US009404096B2

(12) United States Patent
Arnold et al.

(10) Patent No.: US 9,404,096 B2
(45) Date of Patent: *Aug. 2, 2016

(54) ALKANE OXIDATION BY MODIFIED HYDROXYLASES

(71) Applicant: The California Institute of Technology, Pasadena, CA (US)

(72) Inventors: Frances Arnold, Pasadena, CA (US); Peter Meinhold, Pasadena, CA (US); Matthew W. Peters, Pasadena, CA (US); Rudi Fasan, Brea, CA (US); Mike M. Y. Chen, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/788,365

(22) Filed: Jun. 30, 2015

(65) Prior Publication Data

US 2016/0024482 A1 Jan. 28, 2016

Related U.S. Application Data

(60) Continuation of application No. 14/270,268, filed on May 5, 2014, now Pat. No. 9,074,178, which is a division of application No. 11/697,404, which is a continuation-in-part of application No. PCT/US2006/011273, filed on Mar. 28, 2006, now Pat. No. 8,715,988.

(60) Provisional application No. 60/900,243, filed on Feb. 8, 2007, provisional application No. 60/700,781, filed on Jul. 20, 2005, provisional application No. 60/698,872, filed on Jul. 13, 2005, provisional application No. 60/665,903, filed on Mar. 28, 2005.

(51) Int. Cl.
*C12P 7/04* (2006.01)
*C12N 9/02* (2006.01)
*C07K 14/32* (2006.01)

(52) U.S. Cl.
CPC .............. *C12N 9/0077* (2013.01); *C07K 14/32* (2013.01); *C12N 9/0071* (2013.01); *C12P 7/04* (2013.01); *C12Y 114/15* (2013.01); *C12Y 114/15003* (2013.01); *Y02P 20/52* (2015.11)

(58) Field of Classification Search
CPC ........... C12P 7/02; C12P 7/04; C12N 9/0071; C12N 9/0077; C12Y 114/15003; C12Y 114/15
USPC .......................................... 435/157, 132, 189
See application file for complete search history.

(56) References Cited

U.S. PATENT DOCUMENTS

| | | |
|---|---|---|
| 4,599,342 A | 7/1986 | LaHann |
| 5,605,793 A | 2/1997 | Stemmer |
| 5,741,691 A | 4/1998 | Arnold et al. |
| 5,785,989 A | 7/1998 | Stanley et al. |
| 5,811,238 A | 9/1998 | Stemmer et al. |
| 5,830,721 A | 11/1998 | Stemmer et al. |
| 5,837,458 A | 11/1998 | Minshull et al. |
| 5,965,408 A | 10/1999 | Short |
| 6,090,604 A | 7/2000 | Golightly et al. |
| 6,498,026 B2 | 12/2002 | Delagrave et al. |
| 2005/0037411 A1 | 2/2005 | Arnold et al. |
| 2005/0202419 A1 | 9/2005 | Cirino et al. |

FOREIGN PATENT DOCUMENTS

| | | |
|---|---|---|
| EP | 0 505 198 A1 | 9/1992 |
| EP | 0 752 008 | 2/1997 |
| EP | 0 932 670 | 8/2000 |
| WO | WO 89/03424 A1 | 4/1989 |
| WO | WO 95/22625 A1 | 8/1995 |
| WO | WO 97/16553 A1 | 5/1997 |
| WO | WO 97/20078 A1 | 6/1997 |
| WO | WO 97/35957 A1 | 10/1997 |
| WO | WO 97/35966 A1 | 10/1997 |
| WO | WO 98/27230 A1 | 6/1998 |
| WO | WO 98/31837 A1 | 7/1998 |
| WO | WO 98/41653 A1 | 9/1998 |
| WO | WO 98/42832 A1 | 10/1998 |
| WO | WO 99/60096 A2 | 11/1999 |
| WO | WO 00/00632 A1 | 1/2000 |
| WO | WO 00/04190 A1 | 1/2000 |
| WO | WO 00/06718 A2 | 2/2000 |
| WO | WO 00/09679 A1 | 2/2000 |
| WO | WO 00/18906 A3 | 4/2000 |
| WO | WO 00/31273 A2 | 6/2000 |
| WO | WO 01/62938 A2 | 8/2001 |
| WO | WO 03/008563 A2 | 1/2003 |

OTHER PUBLICATIONS

Whittaker, M., et al., "Kinetic Isotope Effects as probes of the Mechanism of Galactose Oxidase," Biochemistry, 1998, pp. 8426-8436 vol. 37, American Chemical Society.
Wilkinson, D., et al., "Structural and Kinetic Studies of a Series of Mutants of Galactose Oxidase Identified by Directed Evolution," Protein Engineering, Design & Selection, Jan. 12, 2004, pp. 141-148, vol. 17, No. 2, Oxford University Press.
Yang, G., et al., "Gal-GalNAc: A biomarker of Colon Carcinogenesis," Histology and Histopathology, 1996, pp. 801-806, vol. 11.
Yano, T., et al., "Directed Evolution of an Aspartate Aminotransferase with New Substrate Specificities," Proc. Natl. Acad. Sci. USA, May 1998, pp. 5511-5515, vol. 95.
Yeom, H., et al., "Oxygen Activation by Cytochrome P450BM-3: Effects of Mutating an Active Site Acidic Residue," Archieves of Biochemistry and Biophysics, Jan. 15, 1997, pp. 209-216, vol. 337, No. 2, Academic Press.

(Continued)

*Primary Examiner* — Younus Meah
(74) *Attorney, Agent, or Firm* — Joseph R. Baker, Jr.; Gavrilovich, Dodd & Lindsey LLP

(57) ABSTRACT

This invention relates to modified hydroxylases. The invention further relates to cells expressing such modified hydroxylases and methods of producing hydroxylated alkanes by contacting a suitable substrate with such cells.

20 Claims, 40 Drawing Sheets

(56) References Cited

OTHER PUBLICATIONS

You, L., et al., "Directed Evolution of Subtilisin E in Bacillus subtilis to Enhance Total Activity in Aqueous Dimethylformamide," Protein Engineering, 1996, pp. 77-83, vol. 9, Oxford University Press.

Zhang, J., et al., "Directed Evolution of a Fucosidase from a Galactosidase by DNA Shuffling and Screening," Proc. Natl. Acad. Sci. USA, Apr. 1997, pp. 4504-4509, vol. 94.

Zhang, T., et al., "Circular Permutation of T4 Lysozyme," Biochemistry, 1993, pp. 12311-12318, vol. 32, No. 46, American Chemical Society.

Zhao, H., et al., "Directed Evolution Converts Subtilisin E into a Functional Equivalent of Thermitase," Protein Engineering,1999, pp. 47-53, vol. 12, No. 1, Oxford University Press.

Zhao, H., et al., "Methods for Optimizing Industrial Enzymes by Directed Evolution," Manual of Industrial Microbiology and Biotechnology (2d Ed.), 1999, pp. 597-604, ASM Press, Washington, D.C.

Zhao, H. et al., "Molecular Evolution by Staggered Extension Process (StEP) In Vitro Recombination," Nature Biotechnology, Mar. 1998, pp. 258-261, vol. 16.

Zhao, H., et al., "Optimization of DNA Shuffling for High Fidelity Recombination," Nucleic Acids Research, 1997, pp. 1307-1308, vol. 25, No. 6, Oxford University Press.

Zimmer, T., et al., "The CYP52 Multigene Family of Candida maltosa Encodes Functionally Diverse n-AlkaneInducible Cytochromes P450," Biochemical and Biophysical Research Communications, 1996, pp. 784-789, vol. 224, No. 3, Academic Press, Inc.

XP-002298548, "Protein Sequence," Database accession No. 355884-87-G.

Maradufu, A. et al., "Stereochemistry of Dehydrogenation by D-Galactose Oxidase," Canadian Journal of Chemistry, Oct. 1971, pp. 3429-3437, vol. 49, No. 19, NCR Research Press, Ottawa Canada.

March, J., Advanced Organic Chemistry: Reactions, Mechanisms, and Structure, 4th Edition, 1992, pp. 882-884, Wiley and Sons NY.

March, J., Advanced Organic Chemistry: Reactions, Mechanisms, and Structure,. 4th Edition, 1992, pp. 1072-1074, Wiley and Sons, NY.

Martin, B. et al., "Highly swelling hydrogels from ordered galactose-based polyacrylates," Biomaterials, 1998, pp. 69-76, 19(1-3), Elsevier.

Martin, I. et al., "Detection of honey adulteration with beet sugar using stable isotope methodology," Food Chemistry, 1998 pp. 281-286, vol. 61, No. 3, Elsevier Science Ltd.

Martineau, P. et al., "Expression of an Antibody Fragment at High Levels in the Bacterial Cytoplasm," J. Mol. Biol., 1998, pp. 117-127, vol. 280, No. 1, Academic Press.

Martinez, C. et al., "Cytochrome P450's: Potential Catalysts for Asymmetric Olefin Epoxidations," Current Organic Chemistry, 2000, pp. 263-282, vol. 4, No. 3, Bentham Science Publishers B.V.

Matson, R. et al., "Characteristics of a Cytochrome P-450-Dependent Fatty Acid $\omega$-2 Hydroxylase From Bacillus Megaterium," Biochimica et Biophysica Acta, 1977, pp. 487-494, 487, Elsevier/ North Holland Biomedical Press.

Mazur, A., "Chapter 8, Galactose Oxidase," ACS Symposium Series 466—Enzymes in Carbohydrate Synthesis, 1991, pp. 99-110. American Chemical Society, Washington, DC, USA.

Mazur, A., et al., "Chemoenzymic Approaches to the Preparation of 5-C-(Hydroxymethyl)hexoses," J. Org. Chem., 1997, pp. 4471-4475, vol. 62, No. 13 American Chemical Society, Washington, DC, USA.

McPherson, M. et al., "Galactose oxidase of Dactylium dendroides. Gene cloning and sequence analysis," Chemical Abstract Service, XP-002298547, Database accession No. M86819.

McPerson, M. et al., "Galactose Oxidase of Dactylium dendroides," Apr. 1992, pp. 8146-8152, The Journal of Biological Chemistry, vol. 267, No. 12, The American Society for Biochemistry and Molecular Biology, Inc.

McPherson, M. et al., "Galactose oxidase: Molecular analysis and mutagenesis studies," Biochemical Society Transactions, 646th Meeting Leeds, 1993, pp. 1992-1994, vol. 21, The Biochemical Society, Portland Press.

Meinhold, P. et al., "Direct Conversion of Ethane to Ethanol by Engineered Cytochrome P450 BM3," ChemBioChem, 2005 PD. 1-4, vol. 6, Wiley-VCH Verlaq GmbH & Co. Weinheim Germany.

Mendonca, M. et al., "Purification and Characterization of Intracellular Galactose Oxidase from Dactylium dendroides," Archives of Biochemistry and Biophysics, Feb. 1987, pp. 507-514, vol. 252, No. 2, Academic Press, Inc.

Mendonca, M. et al., "Role of Carbohydrate Content on the Properties of Galactose Oxidase from Dactylium dendroides," Archives of Biochemistry and Biophysics, Nov. 1988, pp. 427-434, vol. 266, No. 2, Academic Press, Inc.

Miele, R., et al., "Glycosylation of Asparagine-28 of Recombinant Staphylokinase with High-Mannose-type Oligosaccharides Results in a Protein with Highly Attenuated Plasminogen Activator Activity," Journal of Biological Chemistry, Mar. 1999, pp. 7769-7776, vol. 274, No. 12, The American Society for Biochemistry and Molecular Biology, Inc.

Miles, C. et al., "Protein engineering of cytochromes P-450," Biochimica et Biophysica Acta, 2000, pp. 383-407, 1543, Elsevier Science B.V.

Minshull, J. et al., "Protein evolution by molecular breeding," Chemical Biology, 1999, pp. 284-290, 3, Elsevier Science Ltd.

Mitraki, A. et al., "Amino acid substitutions influencing intracellular protein folding pathways," FEBS Letters, Jul. 1992, pp. 20-25, vol. 307, No. 1, Elsevier Science Publishers B.V.

Miura, Y. et al., "$\omega$-1, $\omega$-2 and $\omega$-3 Hydroxylation of Long-Chain Fatty Acids, Amides and Alcohols by a Soluble Enzyme System from Bacillus Megaterium," Biochimica et Biophysica Acta, 1975, pp. 305-317, 388, Elsevier Scientific Publishing Company, Amsterdam, The Netherlands.

Miyazaki, K. et al., "Directed Evolution Study of Temperature Adaptation in a Psychrophilic Enzyme," Journal Mol. Biol., 2000, pp. 1015-1026 297 Academic Press.

Modi, S. et al., "NMR Studies of Substrate Binding to Cytochrome P45OBM3: Comparisons to Cytochrome P450 cam." Biochemistry, 1995, pp. 8982-8988, vol. 34, No. 28, American Chemical Society.

Moore, J. et al., "Directed evolution of a para-nitrobenzyl esterase for aqueous-organic solvents," Nature Biotechnology, Apr. 1996 pp. 458-467, vol. 14.

Moore, J. et al., "Strategies for the in vitro Evolution of Protein Function: Enzyme Evolution by Random Recombination of Improved Sequences," J. Mol. Biol., 1997, pp. 336-347, 272, Academic Press Limited.

Moser, C. et al., "Biological Electron Transfer," Journal of Bioenergetics and Biomembranes, Jun. 1995, pp. 263-274, vol. 27 No. 3 Plenum Publishing Corporation.

Munro, A. et al., "Probing electronic transfer in flavocytochrome P-450 BM3 and its component domains," Eur. J. Biochem., 1996, pp. 403-409, 239, FEBS.

Munro, A. et al., "Alkane Metabnolism by Cytochrome P450 BM3," Biochemical Society Transactions, 1993, p. 412S, 21.

Murrell, J. et al., "Molecular biology and regulation of methane monooxygenase," Arch. Microbial., 2000, pp. 325-332, 173o.

Nagayama, Y. et al., "Role of Asparagine-linked Oligosaccharides in Protein Folding, Membrane Targeting, and Thyrotropin and Autoantibody Binding of the Human Thyrotropin Receptor," Journal of Biological Chemistry, Dec. 1998, pp. 33423-33428, vol. 273, No. 5, The American Society for Biochemistry and Molecular Biology. Inc.

Nakagawa, S. et al., "Construction of Catalase Deficient *Escherichia coli* Strains for the Production of Uricase," Biosci. Biotech. Biochem., 1996, pp. 415-420, 60 (3), Japanese Society for Bioscience, Biotechnology and Agrochemistry.

Nakajima, H. et al.,"Industrial Application of Adenosine 5'—Triphosphate Regeneration to Synthesis of Sugar Phosphates," ACS Symposium Series 466, Enzymes in Carbohydrate Synthesis, Chapter 9, pp. 110-120, American Chemical Society, Washington DC, 1991, Bednarski & Simon, Editors.

(56) References Cited

OTHER PUBLICATIONS

Narhi, L. et al., "Identification and Characterization of Two Functional Domains in Cytochrome P-450BM-3, a Catalytically Self-sufficient Monooxygenase Induced by Barbiturates in Bacillus megaterium," The Journal of Biological Chemistry, May 1987, pp. 6683-6690 vol. 262, No. 14, The American Society of Biological Chemists, Inc.

Narhi, L. et al., "Characterization of a Catalytically Self-sufficient 199,000-Dalton Cytochrome P-450 Monooxygenase Induced by Barbiturates in Bacillus megaterium," The Journal of Biological Chemistry, Jun. 1986, pp. 7160-7169, vol. 261, No. 16, The American Society of Biological Chemists, Inc.

Nelson, D., "Appendix A—Cytochrome P450 Nomenclature and Alignment of Selected Sequences," Cytochrome P450: Structure, Mechanism, and Biochemistry, Second Ed., 1995, pp. 575-606, Plenum Press, NY.

Ness, J. et al., "DNA shuffling of subgenomic sequences of subtilisin," Nature Biotechnology, Sep. 1999, pp. 893-896, vol. 17, No. 9, Nature Publishing Group.

Noble, M. et al., "Roles of key active-site residues in flavocytochrome P450 BM3," Biochem. J., 1999, pp. 371-379, 339, Biochemical Society.

Oliphant, A. et al., "Cloning of random-sequence oligodeoxynucleotides," Gene, 1986, pp. 177-183, 44, Elsevier Science Publishers B.V.

Oliver, C. et al., "Engineering the substrate specificity of Bacillus megaterium cytochrome P-450 BM3: hydroxylation of alkyl trimethylammonium compounds," Biochem. J., 1997, pp. 537-544, 327, The Biochemical Society, London, England.

Omura, T. et al., "The Carbon Monoxide-binding Pigment of Liver Microsomes," The Journal of Biological Chemistry, Jul. 1964 pp. 2370-2378, vol. 239, No. 7, The American Society for Biochemistry and Molecular Biology.

Ortlepp, S. et al., "Expression and characterization of a protein specified by a synthetic horseradish peroxidase gene in *Escherichia coli*," Journal of Biotechnology, 1989, pp. 353-364, 11, Elsevier Science Publishers B.V.

Ost, T. et al., "Rational re-design of the substrate binding site of flavocytochrome P450 BM3," FEBS Letters, 2000, pp. 173-177,486, Elsevier Science B.V.

Ostermeier, M. et al., "Incremental Truncation as a Strategy in the Engineering of Novel Biocatalysts," Bioorganic & Medicinal Chemistry, 1999, pp. 2139-2144, 7, Elsevier Science Ltd.

Parekh, R. et al., "Multicopy Overexpression of Bovine Pancreatic Trypsin Inhibitor Saturates the Protein Folding and Secretory Capacity of *Saccharomyces cerevisiae*," Protein Expression and Purification, 1995, pp. 537-545, 6, Academic Press.

Patten, P. et al., "Applications of DNA shuffling to pharmaceuticals and vaccines," Biotechnology, 1997, pp. 724-733, vol. 8, Elsevier Science Ltd.

Paulsen, M. et al., "Dramatic Differences in the Motions of the Mouth of Open and Closed Cytochrome P450BM-3 by Molecular Dynamics Simulations," Proteins: Structure, Function and Genetics, 1995, pp. 237-243, Wiley-Liss, Inc.

Peterson, J. et al., "Chapter 5—Bacterial P450s," Cytochrome P450: Structure, Mechanism, and Biochemistry, Second Ed., 1995, pp. 151-180, Plenum Press, New York.

Rathore, D., et al., "Expression of Ribonucleolytic Toxin Restrictocin in *Escherichia coli*: Purification and Characterization," FEBS Letters, 1996, pp. 259-262, vol. 392, Federation of European Biochemical Societies.

Reynolds, M., et al., "Structure and Mechanism of Galactose Oxidase: Catalytic Role of Tyrosine 495," JBIC, 1997, pp. 327-335, vol. 2.

Amaral et al., "Galactose Oxidase of Polyporus circinatus1-4," Methods in Enzymology, Carbohydrate Metabolism, 1966, pp. 87-92, vol. 9, Academic Press Inc., New York NY, USA.

Fruetel, J., et al., "Relationship of Active Site Topology to Substrate Specificity for Cytochrome P450terp (CYP108)," The Journal of Biological Chemistry, Nov. 18, 1994, pp. 28815-28821, vol. 269, No. 46, The American Society for Biochemistry and Molecular Biology, Inc.

Gahmberg C., et al., "Nonmetabolic Radiolabeling and Taggin of Glycoconjugates," Methods in Enzymology, 1994, pp. 32-44, vol. 230, Academic Press, Inc.

Gazaryan, I.G., "Heterologous Expression of Heme-Containing Peroxidases," Plant Peroxidase Newsletter, Sep. 1994, pp. 11-13, No. 4, LABPV Newsletters.

Gietz, R., et al., "Studies on the Transformation of Intact Yeast Cells by the LiAc/SS-DNA/PEG Procedure," Yeast, Apr. 15, 1995, pp. 355-360, vol. 11, No. 4, John Wiley & Sons Ltd.

Gillam, E., et al., "Expression of Cytochrome P450 2D6 in *Escherichia coli*, Purification, and Spectral and Catalytic Characterization," Archives of Biochemistry and Biophysics, Jun. 1, 1995, pp. 540-550, vol. 319, No. 2, Academic Press, Inc.

Giver, L., et al., "Combinatorial Protein Design by In Vitro Recombination," Current Opinion in Chemical Biology, 1998, pp. 335-338, vol. 2, Current Biology Ltd.

Giver, L., et al., "Directed Evolution of a Thermostable Esterase," Proc. Natl. Acad. Sci. USA, Oct. 1998, pp. 12809-12813, vol. 95.

Goldman, E., et al., "An Algorithmically Optimized Combinatorial Library Screened by Digital Imaging Spectroscopy," Biotechnology, Dec. 1992, pp. 1557-1561, vol. 10.

Graham-Lorence, S., et al., "An Active Site Substitution, F87V, Converts Cytochrome P450 BM-3 into a Regio-and Stereoselective (14S, 15R)-Arachidonic Acid Epoxygenase," The Journal of Biological Chemistry, Jan. 10, 1997, pp. 1127-1135, vol. 272, No. 2, The American Society for Biochemistry and Molecular Biology, Inc.

Gram, H. et al., "In Vitro Selection and Affinity Maturation of Antibodies from a Naive Combinatorial Immunoglobulin Library," Proc. Natl. Acad. Sci. USA, Apr. 1992, pp. 3576-3580, vol. 89.

Green, J., et al., "Substrate Specificity of Soluble Methane Monooxygenase Mechanistic Implications," The Journal of Biological Chemistry, Oct. 25, 1989, pp. 17698-17703, vol. 264, No. 30, The American Society for Biochemistry and Molecular Biology, Inc.

Griebenow, K., et al., Lyophilization-Induced Reversible Changes in the Secondary Structure of Proteins, Proc. Natl. Acad. Sci. USA, Nov. 1995, pp. 10969-10976, vol. 92.

Groves, J., et al., "Models and Mechanisms of Cytochrome P450 Action," Cytochrome P450: Structure, Mechanism, and Biochemistry (Second Edition), 1995, pp. 3-48, Plenum Press, New York.

Guengerich, F., et al., "Purification of Functional Recombinant P450s from Bacteria," Methods in Enzymology, 1996, pp. 35-44, vol. 272, Academic Press, Inc.

Gossow, D., et al., "Direct Clone Characterization from Plaques and Colonies by the Polymerase Chain Reaction," Nucleic Acids Research, 1989, p. 4000, vol. 17, No. 10, IRL Press.

Haines, D., et al., "Pivotal Role of Water in the Mechanism of P450BM-3," Biochemistry, 2001, pp. 13456-13465, vol. 40, No. 45, American Chemical Society.

Hamilton, G.A., et al., "Galactose Oxidase: The Complexities of a Simple Enzyme," Oxidases and Related Redox Systems, 1973, pp. 103-124, vol. 1, University Park Press.

Hamilton, G.A., et al., "Trivalent Copper, Superoxide, and Galactose Oxidase," Journal of the American Chemical Society, Mar. 15, 1978, pp. 1899-1912, vol. 100, No. 6, American Chemical Society.

Hartmann, M., et al., "Selective Oxidations of Linear Alkanes with Molecular Oxygen on Molecular Sieve Catalysts—A Breakthrough?," Agnew. Chem. Int. Ed. 2000, pp. 888-890, vol. 39, No. 5.

Haschke, R., et al., "Calcium-Related Properties of Horseradish Peroxidase," Biochemical and Biophysical Research Communications, Feb. 28, 1978, pp. 1039-1042, vol. 80, No. 4, Academic Press, Inc.

Helenius, A., "How N-linked Oligosaccharides Affect Glycoprotein Folding in the Endoplasmic Reticulum," Molecular Biology of the Cell, Mar. 1994, pp. 253-265, vol. 5, No. 3, The American Society for Cell Biology.

Hermes, J., et al., "Searching Sequence Space by Definably Random Mutagenesis: Improving the Catalytic Potency of an Enzyme," Proc. Natl. Acad. Sci. USA, Jan. 1990, pp. 696-700, vol. 87.

(56) References Cited

OTHER PUBLICATIONS

Ito, N. et al., "X-Ray Crystallographic Studies of Cofactors in Galactose Oxidase," Methods in Enzymology, Redox-Active Amino Acids in Biology, 1995, pp. 235-262, vol. 258, Academic Press, Inc.

Ito, N. et al., "Crystal Structure of a Free Radical Enzyme, Galactose Oxidase," Journal of Molecular Biology, 1994, pp. 794-814, vol. 238, No. 5, Academic Press Limited.

Ito, N. et al., "Novel thioether bond revealed by a 1.7 Ø crystal structure of galactose oxidase," Nature, Mar. 7, 1991, pp. 87-90.

Joo, H. et al., "Laboratory evolution of peroxide-mediated cytochrome P450 hydroxylation," Nature, Jun. 17, 1999, pp. 671-673 vol. 399.

Joo, H. et al., "A high-throughput digital imaging screen for the discovery and directed evolution of oxygenases," Chemistry & Biology, Oct. 1999, pp. 699-706, vol. 6, No. 10.

Khoslat, C. et al., "Expression of Intracellular Hemoglobin Improves Protein Synthesis in Oxygen-Limited *Escherichia coli*," Bio/Technology, Sep. 1990, pp. 849-853, American Society for Cell Biology, New Orleans, LA, USA.

Kiba, N. et al., "A post-column co-immobilized galactose oxidase/peroxidase reactor for fluorometric detection of saccharides in a liquid chromatographic system," Journal of Chromatography, 1989, pp. 183-187, vol. 463, Elsevier Science Publishes B.V., Amsterdam The Netherlands.

Kim, J. et al., "Use of 4-(Nitrobenzyl)Pyridine (4-NBP) to Test Mutagenic Potential of Slow-Reacting Epoxides. Their Corresponding Olefins, and Other Alkylating Agents," Bull. Environ. Contam. Toxicol., 1992, pp. 879-885, vol. 49, Springer-Verlag New York Inc.

Klibanov, A. et al., "Stereospecific Oxidation of Aliphatic Alcohois Catalyzed by Galactose Oxidase," Biochemical and Biophysical Research Communications, 1982, pp. 804-808, vol. 108, No. 2, Academic Press, Inc.

Knappik, A. et al., "Engineered turns of a recombinant antibody improve its in vivo folding," Protein Engineering, Jan. 1995, pp. 81-89 vol. 8, No. 1, Oxford University Press.

Koroleva, O. et al., "Properties of Fusarium graminearum Galactose Oxidase," 1984, pp. 500-509, Plenum Publishing Corporation.

Kosman, D., "Chapter 1 Galactose Oxidase," in Lontie, R., Eds., Copper Proteins and Copper Enzymes vol. II, pp. 1-26 CRC Press, Inc., Boca Raton, FL, USA.

Koster, R. et al., "Organoboron Monosaccharides; XII1 Quantitative Preparation of D-gluco-Hexodialdose from Sodium D-Giucuronate or D-Giucuronic acid," Synthesis, Aug. 1982, pp. 650-652, No. 8, Georq Thieme Verlaq.

Kuchner, O. et al., "Directed evolution of enzyme catalysts," Biotechnology, Dec. 1997. pp. 523-530, vol. 15, Elsevier Science Ltd.

Kuhn-Velten, W., "Effects of Compatible Solutes on Mammalian Cytochrome P450 Stability," 1997, pp. 132-135, Verlag der Zeitschrift fur Naturforschung.

Kvittingen, L. et al., "Use of Salt Hydrates to Buffer Optimal Water Level During Lipase Catalysed Synthesis in Organic Media: A Practical Procedure for Organic Chemists," Tetrahedron, 1992, pp. 2793-2802, vol. 48, No. 13, Pergamon Press Ltd., Great Britain.

Lei, S. et al., "Characterization of the Erwinia carotovora pelB Gene and its Product Pectate Lyase," Journal of Bacteriology, Sep. 1987, pp. 4379-4383, vol. 169, No. 9, American Society for Microbiology.

Leadbetter, E. R., et al. "Incorporation of Molecular Oxygen in Bacterial Cells Utilizing Hydrocarbons for Growth" Natures; Oct. 31, 1959; vol. 184 pp. 1428-1429.

Leung, D. et al., "A Method for Random Mutagenesis of a Defined DNA Segment Using a Modified Polymerase Chain Reaction," Technique, A Journal of Methods in Cell and Molecular Biology, Aug. 1989, pp. 11-15, vol. 1, No. 1, Saunders Scientific Publications.

Lewis, D., "P450 Substrate Specificity and Metabolism," Cytochromes P450: Structure, Function and Mechanism, Aug. 2001 pp. 115-166, Taylor & Francis Publishers.

Li, H. et al., "The structure of the cytochrome p450BM-3 haem domain complexed with the fatty acid substrate, palmitoleic acid," Nature Structural Biology, Feb. 1997, pp. 140-146, vol. 4, No. 2.

Li, Q. et al., "Rational evolution of a medium chain-specific cytochrome P-450 BM-3 variant," Biochimica et Biophysica Acta, 2001, pp. 114-121, 1545, Elsevier Science B.V.

Lis, M. et al., "Galactose Oxidase-Giucan Binding Domain Fusion Proteins as Targeting Inhibitors of Dental Plaque Bacteria," Antimicrobial Agents & Chemotherapy, May 1997, pp. 999-1003, vol. 41, No. 5, American Society for Microbiology.

Liu, C. et al., "Sugar-containing Polyamines Prepared Using Galactose Oxidase Coupled with Chemical Reduction," J. Am. Chem. Soc., Jan. 20, 1999, pp. 466-467, vol. 121, No. 2, American Chemical Society.

Mannino, S. et al., "Simultaneous Determination of Glucose and Galactose in Dairy Products by Two Parallel Amperometric Biosensors," Italian Journal of Food Science, 1999, pp. 57-65, vol. 11, No. 1, Chiriotti Editori, s.p.a., Pinerolo, Italy.

Maradufu, A. et al., "A Non-Hydrogen-Bonding Role for the 4-Hydroxyl Group of D-Galactose in its Reaction with DGalactose Oxidase," Carbohydrate Research, 1974, pp. 93-99, 32, Elsevier Scientific Publishing Company, Amsterdam, The Netherlands.

Adam et al., "Microbial Asymmetric CH Oxidations of Simple Hydrocarbons: A Novel Monooxygenase Activity of the Topsoil Microorganism *Bacillus megaterium*," Eur. J. Org. Chern., 2000, pp. 2923-2926, Wiley-VCH Verlag GmbH, Weinheim, Germany.

Aisaka et al., "Production of Galactose Oxidase by Gibberella fujikuroi," Agric. Biol. Chem., 1981, pp. 2311-2316, 45(10).

Anfinsen, "Principles that Govern the Folding of Protein Chains," Science, Jul. 20, 1973, pp. 223-230, vol. 181, No. 4096, American Asso for the Advancement of Science, Washington, DC, USA.

Appel et al., "A P450 BM-3 mutant hydroxylates alkanes, cycloalkanes, arenas and heteroarenes," Journal of Biotechnology, 2001, pp. 167-171, Elsevier Science B.V.

Arkin et al., "An algorithm for protein engine ring: Simulations of recursive ensemble mutagenesis," Proc. Natl. Acad. Sci.-USA, Aug. 1992, pp. 7811-7815, vol. 89, Applied Biological Sciences.

Arnold, "Design by Directed Evolution," Accounts of Chemical Research, 1998, pp. 125-131, vol. 31, No. 3, American Chemical Society.

Arnold, "Engineering proteins for nonnatural environments," The FASEB Journal, Jun. 1993, pp. 744-749, vol. 7, No. 6, FASEB, Bethesda, MD, USA.

Arnold et al., "Optimizing Industrial Enzymes by Directed Evolution," Advances in Biochemical Engineering/Biotechnology, 1997, pp. 1-14, vol. 58, Springer-Verlag, Berlin, Germany.

Arts et al., "Hydrogen Peroxide and Oxygen in Catalytic Oxidation of Carbohydrates and Related Compounds," SYNTHESIS Journal of Synthetic Organic Chemistry, Jun. 1997, pp. 597-613.

Ashraf et al., "Bacterial oxidation of propane," FEMS Microbiology Letters, 1994, pp. 1-6, Federation of European MicrobioloQical Societies, Elsevier.

Avigad, "Oxidation Rates of Some Desialylated Glycoproteins by Galactose Oxidase," Archives of Biochemistry and Biophysics, Jun. 1985, pp. 531-537, vol. 239, No. 2, Academic Press, Inc.

Avigad, "An NADH Coupled Assay System for Galactose Oxidase," Analytical Biochemistry, 1978, pp. 470-476, 86, Academic Press Inc.

Avigad, :The D-Galactose Oxidase of Polyporus circinatus. Journal of Biological Chemistry, Sep. 1962, pp. 2736-2743, vol. 237, No. 9, American Society of Biological Chemists, Baltimore, MD, USA.

Barnes, "Maximizing Expression of Eukaryotic Cytochrome P450s in *Escherichia coli*," Methods in Enzymology, Cytochrome P450, Part B, 1996, pp. 3-14, vol. 272, Academic Press, Inc., San Diego, CA, USA.

Baron et al., "Structure and Mechanism of Galactose Oxidase," The Journal of Biological Chemistry, Sep. 23, 1994, pp. 25095-25105, vol. 269, No. 38, American Soc. for Biochemistry and Molecular Biology.

Benson et al., "Regulation of Membrane Peptides by the Pseudomonas Plasmid alk Regulon," Journal of Bacteriology, Dec. 1979 pp. 754-762, vol. 140, No. 3.

Better et al., "*Escherichia coli* Secretion of an Active Chimeric Antibody Fragment," Science, May 20, 1988, pp. 1041-1043, vol. 240, American Asso for the Advancement of Science, Washington, DC, USA.

(56) References Cited

OTHER PUBLICATIONS

Boddupalli et al., "Fatty Acid Monooxygenation by P450BM-3: Product Identification and Proposed Mechanisms for the Sequential Hydroxylation Reactions," Archives of Biochemistry and Biophysics, Jan. 1992, pp. 20-28, vol. 292, No. 1, Academic Press, Inc.

Boddupalli et al., "Fatty Acid Monooxygenation by Cytochrome P-450BM-3," The Journal of Biological Chemistry, 1990, pp. 4233-4239, The American Society for Biochemistry and Molecular Biology.

Borman et al., "Kinetic studies on the reactions of Fusarium galactose oxidase with five different substrates in the presence of dioxygen," Journal of Biological Inorganic Chemistry, 1997, pp. 480-487, Society of Biological Inorganic Chemistry.

Bradford, "A Rapid and Sensitive Method for the Quantitation of Microgram Quantities of Protein Utilizing the Principle of Protein-Dye Binding," Analytical Biochemistry, pp. 248-254.

Calderhead, D. et al., "Labeling of Glucose Transporters at the Cell Surface in 3T3-L 1 Adipocytes," The Journal of Biological Chemistry, Sep. 5, 1988, pp. 12171-12174, vol. 263, No. 25, The American Society for Biochemistry and Molecular Biology.

Calvin, N. et al., "High-Efficiency Transformation of Bacterial Cells by Electroporation," Journal of Bacteriology, Jun. 1988, pp. 2796-2801, vol. 170 No. 6, American Society for Microbiology.

Cameron, A., "Two cradles for the heavy elements," Nature, Jan. 15, 1998, pp. 228-231, vol. 39.

Capdevila, J. et al., "The Highly Stereoselective Oxidation of Polyunsaturated Fatty Acids by Cytochrome P450BM-3," The Journal of Biological Chemistry, Sep. 13, 1996, pp. 22663-22671, vol. 271, No. 37, The American Society for Biochemistry and Molecular Biology, Inc.

Carmichael, A. et al., "Protein engineering of Bacillus megaterium CYP102," Eur. J. Biochem., 2001, pp. 3117-3125, vol. 268, FEBS.

Castelli, L. et al., "High-level secretion of correctly processed β-lactamase from *Saccharomyces cerevisiae* using a highcopy-number secretion vector," Gene, 1994, EE- 113-117, vol. 142, Elsevier Science B.V.

Chang, C. et al., "Evolution of a cytokine using DNA family shuffling," Nature Biotechnology, Aug. 1999, pp. 793-797, vol. 17.

Chang, Y. et al.., "Homology Modeling, Molecular Dynamics Simulations, and Analysis of CYP119, a P450 Enzyme from Extreme Acidothermophilic Archaeon Sulfolobus soifataricus," Biochemistry, 2000, pp. 2484-2498, vol. 39, No. 10, American Chemical Society.

Chen, H. et al., "Thermal, Catalytic, Regiospecific Functionalization of Alkanes," Science, Mar. 17, 2000, pp. 1995-1997, vol. 287.

Chen, K. et al., "Tuning the activity of an enzyme for unusual environments: Sequential random mutagenesis of subtilisin E for catalysis in dimethylformamide," Proc. Natl. Acad. Sci. USA, Jun. 15, 1993, pp. 5618-5622, vol. 90, No. 12.

Cherry, J. et al., "Directed evolution of a fungal peroxidase," Nature Biotechnology, Apr. 1999, pp. 379-384, vol. 17, Nature America Inc., New York, NY, USA.

Christians, F. et al., "Directed evolution of thymidine kinase for AZT phosphorylation using DNA family shuffling," Nature Biotechnology, Mar. 1999, pp. 259-264, vol. 17, Nature America Inc., New York, NY, USA.

Cleland, J. et al., "Cosolvent Assisted Protein Refolding," Biotechnology, Dec. 1990, pp. 1274-1278, vol. 8.

Crameri, A. et al., "Molecular evolution of an arsenate detoxification pathway by DNA shuffling," Nature Biotechnology, May 1997 pp. 436-438, vol. 15, Nature America Inc., New York, NY, USA.

Crameri, A. et al., "Improved Green Fluorescent Protein by Molecular Evolution Using DNA Shuffling," Nature Biotechnology, Mar. 1996, pp. 315-319, vol. 14, Nature America Inc., New York, NY, USA.

Crameri, A. et al., "Construction and evolution of antibody-phage libraries by DNA shuffling," Nature Medicine, Jan. 1996, pp. 100-106 vol. 2, No. 1.

Dahlhoff, W. et al., "L-Giucose or D-gluco-Hexadialdose from D-Glucurono-6,3-lactone by Controlled Reductions," Angew. Chem. Int. Ed. Engl., 1980, pp. 546-547, 19 No. 7, Verlag Chemie, GmbH, Weinheim, Germany.

Danon, A. et al. "Enrichment of Rat Tissue Lipids with Fatty Acids that are Prostaglandin Precursors" Biochimica et Biophysica Acta, 1975, 388: 318-330.

De Bernardez-Clark, E. et al., "Inclusion Bodies and Recovery of Proteins from the Aggregated State," ACS Symposium Series Protein Refolding, 199th Natl Mtg American Chemical Society, Apr. 22-27, 1990, pp. 1-20, American Chemical Society, Washington, DC, USA.

Deacon, S. et al., "Enhanced Fructose Oxidase Activity in a Galactose Oxidase Variant," ChemBioChem: A European Journal of Chemical Biology, 2004, pp. 971-979, 5, Wiley-VCH Verlag GmbH & Co., Weinheim, Germany.

Delagrave, S. et al., "Recursive ensemble mutagenesis," Protein Engineering, Apr. 1993, pp. 327-331, vol. 6, No. 3, Oxford University Press.

Delagrave, S. et al., "Searching Sequence Space to Engineer Proteins: Exponential Ensemble Mutagenesis," Bio/Technology, Dec. 1993, pp. 1548-1552, vol. 11, American Society for Cell Biology, New Orleans, LA, USA.

Dordick, J., "Designing Enzymes for Use in Organic Solvents," Biotechnol. Prog., 1992, pp. 259-267, 8, American Chemical Society and American Institute of Chemical Engineers.

Dower, W. et al., "High efficiency transformation of *E.-coli* by high voltage electroporation," Nucleic Acids Research, 1988, pp. 6127-6145, vol. 16, No. 13, IRL Press Limited, Oxford, England.

Farinas, E., et al., "Directed Evolution of a Cytochrome P450 Monooxygenase for Alkane Oxidation," Adv. Synth. Catal., 2001, pp. 601-606, vol. 343, No. 6-7.

Fiedler, K., et al., The Role of N-Glycans in the Secretory Pathway, Cell, May 5, 1995, pp. 309-312, vol. 81, Cell Press.

Fisher, M., et al., "Positional Specificity of Rabbit CYP4B1 for ω-Hydroxylation of Short-Medium Chain Fatty Acids and Hydrocarbons," Biochemical and Biophysical Research Communications, 1998, pp. 352-355, vol. 248, No. RC988842.

Fox, B., et al., "Methane Monooxygenase from Methylosinus trichosporium OB3b," Methods in Enzymology, 1990, pp. 191-202, vol. 188, Academic Press, Inc.

Fox, B., et al., "Methane Monooxygenase from Methylosinus trichosporium OB3b Purification and Properties of a Three-Component System with High Specific Activity from a Type II Methanotroph," The Journal of Biological Chemistry, Jun. 15, 1989, pp. 10023-10033, vol. 264, No. 17, The American Society for Biochemistry and Molecular Biology, Inc.

Rodriguez-Lopez, J., et al., "Role of Arginine 38 in Horseradish Peroxidase—A Critical Residue for Substrate Binding and Catalysis," The Journal of Biological Chemistry, Feb. 23, 1996, pp. 4023-4030, vol. 271, No. 8, The American Society for Biochemistry and Molecular Biology.

Romanos, M., et al., "Foreign Gene Expression in Yeast: a Review," Yeast, Jun. 1992, pp. 423-488, vol. 8, No. 6, John Wiley & Sons Ltd.

Root, R., et al., "Enzymatic Synthesis of Unusual Sugars: Galactose Oxidase Catalyzed Stereospecific Oxidation of Polyols," Journal of the American Chemical Society, 1985, pp. 2997-2999, vol. 107, No. 10, American Chemical Society.

Ruettinger, R., et al., "Coding Nucleotide, 5' Regulatory, and Deduced Amino Acid Sequences of P-4506M.3 , a Single Peptide Cytochrome P-450:NADPH-P-450 Reductase from Bacillus megaterium," The Journal of Biological Chemistry, Jul. 5, 1989, pp. 10987-10995, vol. 264, No. 19, The American Society for Biochemistry and Molecular Biology, Inc.

Ruettinger, R., et al., "Epoxidation of Unsaturated Fatty Acids by a Soluble Cytochrome P-450-dependent System from Bacillus megaterium," The Journal of Biological Chemistry, Jun. 10, 1981, pp. 5728-5734, vol. 256, No. 11.

Said, I.T., et al., "Comparison of Different Techniques for Detection of Gai-GalNAc, an Early Marker of Colonic Neoplasia," Histology and Histopathology, Apr. 1999, pp. 351-357, vol. 14, No. 2, Jimenez Godoy, SA.

(56) References Cited

OTHER PUBLICATIONS

Savenkova, M., et al. "Improvement of Peroxygenase Activity by Relocation of a Catalytic Histidine within the Active Site of Horseradish Peroxidase," Biochemistry, 1998, pp. 10828-10836, vol. 37, American Chemical Society.

Saysell, C., et al., "Properties of the Trp290His Variant of Fusarium NRRL 2903 Galactose Oxidase: Interactions of the GOasesemi State with Different Buffers, Its Redox Activity and Ability to Bind Azide," JBIC, 1997, pp. 702-709, vol. 2.

Schatz, P., et al., "Genetic Analysis of Protein Export in *Escherichia coli*," Annual Review of Genetics, 1990, pp. 215-248, vol. 24, Annual Reviews, Inc., Palo Alto, CA.

Schein C., "Solubility as a Function of Protein Structure and Solvent Components," Bio/Technology, Apr. 1990, pp. 308-317, vol. 8, No. 4.

Scheller, U., et al., "Characterization of the n-Alkane and Fatty Acid Hydroxylating Cytochrome P450 Forms 52A3 and 52A4," Archives of Biochemistry and Biophysics, Apr. 15, 1996, pp. 245-254, vol. 328, No. 2, Academic Press, Inc.

Schlegel, R., et al.,"Substrate Specificity of D-Galactose Oxidase," Carbohydrate Research, Jun. 1968, pp. 193-199, vol. 7, No. 2, Elsevier Publishing Company, Amsterdam.

Schmid, A., et al., "Industrial Biocatalysis Today and Tomorrow," Nature, Jan. 11, 2001, pp. 258-268, vol. 409, Macmillian Magazines Ltd.

Schneider, S., et al., "Controlled Regioelectivity of Fatty Acid Oxidation by Whole Cells Producing Cytochrome P450sM-3 Monooxygenase Under Varied Dissolved Oxygen Concentrations," Biotechnology and Bioengineering, Aug. 5, 1999, pp. 333-341, vol. 64, No. 3, John Wiley & Sons, Inc.

Schwaneberg, U., et al., "A Continuous Spectrophotometric Assay for P450 BM-3, a Fatty Acid Hydroxylating Enzyme, and its Mutant F87A," Analytical Biochemistry, 1999, pp. 359-366, vol. 269, Academic Press.

Schwaneberg, U., et al., "Cost-Effective Whole-Cell Assay for Laboratory Evolution of Hydroxylases in *Escherichia coli*," Journal of Biomolecular Screening, 2001, pp. 111-117, vol. 6, No. 2, The Society for Biomolecular Screening.

Schwaneberg, U., et al., "P450 Monooxygenase in Biotechnology—Single-Step, Large-Scale Purification Method for Cytochrome P450 BM-3 by Anion-Exchange Chromatography," Journal of Chromatography, 1999, pp. 149-159, vol. 848, Elsevier Science B.V.

Shafikhani, S., et al., "Generation of Large Libraries of Random Mutants in Bacillus subtilis by PCR-Based Plasmid Multimerization," BioTechniques, Aug. 1997, pp. 304-310, vol. 23, No. 2.

Shanklin, J., et al., "Mossbauer Studies of Alkane ω-Hydroxylase: Evidence for a Diiron Cluster in an Integral-Membrane Enzyme," Proc. Natl. Acad. Sci. USA, Apr. 1997, pp. 2981-2986, vol. 94.

Shao, Z., et al., "Random-priming in Vitro Recombination: An Effective Tool for Directed Evolution," Nucleic Acids Research, Jan. 15, 1998, pp. 681-683, vol. 26, No. 2, Oxford University Press.

Shilov, A., et al., "Activation of C-H Bonds by Metal Complexes," Chem. Rev., 1997, pp. 2879-2932, vol. 97, American Chemical Society.

Shindler, J., et al.,"Peroxidase from Human Cervical Mucus—The Isolation and Characterisation," European Journal of Biochemistry, Jun. 1976, pp. 325-331, vol. 65, No. 2.

Sirotkin, K., "Advantages to Mutagenesis Techniques Generating Populations Containing the Complete Spectrum of 1—single Codon Changes,"J. Theor. Biol., 1986, pp. 261-279, vol. 123, Academic Press Inc. (London) Ltd.

Smith, A., et al., "Expression of a Synthetic Gene for Horseradish Peroxidase C in *Escherichia coli* and Folding and Activation of the Recombinant Enzyme with Ca2+ and Heme," The Journal of Biological Chemistry, Aug. 5, 1990, pp. 13335-13343, vol. 265, No. 22, The American Society for Biochemistry and Molecular Biology.

Smith, A., et al., "Substrate Binding and Catalysis in Heme Peroxidases," Current Opinion in Chemical Biology, (1998), pp. 269-278, vol. 2.

Spiro, T., et al., "Is the CO Adduct of Myoglobin Bent, and Does it Matter?," Accounts of Chemical Research, 2001, pp. 137-144, vol. 34, No. 2, American Chemical Society.

Staijen, I., et al., "Expression, Stability and Performance of the Three-Component Alkane Mono-oxygenase of Pseudomonas oleovorans in *Escherichia coli*," Eur. J. Biochem., 2000, pp. 1957-1965, vol. 267.

Stemmer, W., "DNA Shuffling by Random Fragmentation and Reassembly: In Vitro Recombination for Molecular Evolution," Proc. Natl. Acad. Sci. USA, Oct. 25, 1994, pp. 10747-10751, vol. 91, No. 22.

Stemmer, W., "Rapid Evolution of a Protein In Vitro by DNA Shuffling," Nature, Aug. 4, 1994, pp. 389-391, vol. 370, No. 6488.

Stemmer, W., et al., "Selection of an Active Single Chain Fv Antibody from a Protein Linker Library Prepared by Enzymatic Inverse PCR," BioTechniques, 1993, pp. 256-265, vol. 14, No. 2.

Stevenson, J., et al., "The Catalytic Oxidation of Linear and Branched Alkanes by Cytochrome P450cam," J. Am. Chem. Soc., 1996, pp. 12846-12847, vol. 118, No. 50, American Chemical Society.

Studier, F., et al., "Use of T7 RNA Polymerase to Direct Expression of Cloned Genes," Methods in Enzymology, 1990, pp. 60-89 vol. 185 Academic Press, Inc.

Sun, L., et al., "Expression and Stabilization of Galactose Oxidase in *Escherichia coli* by Directed Evolution," Protein Engineering, Sep. 2001, pp. 699-704, vol. 14, No. 9, Oxford University Press.

Sun, L., et al., "Modification of Galactose Oxidase to Introduce Glucose 6-Oxidase Activity," ChemBioChem: A European Journal of Chemical Biology, Aug. 2, 2002, pp. 781-783, vol. 3, No. 8, Wiley-VCH-Vertag GmbH, Weinheim, Germany.

Szabo, E., et al., "Application of Biosensor for Monitoring Galactose Content," Biosensors & Bioelectronics, 1996, pp. 1051-1058, vol. 11, No. 10, Elsevier Science Limited.

Tams, J., et al., "Giycosylation and Thermodynamic Versus Kinetic Stability of Horseradish Peroxidase," FEBS Letters, 1998, pp. 234-236, vol. 421, Federation of European Biochemical Societies.

Thatcher, D., et al., "Protein Folding in Biotechnology," Mechanisms of Protein Folding, 1994, pp. 229-261, IRL Press, Oxford.

Tkac, J., et al., "Rapid and Sensitive Galactose Oxidase-Peroxidase Biosensor for Galactose Detection with Prolonged Stability," Biotechnology Techniques, 1999, pp. 931-936, Kluwer Academic Publishers.

Tonge, G., al., "Purification and Properties of the Methane Monooxygenase nzyme System from Methylosinus trichosporium OB3b," Biochem. J., 1977, pp. 333-344, vol. 161.

Tressel, P., et al., "A Simplified Purification Procedure for Galactose Oxidase," Analytical Biochemistry, Jun. 1980, pp. 150-153, vol. 105, No. 1, Academic Press, Inc.

Tressel, P., et al., "Galactose Oxidase from Dactylium dendroides," Methods in Enzymology, 1982, pp. 163-171, vol. 89, Academic Press.

Truan, G., et al., "Thr268 in Substrate Binding and Catalysis in P450BM-3," Archives of iochemistry and Biophysics, Jan. 1, 1998, pp. 53-64, vol. 349, No. 1, Academic Press.

Vega, F., et al., "On-line Monitoring of Galactoside Conjugates and Glycerol by Flow Injection Analysis," Analytica Chimica Acta, 1998, pp. 57-62, vol. 373, Elsevier Science B.V.

Vrbova, E., et al., "Preparation and Utilization of a Biosensor Based on Galactose Oxidase," Collect. Czech. Chem. Commun., 1992, pp. 2287-2294, vol. 57.

Wachter, R., et al., "Molecular Modeling Studies on Oxidation of Hexopyranoses by Galactose Oxidase. An Active Site Topology Apparently Designed to Catalyze Radical Reactions, Either Concerted or Stepwise," Journal of the American Chemical Society, Mar. 9, 1996, pp. 2782-2789, vol. 118, No. 9.

Watkinson, R., et al., "Physiology of Aliphatic Hydrocarbon-Degrading Microorganisms," Biodegradation, 1990, pp. 79-92, vol. 1, Nos. 2/3 Kluwer Academic Publishers.

(56) References Cited

OTHER PUBLICATIONS

Welinder, K., "Amino Acid Sequence Studies of Horseradish Peroxidase," European Journal of Biochemistry, 1979, pp. 483-502.
Welinder, K., "Supplement to Amino Acid Sequence Studies of Horseradish Peroxidase," pp. 495-502.
Wetzel, R., et al., "Mutations in Human Interferon Gamma Affecting Inclusion Body Formation Identified by a General Immunochemical Screen," Bio/Technology, Aug. 1991, pp. 731-737, vol. 9.
Whittaker, M., et al., "The Active Site of Galactose Oxidase," The Journal of Biological Chemistry, 1988, pp. 6074-6080, vol. 263, No. 13, The American Society for Biochemistry and Molecular Biology, Inc.

Fig. 6A

```
                   201                                              250
SEQ1       (194)  DPAYDENKRQPQE IKV NDL    KI AE  -RKASG Q-SD L  H LN
SEQ2       (195)  QD LMV TKRQFRY IQT FSL    SI AE  -R ANG QDEK L AR LNV
SEQ3       (195)  QD MMV TKLQFQK IEV NSL    R  AE  -RKANP ENIK L  L LY
SEQ4       (197)  D LMW TKRQFQH IQS FSL    NI AE  -RK SGNQEE L R LHV
SEQ5       (201)  QD FMG AHRQAAE IAY RNL  D  RQ  - R VSPTSGM L NL LE
SEQ6       (197)  QIWMQ R  TLAE AF NK    EI AERR SAEGIDDKK   AA  T
SEQ7       (194)  DPAYDENKRQCQE IKV NDL    KI AE  -RKARC Q-SD L   LN
Consensus  (201)  DDK M R KRQFQEDI  MN LVD  IIAE  RKA GDQ    DLLS ML G 251                                              300
SEQ1       (241)   PE GEP    RY I I              SFAL F KN H QKA
SEQ2       (243)   PE GEK    RY I I              SFAT F LKH  K KA
SEQ3       (243)   PV  ET    RY I I              SFA  C LTH  K KA
SEQ4       (245)  Q PE GEK    R  I I              SFA  F LKD  K KA
SEQ5       (249)   PE DRR    RN I I              FAL  L N  AQA
SEQ6       (247)  V RS GEQ   V RY IN              S TL A LKH   KKA
SEQ7       (241)   PE GEP    SY I I              SFAL F KN H QKV
Consensus  (251)  KDPETGE LDDENIRYQIITFLIAGHETTSGLLSFALYFLLKNPDVLKKA 301                                              350
SEQ1       (291)  AE AAR LVDPV---   KQVKQLKY GMV N      W TA  FSLYAKE
SEQ2       (293)  YE VDR LTDAA---   KQVLELTYIRM N      W TA  FSLYPKE
SEQ3       (293)  QE ADR LTDDT---   KQ QQLKYIRMV N      TA  FSLYAKE
SEQ4       (295)  YE VDR LTDPT---   QQVMKLKYIRM N      W TA  FSLYAKE
SEQ5       (298)  YA VDT LPGDA--L V AD AR PV DRV K T     W TA  F APF
SEQ6       (297)  Y  VDR PGPDVNAK   QQVTQLTYITQ  K      W PA   G SPLA
SEQ7       (291)  VE AAR LVDPV---   KQVKQLKY GMV N      W TF  FSLYAKE
Consensus  (301)  YEEVDRVL D       PTYKQV QLKYI MVLNEALRLWPTAPAFSLYAKE 351                                              400
SEQ1       (338)   TVL  EYP EKG-DE MVLIPQ     T  GDDVEE RPER E--NP A
SEQ2       (340)   TV   K P TTN-DRI VLIPQ     DA GKDAEE RPER E--HQQ
SEQ3       (340)   TVL  EYP SKG-QP VLIPK     QNA GFDAE  RPER E--DP S
SEQ4       (342)   TV  KYP RKGEDRI VLIPQ     DA GDNVEE QPER E--DLDK
SEQ5       (346)   VVL  RYP RKD-RRI V TA    PK  N-PER DI R LPENE K
SEQ6       (347)   T   GKY KL KGTYI  LTA    PS  GPNP A DPEN SREAE K
SEQ7       (338)   TVL  EYP EKG-DE MVLIPQ     T  GDDVEE RPER E--NP A
Consensus  (351)  DTVLGG YPI KG D ISVLIPQLHRDK IWG D EEFRPERFE     S
```

Fig. 6B

```
                401                                               450
SEQ1    (385) IP?QH?YK????N?Q????QQ??LH??TLVLGM??KH???FEDHTN??ELDI?
SEQ2    (387) IP?HH?YK????N?Q????MQ??LH??TLVLGM??K???TLIDHHM??ELDI?
SEQ3    (387) IP?HH?YK????N?Q????MQ??LQ??T?VLG???KH???LINHTG??ELKI?
SEQ4    (390) IP?HH?YK????N?Q????MQ??LH??TLV?GM??QH???FID?ED??QLD?
SEQ5    (394) IP?AH?YM????N?Q????RQ??LT??KLAI?????N?AFQDPHD??QFR?
SEQ6    (397) R?IK?YK????N?Q????PG??IH??ALALGM??QR??KLIDHQR??Q?H?
SEQ7    (385) IP?QH?YK????N?Q????QQ??LH??TLVLGM??KH???FEDHTN??ELDI?
Consensus (401) IP HAYKPFGNGQRACIG QFALHEATLVLGMMLKHFDFIDH  YELDIK 451                                               500
SEQ1    (435) ET??L??G?V??A?S??---------IPLG?IPSPSTEQSAKKVRKKAE
SEQ2    (437) QT??L??GD?HISVQSRHQEAIHADVQ?AEK?APDEQKEK-TEA?GA?VI
SEQ3    (437) EA?????D?KITV?PR?---------T?AINVQRKEQADIKAET?PKETK
SEQ4    (440) QT??L??GD?KI??VPRNQNISHTTVL?PTEEKLKNHEIKQQVQ?TP?II
SEQ5    (444) ET??????G?V??V?RR?---------PHERFVTRQASQAVADAAQ?DV
SEQ6    (447) ET?????G?KI?V?PRADR------ED?AYG?PVAAVSSAPRAP?QP?AR
SEQ7    (435) ET??L??G?V??A?S??---------IPLG?IPSPSTGQSAKKVRKKAE
Consensus (451) ETLTLKPE F IKVK RK           AP  G          K  S 501                                               550
SEQ1    (476) N?HNTPLL??YG?N?T?EGT?A?LADIAMSK?PAPQ?AT?DS?A?N??
SEQ2    (486) GL?N?RPLL??YG?DT?T?EG??P?LADTASL??VRTKTAP?NDR??K??
SEQ3    (479) PK?GTPLL??G?N?T?PG?Q?LAAQ?RQM?FTAETAP?DD??K??E
SEQ4    (490) Q?DNLSLL??YG?DT?V?EG??R?LADTASLE?VQTE?AA?NDR??S???
SEQ5    (484) R?HGQA?T??C??S?T?RE??EQ?HAGAIAA?PDAK?AD?DDA??V??T
SEQ6    (492) P?HNTP?L??YG?N?T?EE??T?ADLAEIN?PAVH?GA?D??K??Q
SEQ7    (476) N?HNTPLL??YG?N?T?EGT?A?LADIAMSK?PAPQ?AT?DS?A?N??
Consensus (501) AHNTPLLVLYGSNLGTAEGIARELAD  A     GP    VA LDDHIG LPK 551                                               600
SEQ1    (526) E?A??LIVTAS????HP?DN?KQ?VDW??QAS--ADE?KGVRY?VF??DKN
SEQ2    (536) E?A??IVT?S????KP?SN?GQ?VQW??QEIK--PGE??KGVHYAVF??DHN
SEQ3    (529) E?????IVTAS????AP?DN?AG?VEW??KELE--EGG?KGVSYAVF??NRS
SEQ4    (540) E?A??LIVT?S????KP?SN?GQ?VQW??ELK--PDE?KGVQYAVF??DHN
SEQ5    (534) S?L???VAA????RA?DS?RK?EAM?ADDASGYRANG?RLA?L??N-S
SEQ6    (542) E???LI?CAS????AP?DN?TQ?VKW??CSDLP-KDAFAMVRYAVF??NSD
SEQ7    (526) E?A??LIVTAS????HP?DN?KQ?VDW??QAS--ADE?KGVRY?VF??DKN
Consensus (551) EGAVLIVTASYNG PPDNA QFV WLD       DELKGVRYAVFGCGD N
```

Fig. 6C

```
              601                                              650
SEQ1   (574) WA      V AFIDETLA K  EN  DR  A ASD FEGTYEE   RHMW D
SEQ2   (584) WA      YV RFIDEQLAEK  TRF AR    VSG FEGQLE   KSMW D
SEQ3   (577) WA        RLIDSM K KE SR TAI     A D FKSHRES ENRFW
SEQ4   (588) WA        R IDEQ AQK  TRF TR  A ASG FKEQLEQ  KSMW
SEQ5   (583) QRA    AF RP F FFITA  VP LPR  A NC F QAAER  LAQ WQA
SEQ6   (591) WAA    SV RFIDEQL  H RA YPR  ARS  LGQFQK  FPAAAQV
SEQ7   (574) WA      V AFIDETLA K  EN  DR  A ASD FEGTYEE   RHMW D
Consensus (601) WASTYQKVPRFIDE LAAKGA  IA RGSADAS DFEG  E WK  MWSD 651                                              700
SEQ1   (624) VAAYFNL  ENSE--  N STLSLQFVDSAA MPLA M GAFSTNV AS
SEQ2   (634) AIKAF L  NENAD-K RSTLSLQFVRGL   PLA  EASHAS AEN
SEQ3   (627) TMDAPD NEIAQK--  RP LS TF SEAT  P A A GAFEGIV EN
SEQ4   (638) AMKAF L NKNME-K RSTLSLQFVSRL G PLA T EAVYAS EN K
SEQ5   (633) LQADG GTGGLGVDVQVRSMA RAETLPAG QAFTVLSNDELVGDPSGL
SEQ6   (641) ATKEF   WNFTRTA  DPLY  SPVAVTAVNT VAQGGAVAMKV VNDE
SEQ7   (624) VAAYFNL  ENSE--  N STLSLQFVDSAA MPLA M GAFSTNV AS
Consensus (651)       FGLDI    DDRSTLSLQFV  ADSPLAK YGA   VL NRE 701                                              750
SEQ1   (672) LQQPG----SAR  H EIEL KEA  QE   LGV    YEG   RVTA
SEQ2   (683) LQS D----SDR  HIEIAL PDVE QK   LGV    SQTN SR LH
SEQ3   (675) LQT A----STR  HIE F AGKT  E   G    SRE   RVLS
SEQ4   (687) LQS S----SER  HIEISL EGAT    LGV  I SEKN  R LK
SEQ5   (683) WDP IEAP--RT  DIR QL PGIT  T    VW  DAQ  SE CE
SEQ6   (691) LQNKSGNPSEP  HIE QL SNIT V   LSV   DPT  DSVAR
SEQ7   (672) LQQPG----SAP  H KI EL KEA  QE   LGV    YEGT  RVTA
Consensus (701) LQ A    S RSTRHIEI LP  TYKEGDHLGVLPRN   LVNRV  R 751                                              800
SEQ1   (718) FGLD SQQT LEAEEEK AHL L  TVSVE   QY-V L  PVT TQLRA
SEQ2   (729) FGLK TDQ TLSASGRSA HL L  PVS H   SYSV    AAT AQ RE
SEQ3   (721) FGLQSMHVI  S -SAH AHL  D P KVV   SSYV L  PA  LQLRE
SEQ4   (733) FGLN KDC IL SASGRS NH LDSPVB Y SYSV    AAT AQ RE
SEQ5   (731) LDLDPDAQAT SAPHGMGRGL  DQA PVRQ  F L  VV  QTLRA
SEQ6   (741) FGFLPADQI LQVAEGRRAQL   EAVSVGR  SEFV L  QVAT KQ QI
SEQ7   (718) FGLD SQQI LEAEEEK AHL L  TVSVE   QY-V L  PVT TQLRA
Consensus (751) FGL A  QIRLSA   LAHLPLAK VSV DLLSY VELQD ATR QLR
```

Fig. 6D

```
                801                                                    850
SEQ1    (767) MA?K?V??PHKVELE?L?EKQ-----A??EQVLAK?L?ML?L?EKYP?CE
SEQ2    (779) ?A?F?V??PH?RELEELSA?G-----V?QEQ?LKK??ML DL?EKYE?CE
SEQ3    (770) ?A?Y?V??PHQKELEQL?S?DG-----I??EQVLAK?L?MLDF?EDYP?CE
SEQ4    (783) MVTF?A??PHKKELE?L?E?G-----V?HEQ?LKK??MLDL?EKYP?CE
SEQ5    (781) ?AQA?R??FTKQS?EQLAS?DAEHG--?ATKV?A??LG?LD??VE?P?IA
SEQ6    (791) MAEH?R??VTKPKLL?F?C?EAEPAER??TE??LAM?K??YDL?LEYF?CE
SEQ7    (767) MA?K?V??PHKVELE?L?EKQ-----A??EQVLAK?L?ML?L?EKYP?CE
Consensus (801) MAA TVCPPHK ELEALL D       YKEQVLAKRLSMLDLLEKYPACE 851                                                    900
SEQ1    (812) MKFSEP?ALLP??????Y???S????VDEKQASIT?SV?SGE?W??Y?EY?
SEQ2    (824) MPFERFLELLRPL???Y???S????VNPRQASIT?GV?RGP?W??R?EY?
SEQ3    (816) MPFERFLALLD?L???Y???S????VHANIVS?T?GV?K?S?W??R?EY?
SEQ4    (828) ?RFERFLELLP?L???Y???S???L?AQDRLSIT?GV?N?P?W??E?TYE
SEQ5    (829) ?TLQELLACTVP??????L??????LVSPDVA??L?GT?C?P?L??R?Q??
SEQ6    (841) ?PFHV?LE?LSLLA?Y???S????SVDPARCSIT?GV?EGP?A??R?VY?
SEQ7    (812) MKFSEF?ALLP??????Y???S????VDEKQASIT?SV?SGE?W??Y?EY?
Consensus (851) M P  FLALLPSLKPRYYSISSSPRV   ASITVGVV GPAWSGRGEYK 901                                                    950
SEQ1    (862) ??A?NY?AEL?EGDTITCFISTPQSE?TLPKDPET??IMV?????????
SEQ2    (874) ?VA?ND?AER?AGDD?VMFIRTPESR?QLPKDPET??IMV?????????
SEQ3    (866) ?VA?NY?AEL?TGDAAACFIRTPQSG?Q?PNDPET??IMV?????????
SEQ4    (878) ?VA?NY?AQRHNKDEIICFIRTPQSN?QLPENPET??IMV?????????
SEQ5    (879) ?VA?T??QHLPPGAR?SASIRTF?PP?APDPDPAA??????????????
SEQ6    (891) ??C?NY?ANRRASDAIYAT?RETK?G?RLPDDSSV?IM?????????
SEQ7    (862) ??A?NY?AEL?EGDTITCFISTPQSE?TLPKDPET??IMV?????????
Consensus (901) GVASNYLAELQ GD I CFIRTPQS F LP DPETPIIMVGPGTSIAPFR 951                                                   1000
SEQ1    (912) ????QA?KQL?EQ?Q?LGE?H?Y????SPHE??L?QEELE?AQS????TLR
SEQ2    (934) ???LQA?D?L?RE?K?LGE?H?Y?????N-?R??R?ELERF?K???T??H
SEQ3    (916) ????QA?S?L?KE?S?LGE?L?Y????RP?H??DL?REEL?A?Q??T??R
SEQ4    (928) ???LQA?R?Q?K?MNLGE?H?Y????HP?K??L?RTELE?DER???LR
SEQ5    (929) ???LEE?A?R?MA?NA?TP?Q?Y????HPQH??L?RE??ERWA GQ??E?H
SEQ6    (941) ???LQE?AAR?AK?A?LGP?M??????HP?Q??L?A?ELKALAAS??TELF
SEQ7    (912) ????QA?KQL?EQ?Q?LGE?H?Y????SPHE??L?QEELE?AQS????TLR
Consensus (951) GFLQAR VLK  G SLGEAHLYPGCR PD DYLREELEN   DGIITLR
```

Fig. 6E

```
                1001                                              1050
SEQ1    (962)   TAFSR PNQ KT   HV RQDGKKLIELLD  AHF       SQ A  EA
SEQ2    (973)   TAFSRR GM KT   H ADQADTLIS LDR  R  V     SK A D RA
SEQ3    (966)   RC  R  NE KG   H KQDTQKL TL  K AH  V      SQ A D ER
SEQ4    (978)   TAF R  GH KT   HV KEDRMNLISLLD  AH        SK A D RD
SEQ5    (979)   PA  V PDA   D  WQRREQ WAQ RD AT  V     RR A  RQ
SEQ6    (991)   TAF RA G- KT   HV AAQKDK WPL    AI  V     GQ E D KA
SEQ7    (962)   TAFSR PNQ KT   HV RQDGKKLIELLD  AHF       SQ A  EA
Consensus (1001) TAFSRME  PKTYVQHVL QD   KLI LLDQGAHIYVCGDGSQMAPDVEA 1051                                  1088
SEQ1    (1012)  T  K YA  HQ SEA ARL LQQLE KGR  K  WAG-
SEQ2    (1023)  A QK YQA H TGEQ AQN LRHLQ TGM  K   WAGI
SEQ3    (1016)  T RL YEAEK ASQP  AV LQKLQ QRR VK  WTGM
SEQ4    (1028)  T CQ YG  HE SEQ ARN LDRLQ EGR  K  WAGI
SEQ5    (1028)  T  EIGMAQG    KAASD FGGLVAQGR RQ    --
SEQ6    (1040)  A  AIRH KS SDTATAAR  EE GATNR VL  WAGG
SEQ7    (1012)  T  K YA  HQ SEA ARL LQQLE KGR  K  WAG-
Consensus (1051) TLM AY DVHGVSE EA   WL   L D GRYAKDVWAG
```

Fig. 6F

Fig. 8: SEQ ID NO: 1 (CYP102A1 from *Bacillus megaterium*)

```
   1 TIKEMPQPKT FGELKNLPLL NTDKPVQALM KIADELGEIF KFEAPGRVTR YLSSQRLIKE
  61 ACDESRFDKN LSQALKFVRD FAGDGLFTSW THEKNWKKAH NILLPSFSQQ AMKGYHAMMV
 121 DIAVQLVQKW ERLNADEHIE VPEDMTRLTL DTIGLCGFNY RFNSFYRDQP HPFITSMVRA
 181 LDEAMNKLQR ANPDDPAYDE NKRQFQEDIK VMNDLVDKII ADRKASGEQS DDLLTHMLNG
 241 KDPETGEPLD DENIRYQIIT FLIAGHETTS GLLSFALYFL VKNPHVLQKA AEEAARVLVD
 301 PVPSYKQVKQ LKYVGMVLNE ALRLWPTAPA FSLYAKEDTV LGGEYPLEKG DELMVLIPQL
 361 HRDKTIWGDD VEEFRPERFE NPSAIPQHAF KPFGNGQRAC IGQQFALHEA TLVLGMMLKH
 421 FDFEDHTNYE LDIKETLTLK PEGFVVKAKS KKIPLGGIPS PSTEQSAKKV RKKAENAHNT
 481 PLLVLYGSNM GTAEGTARDL ADIAMSKGFA PQVATLDSHA GNLPREGAVL IVTASYNCHP
 541 PDNAKQFVDW LDQASADEVK GVRYSVFGCG DKNWATTYQK VPAFIDETLA AKGAENIADR
 601 GEADASDDFE GTYEEWREHM WSDVAAYFNL DIENSEDNKS TLSLQFVDSA ADMPLAKMHG
 661 AFSTNVVASK ELQQPGSARS TRHLEIELPK EASYQEGDHL GVIPRNYEGI VNRVTARFGL
 721 DASQQIRLEA EEEKLAHLPL AKTVSVEELL QYVELQDPVT RTQLRAMAAK TVCPPHKVEL
 781 EALLEKQAYK EQVLAKRLTM LELLEKYPAC EMKFSEFIAL LPSIRPRYYS ISSSPRVDEK
 841 QASITVSVVS GEAWSGYGEY KGIASNYLAE LQEGDTITCF ISTPQSEFTL PKDPETPLIM
 901 VGPGTGVAPF RGFVQARKQL KEQGQSLGEA HLYFGCRSPH EDYLYQEELE NAQSEGIITL
 961 HTAFSRMPNQ PKTYVQHVME QDGKKLIELL DQGAHFYICG DGSQMAPAVE ATLMKSYADV
1021 HQVSEADARL WLQQLEEKGR YAKDVWAG
```

Fig. 9: SEQ ID NO: 2 (CYP102A2 from *Bacillus subtilis*, 59% identity to CYP102A1)

```
   1 KETSPIPQPK TFGPLGNLPL IDKDKPTLSL IKLAEEQGPI FQIHTPAGTT IVVSGHELVK
  61 EVCDEERFDK SIEGALEKVR AFSGDGLFTS WTHEPNWRKA HNILMPTFSQ RAMKDYHEKM
 121 VDIAVQLIQK WARLNPNEAV DVPGDMTRLT LDTIGLCGFN YRFNSYYRET PHPFINSMVR
 181 ALDEAMHQMQ RLDVQDKLMV RTKRQFRYDI QTMFSLVDSI IAERRANGDQ DEKDLLARML
 241 NVEDPETGEK LDDENIRFQI ITFLIAGHET TSGLLSFATY FLLKHPDKLK KAYEEVDRVL
 301 TDAAPTYKQV LELTYIRMIL NESLRLWPTA PAFSLYPKED TVIGGKFFIT TNDRISVLIP
 361 QLHRDRDAWG KDAEEFRPER FEHQDCVPHH AYKPFGNGQR ACIGMQFALH EATLVLGMIL
 421 KYFTLIDHEN YELDIKQTLT LKPGDFHISV QSRHQEAIHA DVQAAEKAAP DEQKEKTEAK
 481 GASVIGLNNR PLLVLYGSDT GTAEGVAREL ADTASLHGVR TKTAPLNDRI GKLPKEGAVV
 541 IVTSSYNGKP PSNAGQFVQW LQEIKPGELE GVHYAVFGCG DHNWASTYQY VPRFIDEQLA
 601 EKGATRFSAR GEGDVSGDFE GQLDEWKKSM WADAIKAFGL ELNENADKER STLSLQFVRG
 661 LGESPLARSY EASHASIAEN RELQSADSDR STRHIEIALP PDVEYQEGDH LGVLPKNSQT
 721 NVSRILHRFG LKGTDQVTLS ASGRSAGELP LGRPVSLHDL LSYSVEVQEA ATRAQIRELA
 781 SFTVCPPHRR ELEELSAEGV YQEQILKKRI SMLDLLEKYE ACDMPFERFL ELLRPLKPPY
 841 YSISSSPRVN PRQASITVGV VRGPAWSGRG EYRGVASNDL AERQAGDDVV MFIRTPESRF
 901 QLPKDPETPI IMVGPGTGVA PFRGFLQARD VLKREGKTLG EAHLYFGCRN DRDFIYRDEL
 961 ERFEKDGIVT VHTAFSRKEG MPKTYVQHLM ADQADTLISI LDRGGRLYVC GDGSKMAPDV
1021 EAALQKAYQA VHGTGEQEAQ NWLRHLQDTG MYAKDVWAGI
```

Fig. 10: SEQ ID NO: 3 (CYP102A3 from *Bacillus subtilis*, 58% identity to CYP102A1)

```
   1 KQASAIFQPK TYGPLKNLPH LEKEQLSQSL WRIADELGPI FRFDFPGVSS VFVSGHNLVA
  61 EVCDEKRFDK NLGKGLQKVR EFGGDGLFTS WTHEPNWQKA HRILLPSFSQ KAMKGYHSMM
 121 LDIATQLIQK WSRLNPNEEI DVADDMTRLT LDTIGLCGFN YRFNSFYRDS QHPFITSMLR
 181 ALKEAMNQSK RLGLQDKMMV KTKLQFQKDI EVMNSLVDRM IAERKANPDE NIKDLLSLML
 241 YAKDPVTGET LDDENIRYQI ITFLIAGHET TSGLLSFAIY CLLTHPEKLK KAQEEADRVL
 301 TDDTPEYKQI QQLKYIRMVL NETLRLYPTA PAFSLYAKED TVLGGEYPIS KGQPVTVLIP
 361 KLHRDQNAWG PDAEDFRPER FEDPSSIPHH AYKPFGNGQR ACIGMQFALQ EATMVLGLVL
 421 KHFELINHTG YELKIKEALT IKPDDFKITV KPRKTAAINV QRKEQADIKA ETKPKETKPK
 481 HGTPLLVLFG SNLGTAEGIA GELAAQGRQM GFTAETAPLD DYIGKLPEEG AVVIVTASYN
 541 GAPPDNAAGF VEWLKELEEG QLKGVSYAVF GCGNRSWAST YQRIPRLTDD MMKAKGASRL
 601 TAIGEGDAAD DFESHRESWE NRFWKETMDA FDINEIAQKE DRPSLSITFL SEATETPVAK
 661 AYGAFEGIVL ENRELQTAAS TRSTRHIELE IPAGKTYKEG DHIGILPKNS RELVQRVLSR
 721 FGLQSNHVIK VSGSAHMAHL PMDRPIKVVD LLSSYVELQE PASRLQLREL ASYTVCPPHQ
 781 KELEQLVSDD GIYKEQVLAK RLTMLDFLED YPACEMPFER FLALLPSLKP RYYSISSSPK
 841 VHANIVSMTV GVVKASAWSG RGEYRGVASN YLAELNTGDA AACFIRTPQS GFQMPNDPET
 901 PMIMVGPGTG IAFFRGFIQA RSVLKKEGST LGEALLYFGC RRPDHDDLYR EELDQAEQDG
 961 LVTIRRCYSR VENEPKGYVQ HLLKQDTQKL MTLIEKGAHI YVCGDGSQMA PDVERTLRLA
1021 YEAEKAASQE ESAVWLQKLQ DQRRYVKDVW TGM
```

Fig. 11: SEQ ID NO: 4 (CYP102A5 from *Bacillus cereus*, 60% identity to CYP102A1)

```
   1 MDKKVSAIPQ PKTYGPLCNL PLIDKDKPTL SFIKIAEEYG PIFQIQTLSD TIIVISGHEL
  61 VAEVCDETRF DKSIEGALAK VRAFAGDGLF TSETQEPNWK KAHNILMPTF SQRAMKDYHA
 121 MMVDIAVQLV QKWARLNPNE NVDVPEDMTR LTLDTIGLCG FNYRFNSFYR ETPHPFITSM
 181 TRALDEAMHQ LQRLGIEDKL MWRTKRQFQR DIQSMFSLVD NIIAERKSSG NQEENDLLSR
 241 MLHVQDPETG EKLDDENIRF QIITFLIAGH ETTSGLLSFA IYFLLKNPDK LKKAYEEVDR
 301 VLTDPTPTYQ QVMKLKYIRM ILNESLRLWP TAPAFSLYAK EDTVIGGKYP IKKGEDRISV
 361 LIPQLHRDKD AWGDNVEEFQ PERFEDLDKV PHHAYKPFGN GQRACIGMQF ALHEATLVMG
 421 MLLQHFEFID YEDYQLDVKQ TLTLKPGDFK IRIVPRNQNI SHTTVLAPTE EKLKNHEIKQ
 481 QVQKTPSIIG ADNLSLLVLY GSDTGVAEGI ARELADTASL EGVQTEVAAL NDRIGSLPKE
 541 GAVLIVTSSY NGKPPSNAGQ FVQWLEELKP DELKGVQYAV FGCGDFNWAS TYQRIPRYID
 601 EQMAQKGATR FSTRGEADAS GDFEEQLEQW KESMWSDAMK AFGLELNKNM EKERSTLSLQ
 661 FVSRLGGSPL ARTYEAVYAS ILENPELQSS SSERSTRHIE ISLPEGATYK EGDHLGVLPI
 721 NSEKNVNRIL KRFGLNGKDQ VILSASGRSV NHIPLDSPVR LYDLLSYSVE VQEAATRAQI
 781 REMVTFTACP PHKKELESLL EDGVYHEQIL KKRISMLDLL EKYEACEIRF ERFLELLPAL
 841 KPRYSISSSS PLIAQDRLSI TVGVVNAPAW SGEGTYEGVA SNYLAQRHNK DEIICFIRTP
 901 QSNFQLPENP ETPIIMVGPG TGIAPFRGFL QARRVQKQKG MNLGEAHLYF GCRHPEKDYL
 961 YRTELENDER DGLISLHTAF SRLEGHPKTY VQHVIKEDRM NLISLLDNGA HLYICGDGSK
1021 MAPDVEDTLC QAYQEIHEVS EQEARNWLDR LQDEGRYGKD VWAGI
```

Fig. 12: SEQ ID NO: 5 (CYP102E1 from *Ralstonia metallidurans*, 38% identity to CYP102A1)

```
   1 STATPAAALE PIPRDPGWPI FGNLFQITPG EVGQHLLARS RHEDGIFELD FAGKRVPFVS
  61 SVALASELCD ATRFRKIIGP PLSYLRDMAG DGLFTAHSDE PNWGCAHRIL MPAFSQRAMK
 121 AYFDVMLRVA NRLVGKWDRQ GPDADIAVAD DMTRLTLDTI ALAGEGYDFA SFASDELDPF
 181 VMAMVGALGE AMQKLTRLPI QDRFMGRAHR QAAEDIAYMR NLVDDVIPQR RVSPTSGMDL
 241 LNLMLEARDP ETDRRLDDAN IRNQVITFLI AGHETTSGLL TFALYELLRN PGVLAQAYAE
 301 VDTVLPGDAL PVYADLARMP VLDRVLKETL RLWPTAPAFA VAPFDDVVLG GRYRLRKDRR
 361 ISVVLTALHR DPKVWANPER FDIDRFLPEN EAKLPAHAYM PFGQGERACI GRQFALTEAK
 421 LALALMLRNF AFQDPRDYQF RLKETLTIKP DQFVLRVRRR RPEERFVTRQ ASQAVADAAQ
 481 TDVRGHGQAM TVLCASSLGT ARELAEQIHA GAIAAGFDAK LADLDDAVGV LPTSGLVVVV
 541 AATYNGRAPD SARKFEAMLD ADDASGYRAN GMRLALLGCG NSQWATYQAF PRRVFDFFIT
 601 AGAVPLLPRG EADGNGDFDQ AAERWLAQLW QALQADGAST GGLGVDVQVR SMAAIRAETL
 661 PAGTQAFTVL SNDELVGDPS GLWDFSIEAP RTSTRDIRLQ LPPGITYRTG DHIAVWPQND
 721 AQLVSELCER LDLDPDAQAT ISAPHGMGRG LPIDQALPVR QLLTHFIELQ DVVSRQTLRA
 781 LAQATRCPFT KQSIEQLASD DAEHGYATKV VARRLGILDV LVEHPAIALT LQELLACTVP
 841 MRPRLYSIAS SPLVSPDVAT LLVGTVCAPA LSGRGQFRGV ASTWLQHLPP GARVSASIRT
 901 PNPPFAPDPD PAAPMLLIGP GTGIAPFRGF LEERALRKMA GNAVTPAQLY FGCRHPQHDW
 961 LYREDIERWA GQGVVEVHPA YSVVPDAPRY VQDLLWQRRE QVWAQVRDGA TIYVCGDGRR
1021 MAPAVRQTLI EIGMAQGCMT DKAASDWFGG LVAQGRYRQD VFN
```

Fig. 13: SEQ ID NO: 6 (CYP102A6 from *Bradyrhizobium japonicum*, 46% identity to CYP102A1)

```
   1 SSKNRLDPIP QPPTKPVVGN MLSLDSAAPV QHLTRLAKEL GPIFWLDMMG SPIVVVSGHD
  61 LVDELSDEKR FDKTVRGALR RVRAVGGDGL FTADTREPNW SKAHNILLQF FGNRAMQSYH
 121 PSMVDIAEQL VQKWERLNAD DEIDVVHDMT ALTLDTIGLC GFDYRFNSFY RRDYHPFVES
 181 LVRSLETIMM TRGLPFEQIW MQKRRKTLAE DVAFMNKMVD EIIAERRKSA EGIDDKKDML
 241 AAMMTGVDRS TGEQLDDVNI RYQINTFPLIA GHETTSGLLS YTLYALLKRP DILKKAYDEV
 301 DRVFGPDVNA KPTYQQVTQL TYITQILKEA LRLWPPAPAY GISPLADETI GGGKYKLRKG
 361 TFITILVTAL HRDPSVWGPN PDAFPDFNFS REAEAKRPIN AWKPFGNGQR ACIGRGFAMH
 421 EAALALGMIL QRFKLIDHQR YQMHLKETLT MKPEGFKIKV RPRADRERGA YGGPVAAVSS
 481 APRAPROPTA RPGHNTPMLV LYGSNLGTAE ELATRMADLA EINGFAVHLG ALDEYVGKLP
 541 QEGGVLIICA SYNGAPPDNA TQFVKWLGSD LPKDAFANVR YAVFGCGNSD WAATYQSVPR
 601 FIDEQLSGHG ARAVYPRGEG DARSDLDGQF QKWFPAAAQV ATKEFGIDWN FTRTAEDDPL
 661 YAIEPVAVTA VNTIVAQGGA VAMKVLVNDE LQNKSGSNPS ERSTRHIEVQ LPSNITYRVG
 721 DHLSVVPRND PTLVDSVARR FGFLPADQIR LQVAEGRRAQ LPVGEAVSVG RLLSEFVELQ
 781 QVATRKQIQI MAEHTRCPVT KPKLLAFVGE EAEPAERYRT EILAMRKSVY DLLLEYPACE
 841 LPFHVYLEML SLLAFRYYST SSSPSVDPAR CSITVGVVEG PAASGRGVYK GICSNYLANR
 901 RASDAIYATV RETKAGFRLP DDSSVPIIMI GPGTGLAPFR GFLQERAARK AKGASLGPAM
 961 LFFGCRHPDQ DFLYADELKA LAASGVTELF TAFSRADGPK TYVQHVLAAQ KDKVWPLIEQ
1021 GAIIYVCGDG GQMEPDVKAA LVAIRHEKSG SDTATAARWI EEMGATNRYV LDVWAGG
```

Fig. 14: SEQ ID NO: 7 (35-E11)

```
   1 TIKEMPQPKT FGELKNLPLL NTDKPVQALM KIADELGEIF KFEAPGCVTR YLSSQRLIKE
  61 ACDESRFDKN LSQALKFFRD FSGDGLFTSW THEINWKKAH NILLPSFSQQ AMKGYHAMMV
 121 DIAVQLVQKW ERLNADEHIE VSEDMTRLTL DTIGLCGFNY RFNSFYRDQP HPFIISMVRA
 181 LDEVMNKLQR ANPDDPAYDE NKRQCQEDIK VMNDLVDKII ADRKARGEQS DDLLTQMLNG
 241 KDPETGEPLD DGNISYQIIT FLIAGHETTS GLLSFALYFL VKNPHVLQKV VEEAARVLVD
 301 PVPSYKQVKQ LKYVGMVLNE ALRLWPTFPA FSLYAKEDTV LGGEYPLEKG DEVMVLIPQL
 361 HRDKTIWGDD VEEFRPERFE NPSAIPQHAF KPFGNGQRAC IGQQFALHEA TLVLGMMLKH
 421 FDFEDHTNYE LDIKETLTLK PEGFVVKAKS KKIPLGGIPS PSTGQSAKKV RKKAENAHNT
 481 PLLVLYGSNM GTAEGTARDL ADIAMSKGFA PQVATLDSHA GNLPREGAVL IVTASYNGHP
 541 PDNAKQFVDW LDQASADEVK GVRYSVFGCG DKNWATTYQK VPAFIDETLA AKGAENIADR
 601 GEADASDDFE GTYEEWREHM WSDVAAYFNL DIENSEDNKS TLSLQFVDSA ADMPLAKMHG
 661 AFSTNVVASK ELQQPGSARS TRHLEIELPK EASYQEGDHL GVIPRNYEGT VNRVTARFGL
 721 DASQQIRLEA EEEKLAHLPL AKTVSVEELL QYVELQDPVT RTQLRAMAAK TVCPPHKVEL
 781 EALLEKQAYK EQVLAKRLTM LELLEKYPAC EMKFSEFIAL LPSIRPRYYS ISSSPRVDEK
 841 QASITVSVVS GEAWSGYGEY KGIASNYLAE LQEGDTITCF ISTPQSEFTL PKDPETPLIM
 901 VGPGTGVAPF RGFVQARKQL KEQGQSLGEA HLYFGCRSPH EDYLYQEELE NAQSEGIITL
 961 HTAFSRMPNQ PKTYVQHVME QDGKKLIELL DQGAHFYICG DGSQMAPAVE ATLMKSYADV
1021 HQVSEADARL WLQQLEEKGR YAKDVWAG
```

Fig. 15: SEQ ID NO: 8 (35-E11-E464R)

```
   1 TIKEMPQPKT FGELKNLPLL NTDKPVQALM KIADELGEIF KFEAPGCVTR YLSSQRLIKE
  61 ACDESRFDKN LSQALKFFRD FSGDGLFTSW THEINWKKAH NILLPSFSQQ AMKGYHAMMV
 121 DIAVQLVQKW ERLNADEHIE VSEDMTRLTL DTIGLCGFNY RFNSFYRDQP HPFIISMVRA
 181 LDEVMNKLQR ANPDDPAYDE NKRQCQEDIK VMNDLVDKII ADRKARGEQS DDLLTQMLNG
 241 KDPETGEPLD DGNISYQIIT FLIAGHETTS GLLSFALYFL VKNPHVLQKV VEEAARVLVD
 301 PVPSYKQVKQ LKYVGMVLNE ALRLWPTFPA FSLYAKEDTV LGGEYPLEKG DEVMVLIPQL
 361 HRDKTIWGDD VEEFRPERFE NPSAIPQHAF KPFGNGQRAC IGQQFALHEA TLVLGMMLKH
 421 FDFEDHTNYE LDIKETLTLK PEGFVVKAKS KKIPLGGIPS PSTRQSAKKV RKKAENAHNT
 481 PLLVLYGSNM GTAEGTARDL ADIAMSKGFA PQVATLDSHA GNLPREGAVL IVTASYNGHP
 541 PDNAKQFVDW LDQASADEVK GVRYSVFGCG DKNWATTYQK VPAFIDETLA AKGAENIADR
 601 GEADASDDFE GTYEEWREHM WSDVAAYFNL DIENSEDNKS TLSLQFVDSA ADMPLAKMHG
 661 AFSTNVVASK ELQQPGSARS TRHLEIELPK EASYQEGDHL GVIPRNYEGT VNRVTARFGL
 721 DASQQIRLEA EEEKLAHLPL AKTVSVEELL QYVELQDPVT RTQLRAMAAK TVCPPHKVEL
 781 EALLEKQAYK EQVLAKRLTM LELLEKYPAC EMKFSEFIAL LPSIRPRYYS ISSSPRVDEK
 841 QASITVSVVS GEAWSGYGEY KGIASNYLAE LQEGDTITCF ISTPQSEFTL PKDPETPLIM
 901 VGPGTGVAPF RGFVQARKQL KEQGQSLGEA HLYFGCRSPH EDYLYQEELE NAQSEGIITL
 961 HTAFSRMPNQ PKTYVQHVME QDGKKLIELL DQGAHFYICG DGSQMAPAVE ATLMKSYADV
1021 HQVSEADARL WLQQLEEKGR YAKDVWAG
```

Fig. 16: SEQ ID NO: 9 (35-E11-E464Y)

```
   1 TIKEMPQPKT FGELKNLPLL NTDKPVQALM KIADELGEIF KFEAPGCVTR YLSSQRLIKE
  61 ACDESRFDKN LSQALKFFRD FSGDGLFTSW THEINWKKAH NILLPSFSQQ AMKGYHAMMV
 121 DIAVQLVQKW ERLNADEHIE VSEDMTRLTL DTIGLCGFNY RFNSFYRDQP HPFIISMVRA
 181 LDEVMNKLQR ANPDDPAYDE NKRQCQEDIK VMNDLVDKII ADRKARGEQS DDLLTQMLNG
 241 KDPETGEPLD DGNISYQIIT FLIAGHETTS GLLSFALYFL VKNPHVLQKV VEEAARVLVD
 301 PVPSYKQVKQ LKYVGMVLNE ALRLWPTFPA FSLYAKEDTV LGGEYPLEKG DEVMVLIPQL
 361 HRDKTIWGDD VEEFRPERFE NPSAIPQHAF KPFGNGQRAC IGQQFALHEA TLVLGMMLKH
 421 FDFEDHTNYE LDIKETLTLK PEGFVVKAKS KKIPLGGIPS PSTYQSAKKV RKKAENAHNT
 481 PLLVLYGSNM GTAEGTARDL ADIAMSKGFA PQVATLDSHA GNLPREGAVL IVTASYNGHP
 541 PDNAKQFVDW LDQASADEVK GVRYSVFGCG DKNWATTYQK VPAFIDETLA AKGAENIADR
 601 GEADASDDFE GTYEEWREHM WSDVAAYFNL DIENSEDNKS TLSLQFVDSA ADMPLAKMHG
 661 AFSTNVVASK ELQQPGSARS TRHLEIELPK EASYQEGDHL GVIPRNYEGT VNRVTARFGL
 721 DASQQIRLEA EEEKLAHLPL AKTVSVEELL QYVELQDPVT RTQLRAMAAK TVCPPHKVEL
 781 EALLEKQAYK EQVLAKRLTM LELLEKYPAC EMKFSEFIAL LPSIRPRYYS ISSSPRVDEK
 841 QASITVSVVS GEAWSGYGEY KGIASNYLAE LQEGDTITCF ISTPQSEFTL PKDPETPLIM
 901 VGPGTGVAPF RGFVQARKQL KEQGQSLGEA HLYFGCRSPH EDYLYQEELE NAQSEGIITL
 961 HTAFSRMPNQ PKTYVQHVME QDGKKLIELL DQGAHFYICG DGSQMAPAVE ATLMKSYADV
1021 HQVSEADARL WLQQLEEKGR YAKDVWAG
```

Fig. 17: SEQ ID NO: 10 (35-E11-E464T)

```
   1 TIKEMPQPKT FGELKNLPLL NTDKPVQALM KIADELGEIF KFEAPGCVTR YLSSQRLIKE
  61 ACDESRFDKN LSQALKFFRD FSGDGLFTSW THEINWKKAH NILLPSFSQQ AMKGYHAMMV
 121 DIAVQLVQKW ERLNADEHIE VSEDMTRLTL DTIGLCGFNY RFNSFYRDQP HPFIISMVRA
 181 LDEVMNKLQR ANPDDPAYDE NKRQCQEDIK VMNDLVDKII ADRKARGEQS DDLLTQMLNG
 241 KDPETGEPLD DGNISYQIIT FLIAGHETTS GLLSFALYFL VKNPHVLQKV VEEAARVLVD
 301 PVPSYKQVKQ LKYVGMVLNE ALRLWPTFPA FSLYAKEDTV LGGEYPLEKG DEVMVLIPQL
 361 HRDKTIWGDD VEEFRPERFE NPSAIPQHAF KPFGNGQRAC IGQQFALHEA TLVLGMMLKH
 421 FDFEDHTNYE LDIKETLTLK PEGFVVKAKS KKIPLGGIPS PSTTQSAKKV RKKAENAHNT
 481 PLLVLYGSNM GTAEGTARDL ADIAMSKGFA PQVATLDSHA GNLPREGAVL IVTASYNGHP
 541 PDNAKQFVDW LDQASADEVK GVRYSVFGCG DKNWATTYQK VPAFIDETLA AKGAENIADR
 601 GEADASDDFE GTYEEWREHM WSDVAAYFNL DIENSEDNKS TLSLQFVDSA ADMPLAKMHG
 661 AFSTNVVASK ELQQPGSARS TRHLEIELPK EASYQEGDHL GVIPRNYEGT VNRVTARFGL
 721 DASQQIRLEA EEEKLAHLPL AKTVSVEELL QYVELQDPVT RTQLRAMAAK TVCPPHKVEL
 781 EALLEKQAYK EQVLAKRLTM LELLEKYPAC EMKFSEFIAL LPSIRPRYYS ISSSPRVDEK
 841 QASITVSVVS GEAWSGYGEY KGIASNYLAE LQEGDTITCF ISTPQSEFTL PKDPETPLIM
 901 VGPGTGVAPF RGFVQARKQL KEQGQSLGEA HLYFGCRSPH EDYLYQEELE NAQSEGIITL
 961 HTAFSRMPNQ PKTYVQHVME QDGKKLIELL DQGAHFYICG DGSQMAPAVE ATLMKSYADV
1021 HQVSEADARL WLQQLEEKGR YAKDVWAG
```

Fig. 18: SEQ ID NO: 11 (20-D3)

```
   1 TIKEMPQPKT FGELKNLPLL NTDKPVQALM KIADELGEIF KFEAPGCVTR YLSSQRLIKE
  61 ACDESRFDKN LSQALKFFRD FSGDGLFTSW THEINWKKAH NILLPSFSQQ AMKGYHAMMV
 121 DIAVQLVQKW ERLNADEHIE VSEDMTRLTL DTIGLCGFNY RFNSFYRDQP HPFIISMVRA
 181 LDEVMNKLQR ANPDDPAYDE NKRQCQEDIK VMNDLVDKII ADRKARGEQS DDLLTQMLNG
 241 KDPETGEPLD DGNISYQIIT FLIAGHETTS GLLSFALYFL VKNPRVLQKV VEEAARVLVD
 301 PVPSYKQVKQ LKYVGMVLNE ALRLWPTFPA FSLYAKEDTV LGGEYPLEKG DEVMVLIPQL
 361 HRDKTIWGDD VEEFRPERFE NPSAIPQHAF KPFGNGQRAC IGQQFALHEA TLVLGMMLKH
 421 FDFEDHTNYE LDIKETLTLK PEGFVVKAKS KKIPLGGIPS PSTGQSAKKV RKKAENAHNT
 481 PLLVLYGSNM GTAEGTARDL ADIAMSKGFA PQVATLDSHA GNLPREGAVL IVTASYNGHP
 541 PDNAKQFVDW LDQASADEVK GVRYSVFGCG DKNWATTYQK VPAFIDETLA AKGAENIADR
 601 GEADASDDFE GTYEEWREHM WSDVAAYFNL DIENSEDNKS TLSLQFVDSA ADMPLAKMHG
 661 AFSTNVVASK ELQQPGSARS TRHLEIELPK EASYQEGDHL GVIPRNYEGT VNRVTARFGL
 721 DASQQIRLEA EEEKLAHLPL AKTVSVEELL QYVELQDPVT RTQLRAMAAK TVCPPHKVEL
 781 EALLEKQAYK EQVLAKRLTM LELLEKYPAC EMKFSEFIAL LPSIRPRYYS ISSSPRVDEK
 841 QASITVSVVS GEAWSGYGEY KGIASNYLAE LQEGDTITCF ISTPQSEFTL PKDPETPLIM
 901 VGPGTGVAPF RGFVQARKQL KEQGQSLGEA HLYFGCRSPH EDYLYQEELE NAQSEGIITL
 961 HTAFSRMPNQ PKTYVQHVME QDGKKLIELL DQGAHFYICG DGSQMAPAVE ATLMKSYADV
1021 HQVSEADARL WLQQLEEKGR YAKDVWAG
```

Fig. 19: SEQ ID NO: 12 (23-1D)

```
   1 TIKEMPQPKT FGELKNLPLL NTDKPVQALM KIADELGEIF KFEAPGCVTR YLSSQRLIKE
  61 ACDESRFDKN LSQALKFFRD FSGDGLFTSW THEINWKKAH NILLPSFSQQ AMKGYHAMMV
 121 DIAVQLVQKW ERLNADEHIE VSEDMTRLTL DTIGLCGFNY RFNSFYRDQP HPFIISMVRA
 181 LDEVMNKLQR ANPDDPAYDE NKRQCQEDIK VMNDLVDKII ADRKARGEQS DDLLTQMLNG
 241 KDPETGEPLD DGNISYQIIT FLIAGHETTS GLLSFALYFL VKNPHVLQKV VEEAARVLVD
 301 PVPSYKQVKQ LKYVGMVLNE ALRLWPTFPA FSLYAKEDTV LGGEYPLEKG DEVMVLIPQL
 361 HRDKTIWGDD VEEFRPERFE NPSAIPQHAF KPFGNGQRAC IGQQFALHEA TLVLGMMLKH
 421 FDFEDHTNYE LDIKETLTLK PEGFVVKAKS KKIPLGGIPS PSTGQSAKKV RKKAENAHNT
 481 PLLVLYGSNM GTAEGTARDL ADIAMSKGFA PQVATLDSHA GNLPREGAVL IVTASYNGHP
 541 PDNAKQFVDW LDQASADEVK GVRYSVFGCG DKNWATTYQK VPAFIDETLA AKGAENIADR
 601 GEADASDDFE GTYEEWREHM WSDVAAYFNL DIENSEDNKS TLSLRFVDSA ADMPLAKMHG
 661 AFSTNVVASK ELQQPGSARS TRHLEIELPK EASYQEGDHL GVIPRNYEGT VNRVTARFGL
 721 DASQQIRLEA EEEKLAHLPL AKTVSVEELL QYVELQDPVT RTQLRAMAAK TVCPPHKVEL
 781 EALLEKQAYK EQVLAKRLTM LELLEKYPAC EMKFSEFIAL LPSIRPRYYS ISSSPRVDEK
 841 QASITVSVVS GEAWSGYGEY KGIASNYLAE LQEGDTITCF ISTPQSEFTL PKDPETPLIM
 901 VGPGTGVAPF RGFVQARKQL KEQGQSLGEA HLYFGCRSPH EDYLYQEELE NAQSEGIITL
 961 HTAFSRMLNQ PKTYVQHVME QDGKKLIELL DQGAHFYICG DGSQMAPAVE ATLMKSYADV
1021 HQVSEADARL WLQQLEEKGR YAKDVWAG
```

Fig. 20A:   SEQ ID NO: 13 (21-4G)

```
   1 TIKEMPQPKT FGELKNLPLL NTDKPVQALM KIADELGEIF KFEAPGCVTR YLSSQRLIKE
  61 ACDESRFDKN LSQALKFFRD FSGDGLFTSW THEINWKKAH NILLPSFSQQ AMKGYHAMMV
 121 DIAVQLVQKW ERLNADEHIE VSEDMTRLTL DTIGLCGFNY RPNSFYRDQP HPFIISMVRA
 181 LDEVMNKLQR ANPDDPAYDE NKRQCQEDIK VMNDLVDKII ADRKARGEQS DDLLTQMLNG
 241 KDPETGEPLD DGNISYQIIT FLIAGHETTS GLLSFALYFL VKNPHVLQKV VEEAARVLVD
 301 PVPSYKQVKQ LKYVGMVLNE ALRLWPTFPA FSLYAKEDTV LGGEYPLEKG DEVMVLIPQL
 361 HRDKTIWGDD VEEFRPERFE NPSAIPQHAF KPFGNGQRAC IGQQFALHEA TLVLGMMLKH
 421 FDFEDHTNYE LDIKETLTLK PEGFVVKAKS KKIPLGGIPS PSTGQSAKKV RKKAENAHNT
 481 PLLVLYGSNM GTAEGTARDL ADIAMSKGFA PQVATLDSHA GNLPREGAVL IVTASYNGHP
 541 PDNAKQFVDW LDQASADEVK GVRYSVFGCG DKNWATTYQK VPAFIDETLA AKGAENIADR
 601 GEADASDDFE GTYEEWREHM WSDVAAYFNL NIENSEDNKS TLSLQFVDSA ADMPLAKMHG
 661 AFSTNVVASK ELQQPGSARS TRHLEIELPK EASYQEGDHL GVIPRNYEGT VNRVTARFGL
 721 DASQQIRLEA EEEKLAHLPL AKTVSVEELL QYVELQDPVT RTQLRAMAAK TVCPPHKVEL
 781 EALLEKQAYK EQVLAKRLTM LELLEKYPAC EMKFSEFIAL LPSIRPRYYS ISSSPRVDEK
 841 QASITVSVVS GEAWSGYGEY KGIASNYLAE IQEGDTITCF ISTPQSEFTL PKDPETPLIM
 901 VGPGTGVAPF RGFVQARKQL KEQGQSLGEA HLYFGCRSPH EDYLYQEELE NAQSEGIITL
 961 HTAFSRMPNQ PKTYVQHVME QDGKKLIELL DQGAHFYICG DGSQMAPAVE ATLMKSYADV
1021 HQVSEADARL WLQQLEEKGR YAKDVWAG
```

Fig. 20B:   SEQ ID NO:125 (P450$_{PMO}$)

```
   1 TIKEMPQPKT FGELKNLPLL NTDKPVQALM KIADELGEIF KFEAPGCVTR YISSQRLIKE
  61 ACDESRFDKN LSQELKFFRD FGGDGLFTSW THEINWKKAH NILLPSFSQQ AMKGYHAMMV
 121 DIAVQLVQKW ERLNADEHIE VSEDMTRLTL DTIGLCGFNY RPNSFYRDQP HPFIISMVRA
 181 LDEVMNKPQR ANPDDPAYDE NKRQCQEDIK VMNDLVDKII ADRKARGEQS DDLLTQMLNG
 241 KDPETGEPLD DGNISYQIIT FLIAGHETTS GLLSFALYFL VKNPHVLQKV VEEAARVLVD
 301 PVPSYKQVKQ LKYVGMVLNE ALRLWPTFPA FSLYAKEDTV LGGEYPLEKG DEVMVLIPQL
 361 HRDKTVWGDD VEEFRPERFE NPSAIPQHAF KPFGNGQRAC IGQQFALHEA TLVLGMMLKH
 421 FDFEDHTNYE LDIKETLTLK PEAFVVKAKS KKIPLGGIPS PSTGQSAKKV RKKAENAHNT
 481 PLLVLYGSNM GTAEGTARDL ADIAMSKGFA PQVATLDSHA GNLPREGAVL IVTASYNGHP
 541 PDNAKQFVDW LDQASADEVK GVRYSVFGCG DKNWATTYQK VPAFIDETLA AKGAENIADR
 601 GEADASDDFE GTYEEWREHM WSDVAAYFNL DIENSEDNKS TLSLQFVDSA ADMPLAKMHG
 661 AFSTNVVASK ELQQPGSARS TRHLEIELPK EASYQEGGHL GVIPRNYEGT VNRVTARFGL
 721 DASQQIRLEA EEEKLAHLPL AKTVSVEELL QYVELQDPVT RTQLRAMAAK TVCPPHKVEL
 781 EALLEKQAYK EQVLAKRLTM LELLEKYPAC EMKFSEFIAL LPSIRPRYYS ISSSPRVDEK
 841 QASITVSVVS GEAWSGYGEY KGIASNYLAE IQEGDTITCF ISTPQSEFTL PKDPETPLIM
 901 VGPGTGVAPF RGFVQARKQL KEQGQSLGEA HLYFGCRSPH EDYLYQEELE NAQSEGIITL
 961 HTAFSRMPNQ PKTYVQHVME QDGKKLIELL DQGAHFYICG DGSQMAPAVE ATLMKSYADV
1021 HQVSEADARL WLQQLEEKGR YAKDVWAG
```

Fig. 21: SEQ ID NO:15 - nucleic acid sequence encoding 53-5H polypeptide (heme and reductase domain)

```
atgacaattaaagaaatgcctcagccaaaaacgtttggagagcttaaaaatttaccgttattaaacacagataaa
ccggttcaagctttgatgaaaattgcggatgaattaggagaaatctttaaattcgaggcgcctggttgtgtaacg
cgctacttatcaagtcagcgtctaattaaagaagcatgcgatgaatcacgctttgataaaaacttaagtcaagcg
cttaaattctttcgtgattttagcggagacgggttatttacaagctggacgcatgaaataaattggaaaaaagcg
cataatatcttacttccaagcttttagtcagcaggcaatgaaaggctatcatgcgatgatggtcgatatcgccgtg
cagcttgttcaaaagtgggagcgtctaaatgcagatgagcatattgaagtatcggaagacatgacacgtttaacg
cttgatacaattggtctttgcggctttaactatcgcttaacagcttttaccgagatcagcctcatccatttatt
ataagtatggtccgtgcactggatgaagtaatgaacaagctgcagcgagcaaatccagacgacccagcttatgat
gaaaacaagcgccagtgtcaagaagatatcaaggtgatgaacgacctagtagataaaattattgcagatcgcaaa
gcaaggggtgaacaaagcgatgatttattaacgcagatgctaaacggaaaagatccagaaacgggtgagccgctt
gatgacgggaacattagctatcaaattattacattcttaattgcgggacacgaaacaacaagtggtctttttatca
tttgcgctgtatttcttagtgaaaaatccacatgtattacaaaaagtagcagaagaagcagcacgagttctagta
gatcctgttccaagctacaaacaagtcaaacagcttaaatatgtcggcatggtcttaaacgaagcgctgcgctta
tggccaacttttcctgcgttttccctatatgcaaaagaagatacggtgcttggaggagaatatcctttagaaaaa
ggcgacgaagtaatggttctgattcctcagcttcacgtgataaaacaatttggggagacgatgtggaggagttc
cgtccagagcgttttgaaaatccaagtgcgattccgcagcatgcgtttaaaccgtttggaaacggtcagcgtgcg
tgtatcggtcagcagttcgctcttcatgaagcaacgctggtacttggtatgatgctaaaacactttgactttgaa
gatcatacaaactacgagctcgatattaaagaaactttaacgttaaaacctgaaggctttgtggtaaaagcaaaa
tcgaaaaaattccgcttggcggtattccttcacctagcactgaacagtctgctaaaaaagtacgcaaaaaggca
gaaaacgctcataatacgccgctgcttgtgctatacggttcaaatatgggaacagctgaaggaacggcgcgtgat
ttagcagatattgcaatgagcaaaggatttgcaccgcaggtcgcaacgcttgattcacacgccggaaatcttccg
cgcgaaggagctgtattaattgtaacggcgtcttataacggtcatccgcctgataacgcaaagcaatttgtcgac
tggttagaccaagcgtctgctgatgaagtaaaaggcgttcgctactccgtatttggatgcggcgataaaaactgg
gctactacgtatcaaaaagtgcctgcttttatcgatgaagcacgcttgccgctaaaggggcagaaaacatcgctgac
cgcggtgaagcagatgcaagcgacgactttgaaggcacatatgaagaatggcgtgaacatatgtggagtgacgta
gcagcctactttaacctcgacattgaaaacagtgaagataatasatctactcttcacttcaatttgtcgacagc
gccgcggatatgccgcttgcgaaaatgcacggtgcgttttcaacgaacgtcgtagcaagcaaagaacttcaacag
ccaggcagtgcacgaagcacgcgacatcttgaaattgaacttccaaaagaagcttcttatcaagaaggagatcat
ttaggtgttattcctcgcaactatgaaggaatagtaaaccgtgtaacagcaaggttcggcctagatgcatcacag
caaatccgtctggaagcagaagaagaaaaattagctcatttgccactcgctaaaacagtatccgtagaagagctt
ctgcaatacgtggagcttcaagatcctgttacgcgcacgcagcttcgcgcaatggctgctaaaacggtctgcccg
ccgcataaagtagagcttgaagcctt gcttgaaaagcaagcctacaaagaacaagtgctggcaaaacgtttaaca
atgcttgaactgttgaaaaatacccggcgtgtgaaatgaaattcagcgaatttatcgcccttctgccaagcata
cgccgcgctattactcgatttcttcatcacctcgtgtcgatgaaaaacaagcaagcatcacggtcagcgttgtc
tcaggagaagcgtggagcggatatggagaatataaaggaattgcgtcgaactatcttgccgagctgcaagaagga
gatacgattacgtgctttatttccacaccgcagtcagaatttacgctgccaaaagaccctgaaacgccgcttatc
atggtcggaccgggaacaggcgtcgcgccgtttagaggctttgtgcaggcgcgcaaacagctaaaagaacaagga
cagtcacttggagaagcacatttatacttcggctgccgttcacctcatgaagactatctgtatcaagaagagctt
gaaaacgcccaaagcgaaggcatcattacgcttcataccgcttttctcgcatgccaaatcagccgaaacatac
gttcagcacgtaatggaacaagacggcaagaaattgattgaacttcttgatcaaggagcgcacttctatatttgc
ggagacggaagccaaatggcacctgccgttgaagcaacgcttatgaaaagctatgctgacgttcaccaagtgagt
gaagcagacgctcgcttatggctgcagcagctagaagaaaaaggccgatacgcaaaagacgtgtgggctggg
```

Fig. 22A: SEQ ID NO:16 - nucleic acid sequence of pCWORI-53-5H (expression plasmid for expression of 53-5H polypeptide)

```
atgacaattaaagaaatgcctcagccaaaaacgtttggagagcttaaaaatttaccgttattaaacacagataaa
ccggttcaagctttgatgaaaattgcggatgaattaggagaaatctttaaattcgaggcgcctggttgtgtaacg
cgctacttatcaagtcagcgtctaattaaagaagcatgcgatgaatcacgctttgataaaaacttaagtcaagcg
cttaaattctttcgtgattttagcggagacgggttatttacaagctggacgcatgaaataaattggaaaaaagcg
cataatatcttacttccaagctttagtcagcaggcaatgaaaggctatcatgcgatgatggtcgatatcgccgtg
cagcttgttcaaaagtgggagcgtctaaatgcagatgagcatattgaagtatcggaagacatgacacgtttaacg
cttgatacaattggtctttgcggctttaactatcgctttaacagcttttaccgagatcagcctcatccatttatt
ataagtatggtccgtgcactggatgaagtaatgaacaagctgcagcgagcaaatccagacgacccagcttatgat
gaaaacaagcgccagtgtcaagaagatatcaaggtgatgaacgacctagtagataaaattattgcagatcgcaaa
gcaagggggtgaacaaagcgatgatttattaacgcagatgctaaacggaaaagatccagaaacgggtgagccgctt
gatgacgggaacattagctatcaaattattacattcttaattgcgggacacgaaacaacaagtggtctttttatca
tttgcgctgtatttcttagtgaaaaatccacatgtattacaaaaagtagcagaagaagcagcacgagttctagta
gatcctgttccaagctacaaacaagtcaaacagcttaaatatgtcggcatggtcttaaacgaagcgctgcgctta
tggccaacttttcctgcgttttccctatatgcaaaagaagatacggtgcttggaggagaatatcctttagaaaaa
ggcgacgaagtaatggtctgattcctcagcttcaccgtgataaaacaatttggggagacgatgtggaggagttc
cgtccagagcgttttgaaaatccaagtgcgattccgcagcatgcgtttaaacgtttggaaacggtcagcgtgcg
tgtatcggtcagcagttcgctcttcatgaagcaacgctggtacttggtatgatgctaaaacactttgacttttgaa
gatcatacaaactacgagctcgatattaaagaaactttaacgttaaaacctgaaggctttgtggtaaaagcaaaa
tcgaaaaaaaattccgcttggcggtattccttcacctagcactgaacagtctgctaaaaaagtacgcaaaaaggca
gaaaacgctcataatacgccgctgcttgtgctatacggttcaaatatgggaacagctgaaggaacggcgcgtgat
ttagcagatattgcaatgagcaaaggatttgcaccgcaggtcgcaacgcttgattcacacgccggaaatcttccg
cgcgaaggagctgtattaattgtaacggcgtcttataacggtcatccgcctgataacgcaaagcaatttgtcgac
tggttagaccaagcgtctgctgatgaagtaaaaggcgttcgctactccgtatttggatgcggcgataaaaactgg
gctactacgtatcaaaaagtgcctgcttttatcgatgaaacgcttgccgctaaaggggcagaaaacatcgctgac
cgcggtgaagcagatgcaagcgacgactttgaaggcacatatgaagaatggcgtgaacatatgtggagtgacgta
gcagcctactttaacctcgacattgaaaacagtgaagataataaatctactctttcacttcaatttgtcgacagc
gccgcggatatgccgcttgcgaaaatgcacggtgcgttttcaacgaacgtcgtagcaagcaaagaacttcaacag
ccaggcagtgcacgaagcacgcgacatcttgaaattgaacttccaaaagaagcttcttatcaagaaggagatcat
ttaggtgttattcctcgcaactatgaaggaatagtaaaccgtgtaacagcaaggttcggcctagatgcatcacag
caaatccgtctggaagcagaagaagaaaaaattagctcatttgccactcgctaaaacagtatccgtagaagagctt
ctgcaatacgtggagcttcaagatcctgttacgcgcacgcagcttcgcgcaatggctgctaaaacggtctgcccg
ccgcataaagtagagcttgaagccttgcttgaaaagcaagcctacaaagaacaagtgctggcaaaacgtttaaca
atgcttgaactgcttgaaaaataccggcgtgtgaaatgaaattcagcgaatttatcgcccttctgccaagcata
cgccgcgctattactcgatttcttcatcacctcgtgtcgatgaaaaacaagcaagcatcacggtcagcgttgtc
tcaggagaagcgtggagcggatatgagaatataaaggaattgcgtcgaactatcttgccgagctgcaagaagga
gatacgattacgtgctttatttccacaccgcagtcagaatttacgctgccaaaagaccctgaaacgccgcttatc
atggtcggaccgggaacaggcgtcgcgccgtttagaggctttgtgcaggcgcgcaaacagctaaaagaacaagga
cagtcacttggagaagcacatttatacttcggctgccgttcacctcatgaagactatctgtatcaagaagagctt
gaaaacgcccaaagcgaaggcatcattacgcttcataccgcttttttctcgcatgccaaatcagccgaaacatac
gttcagcacgtaatggaacaagacggcaagaaattgattgaacttcttgatcaaggagcgcacttctatatttgc
ggagacggaagccaaatggcacctgccgttgaagcaacgcttatgaaaagctatgctgacgttcaccaagtgagt
gaagcagacgctcgcttatggctgcagcagctagaagaaaaaggccgatacgcaaaagacgtgtgggctgggtaa
gaattcatcgatgataagctgtcaaacatgagcagatctgagcccgcctaatgagcgggcttttttttcagatct
gcttgaagacgaaagggcctcgtgatacgcctatttttataggttaatgtcatgataataatggttttcttagcgt
caaagcaaccatagtacgcgccctgtagcggcgcattaagcgcggcgggtgtggttacgcgcagcgtgaccg
ctacacttgccagcgccctagcgcccgctcctttcgctttcttcccttcctttctcgccacgttcgccggcttc
cccgtcaagctctaaatcgggggctccctttagggttccgatttagtgctttacggcacctcgaccccaaaaaac
ttgatttgggtgatggttcacgtagtgggccatcgccctgatagacggttttcgccctttgacgttggagtcca
cgttctttaatagtggactcttgttccaaactggaacaacactcaaccctatctcgggctatcttttgatttat
aagggattttgccgatttcggcctattggttaaaaaatgagctgatttaacaaaaatttaacgcgaattttaaca
aaatattaacgtttacaatttcaggtggcacttttcggggaaatgtgcgcggaacccctatttgtttatttttct
aaatacattcaaatatgtatccgctcatgagacaataaccctgataaatgcttcaataatattgaaaaggaaga
gtatgagtattcaacatttccgtgtcgcccttattcccttttttgcggcattttgccttcctgtttttgctcacc
cagaaacgctggtgaaagtaaaagatgctgaagatcagttgggtgcacgagtgggttacatcgaactggatctca
acagcggtaagatccttgagagttttcgccccgaagaacgttttccaatgatgagcacttttaaagttctgctat
gtggcgcggtattatcccgtgttgacgccgggcaagagcaactcggtcgccgcatacactattctcagaatgact
tggttgagtactcaccagtcacagaaaagcatcttacggatggcatgacagtaagagaattatgcagtgctgcca
taaccatgagtgataacactgcggccaacttacttctgacaacgatcggaggaccgaaggagctaaccgcttttt
```

Fig. 22B: SEQ ID NO:16 (continued)

```
tgcacaacatgggggatcatgtaactcgccttgatcgttgggaaccggagctgaatgaagccataccaaacgacg
agcgtgacaccacgatgcctgcagcaatggcaacaacgttgcgcaaactattaactggcgaactacttactctag
cttcccggcaacaattaatagactggatggaggcggataaagttgcaggaccacttctgcgctcggcccttccgg
ctggctggtttattgctgataaatctggagccggtgagcgtgggtctcgcggtatcattgcagcactgggccag
atggtaagccctcccgtatcgtagttatctacacgacggggagtcaggcaactatggatgaacgaaatagacaga
tcgctgagataggtgcctcactgattaagcattggtaactgtcagaccaagttactcatatatactttagattg
attaaaacttcattttttaatttaaaaggatctaggtgaagatccttttttgataatctcatgaccaaaatcccttt
aacgtgagttttcgttccactgagcgtcagaccccgtagaaaagatcaaaggatcttcttgagatcctttttttc
tgcgcgtaatctgctgcttgcaaacaaaaaaaccaccgctaccagcggtggtttgtttgccggatcaagagctac
caactcttttccgaaggtaactggcttcagcagagcgcagataccaaatactgtccttctagtgtagccgtagt
taggccaccacttcaagaactctgtagcaccgcctacatacctcgctctgctaatcctgttaccagtggctgctg
ccagtggcgataagtcgtgtcttaccgggttggactcaagacgatagttaccggataaggcgcagcggtcgggct
gaacggggggttcgtgcacacagcccagcttggagcgaacgacctacaccgaactgagatacctacagcgtgagc
tatgagaaagcgccacgcttcccgaagggagaaaggcggacaggtatccggtaagcggcagggtcggaacaggag
agcgcacgagggagcttccaggggaaacgcctggtatctttatagtcctgtcgggtttcgccacctctgacttg
agcgtcgatttttgtgatgctcgtcaggggggcggagcctatggaaaaacgccagcaacgcggccttttacggt
tcctggccttttgctggcctttgctcacatgttctttcctgcgttatcccctgattctgtggataaccgtatta
ccgcctttgagtgagctgataccgctcgccgcagccgaacgaccgagcgcagcgagtcagtgagcgaggaagcgg
aagagcgcctgatgcggtattttctccttacgcatctgtgcggtatttcacaccgcatatatggtgcactctcag
tacaatctgctctgatgccgcatagttaagccagtatacactccgctatcgctacgtgactgggtcatggctgcg
cccgacacccgccaacaccgcgacgcgccctgacgggcttgtctgctcccggcatccgcttacagacaagct
gtgaccgtctccgggagctgcatgtgtcagaggttttcaccgtcatcaccgaaacgcgcgaggcagaacgccatc
aaaaataattcgcgtctggccttcctgtagccagcttcatcaacattaaatgtgagcgagtaacaacccgtcgg
attctccgtgggaacaaacggcggattgaccgtaatgggataggttacgttggtgtagatgggcgcatcgtaacc
gtgcatctgccagtttgaggggacgacgacagtatcggcctcaggaagatcgcactccagccagctttccggcac
cgcttctggtgccggaaaccaggcaaagcgccattcgccattcaggctgcgcaactgttgggaagggcgatcggt
gcgggcctcttcgctattacgccagctggcgaaaggggatgtgctgcaaggcgattaagttgggtaacgccagg
gttttcccagtcacgacgttgtaaaacgacggccagtgaatccgtaatcatggtcatagctgtttcctgtgtgaa
attgttatccgctcacaattccacacaacatacgagccggaagcataaagtgtaaagcctggggtgcctaatgag
tgagctaactcacattaattgcgttgcgctcactgcccgctttccagtcgggaaacctgtcgtgccagctgcatt
aatgaatcggccaacgcgcggggagaggcggtttgcgtattgggcgccagggtggtttttctttttcaccagtgag
acgggcaacagctgattgcccttcaccgcctggccctgagagagttgcagcaagcggtccacgctggtttgcccc
agcaggcgaaaatcctgtttgatggtggttaacggcgggatataacatgagctgtcttcggtatcgtcgtatccc
actaccgagatatccgcaccaacgcgcagcccggactcggtaatggcgcgcattgcgcccagcgccatctgatcg
ttggcaaccagcatcgcagtgggaacgatgccctcattcagcatttgcatggtttgttgaaaaccggacatggca
ctccagtcgccttcccgttccgctatcggctgaatttgattgcgagtgagatatttatgccagccagccagacgc
agacgcgccgagacagaacttaatgggcccgctaacagcgcgatttgctggtgacccaatgcgaccagatgctcc
acgcccagtcgcgtaccgtcttcatgggagaaaataatactgttgatgggtgtctggtcagagacatcaagaaat
aacgccggaacattagtgcaggcagcttccacagcaatggcatcctggtcatccagcggatagttaatgatcagc
ccactgacgcgttgcgcgagaagattgtgcaccgccgctttacaggcttcgacgccgcttcgttctaccatcgac
accaccacgctggcacccagttgatcggcgcgagatttaatcgccgcgacaatttgcgacggcgcgtgcagggcc
agactggaggtggcaacgccaatcagcaacgactgtttgcccgccagttgttgtgccacgcggttgggaatgtaa
ttcagctccgccatcgccgcttccacttttttccgcgttttcgcagaaacgtggctggcctggttcaccacgcgg
gaaacgtctgataagagacaccggcatactctgcgacatcgtataacgttactggtttcacattcaccaccctg
aattgactctcttccgggcgctatcatgccataccgcgaaaggttttgcgccattcgatggtgtcctggcacgac
aggtttcccgactggaaagcgggcagtgagcgcaacgcaattaatgtgagttagctcactcattaggcaccccag
gctttacactttatgcttccggctcgtataatgtgtggaattgtgagcggataacaatttcacacaggaaacagg
atcgatccatcgatgagcttactccccatcccctgttgacaattaatcatcggctcgtataatgtgtggaattg
tgagcggataacaatttcacacaggaaacaggatcgcttactccccatcccctgttgacaattaatcatcggc
tcgtataatgtgtggaattgtgagcggataacaat
```

Fig. 23: SEQ ID NO:17 - nucleic acid sequence encoding 35-E11 polypeptide (heme and reductase domain)

atgacaattaaagaaatgcctcagccaaaaacgtttggagagcttaaaaatttaccgttattaaacacagataaa
ccggttcaagcttgatgaaaattgcggatgaattaggagaaatctttaaattcgaggcgcctggttgtgtaacg
cgctacttatcaagtcagcgtctaattaaagaagcatgcgatgaatcacgctttgataaaaacttaagtcaagcg
cttaaattcttcgtgattttagcggagacgggttatttacaagctggacgcatgaaataaattggaaaaaagcg
cataatatcttacttccaagctttagtcagcaggcaatgaaaggctatcatgcgatgatggtcgatatcgccgtg
cagcttgttcaaaagtgggagcgtctaaatgcagatgagcatattgaagtatcggaagacatgacacgtttaacg
cttgatacaattggtctttgcggctttaactatcgctttaacagcttttaccgagatcagcctcatccatttatt
ataagtatggtccgtgcactggatgaagtaatgaacaagctgcagcgagcaaatccagacgaccagcttatgat
gaaaacaagcgccagtgtcaagaagatatcaaggtgatgaacgacctagtagataaaattattgcagatcgcaaa
gcaagggtgaacaaagcgatgatttattaacgcagatgctaaacggaaaagatccagaaacgggtgagccgctt
gatgacgggaacattagctatcaaattattacattcttaattgcgggacacgaaacaacaagtggtcttttatca
tttgcgctgtatttcttagtgaaaaatccacatgtattacaaaaagtagcagaagaagcagcacgagttctagta
gatcctgttccaagctacaaacaagtcaaacagcttaaatatgtcggcatggtcttaaacgaagcgctgcgctta
tggccaactttttcctgcgttttccctatatgcaaaagaagatacggtgcttgaggagaatatcctttagaaaaa
ggcgacgaagtaatggttctgattcctcagcttcaccgtgataaaacaatttggggagacgatgtggaggagttc
cgtccagagcgttttgaaaatccaagtgcgattccgcagcatgcgtttaaaccgtttggaaacggtcagcgtgcg
tgtatcggtcagcagttcgctcttcatgaagcaacgctggtacttggtatgatgctaaaacactttgactttgaa
gatcatacaaactacgagctcgatattaaagaaacctttaacgttaaacctgaaggctttgtggtaaaagcaaaa
tcgaaaaaaattccgcttggcggtattccttcacctagcactggacagtctgctaaaaagtacgcaaaaggca
gaaaacgctcataatacgccgctgcttgtgctatacggttcaaatatgggaacagctgaaggaacggcgcgtgat
ttagcagatattgcaatgagcaaaggatttgcaccgcaggtcgcaacgcttgattcacacgccggaaatcttccg
cgcgaaggagctgtattaattgtaacggcgtcttataacggtcatccgcctgataacgcaaagcaatttgtcgac
tggttagaccaagcgtctgctgatgaagtaaaagcgttcgctactccgtatttggatgcggcgataaaaactgg
gctactacgtatcaaaaagtgcctgcttttatcgatgaaacgcttgccgctaaaggggcagaaaacatcgctgac
cgcggtgaagcagatgcaagcgacgacttgaaggcacatatgaagaatggcgtgaacatatgtggagtgacgta
gcagcctactttaacctcgacattgaaaacagtgaagataataaatctactctttcacttcaatttgtcgacagc
gccgcggatatgccgcttgcgaaaatgcaaaatgcgtgtttcaacgaacgtcgtagcaagcaaagaacttcaacag
ccaggcagtgcacgaagcacgcgacatcttgaaattgaacttccaaaagaagcttcttatcaagaaggagatcat
ttaggtgttattcctcgcaactatgaaggaacagtaaaccgtgtaacagcaaggttcggcctagatgcatcacag
caaatccgtctggaagcagaagaagaaaaattagctcatttgccactcgctaaaacagtatccgtagaagagctt
ctgcaatacgtggagcttcaagatcctgttacgcgcacgcagcttcgcgcaatggctgctaagacggtctgcccg
ccgcataaagtagagcttgaagccttgcttgaaaagcaagcctacaaagaacaagtgctggcaaaacgtttaaca
atgcttgaactgcttgaaaaatccggcgtgtgaaatgaaattcagcgaattatcgccttctgccaagcata
cgcccgcgctattactcgattcttcatcacctcgtgtcgatgaaaaacaagcaagcatcacggtcagcgttgtc
tcaggagaagcgtggagcggatatggagaatataaaggaattgcgtcgaactatcttgccgagctgcaagaagga
gatacgattacgtgcttattccacacgcagtcagaatttacgctgccaaaagaccctgaaacgccgcttatc
atggtcggacggggaacaggcgtcgcgccgtttagaggcttgtgcaggcgcgcaaacagctaaagaacaagga
cagtcacttggagaagcacatttatacttcggctgccgttcacctcatgaagactatctgtatcaagaagagctt
gaaaacgcccaaagcgaaggcatcattacgcttcatcccgcttttttctcgcatgccaaatcagccgaaaacatac
gttcagcacgtaatggaacaagacggcaagaaattgattgaacttcttgatcaaggagcgcacttctatatttgc
ggagacggaagccaaatggcacctgccgttgaagcaacgcttatgaaaagctatgctgacgttcaccaagtgagt
gaagcagacgctcgcttatggctgcagcagctagaagaaaaaggccgatacgcaaaagacgtgtgggctggg

Fig. 24A: SEQ ID NO:18 - nucleic acid sequence of pCWORI-35-E11 (expression plasmid for expression of 35-E11 polypeptide)

atgacaattaaagaaatgcctcagccaaaaacgtttggagagcttaaaaatttaccgttattaaacacagataaa
ccggttcaagctttgatgaaaattgcggatgaattaggagaaatctttaaattcgaggcgcctggttgtgtaacg
cgctacttatcaagtcagcgtctaattaaagaagcatgcgatgaatcacgctttgataaaaacttaagtcaagcg
cttaaattctttcgtgatttagcggagacggggtatttacaagctggacgcatgaaataaattggaaaaaagcg
cataatatcttacttccaagctttagtcagcaggcaatgaaaggctatcatgcgatgatggtcgatatcgccgtg
cagcttgttcaaaagtggagcgtctaaatgcagatgagcatattgaagtatcggaagacatgacacgtttaacg
cttgatacaattggtctttgcggctttaactatcgcttaacagcttttaccgagatcagcctcatccatttatt
ataagtatggtccgtgcactggatgaagtaatgaacaagctgcagcgagcaaatccagacgacccagcttatgat
gaaaacaagcgccagtgtcaagaagatatcaaggtgatgaacgacctagtagataaattattgcagatcgcaaa
gcaagcggtgaacaaagcgatgatttattaacgcagatgctaaacggaaaagatccagaaacgggtgagccgctt
gatgacgggaacattagctatcaaattattacattcttaattgcgggacacgaaacaacaagtggtcttttatca
tttgcgctgtatttcttagtgaaaaatccacatgtattacaaaaagtagcagaagaagcagcacgagttctagta
gatcctgttccaagctacaaacaagtcaaacagcttaaatatgtcggcatggtcttaaacgaagcgctgcgctta
tggccaacttttcctgcgttttccctatatgcaaaagaagatacggtgcttggaggagaatatcctttagaaaaa
ggcgacgaagtaatggttctgattcctcagcttcaccgtgataaaacaatttggggagacgatgtggaggagttc
cgtccagagcgttttgaaaatccaagtgcgattccgcagcatgcgtttaaacgtttggaacggtcagcgtgcg
tgtatcggtcagcagttcgctcttcatgaagcaacgctggtacttggtatgatgctaaaacactttgactttgaa
gatcatacaaactacgagctcgatattaaagaaactttaacgttaaaacctgaaggctttgtggtaaaagcaaaa
tcgaaaaaaattccgcttggcggtattccttcacctagcactggacagtctgctaaaaaagtacgcaaaaaggca
gaaaacgctcataatacgccgctgttgtgctatacggttcaaatatgggaacagctgaaggaacggcgcgtgat
ttagcagatattgcaatgagcaaaggatttgcacgcaggtcgcaacgcttgattcacacgccggaaatcttccg
cgcgaaggagctgtattaattgtaacggcgtcttataacggtcatccgcctgataacgcaaagcaatttgtcgac
tggttagaccaagcgtctgctgatgaagtaaaaggcgttcgctactccgtatttggatgcggcgataaaaactgg
gctactacgtatcaaaaagtgcctgcttttatcgatgaaacgcttgccgctaaaggggcagaaaacatcgctgac
cgcggtgaagcagatgcaagcgacgactttgaaggcacatatgaagaatggcgtgaacatatgtggagtgacgta
gcagcctactttaacctcgacattgaaaacagtgaagataataaatctactctttcacttcaatttgtcgacagc
gcgcgcgatatgccgcttgcgaaaatgcacggtgcgttttcaacgaacgtcgtagcaagcaaagaacttcaacag
ccaggcagtgcacgaagcacgcgacatcttgaaattgaacttccaaaagaagcttcttatcaagaaggagatcat
ttaggtgttattcctcgcaactatgaaggaacagtaaaccgtgtaacagcaaggttcggcctagatgcatcacag
caaatccgtctggaagcagaagaagaaaaaattagctcatttgccactcgctaaaacagtatccgtagaagagctt
ctgcaatacgtggagcttcaagatcctgttacgcgcacgcagcttcgcgcaatggctgctaagacggtctgcccg
ccgcataaagtagagcttgaagccttgcttgaaaagcaagcctacaaagaacaagtgctggcaaaacgtttaaca
atgcttgaactgcttgaaaaataccggcgtgtgaaatgaaattcagcgaatttatcgccttctgccaagcata
cgcccgcgctattactcgatttcttcatcacctcgtgtcgatgaaaaacaagcaagcatcacggtcagcgttgtc
tcaggagaagcgtggagcggatatggagaatataaaggaattgcgtcgaactatcttgccgagctgcaagaagga
gatacgattacgtgctttatttccacaccgcagtcagaatttacgctgccaaaagaccctgaaacgccgcttatc
atggtcggaccgggaacaggcgtcgcgccgtttagaggctttgtgcaggcgcgcaaacagctaaaagaacaagga
cagtcacttggagaagcacatttatacttcggctgccgttcacctcatgaagactatctgtatcaagaagagctt
gaaaacgcccaaagcgaaggcatcattacgcttcataccgcttttttctcgcatgccaaatcagccgaaaacatac
gttcagcacgtaatggaacaagacggcaagaaattgattgaacttcttgatcaaggagcgcacttctatatttgc
ggagacggaagccaaatggcacctgccgttgaagcaacgcttatgaaaagctatgctgacgttcaccaagtgagt
gaagcagacgctcgcttatggctgcagcgactagaagaaaaggccgatacgcaaaagacgtgtgggctgggtaa
gaattcatcgatgataagctgtcaaacatgagcagatctgagcccgcctaatgagcgggcttttttttcagatct
gcttgaagacgaaagggcctcgtgatacgcctatttttataggttaatgtcatgataataatggtttcttagcgt
caaagcaaccatagtacgcgccctgtagcggcgcattaagcgcggcgggtgtggtggttacgcgcagcgtgaccg
ctacacttgccagcgccctagcgcccgctcctttcgctttcttcccttcctttctcgccacgttcgccggcttc
cccgtcaagctctaaatcggggctccctttagggttccgatttagtgctttacggcacctcgaccccaaaaaac
ttgatttgggtgatggttcacgtagtgggccatcgccctgatagacggttttcgccctttgacgttggagtcca
cgttctttaatagtggactcttgttccaaactggaacaacactcaaccctatctcgggctattcttttgatttat
aagggattttgccgatttcggcctattggttaaaaaatgagctgatttaacaaaaatttaacgcgaattttaaca
aaatattaacgtttacaatttcaggtggcacttttcggggaaatgtgcgcggaacccctatttgtttatttttct
aaatacattcaaatatgtatccgctcatgagacaataaccctgataaatgcttcaataatattgaaaaaggaaga
gtatgagtattcaacatttccgtgtcgcccttattcccttttttgcggcattttgccttcctgtttttgctcacc
cagaaacgctggtgaaagtaaaagatgctgaagatcagttgggtgcacgagtgggttacatcgaactggatctca
acagcggtaagatccttgagagttttcgccccgaagaacgttttccaatgatgagcacttttaaagttctgctat
gtggcgcggtattatcccgtgttgacgccgggcaagagcaactcggtcgccgcatacactattctcagaatgact
tggttgagtactcaccagtcacagaaaagcatcttacggatggcatgacagtaagagaattatgcagtgctgcca
taaccatgagtgataacactgcggccaacttacttctgacaacgatcggaggaccgaaggagctaaccgcttttt

Fig. 24B: SEQ ID NO:18 (continued)

```
tgcacaacatgggggatcatgtaactcgccttgatcgttgggaaccggagctgaatgaagccataccaaacgacg
agcgtgacaccacgatgcctgcagcaatggcaacaacgttgcgcaaactattaactggcgaactacttactctag
cttcccggcaacaattaatagactggatggaggcggataaagttgcaggaccacttctgcgctcggccttccgg
ctggctggtttattgctgataaatctggagccggtgagcgtgggtctcgcggtatcattgcagcactggggccag
atggtaagccctcccgtatcgtagttatctacacgacggggagtcaggcaactatggatgaacgaaatagacaga
tcgctgagataggtgcctcactgattaagcattgtgtaactgtcagaccaagtttactcatatatactttagattg
atttaaaacttcattttaatttaaaaggatctaggtgaagatcctttttgataatctcatgaccaaaatcccct
aacgtgagttttcgttccactgagcgtcagaccccgtagaaaagatcaaaggatcttcttgagatccttttttc
tgcgcgtaatctgctgcttgcaaacaaaaaaaccaccgctaccagcggtggtttgtttgccggatcaagagctac
caactcttttccgaaggtaactggcttcagcagagcgcagataccaaatactgtccttctagtgtagccgtagt
taggccaccacttcaagaactctgtagcaccgcctacatacctcgctctgctaatcctgttaccagtggctgctg
ccagtggcgataagtcgtgtcttaccgggttggactcaagacgatagttaccggataaggcgcagcggtcgggct
gaacggggggttcgtgcacacagcccagcttggagcgaacgacctacaccgaactgagatacctacagcgtgagc
tatgagaaagcgccacgcttcccgaagggagaaaggcggacaggtatccggtaagcggcagggtcggaacaggag
agcgcacgagggagcttccaggggggaaacgcctggtatctttatagtcctgtcgggtttcgccacctctgacttg
agcgtcgattttgtgatgctcgtcagggggcggagcctatggaaaaacgccagcaacgcggccttttttacggt
tcctggccttttgctggccttttgctcacatgttctttcctgcgttatccctgattctgtggataaccgtatta
ccgcctttgagtgagctgataccgctcgccgcagccgaacgaccgagcgcagcgagtcagtgagcgaggaagcgg
aagagcgcctgatgcggtatttttctccttacgcatctgtgcggtatttcacaccgcatatatggtgcactctcag
tacaatctgctctgatgccgcatagttaagccagtatacactccgctatcgctacgtgactgggtcatggctgcg
ccccgacacccgccaacacccgctgacgcgccctgacgggcttgtctgctcccggcatccgcttacagacaagct
gtgaccgtctccgggagctgcatgtgtcagaggttttcaccgtcatcaccgaaacgcgcgaggcagaacgccatc
aaaaataattcgcgtctggccttcctgtagccagctttcatcaacattaaatgtgagcgagtaacaacccgtcgg
attctccgtgggaacaaacggcggattgaccgtaatgggataggttacgttggtgtagatgggcgcatcgtaacc
gtgcatctgccagtttgaggggacgacgacagtatcggcctcaggaagatcgcactccagccagctttccggcac
cgcttctggtgccggaaaccaggcaaagcgccattcgccattcaggctgcgcaactgttgggaagggcgatcggt
gcgggcctcttcgctattacgccagctggcgaaagggggatgtgctgcaaggcgattaagttgggtaacgccagg
gttttcccagtcacgacgttgtaaaacgacggccagtgaatccgtaatcatggtcatagctgtttcctgtgtgaa
attgttatccgctcacaattccacacaacatacgagccggaagcataaagtgtaaagcctggggtgcctaatgag
tgagctaactcacattaattgcgttgcgctcactgcccgctttccagtcgggaaacctgtcgtgccagctgcatt
aatgaatcggccaacgcgcggggagaggcggtttgcgtattgggcgccagggtggtttttcttttcaccagtgag
acgggcaacagctgattgcccttcaccgcctggccctgagagagttgcagcaagcggtccacgctggtttgcccc
agcaggcgaaaatcctgtttgatggtggttaacggcgggatataacatgagctgtcttcggtatcgtcgtatccc
actaccgagatatccgcaccaacgcgcagcccggactcggtaatggcgcgcattgcgcccagcgccatctgatcg
ttggcaaccagcatcgcagtgggaacgatgccctcattcagcatttgcatggtttgttgaaaaccggacatggca
ctccagtcgccttcccgttccgctatcggctgaatttgattgcgagtgagatatttatgccagccagccagacgc
agacgcgccgagacagaacttaatgggcccgctaacagcgcgatttgctggtgacccaatgcgaccagatgctcc
acgcccagtcgcgtaccgtcttcatggagaaaataatactgttgatgggtgtctggtcagagacatcaagaaat
aacgccggaacattagtgcaggcagcttccacagcaatggcatcctggtcatccagcggatagttaatgatcagc
ccactgacgcgttgcgcgagaagattgtgcaccgccgctttacaggcttcgacgccgcttcgttctaccatcgac
accaccacgctggcaccagttgatcggcgcgagatttaatcgccgcgacaattgcgacggcgcgtgcagggcc
agactggaggtggcaagccaatcagcaacgactgtttgcccgccagttgttgtgccacgcggttgggaatgtaa
ttcagctccgccatcgccgcttccactttttccgcgttttcgcagaaacgtggctggcctggttcaccacgcgg
gaaacggtctgataagagacaccggcatactctgcgacatcgtataacgttactggtttcacattcaccaccctg
aattgactctcttccgggcgctatcatgccataccgcgaaaggttttgcgccattcgatggtgtcctggcacgac
aggtttcccgactggaaagcgggcagtgagcgcaacgcaattaatgtgagttagctcactcattaggcaccccag
gctttacactttatgcttccggctcgtataatgtgtggaattgtgagcggataacaatttcacacaggaaacagg
atcgatccatcgatgagcttactccccatcccctgttgacaattaatcatcggctcgtataatgtgtggaattg
tgagcggataacaatttcacacaggaaacaggatcgcttactccccatcccctgttgacaattaatcatcggc
tcgtataatgtgtggaattgtgagcggataacaat
```

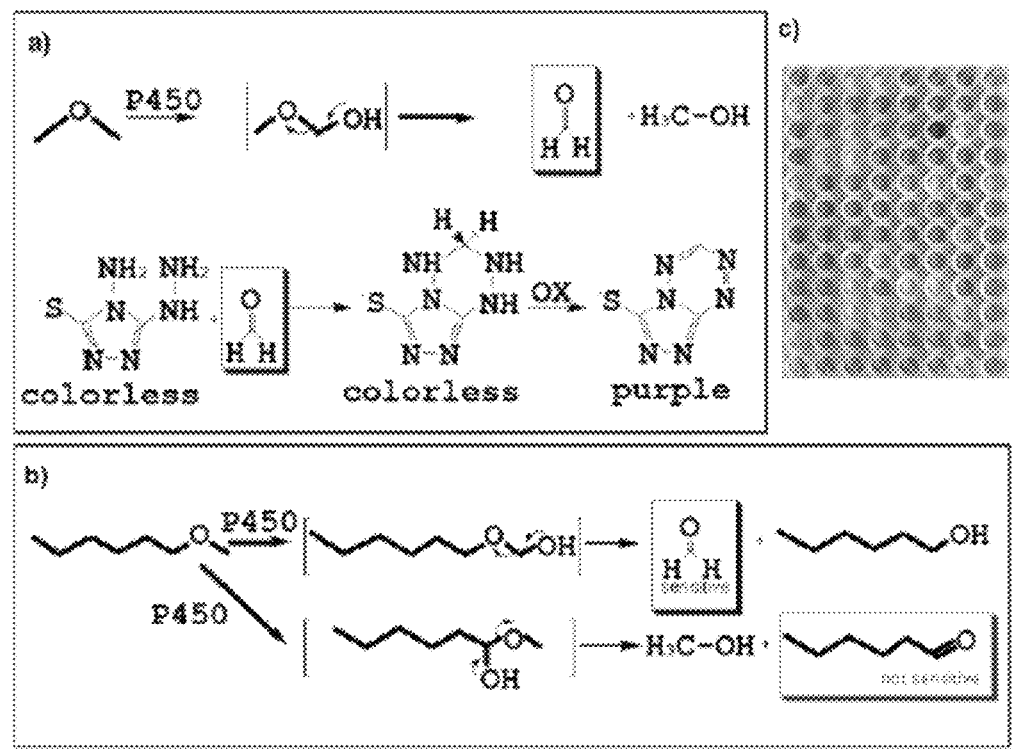
Fig. 25A-C
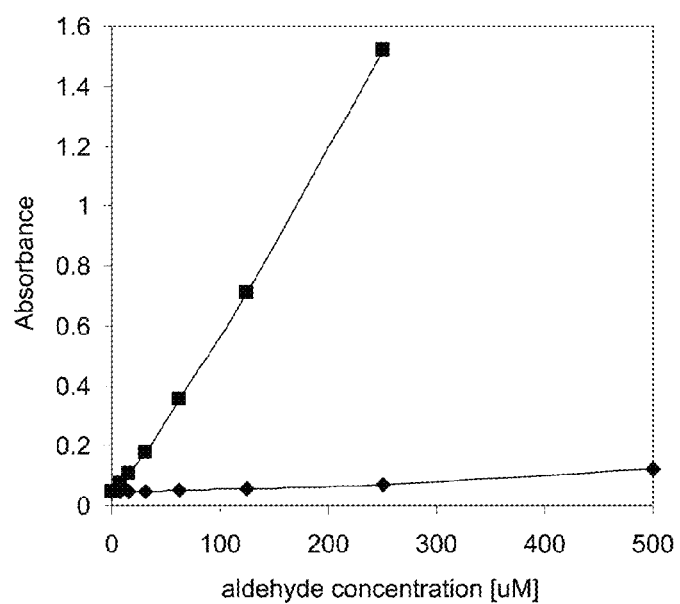
Fig. 26

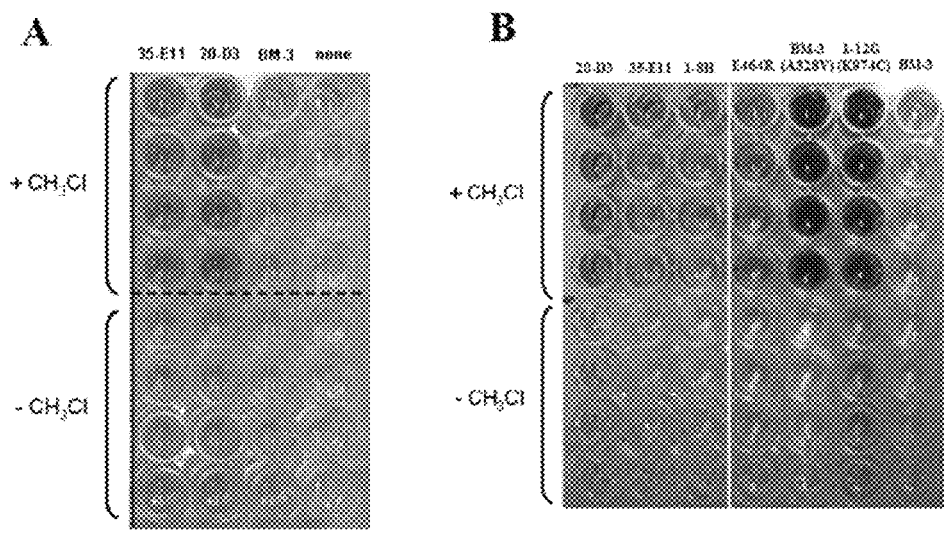
Fig. 27A-B
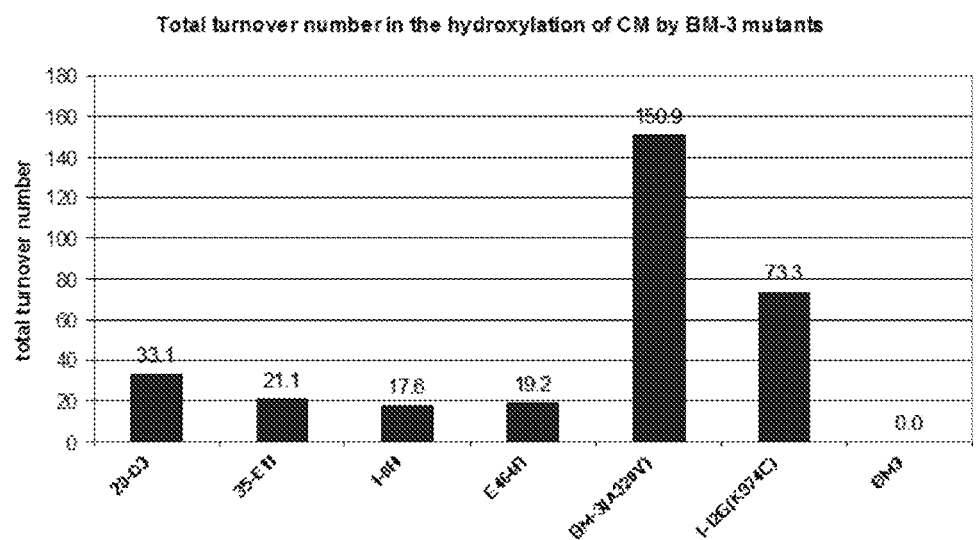
Fig. 28

```
                            1                                               50
SEQ1 HEME     (1)   --------T KE QPKT GELK LPLLNTDKPVQ L KIA ELG  KF
SEQ2 HEME     (1)   ------KETSPI QPKT GPLG LPL  KDKPTL L  A EQGP  Q H
SEQ3 HEME     (1)   ------KQASAI QPKT GPLK LPHLEK QLSQ LW IA ELGP  RF
SEQ4 HEME     (1)   ----MDKK SAI QPKT GPLG LPL  KDKPTL F KIA EYGP  Q Q
SEQ5 HEME     (1)   STATPAAA EPI RDPG PIFG LFQ TPGEVGQHL AR RHHDG   
SEQ6 HEME     (1)   ---SSKNR DPI QPPTKPV G  LSL SAAPVQHLT AKELGP  W
SEQ7 HEME     (1)   --------T KE QPKT GELK LPLLNTDKPVQ L KIA ELG  KF
Consensus     (1)          I   IPQPKTFG LGNLPLLD DKP QSLIKIADELGPIF ID
                            51                                              100
SEQ1 HEME    (44)   APGRV R   SQR  K AC E   D N SQA KFV  F         SWTH
SEQ2 HEME    (45)   TP GT VV GHE VK C EE D S EGA R V AP          SWTH
SEQ3 HEME    (45)   PPGVS  V GHN VA C EK D N GK Q V F           SWTH
SEQ4 HEME    (47)   TLSDTI V GHE VA C E  D S EGA A V AP          SETQ
SEQ5 HEME    (51)   FAGKRVP V SVA AS C A  R I GPP SY MA          HSD
SEQ6 HEME    (48)   MMGSPI VV GHD VD S EK D T RGA R V AVQ         DTH
SEQ7 HEME    (44)   APGCV R   SQR  K AC E   D N SQA KFF  P         SWTH
Consensus    (51)          PG    TIFVSGH LV  EVCDESRPDK I   AL  KVRDFAGDGLFTSWTHE
                            101                                             150
SEQ1 HEME    (94)   K  K N LP SQQ  K H M VDI VQ VQ    LNADEHI  P
SEQ2 HEME    (95)   P  K K  P SQR  KD HEK VDI VQ Q   A LNPNEA D PG
SEQ3 HEME    (95)   P  QK R LP SQQ  K H M DI TQ Q S LNPNEEID A
SEQ4 HEME    (97)   P  K N  P SQR  KD H M VDI VQ VQ   A LNPNEN D P
SEQ5 HEME   (101)   P  QC R  PA SQR  K  FD  R NR VD    QGPDADIA A
SEQ6 HEME    (98)   P  SK N LQP  R  QS HPS VDI EQ VQ    LNAD EID VH
SEQ7 HEME    (94)   I  K N LP SQQ  K H M VDI VQ VQ    LNADEHI  S
Consensus   (101)   PNWKKAHNILLPSFSQRAMKGYHAMMVDIAVQLVQKWERLNPDE  IDV E
                            151                                             200
SEQ1 HEME   (144)           R      G C  N R N FYRDQPH   ITSMVRA DEA  KLQRANP
SEQ2 HEME   (145)           R      G C  N R N YR TPH   INSMVRA DEA  HQ QRLD
SEQ3 HEME   (145)           R      G C  N R N FYRDSQH   ITSM RA KEA  QSKRLG
SEQ4 HEME   (147)           P      G C  N R N FYR TPH   ITSMTRA DEA  HQLQRLD
SEQ5 HEME   (151)           R      A  G D A FASDELD   M MVGA GEA  KLTRLP
SEQ6 HEME   (148)           A      G C  D R N FYRBDYH   ES VR    TISMTRG-LPF
SEQ7 HEME   (144)           P      G C  N R N FYRDQPH   IISMVRA DEV  KLQRANP
Consensus   (151)   DMTRLTLDTIGLCGFNYRFNSFYRD PHPFI  SMVRALDEAMN  LQRL  I
```

Fig. 31A

```
                      201                                              250
SEQ1 HEME    (194)  DDPAYDENKRQFQEDIKVMNDLVDKIIADR--KASGEQS-DLLTHMLNG
SEQ2 HEME    (195)  QDKLMVRTKRQFRVDIQTMFSLVDSIIAER--RANGDQDEKDLLARMLNV
SEQ3 HEME    (195)  QDRMMVRTKLQFQKDIEVMNSLVDRMIAER--KANPDENIKDLLSLMLYR
SEQ4 HEME    (197)  EDKLMWRTKRQFQHDIQSMFSLVDNIIAER--KSSGNQEENDLLSRMLHV
SEQ5 HEME    (201)  QDRPMGRAHRQAAEDIAVMRNLVDQVIRQR---RVSPTSGMDLINLMLER
SEQ6 HEME    (197)  EQIWMQRRRILAEDVAFMNRMVDEIIAERRKSAEGIDDKKDMLAAMMTG
SEQ7 HEME    (194)  DDPAYDENKRQCQEDIKVMNDLVDKIIADR--KARGEQS-DLLTQMLNG
Consensus    (201)  DDK M R KRQFQEDI  MN LVD IIAER  KA GDQ  DLLS ML G
                      251                                              300
SEQ1 HEME    (241)  KDPETGEPLDDENIRYQIITFLIAGHETTSGLLSFALYFLVKNPHVLQKA
SEQ2 HEME    (243)  EDPETGEKLDDENIRFQIITFLIAGHETTSGLLSFATYFLLKHPDKLKKA
SEQ3 HEME    (243)  KDPVTGETLDDENIRYQIITFLIAGHETTSGLISFATYCLLTHPEKLKKA
SEQ4 HEME    (245)  QDPETGEKLDDENIRFQIITFLIAGHETTSGLLSFATYFLLKNPDKLKKA
SEQ5 HEME    (248)  RDPETDRRLDDANIRNQVITFLIAGHETTSGLLTFALYELLRNPGVLAQA
SEQ6 HEME    (247)  VDRSTGEQLDDVNIRYQINTFLIAGHETTSGLLSYTLYALLKHPDILKKA
SEQ7 HEME    (241)  KDPETGEPLDDGNISYQIITFLIAGHETTSGLLSFALYFLVKNPHVLQKV
Consensus    (251)  KDPETGE LDDENIRYQIITFLIAGHETTSGLLSFALYFLLKNPDVLKKA
                      301                                              350
SEQ1 HEME    (291)  AEEAARVL---VDPVPSYKQVKQLKYVGMVLNEALRLWPTAPAFSLYAKE
SEQ2 HEME    (293)  YEEVDRVL---TDAAPTYKQVLELTYIRMIINESLRLWPTAPAFSLYPKE
SEQ3 HEME    (293)  QEEADRVL---TDDTPKYKQIQQLKYIRMVLNETLRLYPTAPAFSLYAKE
SEQ4 HEME    (295)  YEEVDRVL---TDPTPTYQQVMKLKYIRMIINESLRLWPTAPAFSLYAKE
SEQ5 HEME    (298)  YAEVDTVLPG-DALEVVADLARMPVLDRVLKETLRLWPTAPAPAVAPFD
SEQ6 HEME    (297)  YDEVDRVFGPDVNAKPTYQQVTQLTYITQILKEALRLWPAPAYGISPLA
SEQ7 HEME    (291)  VEEAARVL---VDPVFSYKQVKQLKYVGMVLNEALRLWPTPPAFSLYAKE
Consensus    (301)  YEEVDRVL    D  PTYKQV QLKYI MVLNEALRLWPTAPAFSLYAKE
                      351                                              400
SEQ1 HEME    (338)  DTVLGG-EYPLEKG-DELMVLIPQLHRDKTIWGDDVEEFRPERFE--NPS
SEQ2 HEME    (340)  DTVIGG-KRPTTTN-DRISVLIPQLHRDRDAWGKDAEEFRPERFE--RQD
SEQ3 HEME    (340)  DTVLGG-EYPTSKG-QRVVLIPKLHRDQNAWGPDAEDFRPERFE--DPG
SEQ4 HEME    (342)  DTVIGG-KYPTKKGEDRISVLIPQLHRDKDAWGDNVEEFQPERFE--DLD
SEQ5 HEME    (346)  DVVLGG-RYRLRKD-RRISVVLTALHRDPKVWAN-PERFDIDRFLPENEA
SEQ6 HEME    (347)  DETIGGGKYKLRKG-TFIFILVTALHRDPSVWGPNPDAFDPENFSREAEA
SEQ7 HEME    (338)  DTVLGG-EYPLEKG-DEYMVLIPQLHRDKTIWGDDVEEFRPERFE--NPS
Consensus    (351)  DTVLGG KYPL KG D ISVLIPQLHRDK IWG D EEFRPERFE    S
```

Fig. 31B

```
              401                                                    450
SEQ1 HEME  (384) A  QH  K   M Q       QQ  LH  TLVLGM  KH  FEDHTN ELDI
SEQ2 HEME  (386) Q  HH YK   N Q       MQ  LH  TLVLGM  K   TLIDHEN ELDI
SEQ3 HEME  (386) S  HH YK   N Q       MQ  LQ  T VLG   KH  LINHTG ELKI
SEQ4 HEME  (389) K  HH YK   N Q       MQ  LH  TLV GM  QH  FID ED QLD
SEQ5 HEME  (393) K  AH YM     E       RQ  LT  KLAL        AFQDPHD QFR
SEQ6 HEME  (396) KR IN  K   N Q       RG  H   ALALGM  QR  KLIDHQR Q
SEQ7 HEME  (384) A  QH  K   M Q       QQ  LH  TLVLGM  KH  FEDHTN ELDI
Consensus  (401)    IP HAYKPPGNGQRACIG QFALHEATLVLGMMLKHPDFIDH  YELDI 451              472
SEQ1 HEME  (434)  ET  L   GFV KAKS KIPL
SEQ2 HEME  (436)  QT  L   GDFH SVQS HQ--
SEQ3 HEME  (436)  EA      DFK TVKP KT--
SEQ4 HEME  (439)  QT  L   GDFK RIVP-----
SEQ5 HEME  (443)  ET      QFV ---------
SEQ6 HEME  (446)  ET      G-------------
SEQ7 HEME  (434)  ET  L   GFV KAKS KIPL
Consensus  (451) KETLTLKPE F I    K
```

Fig. 31C

Fig. 32A: Protein Similarity Scores
Full Length Protein

| SEQ ID NO: | 1 | 2 | 3 | 4 | 5 | 6 | 7 |
|---|---|---|---|---|---|---|---|
| 1 | 5457 | 3303 | 3272 | 3375 | 1860 | 2400 | 5352 |
| 2 | | 5536 | 3395 | 4208 | 1812 | 2514 | 3251 |
| 3 | | | 5480 | 3347 | 1931 | 2386 | 3226 |
| 4 | | | | 5548 | 1848 | 2437 | 3310 |
| 5 | | | | | 5523 | 1964 | 1831 |
| 6 | | | | | | 5607 | 2372 |
| 7 | | | | | | | 5463 |

Fig. 32B: Heme Domain (amino acids 1-455)

| SEQ ID NO: | 1 | 2 | 3 | 4 | 5 | 6 | 7 |
|---|---|---|---|---|---|---|---|
| 1 | 2386 | 1600 | 1610 | 1615 | 985 | 1143 | 2293 |
| 2 | | 2397 | 1675 | 1977 | 969 | 1233 | 1551 |
| 3 | | | 2386 | 1651 | 997 | 1158 | 1568 |
| 4 | | | | 2386 | 1007 | 1214 | 1553 |
| 5 | | | | | 2361 | 979 | 959 |
| 6 | | | | | | 2386 | 1118 |
| 7 | | | | | | | 2390 |

Fig. 33A: Protein % Identity
Full Length Protein

| SEQ ID NO: | 1 | 2 | 3 | 4 | 5 | 6 | 7 |
|---|---|---|---|---|---|---|---|
| 1 | 100 | 59 | 58 | 60 | 40 | 47 | 98 |
| 2 |  | 100 | 60 | 75 | 39 | 48 | 58 |
| 3 |  |  | 100 | 59 | 41 | 46 | 57 |
| 4 |  |  |  | 100 | 38 | 46 | 59 |
| 5 |  |  |  |  | 100 | 40 | 39 |
| 6 |  |  |  |  |  | 100 | 46 |
| 7 |  |  |  |  |  |  | 100 |

Fig. 33B: Heme Domain (amino acids 1-455)

| SEQ ID NO: | 1 | 2 | 3 | 4 | 5 | 6 | 7 |
|---|---|---|---|---|---|---|---|
| 1 | 100 | 66 | 67 | 67 | 45 | 50 | 97 |
| 2 |  | 100 | 69 | 82 | 45 | 53 | 65 |
| 3 |  |  | 100 | 68 | 46 | 50 | 66 |
| 4 |  |  |  | 100 | 47 | 52 | 64 |
| 5 |  |  |  |  | 100 | 45 | 44 |
| 6 |  |  |  |  |  | 100 | 49 |
| 7 |  |  |  |  |  |  | 100 |

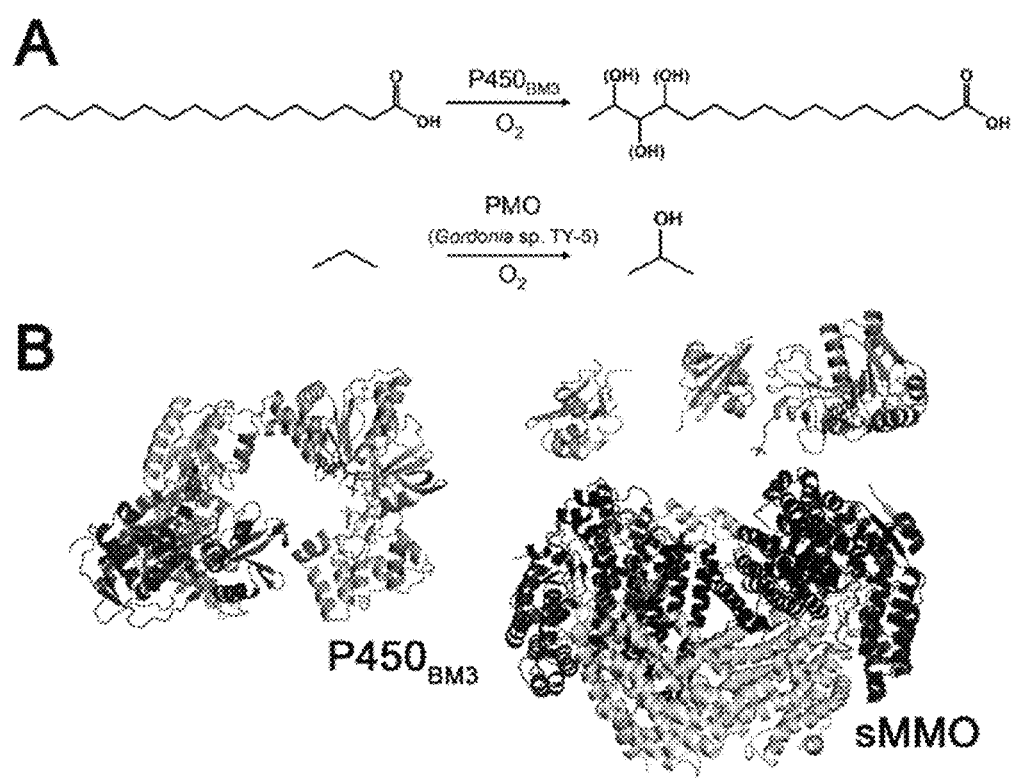
Fig. 34A-B

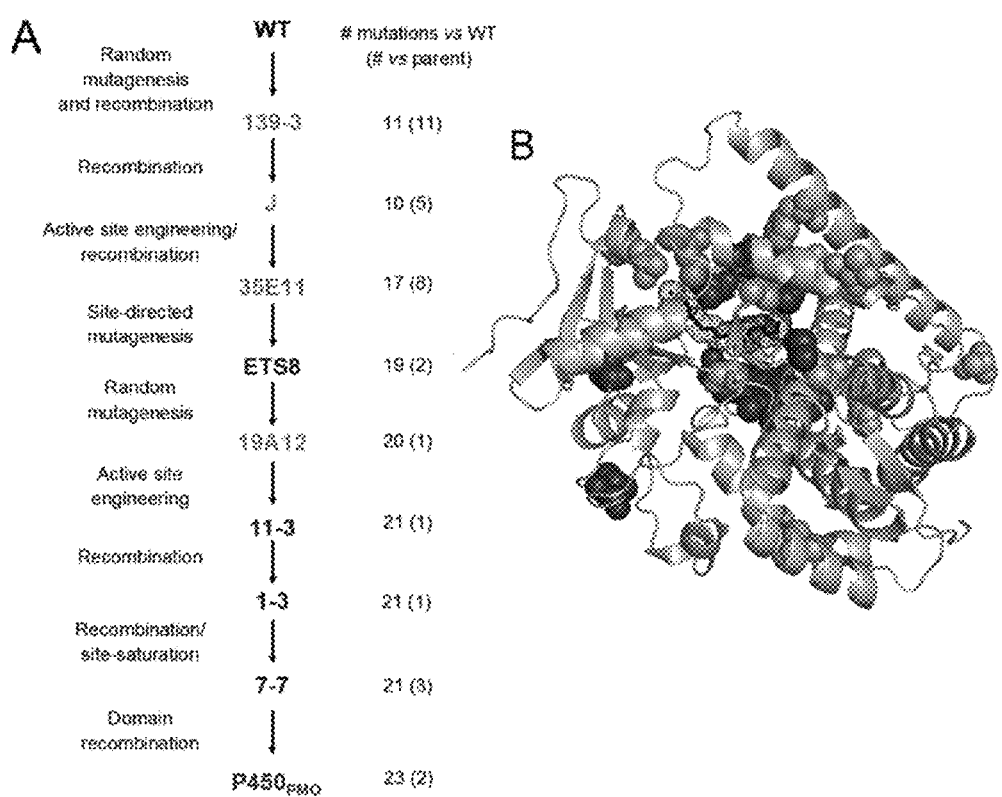
Fig. 35A-B

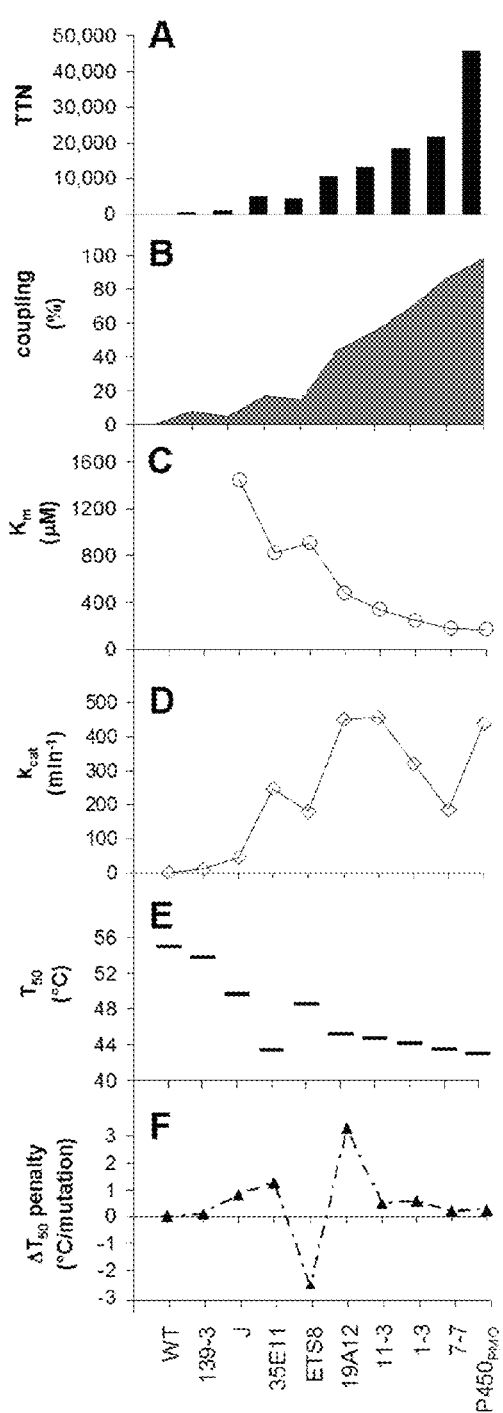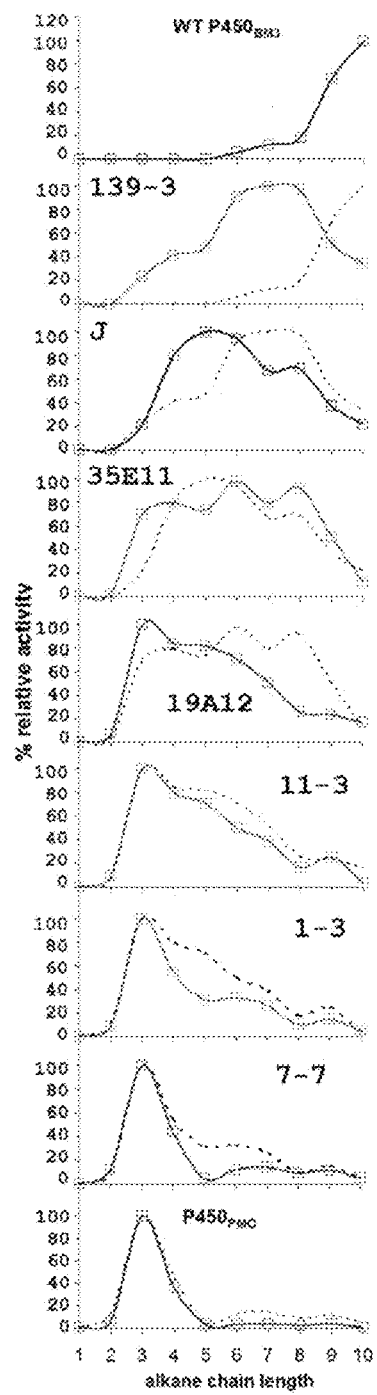
Fig. 37A-F
Fig. 38

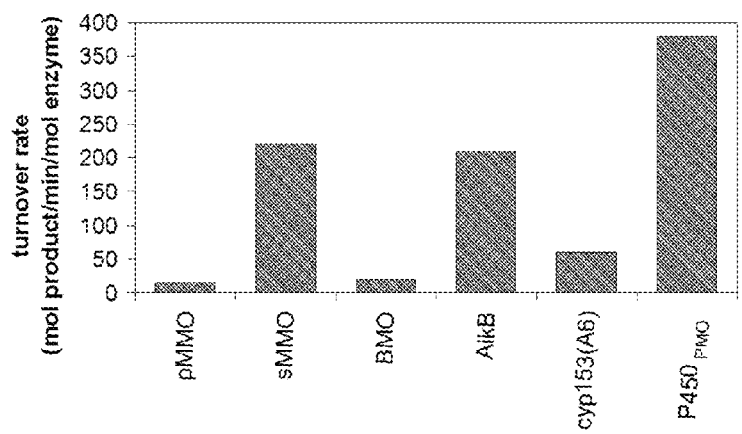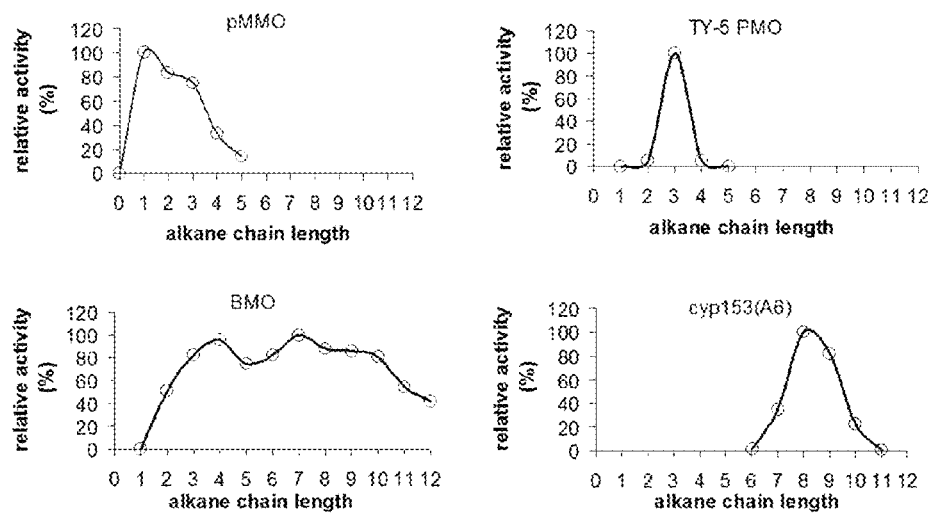
Fig. 40A-B

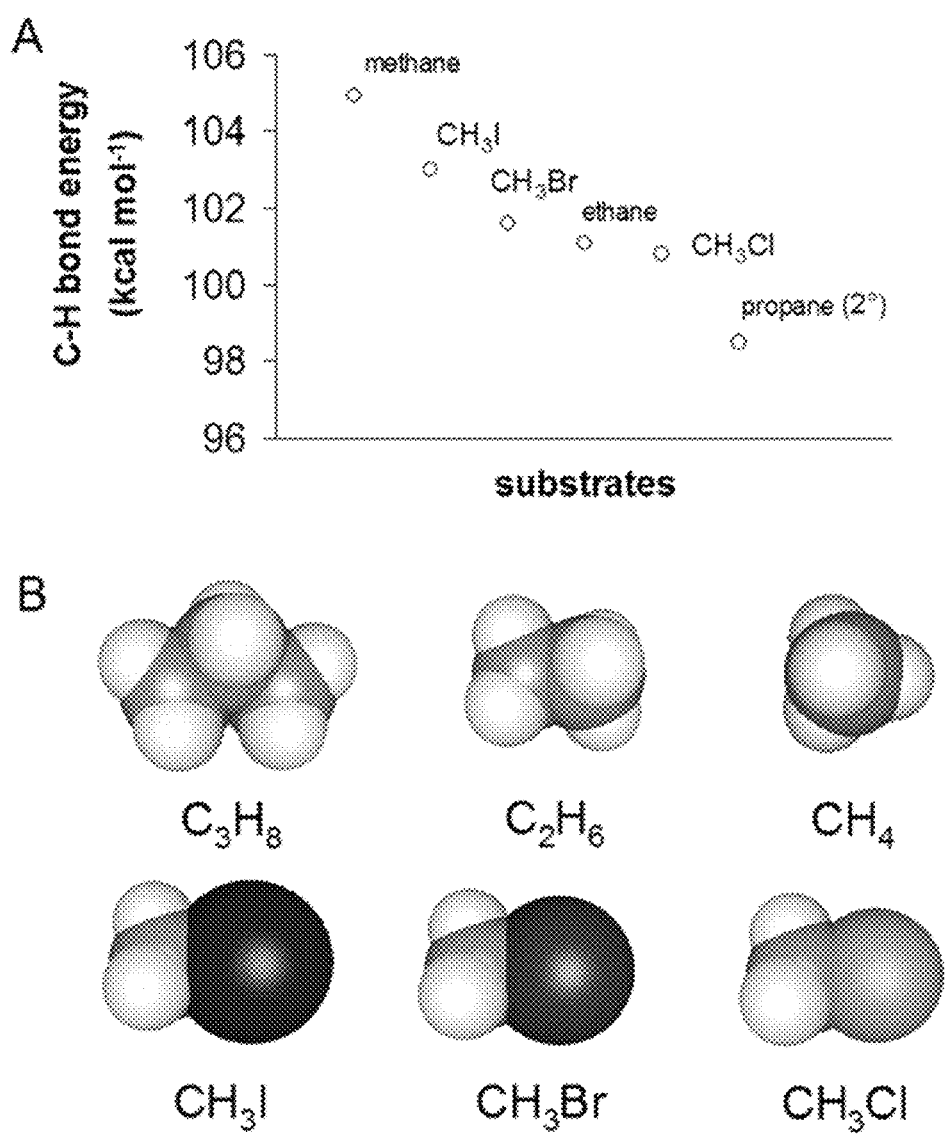
Fig. 41A-B

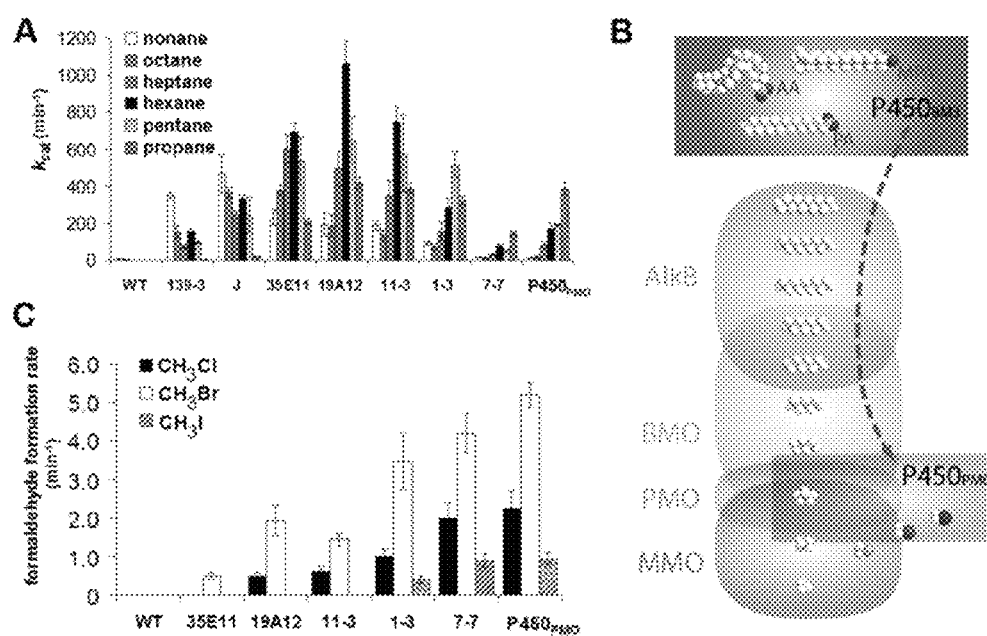
Fig. 43A-C

ALKANE OXIDATION BY MODIFIED HYDROXYLASES

CROSS REFERENCE TO RELATED APPLICATIONS

This application claims priority under 35 U.S.C. 120 as a continuation of U.S. Ser. No. 14/270,268, filed May 5, 2014 (now U.S. Pat. No. 9,074,178), which application claims priority under 35 U.S.C. 120 as a divisional application of U.S. Ser. No. 11/697,404, filed Apr. 6, 2007 (now U.S. Pat. No. 8,715,988), which application is a continuation-in-part of PCT/US2006/011273, filed Mar. 28, 2006, which application claims priority to U.S. Provisional Application Ser. No. 60/665,903 filed Mar. 28, 2005, and to U.S. Provisional Application Ser. No. 60/698,872, filed Jul. 13, 2005, and also to U.S. Provisional Application Ser. No. 60/700,781 filed Jul. 20, 2005. The application also claims priority to U.S. Provisional Application Ser. No. 60/900,243, filed Feb. 8, 2007, entitled, "Engineered Cytochromes P450 with Tailored Propane Specificity and Haloalkanes Dechalogenase Activity." All of the above disclosures are incorporated herein by reference.

STATEMENTS REGARDING FEDERALLY SPONSORED RESEARCH

The invention was funded by Grant No. BES-0313567 awarded by National Science Foundation (NSF) and Grant No. DAAD19-03-0004 awarded by the U.S. Army. The government has certain rights in the invention.

TECHNICAL FIELD

This invention relates to modified hydroxylases. The invention further relates to cells expressing such modified hydroxylases and methods of producing hydroxylated alkanes by contacting a suitable substrate with such modified hydroxylases and/or such cells. Also included may have modified hydroxylases comprising unique regioselectivities.

BACKGROUND

Hydroxylation of linear alkanes has the important practical implication of providing valuable intermediates for chemical synthesis. Nevertheless, selective oxyfunctionalization of hydrocarbons remains one of the great challenges for contemporary chemistry. Many chemical methods for hydroxylation require severe conditions of temperature or pressure, and the reactions are prone to over-oxidation, producing a range of products, many of which are not desired.

Enzymes are an attractive alternative to chemical catalysts. In particular, monooxygenases have the ability to catalyze the specific hydroxylation of non-activated C—H bonds. These cofactor-dependent oxidative enzymes have multiple domains and function via complex electron transfer mechanisms to transport a reduction equivalent to the catalytic center. Exemplary monooxygenases include the cytochrome P450 monooxygenases ("P450s"). The P450s are a group of widely-distributed heme-containing enzymes that insert one oxygen atom from diatomic oxygen into a diverse range of hydrophobic substrates, often with high regio- and stereoselectivity. Their ability to catalyze these reactions with high specificity and selectivity makes P450s attractive catalysts for chemical synthesis and other applications, including oxidation chemistry.

Despite the ability of these enzymes to selectively hydroxylate a wide range of compounds, including fatty acids, aromatic compounds, alkanes, alkenes, and natural products, only a few members of this large superfamily of proteins are capable of hydroxylating alkanes. Accordingly, there is a need for modified hydroxylases that have the ability to efficiently hydroxylate alkanes in vivo. In addition, there is a need for cells that can express such modified hydroxylases while producing recoverable quantities of alkane-derived alcohols.

SUMMARY

Provided herein are polypeptides that convert alkanes to alcohols. Also provided are nucleic acid molecules that encode such polypeptides, cells expressing such polypeptides, and methods of synthesizing alcohols from a suitable alkane substrate. Accordingly, in various embodiments, isolated or recombinant polypeptides comprising residues 1 or about 455 of the amino acid sequence set forth in SEQ ID NO:1, 2, 3, 4, 5 or 6, are provided. The polypeptides include up to 50, 25, 10, or 5 conservative amino acid substitutions excluding residues: (a) 47, 78, 82, 94, 142, 175, 184, 205, 226, 236, 252, 255, 290, 328, and 353 of SEQ ID NO:1; (b) 48, 79, 83, 95, 143, 176, 185, 206, 227, 238, 254, 257, 292, 330, and 355 of SEQ ID NO:2 or SEQ ID NO:3; (c) 49, 80, 84, 96, 144, 177, 186, 207, 228, 239, 255, 258, 293, 331, and 357 of SEQ ID NO:4; (d) 54, 85, 89, 101, 149, 182, 191, 212, 232, 243, 259, 262, 297, 336, and 361 of SEQ ID NO:5; and (e) 51, 82, 86, 98, 146, 179, 188, 208, 231, 242, 258, 262, 296, 337, and 363 of SEQ ID NO:6. The amino acid sequence includes the following residues:

(1) a Z1 amino acid residue at positions: (a) 47, 82, 142, 205, 236, 252, and 255 of SEQ ID NO:1; (b) 48, 83, 143, 206, 238, 254, and 257 of SEQ ID NO:2 or SEQ ID NO:3; (c) 49, 84, 144, 207, 239, 255, and 258 of SEQ ID NO:4; (d) 54, 89, 149, 212, 243, 259, and 262 of SEQ ID NO:5; and (e) 51, 86, 146, 208, 242, 258, and 262 of SEQ ID NO:6;

(2) a Z2 amino acid residue at positions: (a) 94, 175, 184, 290, and 353 of SEQ ID NO:1; (b) 95, 176, 185, 292, and 355 of SEQ ID NO:2 or SEQ ID NO:3; (c) 96, 177, 186, 293, and 357 of SEQ ID NO:4; (d) 101, 182, 191, 297, and 361 of SEQ ID NO:5; and (e) 98, 179, 188, 296, and 363 of SEQ ID NO:6;

(3) a Z3 amino acid residue at position: (a) 226 of SEQ ID NO:1; (b) 227 of SEQ ID NO:2 or SEQ ID NO:3; (c) 228 of SEQ ID NO:4; (d) 232 of SEQ ID NO:5; and (e) 231 of SEQ ID NO:6; and (4) a Z4 amino acid residue at positions: (a) 78 and 328 of SEQ ID NO:1; (b) 79 and 330 of SEQ ID NO:2 or SEQ ID NO:3; (c) 80 and 331 of SEQ ID NO:4; (d) 85 and 336 of SEQ ID NO:5; and (e) 82 and 337 of SEQ ID NO:6.

In general, a Z1 amino acid residue includes glycine (G), asparagine (N), glutamine (Q), serine (S), threonine (T), tyrosine (Y), or cysteine (C). A Z2 amino acid residue includes alanine (A), valine (V), leucine (L), isoleucine (I), proline (P), or methionine (M). A Z3 amino acid residue includes lysine (K), or arginine (R). A Z4 amino acid residue includes tyrosine (Y), phenylalanine (F), tryptophan (W), or histidine (H).

In other embodiments, the polypeptide further includes a Z3 amino acid residue at position: (a) 285 of SEQ ID NO:1; (b) 287 of SEQ ID NO:2 or 3; (c) 288 of SEQ ID NO:4; (d) 292 of SEQ ID NO:5; and (e) 291 of SEQ ID NO:6. A Z3 amino acid residue includes lysine (K), arginine (R), or histidine (H). In some aspects, the amino acid residue at this position is an arginine (R).

In yet another embodiment, the polypeptide comprises, in addition to one or more of the residue replacements above, an isoleucine at position 52, a glutamic acid at position 74, proline at position 188, a valine at position 366, an alanine at position 443, a glycine at position 698 of SEQ ID NO:1; isoleucine at position 53, a glutamic acid at position 75, proline at position 189, a valine at position 368 of SEQ ID NO:2; an isoleucine at position 53, a glutamic acid at position 75, proline at position 189, a valine at position 368 of SEQ ID NO:3; an isoleucine at position 55, a gluatmic acid at position 77, proline at position 191, a valine at position 371 of SEQ ID NO:4; an isoleucine at position 59, a glutamic acid at position 81, proline at position 195, a valine at position 374 of SEQ ID NO:5; an isoleucine at position 56, a gluatmic acid at position 78, proline at position 192, a valine at position 376 of SEQ ID NO:6; and an isoleucine at position 52, a glutamic acid at position 74, proline at position 188, a valine at position 366 of SEQ ID NO:7.

In general, polypeptides provided herein display hydroxylase activity that converts an alkane to an alcohol. In general, alkanes include methane ($CH_4$), ethane ($C_2H_6$), propane ($C_3H_8$), butane ($C_4H_{10}$), pentane ($C_5H_{12}$), hexane ($C_6H_{14}$), heptane ($C_7H_{16}$), octane ($C_8H_{18}$), nonane ($C_9H_{20}$), decane ($C_{10}H_{22}$), undecane ($C_{11}H_{24}$), and dodecane ($C_{12}H_{26}$). Also in general, alcohols include methanol, ethanol, propanol, butanol, pentanol, hexanol, heptanol, octanol, nonanol, decanol, undecanol, and dodecanol.

In other embodiments, the amino acid sequence of the polypeptide includes residues at the following positions:

(1) a glycine (G), glutamine (Q), serine (S), threonine (T), or cysteine (C) amino acid residue at position: (a) 47, 82, 142, 205, 236, 252, and 255 of SEQ ID NO:1; (b) 48, 83, 143, 206, 238, 254, and 257 of SEQ ID NO:2 or SEQ ID NO:3; (c) 49, 84, 144, 207, 239, 255, and 258 of SEQ ID NO:4; (d) 54, 89, 149, 212, 243, 259, and 262 of SEQ ID NO:5; and (e) 51, 86, 146, 208, 242, 258, and 262 of SEQ ID NO:6;

(2) a valine (V) or isoleucine (I) amino acid residue at position: (a) 94, 175, 184, 290, and 353 of SEQ ID NO:1; (b) 95, 176, 185, 292, and 355 of SEQ ID NO:2 or SEQ ID NO:3; (c) 96, 177, 186, 293, and 357 of SEQ ID NO:4; (d) 101, 182, 191, 297, and 361 of SEQ ID NO:5; and (e) 98, 179, 188, 296, and 363 of SEQ ID NO:6;

(3) an arginine amino acid residue at position: (a) 226 of SEQ ID NO:1; (b) 227 of SEQ ID NO:2 or SEQ ID NO:3; (c) 228 of SEQ ID NO:4; (d) 232 of SEQ ID NO:5; and (e) 231 of SEQ ID NO:6; and (4) a phenylalanine (F) or histidine (H) amino acid residue at position: (a) 78 and 328 of SEQ ID NO:1; (b) 79 and 330 of SEQ ID NO:2 or SEQ ID NO:3; (c) 80 and 331 of SEQ ID NO:4; (d) 85 and 336 of SEQ ID NO:5; and (e) 82 and 337 of SEQ ID NO:6.

In other embodiments, the amino acid sequence of the polypeptide includes residues at the following positions:

(1) a serine (S) residue at position: (a) 82, 142, and 255 of SEQ ID NO:1; (b) 83, 143 and 257 of SEQ ID NO:2 or SEQ ID NO:3; (c) 84, 144, and 258 of SEQ ID NO:4; (d) 89, 149, and 262 of SEQ ID NO:5; (e) 86, 146 and 262 of SEQ ID NO:6;

(2) a cysteine (C) amino acid residue at position: (a) 47 and 205 of SEQ ID NO:1; (b) 48 and 206 of SEQ ID NO:2 or SEQ ID NO:3; (c) 49 and 207 of SEQ ID NO:4; (d) 54 and 212 of SEQ ID NO:5; (e) 51 and 208 of SEQ ID NO:6;

(3) a glutamine (Q) amino acid residue at position: (a) 236 of SEQ ID NO:1; (b) 238 of SEQ ID NO:2 or SEQ ID NO:3; (c) 239 of SEQ ID NO:4; (d) 243 of SEQ ID NO:5; (e) 242 of SEQ ID NO:6;

(4) a glycine (G) amino acid residue at position: (a) 252 of SEQ ID NO:1; (b) 254 of SEQ ID NO:2 or SEQ ID NO:3; (c) 255 of SEQ ID NO:4; (d) 259 of SEQ ID NO:5; (e) 258 of SEQ ID NO:6;

(5) a valine (V) amino acid residue at position: (a) 184, 290 and 353 of SEQ ID NO:1; (b) 185, 292, and 355 of SEQ ID NO:2 or SEQ ID NO:3; (c) 186, 293 and 357 of SEQ ID NO:4; (d) 191, 297, and 361 of SEQ ID NO:5; (e) 188, 296, and 363 of SEQ ID NO:6;

(6) an isoleucine (I) amino acid residue at position: (a) 94 and 175 of SEQ ID NO:1; (b) 95 and 176 of SEQ ID NO:2 or SEQ ID NO:3; (c) 96 and 177 of SEQ ID NO:4; (d) 101 and 182 of SEQ ID NO:5; (e) 98 and 179 of SEQ ID NO:6; and (7) a phenylalanine (F) amino acid residue at position: (a) 78 and 328 of SEQ ID NO:1; (b) 79 and 330 of SEQ ID NO:2 or SEQ ID NO:3; (c) 80 and 331 of SEQ ID NO:4; (d) 85 and 336 of SEQ ID NO:5; (e) 82 and 337 of SEQ ID NO:6.

In another embodiment, an isolated or recombinant polypeptide that includes residues 1 to about 455 of the amino acid sequence set forth in SEQ ID NO:1, 2, 3, 4, 5 or 6 is provided. The polypeptide includes, at least, 80%, 85%, 90%, or 95% of the amino acid residues in the amino acid sequence at the following positions:

(1) a serine (S) residue at position: (a) 82, 142, and 255 of SEQ ID NO:1; (b) 83, 143 and 257 of SEQ ID NO:2 or SEQ ID NO:3; (c) 84, 144, and 258 of SEQ ID NO:4; (d) 89, 149, and 262 of SEQ ID NO:5; (e) 86, 146 and 262 of SEQ ID NO:6;

(2) a cysteine (C) amino acid residue at position: (a) 47 and 205 of SEQ ID NO:1; (b) 48 and 206 of SEQ ID NO:2 or SEQ ID NO:3; (c) 49 and 207 of SEQ ID NO:4; (d) 54 and 212 of SEQ ID NO:5; (e) 51 and 208 of SEQ ID NO:6;

(3) a glutamine (Q) amino acid residue at position: (a) 236 of SEQ ID NO:1; (b) 238 of SEQ ID NO:2 or SEQ ID NO:3; (c) 239 of SEQ ID NO:4; (d) 243 of SEQ ID NO:5; (e) 242 of SEQ ID NO:6;

(4) a glycine (G) amino acid residue at position: (a) 252 of SEQ ID NO:1; (b) 254 of SEQ ID NO:2 or SEQ ID NO:3; (c) 255 of SEQ ID NO:4; (d) 259 of SEQ ID NO:5; (e) 258 of SEQ ID NO:6;

(5) a valine (V) amino acid residue at position: (a) 184, 290 and 353 of SEQ ID NO:1; (b) 185, 292, and 355 of SEQ ID NO:2 or SEQ ID NO:3; (c) 186, 293 and 357 of SEQ ID NO:4; (d) 191, 297, and 361 of SEQ ID NO:5; (e) 188, 296, and 363 of SEQ ID NO:6;

(6) an isoleucine (I) amino acid residue at position: (a) 94 and 175 of SEQ ID NO:1; (b) 95 and 176 of SEQ ID NO:2 or SEQ ID NO:3; (c) 96 and 177 of SEQ ID NO:4; (d) 101 and 182 of SEQ ID NO:5; (e) 98 and 179 of SEQ ID NO:6; and (7) a phenylalanine (F) amino acid residue at position: (a) 78 and 328 of SEQ ID NO:1; (b) 79 and 330 of SEQ ID NO:2 or SEQ ID NO:3; (c) 80 and 331 of SEQ ID NO:4; (d) 85 and 336 of SEQ ID NO:5; (e) 82 and 337 of SEQ ID NO:6; and (8) an arginine (R) amino acid residue at position: (a) 226 of SEQ ID NO:1; b) 227 of SEQ ID NO:2 or SEQ ID NO:3; (c) 228 of SEQ ID NO:4; (d) 232 of SEQ ID NO:5; (e) 231 of SEQ ID NO:6.

In other embodiments, the polypeptide further includes a Z3 amino acid residue at position: (a) 285 of SEQ ID NO:1; (b) 287 of SEQ ID NO:2 or 3; (c) 288 of SEQ ID NO:4; (d) 292 of SEQ ID NO:5; and (e) 291 of SEQ ID NO:6. A Z3 amino acid residue includes lysine (K), arginine (R), or histidine (H). In some aspects, the amino acid residue at this position is an arginine (R).

In yet another embodiment, an isolated or recombinant polypeptide that includes residues 456-1048 of SEQ ID NO:1, 456-1059 of SEQ ID NO:2, 456-1053 of SEQ ID NO:3, 456-1064 of SEQ ID NO:4, 456-1063 of SEQ ID NO:5, or 456-1077 of SEQ ID NO:6, is provided. The polypeptide includes an amino acid sequence with up to 65, 40, 25, or 10 conservative amino acid substitutions excluding residues: (a) 464, 631, 645, 710 and 968 of SEQ ID NO:1; (b) 475, 641, 656, 721 and 980 of SEQ ID NO:2; (c) 467, 634, 648, 713 and 972 of SEQ ID NO:3; (d) 477, 644, 659, 724 and 983 of SEQ ID NO:4; (e) 472, 640, 656, 723 and 985 of SEQ ID NO:5; and (f) 480, 648, 664, 733 and 997 of SEQ ID NO:6. The amino acid sequence includes the following residues:

(1) a Z1, Z3, Z4, or Z5 amino acid residue at position: (a) 464 of SEQ ID NO:1; (b) 475 of SEQ ID NO:2; (c) 467 of SEQ ID NO:3; (d) 477 of SEQ ID NO:4; (e) 472 of SEQ ID NO:5; and (f) 480 of SEQ ID NO:6;

(2) a Z1 amino acid residue at position: (a) 631 and 710 of SEQ ID NO1; (b) 641 and 721 of SEQ ID NO:2; (c) 634 and 713 of SEQ ID NO:3; (d) 644 and 724 of SEQ ID NO:4; (e) 640 and 723 of SEQ ID NO:5; and (f) 648 and 733 of SEQ ID NO:6;

(3) a Z3 amino acid residue at position: (a) 645 of SEQ ID NO:1; (b) 656 of SEQ ID NO:2; (c) 648 of SEQ ID NO:3; (d) 659 of SEQ ID NO:4; (e) 656 of SEQ ID NO:5; and (f) 664 of SEQ ID NO:6; and (4) a Z2 amino acid residue at position: (a) 968 of SEQ ID NO:1; (b) 980 of SEQ ID NO:2; (c) 972 of SEQ ID NO:3; (d) 983 of SEQ ID NO:4; (e) 985 of SEQ ID NO:5; and (f) 997 of SEQ ID NO:6. Z1 is an amino acid residue selected from the group consisting of glycine (G), asparagine (N), glutamine (Q), serine (S), threonine (T), tyrosine (Y), and cysteine (C); Z2 is an amino acid residue selected from the group consisting of alanine (A), valine (V), leucine (L), isoleucine (I), proline (P), and methionine (M); Z3 is an amino acid residue selected from the group consisting of lysine (K), and arginine (R); Z4 is an amino acid residue selected from the group consisting of tyrosine (Y), phenylalanine (F), tryptophan (W), and histidine (H); and is an amino acid residue selected from the group consisting of threonine (T), valine (V), and isoleucine (I).

In other embodiments, the amino acid sequence of the polypeptide includes residues at the following positions:

(1) a glycine (G), arginine (R), tyrosine (Y), or threonine (T) amino acid residue at position: (a) 464 of SEQ ID NO:1; (b) 475 of SEQ ID NO:2; (c) 467 of SEQ ID NO:3; (d) 477 of SEQ ID NO:4; (e) 472 of SEQ ID NO:5; and (f) 480 of SEQ ID NO:6;

(2) an asparagine (N) amino acid residue at position: (a) 631 of SEQ ID NO:1; (b) 641 of SEQ ID NO:2; (c) 634 of SEQ ID NO:3; (d) 644 of SEQ ID NO:4; (e) 640 of SEQ ID NO:5; and (f) 648 of SEQ ID NO:6;

(3) an arginine (R) amino acid residue at position: (a) 645 of SEQ ID NO:1; (b) 656 of SEQ ID NO:2; (c) 648 of SEQ ID NO:3; (d) 659 of SEQ ID NO:4; (e) 656 of SEQ ID NO:5; and (f) 664 of SEQ ID NO:6;

(4) a threonine (T) amino acid residue at position: (a) 710 of SEQ ID NO:1; (b) 721 of SEQ ID NO:2; (c) 713 of SEQ ID NO:3; (d) 724 of SEQ ID NO:4; (e) 723 of SEQ ID NO:5; and (f) 733 of SEQ ID NO:6; and (5) a lysine (L) amino acid residue at position: (a) 968 of SEQ ID NO:1; (b) 980 of SEQ ID NO:2; (c) 972 of SEQ ID NO:3; (d) 983 of SEQ ID NO:4; (e) 985 of SEQ ID NO:5; and (f) 997 of SEQ ID NO:6.

An isolated or recombinant polypeptide comprising residues 1 to about 455 of the amino acid sequence set forth in SEQ ID NO:1 with up to 50 conservative amino acid substitutions excluding residues 47, 52, 74, 78, 82, 94, 142, 175, 184, 188, 205, 226, 236, 252, 255, 290, 328, 353, 366 and 443 wherein the amino acid sequence comprises residues selected from the group consisting of: (a) at positions 47, 82, 142, 205, 236, 252, and 255, a Z1 amino acid residue; (b) at positions 52, 94, 175, 184, 188, 290, 353, 366 and 443, a Z2 amino acid residue; (c) at position 226, a Z3 amino acid residue; (d) at positions 78 and 328, a Z4 amino acid residue, (e) at position 74, an amino acid selected from the group consisting of alanine (A), serine (S), and glutamic acid (E); wherein Z1 is an amino acid residue selected from the group consisting of glycine (G), asparagine (N), glutamine (Q), serine (S), threonine (T), tyrosine (Y), and cysteine (C); wherein Z2 is an amino acid residue selected from the group consisting of alanine (A), valine (V), leucine (L), isoleucine (I), proline (P), and methionine (M); wherein Z3 is an amino acid residue selected from the group consisting of lysine (K), and arginine (R); and wherein Z4 is an amino acid residue selected from the group consisting of tyrosine (Y), phenylalanine (F), tryptophan (W), and histidine (H), and wherein the polypeptide catalyzes the conversion of an alkane to an alcohol.

In another embodiment, an isolated or recombinant polypeptide that includes the amino acid sequence set forth in SEQ ID NO:7 with up to 75, 50, 25, or 10 conservative amino acid substitutions excluding residues 47, 78, 82, 94, 142, 175, 184, 205, 226, 236, 252, 255, 290, 328, 353, 464, and 710, is provided. The polypeptide can display hydroxylase activity that converts an alkane to an alcohol.

In yet another embodiment, an isolated or recombinant polypeptide that includes the amino acid sequence set forth in SEQ ID NO:8 with up to 75, 50, 25, or 10 conservative amino acid substitutions excluding residues 47, 78, 82, 94, 142, 175, 184, 205, 226, 236, 252, 255, 290, 328, 353, 464, and 710, is provided.

In another embodiment, an isolated or recombinant polypeptide that includes the amino acid sequence set forth in SEQ ID NO:9 with up to 75, 50, 25, or 10 conservative amino acid substitutions excluding residues 47, 78, 82, 94, 142, 175, 184, 205, 226, 236, 252, 255, 290, 328, 353, 464, and 710, is provided.

In another embodiment, an isolated or recombinant polypeptide that includes the amino acid sequence set forth in SEQ ID NO:10 with up to 75, 50, 25, or 10 conservative amino acid substitutions excluding residues 47, 78, 82, 94, 142, 175, 184, 205, 226, 236, 252, 255, 290, 328, 353, 464, and 710, is provided.

The polypeptides of SEQ ID NO:7, 8, 9 or 10, further optionally include an arginine (R) at amino acid residue position 285.

As previously noted, polypeptides provided herein can display hydroxylase activity that converts an alkane to an alcohol. In general an alkane includes methane ($CH_4$), ethane ($C_2H_6$), propane ($C_3H_8$), butane ($C_4H_{10}$), pentane ($C_5H_{12}$), hexane ($C_6H_{14}$), heptane ($C_7H_{16}$), octane ($C_8H_{18}$), nonane ($C_8H_{20}$), decane ($C_{10}H_{22}$), undecane ($C_{11}H_{24}$), and dodecane ($C_{12}H_{26}$). In general, an alcohol includes methanol, ethanol, propanol, butanol, pentanol, hexanol, heptanol, octanol, nonanol, decanol, undecanol, and dodecanol.

In another embodiment, an isolated or recombinant polypeptide that includes the amino acid sequence set forth in SEQ ID NO:11 with up to 75, 50, 25, or 10 conservative amino acid substitutions excluding residues 47, 78, 82, 94, 142, 175, 184, 205, 226, 236, 252, 255, 285, 290, 328, 353, 464, and 710, is provided.

In another embodiment, an isolated or recombinant polypeptide that includes the amino acid sequence set forth in SEQ ID NO:12 with up to 75, 50, 25, or 10 conservative amino acid substitutions excluding residues 47, 78, 82, 94, 142, 175, 184, 205, 226, 236, 252, 255, 290, 328, 353, 464, 645, and 710, is provided.

In another embodiment, an isolated or recombinant polypeptide that includes the amino acid sequence set forth in SEQ ID NO:13 with up to 75, 50, 25, or 10 conservative amino acid substitutions excluding residues 47, 78, 82, 94, 142, 175, 184, 205, 226, 236, 252, 255, 290, 328, 353, 464, 631, and 710, is provided.

In other embodiments, isolated or recombinant polypeptides of the invention include: (a) a polypeptide comprising the amino acid sequence set forth in SEQ ID NO:7; (b) a polypeptide consisting of the amino acid sequence set forth in SEQ ID NO:7; (c) a polypeptide comprising an amino acid sequence having at least 60%, 70%, 80%, 90%, or 98% sequence identity to the amino acid sequence set forth in SEQ ID NO:7 excluding amino acid residues 47, 78, 82, 94, 142, 175, 184, 205, 226, 236, 252, 255, 290, 328, 353, 464, and 710 of SEQ ID NO:7; or (d) a polypeptide comprising an amino acid sequence that can be optimally aligned with the sequence of SEQ ID NO:7 to generate a similarity score of at least 1830, using the BLOSUM62 matrix, a gap existence penalty of 11, and a gap extension penalty of 1, excluding amino acid residues 47, 78, 82, 94, 142, 175, 184, 205, 226, 236, 252, 255, 290, 328, 353, 464, and 710 of SEQ ID NO:7.

In other embodiments, isolated or recombinant polypeptides of the invention include: (a) a polypeptide comprising the amino acid sequence set forth in SEQ ID NO:8; (b) a polypeptide consisting of the amino acid sequence set forth in SEQ ID NO:8; or (c) a polypeptide comprising an amino acid sequence having at least 60%, 70%, 80%, 90%, or 98% sequence identity to the amino acid sequence set forth in SEQ ID NO:8 excluding amino acid residues 47, 78, 82, 94, 142, 175, 184, 205, 226, 236, 252, 255, 290, 328, 353, 464, and 710 of SEQ ID NO:8.

In other embodiments, isolated or recombinant polypeptides of the invention include: (a) a polypeptide comprising the amino acid sequence set forth in SEQ ID NO:9; (b) a polypeptide consisting of the amino acid sequence set forth in SEQ ID NO:9; or (c) a polypeptide comprising an amino acid sequence having at least 60%, 70%, 80%, 90%, or 98% sequence identity to the amino acid sequence set forth in SEQ ID NO:9 excluding amino acid residues 47, 78, 82, 94, 142, 175, 184, 205, 226, 236, 252, 255, 290, 328, 353, 464, and 710 of SEQ ID NO:9.

In other embodiments, isolated or recombinant polypeptides of the invention include: (a) a polypeptide comprising the amino acid sequence set forth in SEQ ID NO:10; (b) a polypeptide consisting of the amino acid sequence set forth in SEQ ID NO:10; or (c) a polypeptide comprising an amino acid sequence having at least 60%, 70%, 80%, 90%, or 98% sequence identity to the amino acid sequence set forth in SEQ ID NO:10 excluding amino acid residues 47, 78, 82, 94, 142, 175, 184, 205, 226, 236, 252, 255, 290, 328, 353, 464, and 710 of SEQ ID NO:10.

In other embodiments, isolated or recombinant polypeptides of the invention include: (a) a polypeptide comprising the amino acid sequence set forth in SEQ ID NO:11; (b) a polypeptide consisting of the amino acid sequence set forth in SEQ ID NO:11; or (c) a polypeptide comprising an amino acid sequence having at least 60%, 70%, 80%, 90%, or 98% sequence identity to the amino acid sequence set forth in SEQ ID NO:11 excluding amino acid residues 47, 78, 82, 94, 142, 175, 184, 205, 226, 236, 252, 255, 285, 290, 328, 353, 464, and 710 of SEQ ID NO:11.

In other embodiments, isolated or recombinant polypeptides of the invention include: (a) a polypeptide comprising the amino acid sequence set forth in SEQ ID NO:12; (b) a polypeptide consisting of the amino acid sequence set forth in SEQ ID NO:12; or (c) a polypeptide comprising an amino acid sequence having at least 60%, 70%, 80%, 90%, or 98% sequence identity to the amino acid sequence set forth in SEQ ID NO:12 excluding amino acid residues 47, 78, 82, 94, 142, 175, 184, 205, 226, 236, 252, 255, 290, 328, 353, 464, 645, and 710 of SEQ ID NO:12.

In other embodiments, isolated or recombinant polypeptides of the invention include: (a) a polypeptide comprising the amino acid sequence set forth in SEQ ID NO:13; (b) a polypeptide consisting of the amino acid sequence set forth in SEQ ID NO:13; or (c) a polypeptide comprising an amino acid sequence having at least 60%, 70%, 80%, 90%, or 98% sequence identity to the amino acid sequence set forth in SEQ ID NO:13 excluding amino acid residues 47, 78, 82, 94, 142, 175, 184, 205, 226, 236, 252, 255, 290, 328, 353, 464, 631, and 710 of SEQ ID NO:13.

In other embodiments, isolated nucleic acid molecules are provided. Such nucleic acid molecules include: (a) a nucleic acid molecule which encodes a polypeptide comprising the amino acid sequence set forth in SEQ ID NO:7, 8, 9, 10, 11, 12, 13 or 125; (b) a nucleic acid molecule which encodes a polypeptide consisting of the amino acid sequence set forth in SEQ ID NO:7, 8, 9, 10, 11, 12, 13 or 125; (c) a nucleic acid molecule which encodes a polypeptide comprising residues 1 to about 455 of the amino acid sequence set forth in SEQ ID NO:7 or 11; (d) a nucleic acid molecule which encodes a polypeptide comprising residues about 456 to about 1088 of the amino acid sequence set forth in SEQ ID NO:7, 8, 9, 10, 12, 13 or 125; (e) a nucleic acid molecule comprising the nucleotide sequence set forth in SEQ ID NO:15; (f) a nucleic acid molecule consisting of the nucleotide sequence set forth in SEQ ID NO:15; (g) a nucleic acid molecule comprising the nucleotide sequence set forth in SEQ ID NO:17; (h) a nucleic acid molecule consisting of the nucleotide sequence set forth in SEQ ID NO:17.

In other embodiments, nucleic acid molecules of the invention include: (a) a nucleic acid molecule which encodes a polypeptide comprising residues 1 to about 455 of the amino acid sequence set forth in SEQ ID NO:2 or 3 with the following amino acid residues: 48 and 206 are cysteine (C); 79 and 330 are phenylalanine (F); 83, 143, and 257 are serine (S); 95 and 176 are isoleucine (I); 185, 292, and 355 are valine (V); 227 is arginine (R); 238 is glutamine (Q); and 254 is glycine (G); (b) a nucleic acid molecule which encodes a polypeptide consisting of residues 1 to about 455 of the amino acid sequence set forth in SEQ ID NO:2 or 3 with the following amino acid residues: 48 and 206 are cysteine (C); 79 and 330 are phenylalanine (F); 83, 143, and 257 are serine (S); 95 and 176 are isoleucine (I); 185, 292, and 355 are valine (V); 227 is arginine (R); 238 is glutamine (Q); and 254 is glycine (G); (c) a nucleic acid molecule which encodes a polypeptide comprising residues 1 to about 455 of the amino acid sequence set forth in SEQ ID NO:4 with the following amino acid residues: 49 and 207 are cysteine (C); 80 and 331 are phenylalanine (F); 84, 144, and 258 are serine (S); 96 and 177 are isoleucine (I); 186, 293, and 357 are valine (V); 228 is arginine (R); 239 is glutamine (Q); and 255 is glycine (G); (d) a nucleic acid molecule which encodes a polypeptide consisting of residues 1 to about 455 of the amino acid sequence set forth in SEQ ID NO:4 with the following amino acid residues: 49 and 207 are cysteine (C); 80 and 331 are phenylalanine (F); 84, 144, and 258 are serine (S); 96 and 177 are isoleucine (I); 186, 293, and 357 are valine (V); 228 is arginine (R); 239 is glutamine (Q); and 255 is glycine (G); (e) a nucleic acid molecule which encodes a polypeptide comprising residues 1 to about 455 of the amino acid sequence set forth in SEQ ID NO:5 with the following amino acid residues: 54 and 212 are cysteine (C); 85 and 336 are phenylalanine (F); 89, 149, and 262 are serine (S); 101 and 182 are isoleucine (I); 191, 297, and 361 are valine (V); 232 is arginine (R); 243 is glutamine (Q); and 259 is glycine (G); (f) a nucleic acid molecule which encodes a polypeptide consisting of residues 1 to about 455 of the amino acid sequence set forth in SEQ ID NO:5 with the following amino acid residues: 54 and 212 are cysteine (C); 85 and 336 are phenylalanine (F); 89, 149, and 262 are serine (S); 101 and 182 are isoleucine (I); 191, 297, and 361 are valine (V); 232 is arginine (R); 243 is glutamine (Q); and 259 is glycine (G); (g) a nucleic acid molecule which encodes a polypeptide comprising residues 1 to about 455 of the amino acid sequence set forth in SEQ ID NO:6 with the following amino acid residues: 51 and 208 are cysteine (C); 82 and 337 are phenylalanine (F); 86, 146, and 262 are serine (S); 98 and 179 are isoleucine (I); 188, 296, and 363 are valine (V); 231 is arginine (R); 243 is glutamine (Q); and 258 is glycine (G); and (h) a nucleic acid molecule which encodes a polypeptide consisting of residues 1 to about 455 of the amino acid sequence set forth in SEQ ID NO:6 with the following amino acid residues: 51 and 208 are cysteine (C); 82 and 337 are phenylalanine (F); 86, 146, and 262 are serine (S); 98 and 179 are isoleucine (I); 188, 296, and 363 are valine (V); 231 is arginine (R); 243 is glutamine (Q); and 258 is glycine (G).

In other embodiments, nucleic acid molecules of the invention include: (a) a nucleic acid molecule which encodes a polypeptide comprising the amino acid sequence set forth in SEQ ID NO:2 with the following amino acid residues: 48 and 206 are cysteine (C); 79 and 330 are phenylalanine (F); 83, 143, and 257 are serine (S); 95 and 176 are isoleucine (I); 185, 292, and 355 are valine (V); 227, 287, and 656 are arginine (R); 238 is glutamine (Q); 254 is glycine (G); 475 is glycine (G), arginine (R), tyrosine (Y), or threonine (T); 641 is asparagine (N); 721 is threonine (T); and 980 is leucine; (b) a nucleic acid molecule which encodes a polypeptide consisting of the amino acid sequence set forth in SEQ ID NO:2 with the following amino acid residues: 48 and 206 are cysteine (C); 79 and 330 are phenylalanine (F); 83, 143, and 257 are serine (S); 95 and 176 are isoleucine (I); 185, 292, and 355 are valine (V); 227, 287, and 656 are arginine (R); 238 is glutamine (Q); 254 is glycine (G); 475 is glycine (G), arginine (R), tyrosine (Y), or threonine (T); 641 is asparagine (N); 721 is threonine (T); and 980 is leucine; (c) a nucleic acid molecule which encodes a polypeptide comprising the amino acid sequence set forth in SEQ ID NO:3 with the following amino acid residues: 48 and 206 are cysteine (C); 79 and 330 are phenylalanine (F); 83, 143, and 257 are serine (S); 95 and 176 are isoleucine (I); 185, 292, and 355 are valine (V); 227, 287, and 648 are arginine (R); 238 is glutamine (Q); 254 is glycine (G); 467 is glycine (G), arginine (R), tyrosine (Y), or threonine (T); 634 is asparagine (N); 713 is threonine (T); and 972 is leucine; (d) a nucleic acid molecule which encodes a polypeptide consisting of the amino acid sequence set forth in SEQ ID NO:3 with the following amino acid residues: 48 and 206 are cysteine (C); 79 and 330 are phenylalanine (F); 83, 143, and 257 are serine (S); 95 and 176 are isoleucine (I); 185, 292, and 355 are valine (V); 227, 287, and 648 are arginine (R); 238 is glutamine (Q); 254 is glycine (G); 467 is glycine (G), arginine (R), tyrosine (Y), or threonine (T); 634 is asparagine (N); 713 is threonine (T); and 972 is leucine; (e) a nucleic acid molecule which encodes a polypeptide comprising the amino acid sequence set forth in SEQ ID NO:4 with the following amino acid residues: 49 and 207 are cysteine (C); 80 and 331 are phenylalanine (F); 84, 144, and 258 are serine (S); 96 and 177 are isoleucine (I); 186, 293, and 357 are valine (V); 228, 288, and 659 are arginine (R); 239 is glutamine (Q); and 255 is glycine (G); 477 is glycine (G), arginine (R), tyrosine (Y), or threonine (T); 644 is asparagine (N); 724 is threonine (T); and 983 is leucine; (f) a nucleic acid molecule which encodes a polypeptide consisting of the amino acid sequence set forth in SEQ ID NO:4 with the following amino acid residues: 49 and 207 are cysteine (C); 80 and 331 are phenylalanine (F); 84, 144, and 258 are serine (S); 96 and 177 are isoleucine (I); 186, 293, and 357 are valine (V); 228, 288, and 659 are arginine (R); 239 is glutamine (Q); and 255 is glycine (G); 477 is glycine (G), arginine (R), tyrosine (Y), or threonine (T); 644 is asparagine (N); 724 is threonine (T); and 983 is leucine; (g) a nucleic acid molecule which encodes a polypeptide comprising the amino acid sequence set forth in SEQ ID NO:5 with the following amino acid residues: 54 and 212 are cysteine (C); 85 and 336 are phenylalanine (F); 89, 149, and 262 are serine (S); 101 and 182 are isoleucine (I); 191, 297, and 361 are valine (V); 232, 292, and 656 are arginine (R); 243 is glutamine (Q); and 259 is glycine (G); 472 is glycine (G), arginine (R), tyrosine (Y), or threonine (T); 640 is asparagine (N); 723 is threonine (T); and 985 is leucine; (h) a nucleic acid molecule which encodes a polypeptide consisting of the amino acid sequence set forth in SEQ ID NO:5 with the following amino acid residues: 54 and 212 are cysteine (C); 85 and 336 are phenylalanine (F); 89, 149, and 262 are serine (S); 101 and 182 are isoleucine (I); 191, 297, and 361 are valine (V); 232, 292, and 656 are arginine (R); 243 is glutamine (Q); and 259 is glycine (G); 472 is glycine (G), arginine (R), tyrosine (Y), or threonine (T); 640 is asparagine (N); 723 is threonine (T); and 985 is leucine; (i) a nucleic acid molecule which encodes a polypeptide comprising the amino acid sequence set forth in SEQ ID NO:6 with the following amino acid residues: 51 and 208 are cysteine (C); 82 and 337 are phenylalanine (F); 86, 146, and 262 are serine (S); 98 and 179 are isoleucine (I); 188, 296, and 363 are valine (V); 231, 291, and 664 are arginine (R); 243 is glutamine (Q); and 258 is glycine (G); 480 is glycine (G), arginine (R), tyrosine (Y), or threonine (T); 648 is asparagine (N); 733 is threonine (T); and 997 is leucine; and (j) a nucleic acid molecule which encodes a polypeptide consisting of the amino acid sequence set forth in SEQ ID NO:6 with the following amino acid residues: 51 and 208 are cysteine (C); 82 and 337 are phenylalanine (F); 86, 146, and 262 are serine (S); 98 and 179 are isoleucine (I); 188, 296, and 363 are valine (V); 231, 291, and 664 are arginine (R); 243 is glutamine (Q); and 258 is glycine (G); 480 is glycine (G), arginine (R), tyrosine (Y), or threonine (T); 648 is asparagine (N); 733 is threonine (T); and 997 is leucine.

In one embodiment, an isolated nucleic acid molecule that includes a nucleic acid molecule of the invention and a nucleotide sequence encoding a heterologous polypeptide, is provided.

In other embodiments, vectors that include a nucleic acid molecule of the invention are provided.

In other embodiments, host cells transfected with a nucleic acid molecule of the invention, or a vector that includes a nucleic acid molecule of the invention, are provided. Host cells include eucaryotic cells such as yeast cells, insect cells, or animal cells. Host cells also include procaryotic cells such as bacterial cells.

In other embodiments, methods for producing a cell that converts an alkane to alcohol, are provided. Such methods generally include: (a) transforming a cell with an isolated nucleic acid molecule encoding a polypeptide that includes an amino acid sequence set forth in SEQ ID NO: 7, 8, 9, 10, 11, 12, 13 or 125; (b) transforming a cell with an isolated nucleic acid molecule encoding a polypeptide of the invention; or (c) transforming a cell with an isolated nucleic acid molecule of the invention.

In other embodiments, methods for selecting a cell that converts an alkane to an alcohol, are provided. The methods generally include: (a) providing a cell containing a nucleic acid construct that includes a nucleotide sequence that encodes a modified cytochrome P450 polypeptide, the nucleotide sequence selected from: (i) a nucleic acid molecule encoding a polypeptide comprising an amino acid sequence set forth in SEQ ID NO: 7, 8, 9, 10, 11, 12, 13 or 125; (ii) a nucleic acid molecule encoding a polypeptide of the invention; or (iii) a nucleic acid molecule of the invention. The methods further include (b) culturing the cell in the presence of a suitable alkane and under conditions where the modified cytochrome P450 is expressed at a level sufficient to convert an alkane to an alcohol. Such conditions are met when an alcohol is produced at a level detectable by a method provided herein, or a method known to one skilled in the art of enzymology.

In other embodiments, methods for producing an alcohol, are provided. The methods include: (a) providing a cell containing a nucleic acid construct comprising a nucleotide sequence that encodes a modified cytochrome P450 polypeptide, the nucleotide sequence selected from: (i) a nucleic acid molecule encoding a polypeptide comprising an amino acid sequence set forth in SEQ ID NO: 7, 8, 9, 10, 11, 12, 13 or 125; (ii) a nucleic acid molecule encoding a polypeptide of the invention; or (iii) a nucleic acid molecule of the invention. The methods further include (b) culturing the cell in the presence of a suitable alkane and under conditions where the modified cytochrome P450 is expressed at an effective level; and (c) producing an alcohol by hydroxylation of the suitable alkane such as methane ($CH_4$), ethane ($C_2H_6$), propane ($C_3H_8$), butane ($C_4H_{10}$), pentane ($C_5H_{12}$), hexane ($C_6H_{14}$), heptane ($C_8H_{16}$), octane ($C_8H_{18}$), nonane ($C_8H_{20}$), decane ($C_{10}H_{22}$), undecane ($C_{11}H_{24}$), and dodecane ($C_{12}H_{26}$). In general an alcohol produced by a method the invention can include methanol, ethanol, propanol, butanol, pentanol, hexanol, heptanol, octanol, nonanol, decanol, undecanol, and dodecanol.

In yet another embodiment, methods for producing a cytochrome P450 variant that hydroxylates an alkane are provided. Such methods include selecting a parent cytochrome P450 polypeptide and modifying at least one amino acid residue positioned in or near the active site of the heme domain of the parent cytochrome P450 polypeptide. In general the modification reduces the volume of the active site. The method further includes contacting the polypeptide comprising the modified amino acid with at least one alkane under conditions suitable for hydroxylation of the alkane and detecting a hydroxylated alkane. The modification may include a substitution of the parent amino acid for a different amino acid or it may include modifying the parent amino acid to include an additional group. If the modification is a substitution, such substitutions can include a phenylalanine, tyrosine, histidine, or serine for the parent amino acid residue positioned in or near the active site of the heme domain of the parent cytochrome P450 polypeptide.

The details of one or more embodiments of the disclosure are set forth in the accompanying drawings and the description below. Other features, objects, and advantages will be apparent from the description and drawings, and from the claims.

BRIEF DESCRIPTION OF DRAWINGS

FIG. 5 depicts an absorption spectrum of 53-5H. The ferric heme iron is in low-spin form. A shift to high-spin ferric iron upon addition of ethane could not be detected. Addition of octane did not induce an increase at 390 nm. The spectrum of 35-E11 is substantially similar.

FIGS. 6A-6F depict an amino acid sequence alignment of 6 CYP102 homologs and BM-3 mutant 35-E11. Corresponding mutations in homologs are provided in Table 4.

FIG. 8 depicts SEQ ID NO: 1 (CYP102A1 from *Bacillus megaterium*).

FIG. 9 depicts SEQ ID NO: 2 (CYP102A2 from *Bacillus subtilis*, 59% identity to CYP102A1).

FIG. 10 depicts SEQ ID NO: 3 (CYP102A3 from *Bacillus subtilis*, 58% identity to CYP102A1).

FIG. 11 depicts SEQ ID NO: 4 (CYP102A5 from *Bacillus cereus*, 60% identity to CYP102A1).

FIG. 12 depicts SEQ ID NO: 5 (CYP102E1 from *Ralstonia metallidurans*, 38% identity to CYP102A1).

FIG. 13 depicts SEQ ID NO: 6 (CYP102A6 from *Bradyrhizobium japonicum*, 46% identity to CYP102A1).

FIG. 14 depicts SEQ ID NO: 7 (35-E11).

FIG. 15 depicts SEQ ID NO: 8 (35-E11-E464R).

FIG. 16 depicts SEQ ID NO: 9 (35-E11-E464Y).

FIG. 17 depicts SEQ ID NO: 10 (35-E11-E464T).

FIG. 18 depicts SEQ ID NO: 11 (20-D3).

FIG. 19 depicts SEQ ID NO: 12 (23-1D).

FIG. 20A-B depicts SEQ ID NO: 13 (21-4G) and 125 ($P450_{PMO}$).

FIG. 21 depicts SEQ ID NO: 15 (53-5H).

FIGS. 22A and 22B depict SEQ ID NO: 16 (expression plasmid pCWORI-53-H containing the heme and reductase domain of variant 53-5H).

FIG. 23 depicts SEQ ID NO: 17 (nucleic acid sequence encoding variant 35-E11).

FIGS. 24A and 24B depict SEQ ID NO: 18 (expression plasmid pCWORI-35-E11 containing heme and reductase domain of variant 35-E11).

FIG. 25A-C depicts alkyl methyl ether assays. (A) shows hydroxylation of the propane surrogate dimethyl ether produces formaldehyde which can easily be detected using the dye Purpald. (B) shows hexyl methyl ether can be used as an octane surrogate. (C) shows a typical screening plate with P450-containing cell lysate, which, upon hydroxylation of the methoxy group of DME or HME and addition of Purpald, forms a purple color. Each well represents a different BM-3 variant.

FIG. 26 depicts standard curves for formaldehyde (■) and hexanal (♦) using Purpald. The assay was performed in a 96-well microtiter plate and the final volume was 250 µL per well.

FIG. 27A-B depicts a colorimetric reaction after addition of Purpald to reaction mixtures containing BM-3 mutants, chloromethane and cofactor regeneration system. (A) and (B) refer to independent experiments.

FIG. 28 depicts total turnover numbers for the reaction of CM dehalogenation catalyzed by BM-3 mutants.

FIGS. 31A-31C depict an amino acid sequence alignment of the heme domain (residues 1-455) of 6 CYP102 homologs and BM-3 mutant 35-E11. Corresponding mutations in homologs are provided in Table 4.

FIG. 32A-B depicts protein similarity scores for polypeptides provided herein. (A) shows exemplary similarity scores for full length polypeptides (e.g., SEQ ID NOs: 1-7). (B) shows exemplary similarity scores for residues 1-455 of SEQ ID NOs: 1-7 corresponding to the heme domain of P450 polypeptides.

FIG. 33A-B depicts protein percent (%) identities for polypeptides provided herein. (A) shows exemplary percent (%) identities for full length polypeptides (e.g., SEQ ID NOs: 1-7). (B) shows exemplary percent (%) identities for residues 1-455 of SEQ ID NOs: 1-7 corresponding to the heme domain of P450 polypeptides.

FIG. 34A-B shows $P450_{BM3}$ and naturally-occurring non-heme gaseous alkane monooxygenases. (A) $P450_{BM3}$ (from *Bacillus megaterium*) catalyzes sub-terminal hydroxylation of long-chain fatty acids and propane monooxygenase from *Gordonia* sp. TY-5 catalyzes hydroxylation of propane to 2-propanol. $P450_{BM3}$ has no measurable activity on propane, while TY-5 PMO specificity is restricted to propane. (B) Structures of $P450_{BM3}$ and soluble gaseous alkane monooxygenase (represented by the soluble methane monoxygenase, sMMO) redox systems. Single-component $P450_{BM3}$ (119 kDa) consists of three functional sub-domains, heme-, FMN-, and FAD-binding domain (modeled on rat CPR structure). sMMO (and presumably other bacterial multi-component monooxygenases including PMO and BMO) comprises a 250 kDa $\alpha_2\beta_2\gamma_2$ hydroxylase, a 15 kDa cofactorless effector protein, and a 40 kDa [2Fe-2S]- and FAD-containing reductase.

FIG. 35A-C depicts directed evolution of $P450_{PMO}$ from wild-type $P450_{BM3}$. (A) Protein engineering steps and selected variants from each round. (B) Map of mutated residues (sphere models) on $P450_{BM3}$ heme domain crystal structure (PDB entry 1FAG). L188 (mutated to proline in ETS8→19A12 transition) is shown. Heme (sphere models) is shown while bound palmitate (stick model) is shown. (C) shows domain-based engineering strategy. The heme-, FMN- and FAD-binding domains of $P450_{BM3}$ variant 35E11 were independently evolved preparing separate mutagenesis libraries of each region. The heme domain was optimized for propane activity over several rounds of directed evolution. Upon screening of 35E11 reductase domain libraries, sites important for activity were identified and further optimized using the heme domain of 11-3. $P450_{PMO}$ was obtained by recombination of the most beneficial reductase domain mutations obtained from these libraries using the heme domain of 7-7.

FIG. 37A-F shows the functional and stability properties of variants on the lineage from $P450_{BM3}$ to $P450_{PMO}$. (A) Total turnover numbers for propane hydroxylation (mol propanol/mol P450). (B) Coupling efficiency as given by propanol formation rate/NADPH oxidation rate. (C) $K_m$ values for propanol formation. (D) Catalytic rate constants ($k_{cat}$) for propanol formation. (E) Enzyme thermostability, reported as $T_{50}$ values from heat inactivation of heme domain. (F) Stability penalty for each round of directed evolution, normalized by the number of mutations accumulated in each round.

FIG. 38 depicts re-specialization of $P450_{BM3}$ for activity on propane. Activities of the engineered variants on $C_2$ to $C_{10}$ alkanes, reported relative to activity on the substrate preferred by each variant (=100%). The dashed line indicates the profile of the preceding variant to highlight the change in substrate specificity in each directed evolution step.

FIG. 40A-B (A) Comparison between catalytic rate of $P450_{PMO}$ on propane and those of naturally-occurring alkane monooxygenases (pMMO, sMMO, BMO, AlkB, cyp153 (A6)) on their preferred substrates. (B) Reported substrate specificity profiles of pMMO (based on in vitro activity), PMO from *Gordonia* sp. TY-5 (based on growth rate), BMO from *Nocardioides* sp. CF8 (based on growth rate), and cyp153(A6) from *Mycobacterium* sp. HXN-1500 (based on in vitro activity).

FIG. 41A-B shows C—H bond dissociation energy (A) and molecular size (B) of $C_1$-$C_3$ alkanes and halogenated methane derivatives. Experimental C—H BDE values are derived from Cherkasov et al.

FIG. 43A-C shows convergent evolution in propane hydroxylation and emergence of new functions. (A) $k_{cat}$ values for alkanes as measured from Michaelis-Menten plots. (B) Overlap of substrate range of the evolving $P450_{BM3}$ with those of naturally-occurring non-heme oxygenases (AlkB: integral membrane alkane hydroxylase). $P450_{PMO}$ has re-specialized for propane hydroxylation with complete loss of the original activity on fatty acids (AA: arachidonic acid, PA: palmitic acid, MPA: 13-methyl-PA). Overall, 34 mutational events separate $P450_{PMO}$ and $P450_{BM3}$ leading to 23 amino acid differences. (C) Halomethane dehalogenase activity of $P450_{PMO}$ and its precursors, as measured by the rate of formaldehyde formation.

Like reference symbols in the various drawings indicate like elements.

DETAILED DESCRIPTION

Figure 1:
FIG. 1 depicts the reduction of substrate size and increase in C—H bond dissociation energy achieved by directed evolution. Directed evolution was used to convert wild-type P450 BM-3 stepwise from a fatty acid hydroxylase into an enzyme capable of activating the higher-energy C—H bond of ethane. The figure shows the substrate range of wild-type P450 BM-3 and its mutant 53-5H and, for comparison, the range of substrates of other alkane monooxygenases.

Before describing the invention in detail, it is to be understood that this invention is not limited to particular compositions or biological systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. Unless defined otherwise, all technical and scientific terms used herein have the same meaning as commonly understood by one of ordinary skill in the art to which the invention pertains. Although any methods and materials similar or equivalent to those described herein can be used in the practice for testing of the invention(s), specific examples of appropriate materials and methods are described herein.

World reserves of methane in natural gas are more abundant than oil. Methane in methane hydrates increases this by orders of magnitude. Methane is also emitted from coal beds and renewably produced by the anaerobic decomposition of organic matter in landfills and human and animal waste streams. Most of these sources, deemed "stranded" by the energy industries, are not used because they are either too remote to transport the gas to a power generating facility or too small to economically convert with existing technology into the more easily transported methanol. A practical catalyst for the conversion of methane to methanol could allow these sources of methane gas to be converted into easily transported liquid fuel. Accessing these reserves with a new technology will have a dramatic effect on both the energy and chemical commodity industries.

The wide scale production of methanol from these sources would also have a favorable impact on the concentration of greenhouse gases in the atmosphere. Methane has a 20 fold higher global warming potential than carbon dioxide. Human activities release about 300 MMT/year of methane into the atmosphere, accounting for about a quarter of the measured increase in global temperatures. Conversion of this wasted methane into methanol could have a dramatic effect on the concentrations of global warming gases in the atmosphere, since in addition to removing methane from the atmosphere by this process, the methanol when burned as a fuel releases less (~½) carbon dioxide than is released by burning an equivalent amount of gasoline. Converting methane released into the environment from human activities into a usable alternative fuel is therefore one of the most effective means of curbing global warming.

The engineered cytochromes P450 mutants described throughout the present disclosure were acquired by accumulating point mutations in directed evolution experiments. An alternative method for making libraries for directed evolution to obtain P450s with new or altered properties is recombination, or chimeragenesis, in which portions of homologous P450s are swapped to form functional chimeras. Recombining equivalent segments of homologous proteins generates variants in which every amino acid substitution has already proven to be successful in one of the parents. Therefore, the amino acid mutations made in this way are less disruptive, on average, than random mutations. A structure-based algorithm, such as SCHEMA, identifies fragments of proteins that can be recombined to minimize disruptive interactions that would prevent the protein from folding into its active form. SCHEMA has been used to design chimeras of P450 BM-3 and its homolog CYP102A2, sharing 63% amino acid sequence identity. Fourteen of the seventeen constructed hybrid proteins were able to fold correctly and incorporate the heme cofactor, as determined by CO difference spectra. Half of the chimeras had altered substrate specificities, while three mutants acquired activities towards a new substrate not hydroxylated by either parent. A large library of chimeras made by SCHEMA-guided recombination of BM-3 with its homologs CYP102A2 and CYP102A3 contains more than 3000 new properly folded variants of BM-3. In addition to creating new biocatalysts, these chimeragenesis studies demonstrate that the homologous P450 enzymes CYP102A2 and CYP102A3 are similar enough to BM-3 to recombine in this fashion and still retain a high probability of folding.

Provided herein are variants of cytochrome P450 BM-3 that catalyze the direct conversion of methane to methanol. The reaction uses dioxygen from the air and the reduced form of the biological cofactor nicotinamide adenine dinucleotide phosphate (NADPH). The stoichiometry of the reactions catalyzed by the BM-3 variant is $CH_4+O_2+NADPH+H^+\rightarrow CH_3OH+H_2O+NADP^+$.

The term "total turnover number" (TTN) is the total number of substrate molecules converted to product (or turned over) by a single enzyme over its lifetime or during a specified time period. TTN is an important figure of merit for a catalyst because it allows for the calculation of the total amount of product that can be made from a given quantity of catalyst. The term "coupling" means the ratio, in percent, of product formed to cofactor (NAD(P)H) consumed during the enzyme-catalyzed reaction. If 2 moles of cofactor are consumed for every mole of product made, then the coupling for the reaction is 50%. Coupling is also an important figure of merit because it allows one to assess how much cofactor is required to produce a given amount of product.

The BM-3-based catalyst functions at ambient temperature and pressure. Unlike methane monooxygenase enzymes, this BM-3 based biocatalyst can be expressed in host organisms that do not consume the methanol as it is produced. Thus it may be incorporated into a whole-cell biocatalysis system that can accumulate methanol in the presence of methane and air.

Cytochrome P450 enzymes (P450s) are exceptional oxidizing catalysts, effecting highly selective transformations that are sometimes impossible to achieve by chemical methods under similarly mild conditions. These versatile enzymes have enormous potential for applications in drug discovery, chemical synthesis, bioremediation, and biotechnology. However, tailoring P450s to accept nonnatural substrates, as required by many applications, is exceptionally difficult in this complex catalytic system, which involves multiple cofactors, substrates and protein domains. Compared to their natural counterparts, engineered P450s exhibit poor catalytic and coupling efficiencies; obtaining native-like proficiencies is a mandatory first step towards utilizing the catalytic power of these versatile oxygenases in chemical synthesis.

The P450 catalytic cycle is initiated by a substrate binding event that is accompanied by large conformational changes and a shift in the heme redox potential. This induces electron transfer from the NAD(P)H cofactor to the heme, resulting in the formation of the highly reactive iron-oxo species that activates the substrate. Mechanisms controlling efficient catalysis are disrupted when P450s bind nonnative substrates or when amino acid substitutions are made, both of which result in uncoupling of cofactor utilization and product formation and rapid enzyme inactivation due to the formation of reactive oxygen species.

P450s insert oxygen into a broad range of compounds. No P450, however, is known to have specialized in reactions on small alkanes. Gaseous alkanes (methane, propane, butane) and halomethanes ($CH_3Cl$, $CH_3Br$) serve as sole carbon and energy sources for numerous aerobic microorganisms, where the first oxidative step is catalyzed by non-heme methane, propane and butane monooxygenases (MMO, PMO, BMO).

Accordingly, the term "hydroxylase" or "monooxygenase" should be considered to include any enzyme that can insert one oxygen atom from diatomic oxygen into a substrate.

Exemplary enzymes include the cytochrome P450 monooxygenases. "Cytochrome P450 monooxygenase" or "P450 enzyme" means an enzyme in the superfamily of P450 heme-thiolate proteins, which are widely distributed in bacteria, fungi, plants and animals. The unique feature which defines whether an enzyme is a cytochrome P450 enzyme is traditionally considered to be the characteristic absorption maximum ("Soret band") near 450 nm observed upon binding of carbon monoxide (CO) to the reduced form of the heme iron of the enzyme. Reactions catalyzed by cytochrome P450 enzymes include epoxidation, N-dealkylation, O-dealkylation, S-oxidation and hydroxylation. The most common reaction catalyzed by P450 enzymes is the monooxygenase reaction, i.e., insertion of one atom of oxygen into a substrate while the other oxygen atom is reduced to water.

The term "substrate" or "suitable substrate" means any substance or compound that is converted or meant to be converted into another compound by the action of an enzyme catalyst. The term includes alkanes, and includes not only a single compound, but also combinations of compounds, such as solutions, mixtures and other materials which contain at least one substrate. Substrates for hydroxylation using the cytochrome P450 enzymes of the invention include para-nitrophenoxycarboxylic acids ("pNCAs") such as 12-pNCA, as well as decanoic acid, myristic acid, lauric acid, and other fatty acids and fatty acid-derivatives. For alkane/alkene-substrates, propane, propene, ethane, ethene, butane, butene, pentane, pentene, hexane, hexene, cyclohexane, octane, octene, styrene, p-nitrophenoxyoctane (8-pnpane), and various derivatives thereof, can be used. The term "derivative" refers to the addition of one or more functional groups to a substrate, including, but not limited, alcohols, amines, halogens, thiols, amides, carboxylates, etc.

As will be described in more detail below, the invention is based, at least in part, on the generation and expression of novel enzymes that catalyze the hydroxylation of alkanes to alcohols. In one embodiment, novel polypeptides that have been engineered to convert an alkane to an alcohol are provided. Such polypeptides include P450 variants that have been altered to include amino acid substitutions at specified residues.

While these variants will be described in more detail below, it is understood that polypeptides of the invention may contain one or more modified amino acids. The presence of modified amino acids may be advantageous in, for example, (a) increasing polypeptide in vivo half-life, (b) reducing or increasing polypeptide antigenicity, and (c) increasing polypeptide storage stability. Amino acid(s) are modified, for example, co-translationally or post-translationally during recombinant production (e.g., N-linked glycosylation at N-X-S/T motifs during expression in mammalian cells) or modified by synthetic means. Accordingly, A "mutant", "variant" or "modified" protein, enzyme, polynucleotide, gene, or cell, means a protein, enzyme, polynucleotide, gene, or cell, that has been altered or derived, or is in some way different or changed, from a parent protein, enzyme, polynucleotide, gene, or cell. A mutant or modified protein or enzyme is usually, although not necessarily, expressed from a mutant polynucleotide or gene.

A "parent" protein, enzyme, polynucleotide, gene, or cell, is any protein, enzyme, polynucleotide, gene, or cell, from which any other protein, enzyme, polynucleotide, gene, or cell, is derived or made, using any methods, tools or techniques, and whether or not the parent is itself native or mutant. A parent polynucleotide or gene encodes for a parent protein or enzyme.

The disclosure demonstrates, for example, that directed evolution converted a long-chain fatty acid P450 hydroxylase into a proficient propane hydroxylase. To achieve high activity and catalytic efficiency on this small alkane, the active site was progressively optimized in the evolving P450, as judged by narrowing of the substrate range and decreasing $K_m$. This is consistent with the sequence of mutational events leading to $P450_{PMO}$, which indicate a continuous re-arrangement of active site residues in the search of a configuration optimal for the new substrate. For example, the evolution of $P450_{BM3}$ into $P450_{PMO}$ shows that a specialized member of the P450 enzyme family can evolve by point mutations and selection for function on progressively different substrates to a new, re-specialized function. Particularly noteworthy is that the native enzymatic function eventually disappeared solely under the pressure of positive selection for the new function; no negative selection was needed. The disclosure provides an engineered P450, $P450_{PMO}$, comprising a catalytic rate and specificity comparable to natural alkane monooxygenases (FIG. 40).

A "mutation" means any process or mechanism resulting in a mutant protein, enzyme, polynucleotide, gene, or cell. This includes any mutation in which a protein, enzyme, polynucleotide, or gene sequence is altered, and any detectable change in a cell arising from such a mutation. Typically, a mutation occurs in a polynucleotide or gene sequence, by point mutations, deletions, or insertions of single or multiple nucleotide residues. A mutation includes polynucleotide alterations arising within a protein-encoding region of a gene as well as alterations in regions outside of a protein-encoding sequence, such as, but not limited to, regulatory or promoter sequences. A mutation in a gene can be "silent", i.e., not reflected in an amino acid alteration upon expression, leading to a "sequence-conservative" variant of the gene. This generally arises when one amino acid corresponds to more than one codon.

Non-limiting examples of a modified amino acid include a glycosylated amino acid, a sulfated amino acid, a prenlyated (e.g., farnesylated, geranylgeranylated) amino acid, an acetylated amino acid, an acylated amino acid, a pegylated amino acid, a biotinylated amino acid, a carboxylated amino acid, a phosphorylated amino acid, and the like. References adequate to guide one of skill in the modification of amino acids are replete throughout the literature. Example protocols are found in Walker (1998) Protein Protocols on CD-ROM (Humana Press, Towata, N.J.).

Recombinant methods for producing and isolating modified P450 polypeptides of the invention are described herein. In addition to recombinant production, the polypeptides may be produced by direct peptide synthesis using solid-phase techniques (e.g., Stewart et al. (1969) Solid-Phase Peptide Synthesis (WH Freeman Co, San Francisco); and Merrifield (1963) J. Am. Chem. Soc. 85: 2149-2154; each of which is incorporated by reference). Peptide synthesis may be performed using manual techniques or by automation. Automated synthesis may be achieved, for example, using Applied Biosystems 431A Peptide Synthesizer (Perkin Elmer, Foster City, Calif.) in accordance with the instructions provided by the manufacturer.

"Cytochrome P450 monooxygenase" or "P450 enzyme" means an enzyme in the superfamily of P450 haem-thiolate proteins, which are widely distributed in bacteria, fungi, plants and animals. The enzymes are involved in metabolism of a plethora of both exogenous and endogenous compounds. Usually, P450 enzymes act as terminal oxidases in multicomponent electron transfer chains, i.e., P450-containing monooxygenase systems. The unique feature which defines whether an enzyme is a cytochrome P450 enzyme is traditionally considered to be the characteristic absorption maximum ("Soret band") near 450 nm observed upon binding of carbon monoxide (CO) to the reduced form of the heme iron of the enzyme. Reactions catalyzed by cytochrome P450 enzymes include epoxidation, N-dealkylation, 0-dealkylation, S-oxidation and hydroxylation. The most common reaction catalyzed by P450 enzymes is the monooxygenase reaction, i.e., insertion of one atom of oxygen into a substrate while the other oxygen atom is reduced to water.

"Heme domain" refers to an amino acid sequence within an oxygen carrier protein, which sequence is capable of binding an iron-complexing structure such as a porphyrin. Compounds of iron are typically complexed in a porphyrin (tetrapyrrole) ring that may differ in side chain composition. Heme groups can be the prosthetic groups of cytochromes and are found in most oxygen carrier proteins. Exemplary heme domains include that of P450 BM-3 ($P450_{BM}$-P), SEQ ID NO:3, as well as truncated or mutated versions that retain the capability to bind the iron-complexing structure. The skilled artisan can readily identify the heme domain of a specific protein using methods known in the art.

As noted above, polypeptides provided herein generally include a "heme domain" which includes amino acid residues 1 to about 455 of the various P450 sequences provided in, for example, SEQ ID NO:1 through SEQ ID NO:13 and SEQ ID NO:125. As used herein, the term "heme domain" refers to a catalytically functional region of the polypeptide that exhibits monooxygenase/hydroxylase activity. A heme domain is a redox domain capable of binding an iron-complexing structure such as a porphyrin. Compounds of iron are typically complexed in a porphyrin (tetrapyrrole) ring that may differ in side chain composition. Heme groups can be the prosthetic groups of cytochromes and are found in most oxygen carrier proteins. Exemplary heme domains include that of P450 BM-3 (e.g., amino acid residues 1 to about 455 of SEQ ID NO:1), as well as truncated or mutated versions of these that retain the capability to bind the iron-complexing structure. The skilled artisan can readily identify the heme domain of a specific protein using methods known in the art. Accordingly, the skilled artisan will recognize that amino acid residues 1 to "about" or "approximately" 430 means within an acceptable error range for the particular value as determined by one of ordinary skill in the art, which will depend in part on how the value is measured or determined, i.e., the limitations of the measurement system. For example, "about" can mean a range of up to 20%, up to 10%, up to 5%, up to 1% of a given value, such as the number of amino acid residues in a heme domain or a reductase domain.

A "protein" or "polypeptide", which terms are used interchangeably herein, comprises one or more chains of chemical building blocks called amino acids that are linked together by chemical bonds called peptide bonds. An "enzyme" means any substance, composed wholly or largely of protein, that catalyzes or promotes, more or less specifically, one or more chemical or biochemical reactions. The term "enzyme" can also refer to a catalytic polynucleotide (e.g., RNA or DNA). A "native" or "wild-type" protein, enzyme, polynucleotide, gene, or cell, means a protein, enzyme, polynucleotide, gene, or cell that occurs in nature.

Referring to the sequence comparison of various cytochromes P450 in FIG. 6A-6F, SEQ ID NO:1 includes the amino acid sequence of cytochrome P450 BM-3 isolated from *Bacillus megaterium*. This wild-type P450 BM-3 is also designated CYP102A1. SEQ ID NO:2 provides the amino acid sequence of wild-type cytochrome P450 from *Bacillus subtilis* strain 1A1.15. This wild-type P450 is designated CYP102A2 and shares 59% amino acid sequence identity to CYP102A1 (SEQ ID NO:1). SEQ ID NO:3 includes the amino acid sequence of wild-type cytochrome P450 from *Bacillus subtilis* strain 1A1.15). This wild-type P450 is designated CYP102A3 and shares 58% amino acid sequence identity to CYP102A1 (SEQ ID NO:1). SEQ ID NO:4 includes the amino acid sequence of wild-type cytochrome P450 from *Bacillus cereus*. This wild-type P450 is also designated CYP102A5 and shares 60% amino acid sequence identity to CYP102A1 (SEQ ID NO:1). SEQ ID NO:5 includes the amino acid sequence of wild-type cytochrome P450 from *Ralstonia metallidurans*. This wild-type P450 is designated CYP102E1 and shares 38% amino acid identity to CYP102A1 (SEQ ID NO:1). SEQ ID NO:6 includes the amino acid sequence of wild-type cytochrome P450 from *Bradyrhizobium japonicum*. This wild-type P450 is also designated CYP102A6 and shares 38% amino acid sequence identity to CYP102A1 (SEQ ID NO:1).

The cytochromes P450 set forth in SEQ ID NOs:1-6 are closely related to one another and show a high degree of sequence identity. The sequences can be aligned based on the sequence homology. The alignment provided in FIG. 6A-6F identifies "equivalent positions" in the sequences. An equivalent position denotes a position which, on the basis of the alignment of the sequence of the parent cytochrome P450 in question with the "reference" cytochrome P450 amino acid sequence in question (e.g. SEQ ID NO: 1) so as to achieve juxtapositioning of amino acid residues which are common to both, corresponds most closely to a particular position in the reference sequence in question. This process can cause gaps or insertions to appear in the sequences. In the alignment of FIGS. 6A-6F or FIGS. 31A-31C, equivalent positions are shown lined up vertically with one another. For example, position 87 in SEQ ID NO: 1 is equivalent to position 88 in SEQ ID NO: 2 and 3 and position 89 in SEQ ID NO: 4. As shown in FIG. 6A-6F and more particularly in FIGS. 31A-31C, the identity in the heme domain is often higher than reported because of large differences in the linker region (~residue 470) between the heme and reductase domains (see Gonindaraj & Poulos, J. Biol. Chem. 272:7915).

Provided herein are novel modified cytochrome P450 enzymes capable of hydroxylating various alkanes to alcohols (e.g., methane to produce methanol). Because the heme domain is capable of this reaction, protein engineering of cytochrome P450s from other sources can be expected to lead to a similar result. It is well known in the art that amino acid substitutions having a particular effect (e.g. that confer activity towards a new substrate) can have the same effect in closely related proteins. For example, the alignment of these four homologs and 35-E11 shown in FIGS. 6A-6F illustrate the high degree of sequence similarity among the four cytochromes P450, particularly in the heme domain. It has been shown on multiple occasions that amino acid substitutions at equivalent positions in these enzymes have equivalent effects on function. For example, the substitution of F87 by A in CYP102A1 increases the peroxygenase activity of the enzyme. The same substitution of the equivalent position in CYP102A2 and CYP102A3, which is F88A, has the same effect: it increases the peroxygenase.31 Appel et al. showed that the substitutions A74G, F87A and L188Q in CYP102A1 together broaden the enzyme's substrate range, so that it hydroxylates octane and naphthalene. Lentz et al. demonstrated that substituting the equivalent positions in CYP102A3 (no substitution was required at A74G because there was a G at this position already), F88 to V and S188 to Q, had a similar effect of conferring the ability to hydroxylate octane and naphthalene. Thus on the basis of this experience, it is reasonable to assume that substitutions equivalent to those described here in CYP102A2 as conferring methane hydroxylation activity will have the same effect in CYP102A2, CYP102A3 as well as other cytochromes P450 that show high identity (55% or greater) to CYP102A such as the one from *B. cereus*. Additionally, these P450 enzymes can be subjected to rounds of directed evolution using the techniques and screens described herein to obtain and/or increase methane hydroxylation activity. Less closely-related cytochromes P450 with similar domain architecture to BM-3 have also been reported in the literature, including P450s from the unrelated β-proteobacterium *Ralstonia metallidurans* (CYP102E1) and the gram negative bacterium *Bradyrhizobium japonicum* (CYP102A6), and could potentially be similarly engineered for methane oxidation (see FIGS. 6A-6F and Table 4 for corresponding mutations in these two P450s).

Accordingly, in various embodiments, isolated or recombinant polypeptides comprising residues 1 to about 455 of the amino acid sequence set forth in SEQ ID NO:1, 2, 3, 4, 5 or 6, are provided. The polypeptides include up to 50, 25, 10, or 5 conservative amino acid substitutions excluding residues: (a) 47, 78, 82, 94, 142, 175, 184, 205, 226, 236, 252, 255, 290, 328, and 353 of SEQ ID NO:1; (b) 48, 79, 83, 95, 143, 176, 185, 206, 227, 238, 254, 257, 292, 330, and 355 of SEQ ID NO:2 or SEQ ID NO:3; (c) 49, 80, 84, 96, 144, 177, 186, 207, 228, 239, 255, 258, 293, 331, and 357 of SEQ ID NO:4; (d) 54, 85, 89, 101, 149, 182, 191, 212, 232, 243, 259, 262, 297, 336, and 361 of SEQ ID NO:5; and (e) 51, 82, 86, 98, 146, 179, 188, 208, 231, 242, 258, 262, 296, 337, and 363 of SEQ ID NO:6. The amino acid sequence includes the following residues at the following positions:

(1) a Z1 amino acid residue at positions: (a) 47, 82, 142, 205, 236, 252, and 255 of SEQ ID NO:1; (b) 48, 83, 143, 206, 238, 254, and 257 of SEQ ID NO:2 or SEQ ID NO:3; (c) 49, 84, 144, 207, 239, 255, and 258 of SEQ ID NO:4; (d) 54, 89, 149, 212, 243, 259, and 262 of SEQ ID NO:5; and (e) 51, 86, 146, 208, 242, 258, and 262 of SEQ ID NO:6;

(2) a Z2 amino acid residue at positions: (a) 94, 175, 184, 290, and 353 of SEQ ID NO:1; (b) 95, 176, 185, 292, and 355 of SEQ ID NO:2 or SEQ ID NO:3; (c) 96, 177, 186, 293, and 357 of SEQ ID NO:4; (d) 101, 182, 191, 297, and 361 of SEQ ID NO:5; and (e) 98, 179, 188, 296, and 363 of SEQ ID NO:6;

(3) a Z3 amino acid residue at position: (a) 226 of SEQ ID NO:1; (b) 227 of SEQ ID NO:2 or SEQ ID NO:3; (c) 228 of SEQ ID NO:4; (d) 232 of SEQ ID NO:5; and (e) 231 of SEQ ID NO:6; and (4) a Z4 amino acid residue at positions: (a) 78 and 328 of SEQ ID NO:1; (b) 79 and 330 of SEQ ID NO:2 or SEQ ID NO:3; (c) 80 and 331 of SEQ ID NO:4; (d) 85 and 336 of SEQ ID NO:5; and (e) 82 and 337 of SEQ ID NO:6.

In other embodiments, the polypeptide further includes a Z3 amino acid residue at position: (a) 285 of SEQ ID NO:1; (b) 287 of SEQ ID NO:2 or 3; (c) 288 of SEQ ID NO:4; (d) 292 of SEQ ID NO:5; and (e) 291 of SEQ ID NO:6. A Z3 amino acid residue includes lysine (K), arginine (R), or histidine (H). In some aspects, the amino acid residue at this position is an arginine (R).

In some embodiments, the polypeptide can further comprise, in addition to one or more of the residue replacements above, an isoleucine at position 52, a glutamic acid at position 74, proline at position 188, valine at position 366, an alanine at position 443, a glycine at position 698 of SEQ ID NO:1; isoleucine at position 53, a glutamic acid at position 75, proline at position 189, a valine at position 368, an alanine at position 445, a glycine at position 709 of SEQ ID NO:2; an isoleucine at position 53, a glutamic acid at position 75, proline at position 189, a valine at position 368, an alanine at position 445, a glycine at position 701 of SEQ ID NO:3; an isoleucine at position 55, a gluatmic acid at position 77, proline at position 191, a valine at position 371, an alanine at position 448, a glycine at position 813 of SEQ ID NO:4; an isoleucine at position 59, a glutamic acid at position 81, proline at position 195, a valine at position 374, an alanine at position 452, a glycine at position 811 of SEQ ID NO:5; an isoleucine at position 56, a gluatmic acid at position 78, proline at position 192, a valine at position 376, an alanine at position 455, a glycine at position 821 of SEQ ID NO:6; and an isoleucine at position 52, a glutamic acid at position 74, proline at position 188, a valine at position 366, an alanine at position 443, a glycine at position 698 of SEQ ID NO:7.

"Conservative amino acid substitution" or, simply, "conservative variations" of a particular sequence refers to the replacement of one amino acid, or series of amino acids, with essentially identical amino acid sequences. One of skill will recognize that individual substitutions, deletions or additions which alter, add or delete a single amino acid or a percentage of amino acids in an encoded sequence result in "conservative variations" where the alterations result in the deletion of an amino acid, addition of an amino acid, or substitution of an amino acid with a chemically similar amino acid.

Conservative substitution tables providing functionally similar amino acids are well known in the art. For example, one conservative substitution group includes Alanine (A), Serine (S), and Threonine (T). Another conservative substitution group includes Aspartic acid (D) and Glutamic acid (E). Another conservative substitution group includes Asparagine (N) and Glutamine (Q). Yet another conservative substitution group includes Arginine (R) and Lysine (K). Another conservative substitution group includes Isoleucine, (I) Leucine (L), Methionine (M), and Valine (V). Another conservative substitution group includes Phenylalanine (F), Tyrosine (Y), and Tryptophan (W).

Thus, "conservative amino acid substitutions" of a listed polypeptide sequence (e.g., SEQ ID NOs: 1-6) include substitutions of a percentage, typically less than 10%, of the amino acids of the polypeptide sequence, with a conservatively selected amino acid of the same conservative substitution group. Accordingly, a conservatively substituted variation of a polypeptide of the invention can contain 100, 75, 50, 25, or 10 substitutions with a conservatively substituted variation of the same conservative substitution group.

It is understood that the addition of sequences which do not alter the encoded activity of a nucleic acid molecule, such as the addition of a non-functional or non-coding sequence, is a conservative variation of the basic nucleic acid. The "activity" of an enzyme is a measure of its ability to catalyze a reaction, i.e., to "function", and may be expressed as the rate at which the product of the reaction is produced. For example, enzyme activity can be represented as the amount of product produced per unit of time or per unit of enzyme (e.g., concentration or weight), or in terms of affinity or dissociation constants. As used interchangeably herein a "cytochrome P450 activity", "biological activity of cytochrome P450" or "functional activity of cytochrome P450", refers to an activity exerted by a cytochrome P450 protein, polypeptide or nucleic acid molecule on a cytochrome P450 polypeptide substrate, as determined in vivo, or in vitro, according to standard techniques. The biological activity of cytochrome P450 is described herein.

One of skill in the art will appreciate that many conservative variations of the nucleic acid constructs which are disclosed yield a functionally identical construct. For example, owing to the degeneracy of the genetic code, "silent substitutions" (i.e., substitutions in a nucleic acid sequence which do not result in an alteration in an encoded polypeptide) are an implied feature of every nucleic acid sequence which encodes an amino acid. Similarly, "conservative amino acid substitutions," in one or a few amino acids in an amino acid sequence are substituted with different amino acids with highly similar properties, are also readily identified as being highly similar to a disclosed construct. Such conservative variations of each disclosed sequence are a feature of the polypeptides provided herein.

It will be appreciated by those skilled in the art that due to the degeneracy of the genetic code, a multitude of nucleotide sequences encoding modified P450 polypeptides of the invention may be produced, some of which bear substantial identity to the nucleic acid sequences explicitly disclosed herein. For instance, codons AGA, AGG, CGA, CGC, CGG, and CGU all encode the amino acid arginine. Thus, at every position in the nucleic acids of the invention where an arginine is specified by a codon, the codon can be altered to any of the corresponding codons described above without altering the encoded polypeptide. It is understood that U in an RNA sequence corresponds to T in a DNA sequence.

"Conservative variants" are proteins or enzymes in which a given amino acid residue has been changed without altering overall conformation and function of the protein or enzyme, including, but not limited to, replacement of an amino acid with one having similar properties, including polar or nonpolar character, size, shape and charge. Amino acids other than those indicated as conserved may differ in a protein or enzyme so that the percent protein or amino acid sequence similarity between any two proteins of similar function may vary and can be, for example, at least 30%, at least 50%, at least 70%, at least 80%, at least 90%, at least 95%, at least 98% or at least 99%, as determined according to an alignment scheme. As referred to herein, "sequence similarity" means the extent to which nucleotide or protein sequences are related. The extent of similarity between two sequences can be based on percent sequence identity and/or conservation. "Sequence identity" herein means the extent to which two nucleotide or amino acid sequences are invariant. "Sequence alignment" means the process of lining up two or more sequences to achieve maximal levels of identity (and, in the case of amino acid sequences, conservation) for the purpose of assessing the degree of similarity. Numerous methods for aligning sequences and assessing similarity/identity are known in the art such as, for example, the Cluster Method, wherein similarity is based on the MEGALIGN algorithm, as well as BLASTN, BLASTP, and FASTA (Lipman and Pearson, 1985; Pearson and Lipman, 1988). When using all of these programs, the preferred settings are those that results in the highest sequence similarity.

Non-conservative modifications of a particular polypeptide are those which substitute any amino acid not characterized as a conservative substitution. For example, any substitution which crosses the bounds of the six groups set forth above. These include substitutions of basic or acidic amino acids for neutral amino acids, (e.g., Asp, Glu, Asn, or Gln for Val, Ile, Leu or Met), aromatic amino acid for basic or acidic amino acids (e.g., Phe, Tyr or Trp for Asp, Asn, Glu or Gln) or any other substitution not replacing an amino acid with a like amino acid. Basic side chains include lysine (K), arginine (R), histidine (H); acidic side chains include aspartic acid (D), glutamic acid (E); uncharged polar side chains include glycine (G), asparagine (N), glutamine (Q), serine (S), threonine (T), tyrosine (Y), cysteine (C); nonpolar side chains include alanine (A), valine (V), leucine (L), isoleucine (I), proline (P), phenylalanine (F), methionine (M), tryptophan (W); beta-branched side chains include threonine (T), valine (V), isoleucine (I); aromatic side chains include tyrosine (Y), phenylalanine (F), tryptophan (W), histidine (H).

Accordingly, some amino acid residues at specific positions in a polypeptide are "excluded" from conservative amino acid substitutions. Instead, these restricted amino acids are generally chosen from a "Z" group. "Z" groups are amino acid groups designated Z1, Z2, Z3, Z4, Z5, and Z6. These amino acid residues can be substituted at a designated position to obtain a modified or variant polypeptide. While some overlap may occur, the members of each "Z" group are not "conservative amino acid substitutions" as defined above. The "Z" group members are established based upon the substitutions set forth in Table 4. In general, these mutations represent non-conservative substitutions at the indicated position in the designated sequence. For example, as shown in the first column at the first row, an arginine (R) to cysteine (C) substitution is made in SEQ ID NO:1 at position 47. This substitution is generally not considered a "conservative" substitution. Similar substitutions are made throughout the various sequences at the indicated positions in order to modify the activity of the polypeptide. Such modifications are made in order to generate polypeptides that are active on substrates such as alkanes. Referring again to Table 4, a parent polypeptide (e.g., SEQ ID NO:1, 2, 3, 4, 5 or 6) can be modified to include an amino acid substitution at a particular residue by modifying the nucleic acid sequence that encodes the parent polypeptide (see below for additional information regarding modifying nucleic acid sequences). The region of P450 modified is identified on the left side of Table 4. The specific substitutions are identified throughout Table 4. Accordingly, "Z" groups are identified as follows: a Z1 amino acid residue includes glycine (G), asparagine (N), glutamine (Q), serine (S), threonine (T), tyrosine (Y), or cysteine (C); a Z2 amino acid residue includes alanine (A), valine (V), leucine (L), isoleucine (I), proline (P), or methionine (M); a Z3 amino acid residue includes lysine (K), or arginine (R); a Z4 amino acid residue includes tyrosine (Y), phenylalanine (F), tryptophan (W), or histidine (H); a Z5 amino acid residue includes threonine (T), valine (V), and isoleucine (I); and a Z6 amino acid residue includes aspartic acid (D) and glutamic acid (E).

Accordingly, a polypeptide provided herein can include amino acids that are "restricted" to particular amino acid substitutions. For example, residues 47, 78, 82, 94, 142, 175, 184, 205, 226, 236, 252, 255, 290, 328, and 353 can be restricted to substitutions set forth in a "Z" group as defined below and throughout the specification. It is understood that not all of the identified restricted residues need be altered in the same polypeptide. In some embodiments, the invention encompasses polypeptides where only about 80%, 85%, 90% or 95% of the restricted amino acid residues are altered in a given polypeptide.

Member residues of each "Z" group can be included at the appropriate position in a designated polypeptide. Accordingly, in other embodiments, the amino acid sequence of the polypeptide includes residues at the following positions:

(1) a glycine (G), glutamine (Q), serine (S), threonine (T), or cysteine (C) amino acid residue at position: (a) 47, 82, 142, 205, 236, 252, and 255 of SEQ ID NO:1; (b) 48, 83, 143, 206, 238, 254, and 257 of SEQ ID NO:2 or SEQ ID NO:3; (c) 49, 84, 144, 207, 239, 255, and 258 of SEQ ID NO:4; (d) 54, 89, 149, 212, 243, 259, and 262 of SEQ ID NO:5; and (e) 51, 86, 146, 208, 242, 258, and 262 of SEQ ID NO:6;

(2) a valine (V) or isoleucine (I) amino acid residue at position: (a) 94, 175, 184, 290, and 353 of SEQ ID NO:1; (b) 95, 176, 185, 292, and 355 of SEQ ID NO:2 or SEQ ID NO:3;

(c) 96, 177, 186, 293, and 357 of SEQ ID NO:4; (d) 101, 182, 191, 297, and 361 of SEQ ID NO:5; and (e) 98, 179, 188, 296, and 363 of SEQ ID NO:6;

(3) an arginine amino acid residue at position: (a) 226 of SEQ ID NO:1; (b) 227 of SEQ ID NO:2 or SEQ ID NO:3; (c) 228 of SEQ ID NO:4; (d) 232 of SEQ ID NO:5; and (e) 231 of SEQ ID NO:6; and (4) a phenylalanine (F) or histidine (H) amino acid residue at position: (a) 78 and 328 of SEQ ID NO:1; (b) 79 and 330 of SEQ ID NO:2 or SEQ ID NO:3; (c) 80 and 331 of SEQ ID NO:4; (d) 85 and 336 of SEQ ID NO:5; and (e) 82 and 337 of SEQ ID NO:6.

In other embodiments, the amino acid sequence of the polypeptide includes residues at the following positions:

(1) a serine (S) residue at position: (a) 82, 142, and 255 of SEQ ID NO:1; (b) 83, 143 and 257 of SEQ ID NO:2 or SEQ ID NO:3; (c) 84, 144, and 258 of SEQ ID NO:4; (d) 89, 149, and 262 of SEQ ID NO:5; (e) 86, 146 and 262 of SEQ ID NO:6;

(2) a cysteine (C) amino acid residue at position: (a) 47 and 205 of SEQ ID NO:1; (b) 48 and 206 of SEQ ID NO:2 or SEQ ID NO:3; (c) 49 and 207 of SEQ ID NO:4; (d) 54 and 212 of SEQ ID NO:5; (e) 51 and 208 of SEQ ID NO:6;

(3) a glutamine (Q) amino acid residue at position: (a) 236 of SEQ ID NO:1; (b) 238 of SEQ ID NO:2 or SEQ ID NO:3; (c) 239 of SEQ ID NO:4; (d) 243 of SEQ ID NO:5; (e) 242 of SEQ ID NO:6;

(4) a glycine (G) amino acid residue at position: (a) 252 of SEQ ID NO:1; (b) 254 of SEQ ID NO:2 or SEQ ID NO:3; (c) 255 of SEQ ID NO:4; (d) 259 of SEQ ID NO:5; (e) 258 of SEQ ID NO:6;

(5) a valine (V) amino acid residue at position: (a) 184, 290 and 353 of SEQ ID NO:1; (b) 185, 292, and 355 of SEQ ID NO:2 or SEQ ID NO:3; (c) 186, 293 and 357 of SEQ ID NO:4; (d) 191, 297, and 361 of SEQ ID NO:5; (e) 188, 296, and 363 of SEQ ID NO:6;

(6) an isoleucine (I) amino acid residue at position: (a) 94 and 175 of SEQ ID NO:1; (b) 95 and 176 of SEQ ID NO:2 or SEQ ID NO:3; (c) 96 and 177 of SEQ ID NO:4; (d) 101 and 182 of SEQ ID NO:5; (e) 98 and 179 of SEQ ID NO:6; and (7) a phenylalanine (F) amino acid residue at position: (a) 78 and 328 of SEQ ID NO:1; (b) 79 and 330 of SEQ ID NO:2 or SEQ ID NO:3; (c) 80 and 331 of SEQ ID NO:4; (d) 85 and 336 of SEQ ID NO:5; (e) 82 and 337 of SEQ ID NO:6.

In some embodiments, the polypeptide can further comprise, in addition to one or more of the residue replacements above, an isoleucine at position 52, a glutamic acid at position 74, proline at position 188, valine at position 366, an alanine at position 443, a glycine at position 698 of SEQ ID NO:1; isoleucine at position 53, a glutamic acid at position 75, proline at position 189, a valine at position 368 of SEQ ID NO:2; an isoleucine at position 53, a glutamic acid at position 75, proline at position 189, a valine at position 368 of SEQ ID NO:3; an isoleucine at position 55, a gluatmic acid at position 77, proline at position 191, a valine at position 371 of SEQ ID NO:4; an isoleucine at position 59, a glutamic acid at position 81, proline at position 195, a valine at position 374 of SEQ ID NO:5; an isoleucine at position 56, a gluatmic acid at position 78, proline at position 192, a valine at position 376 of SEQ ID NO:6; and an isoleucine at position 52, a glutamic acid at position 74, proline at position 188, a valine at position 366 of SEQ ID NO:7.

A polynucleotide, polypeptide, or other component is "isolated" when it is partially or completely separated from components with which it is normally associated (other proteins, nucleic acids, cells, synthetic reagents, etc.). A nucleic acid or polypeptide is "recombinant" when it is artificial or engineered, or derived from an artificial or engineered protein or nucleic acid. For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant. For example, an "isolated" nucleic acid molecule is one which is separated from other nucleic acid molecules which are present in the natural source of the nucleic acid. For example, with regards to genomic DNA, the term "isolated" includes nucleic acid molecules which are separated from the chromosome with which the genomic DNA is naturally associated. Typically, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

It is envisioned that modifying the regions of a P450 polypeptide associated with the "linker" region and "reductase" domain. The "linker" region generally includes those residues from positions about 450 to about 480 of, for example, SEQ ID NO:1-6. In addition, the "reductase" domain generally includes those residues from positions about 470 to about 1050 of SEQ ID NOs:1-6. As shown in Table 4, polypeptides that include amino acid substitutions at these residues are provided. These substitutions can be made in conjunction with substitutions in the "heme" domain or they can be made in isolation from those in the heme domain.

Accordingly, in yet another embodiment, an isolated or recombinant polypeptide that includes residues 456-1048 of SEQ ID NO:1, 456-1059 of SEQ ID NO:2, 456-1053 of SEQ ID NO:3, 456-1064 of SEQ ID NO:4, 456-1063 of SEQ ID NO:5, or 456-1077 of SEQ ID NO:6, is provided. The polypeptide includes an amino acid sequence with up to 65, 40, 25, or 10 conservative amino acid substitutions excluding residues: (a) 464, 631, 645, 710 and 968 of SEQ ID NO:1; (b) 475, 641, 656, 721 and 980 of SEQ ID NO:2; (c) 467, 634, 648, 713 and 972 of SEQ ID NO:3; (d) 477, 644, 659, 724 and 983 of SEQ ID NO:4; (e) 472, 640, 656, 723 and 985 of SEQ ID NO:5; and (f) 480, 648, 664, 733 and 997 of SEQ ID NO:6. The amino acid sequence includes the following residues:

(1) a Z1, Z3, Z4, or Z5 amino acid residue at position: (a) 464 of SEQ ID NO:1; (b) 475 of SEQ ID NO:2; (c) 467 of SEQ ID NO:3; (d) 477 of SEQ ID NO:4; (e) 472 of SEQ ID NO:5; and (f) 480 of SEQ ID NO:6;

(2) a Z1 amino acid residue at position: (a) 631 and 710 of SEQ ID NO1; (b) 641 and 721 of SEQ ID NO:2; (c) 634 and 713 of SEQ ID NO:3; (d) 644 and 724 of SEQ ID NO:4; (e) 640 and 723 of SEQ ID NO:5; and (f) 648 and 733 of SEQ ID NO:6;

(3) a Z3 amino acid residue at position: (a) 645 of SEQ ID NO:1; (b) 656 of SEQ ID NO:2; (c) 648 of SEQ ID NO:3; (d) 659 of SEQ ID NO:4; (e) 656 of SEQ ID NO:5; and (f) 664 of SEQ ID NO:6; and (4) a Z2 amino acid residue at position: (a) 968 of SEQ ID NO:1; (b) 980 of SEQ ID NO:2; (c) 972 of SEQ ID NO:3; (d) 983 of SEQ ID NO:4; (e) 985 of SEQ ID NO:5; and (f) 997 of SEQ ID NO:6.

Z1 is an amino acid residue selected from the group consisting of glycine (G), asparagine (N), glutamine (Q), serine (S), threonine (T), tyrosine (Y), and cysteine (C); Z2 is an amino acid residue selected from the group consisting of alanine (A), valine (V), leucine (L), isoleucine (I), proline (P), and methionine (M); Z3 is an amino acid residue selected from the group consisting of lysine (K), and arginine (R); Z4 is an amino acid residue selected from the group consisting of tyrosine (Y), phenylalanine (F), tryptophan (W), and histidine (H); and is an amino acid residue selected from the group consisting of threonine (T), valine (V), and isoleucine (I).

In other embodiments, the amino acid sequence of the polypeptide includes residues at the following positions:

(1) a glycine (G), arginine (R), tyrosine (Y), or threonine (T) amino acid residue at position: (a) 464 of SEQ ID NO:1; (b) 475 of SEQ ID NO:2; (c) 467 of SEQ ID NO:3; (d) 477 of SEQ ID NO:4; (e) 472 of SEQ ID NO:5; and (f) 480 of SEQ ID NO:6;

(2) an asparagine (N) amino acid residue at position: (a) 631 of SEQ ID NO:1; (b) 641 of SEQ ID NO:2; (c) 634 of SEQ ID NO:3; (d) 644 of SEQ ID NO:4; (e) 640 of SEQ ID NO:5; and (f) 648 of SEQ ID NO:6;

(3) an arginine (R) amino acid residue at position: (a) 645 of SEQ ID NO:1; (b) 656 of SEQ ID NO:2; (c) 648 of SEQ ID NO:3; (d) 659 of SEQ ID NO:4; (e) 656 of SEQ ID NO:5; and (f) 664 of SEQ ID NO:6;

(4) a threonine (T) amino acid residue at position: (a) 710 of SEQ ID NO:1; (b) 721 of SEQ ID NO:2; (c) 713 of SEQ ID NO:3; (d) 724 of SEQ ID NO:4; (e) 723 of SEQ ID NO:5; and (f) 733 of SEQ ID NO:6; and (5) a lysine (L) amino acid residue at position: (a) 968 of SEQ ID NO:1; (b) 980 of SEQ ID NO:2; (c) 972 of SEQ ID NO:3; (d) 983 of SEQ ID NO:4; (e) 985 of SEQ ID NO:5; and (f) 997 of SEQ ID NO:6.

The invention envisions the synthesis of chimeric polypeptides that include a heme catalytic domain derived from a first source and an electron transfer domain (e.g., a reductase domain) derived from a second source. The first source and the second source may differ by the genus, or the species from which they are derived, or they may be derived from the same species as one another but from different organelles or compartments in the same species. Generally the electron transfer domain is a heme reductase domain.

Accordingly, in addition to providing variants of full-length P450 polypeptides, chimeric polypeptides that comprise: 1) a variant heme domain isolated from a first organism and modified to include a new activity; and 2) a variant reductase domain isolated from a second organism and modified to include a new activity or an activity that a complements the heme domain, are provided. Methods for engineering a chimeric polypeptide of the invention are disclosed in U.S. Patent Application Publication Number 20050124025, the contents of which are incorporated herein by reference.

In another embodiment, an isolated or recombinant polypeptide that includes residues 1 to about 455 of the amino acid sequence set forth in SEQ ID NO:1, 2, 3, 4, 5 or 6 is provided. The polypeptide comprises amino acid residues in the amino acid sequence that correspond to the following positions, at least 80%, 85%, 90%, or 95% of the amino acid residues in the amino acid sequence at the positions specified below are present:

(1) a serine (S) residue at position: (a) 82, 142, and 255 of SEQ ID NO:1; (b) 83, 143 and 257 of SEQ ID NO:2 or SEQ ID NO:3; (c) 84, 144, and 258 of SEQ ID NO:4; (d) 89, 149, and 262 of SEQ ID NO:5; (e) 86, 146 and 262 of SEQ ID NO:6;

(2) a cysteine (C) amino acid residue at position: (a) 47 and 205 of SEQ ID NO:1; (b) 48 and 206 of SEQ ID NO:2 or SEQ ID NO:3; (c) 49 and 207 of SEQ ID NO:4; (d) 54 and 212 of SEQ ID NO:5; (e) 51 and 208 of SEQ ID NO:6;

(3) a glutamine (Q) amino acid residue at position: (a) 236 of SEQ ID NO:1; (b) 238 of SEQ ID NO:2 or SEQ ID NO:3; (c) 239 of SEQ ID NO:4; (d) 243 of SEQ ID NO:5; (e) 242 of SEQ ID NO:6;

(4) a glycine (G) amino acid residue at position: (a) 252 of SEQ ID NO:1; (b) 254 of SEQ ID NO:2 or SEQ ID NO:3; (c) 255 of SEQ ID NO:4; (d) 259 of SEQ ID NO:5; (e) 258 of SEQ ID NO:6;

(5) a valine (V) amino acid residue at position: (a) 184, 290 and 353 of SEQ ID NO:1; (b) 185, 292, and 355 of SEQ ID NO:2 or SEQ ID NO:3; (c) 186, 293 and 357 of SEQ ID NO:4; (d) 191, 297, and 361 of SEQ ID NO:5; (e) 188, 296, and 363 of SEQ ID NO:6;

(6) an isoleucine (I) amino acid residue at position: (a) 94 and 175 of SEQ ID NO:1; (b) 95 and 176 of SEQ ID NO:2 or SEQ ID NO:3; (c) 96 and 177 of SEQ ID NO:4; (d) 101 and 182 of SEQ ID NO:5; (e) 98 and 179 of SEQ ID NO:6; and (7) a phenylalanine (F) amino acid residue at position: (a) 78 and 328 of SEQ ID NO:1; (b) 79 and 330 of SEQ ID NO:2 or SEQ ID NO:3; (c) 80 and 331 of SEQ ID NO:4; (d) 85 and 336 of SEQ ID NO:5; (e) 82 and 337 of SEQ ID NO:6; and (8) an arginine (R) amino acid residue at position: (a) 226 of SEQ ID NO:1; b) 227 of SEQ ID NO:2 or SEQ ID NO:3; (c) 228 of SEQ ID NO:4; (d) 232 of SEQ ID NO:5; (e) 231 of SEQ ID NO:6.

In other embodiments, the polypeptide further includes a Z3 amino acid residue at position: (a) 285 of SEQ ID NO:1; (b) 287 of SEQ ID NO:2 or 3; (c) 288 of SEQ ID NO:4; (d) 292 of SEQ ID NO:5; and (e) 291 of SEQ ID NO:6. A Z3 amino acid residue includes lysine (K), arginine (R), or histidine (H). In some aspects, the amino acid residue at this position is an arginine (R).

In some embodiments, the polypeptide can further comprise, in addition to one or more of the residue replacements above, an isoleucine at position 52, a glutamic acid at position 74, proline at position 188, valine at position 366, an alanine at position 443, a glycine at position 698 of SEQ ID NO:1; isoleucine at position 53, a glutamic acid at position 75, proline at position 189, a valine at position 368 of SEQ ID NO:2; an isoleucine at position 53, a glutamic acid at position 75, proline at position 189, a valine at position 368 of SEQ ID NO:3; an isoleucine at position 55, a gluatmic acid at position 77, proline at position 191, a valine at position 371 of SEQ ID NO:4; an isoleucine at position 59, a glutamic acid at position 81, proline at position 195, a valine at position 374 of SEQ ID NO:5; an isoleucine at position 56, a gluatmic acid at position 78, proline at position 192, a valine at position 376 of SEQ ID NO:6; and an isoleucine at position 52, a glutamic acid at position 74, proline at position 188, a valine at position 366 of SEQ ID NO:7.

Accordingly, in some embodiments, a polypeptide provided herein includes amino acid residue substitutions that correspond to positions in a particular sequence at least 80%, 85%, 90%, or 95% of the time. In other words, the invention encompasses polypeptides that contain the recited amino acid substitutions at 80%, 85%, 90%, or 95% of the recited positions in a given sequence. The skilled artisan will recognize that not every substitution from a group of substitutions is necessary to obtain a modified polypeptide that is active on an alkane substrate.

In another embodiment, an isolated or recombinant polypeptide that includes the amino acid sequence set forth in SEQ ID NO:7, is provided. SEQ ID NO:7 (see FIG. 14) provides an amino acid sequence of a P450 BM-3 variant. This variant is also designated 35-E11. The polypeptide may contain up to 75, 50, 25, or 10 conservative amino acid substitutions excluding residues 47, 78, 82, 94, 142, 175, 184, 205, 226, 236, 252, 255, 290, 328, 353, 464, and 710.

In yet another embodiment, an isolated or recombinant polypeptide that includes the amino acid sequence set forth in SEQ ID NO:8, is provided. SEQ ID NO:8 (see FIG. 15) provides an amino acid sequence of a P450 BM-3 variant. This variant is also designated 35-E11-E464R. The polypeptide may contain up to 75, 50, 25, or 10 conservative amino acid substitutions excluding residues 47, 78, 82, 94, 142, 175, 184, 205, 226, 236, 252, 255, 290, 328, 353, 464, and 710.

In another embodiment, an isolated or recombinant polypeptide that includes the amino acid sequence set forth in SEQ ID NO:9, is provided. SEQ ID NO:9 (see FIG. 16) provides an amino acid sequence of a P450 BM-3 variant. This variant is also designated 35-E11-E464Y. The polypeptide may contain up to 75, 50, 25, or 10 conservative amino acid substitutions excluding residues 47, 78, 82, 94, 142, 175, 184, 205, 226, 236, 252, 255, 290, 328, 353, 464, and 710.

In another embodiment, an isolated or recombinant polypeptide that includes the amino acid sequence set forth in SEQ ID NO:10, is provided. SEQ ID NO:10 (see FIG. 17) provides an amino acid sequence of a P450 BM-3 variant. This variant is also designated 35-E11-E464T. The polypeptide may contain up to 75, 50, 25, or 10 conservative amino acid substitutions excluding residues 47, 78, 82, 94, 142, 175, 184, 205, 226, 236, 252, 255, 290, 328, 353, 464, and 710.

In yet another embodiment, the polypeptides of SEQ ID NO:7, 8, 9 or 10, further optionally include an arginine (R) at amino acid residue position 285.

In another embodiment, an isolated or recombinant polypeptide that includes the amino acid sequence set forth in SEQ ID NO:11, is provided. SEQ ID NO:11 (see FIG. 18) provides an amino acid sequence of a P450 BM-3 variant. This variant is also designated 20-D3. The polypeptide may contain up to 75, 50, 25, or 10 conservative amino acid substitutions excluding residues 47, 78, 82, 94, 142, 175, 184, 205, 226, 236, 252, 255, 285, 290, 328, 353, 464, and 710.

In another embodiment, an isolated or recombinant polypeptide that includes the amino acid sequence set forth in SEQ ID NO:12, is provided. SEQ ID NO:12 (see FIG. 19) provides an amino acid sequence of a P450 BM-3 variant. This variant is also designated 23-1D. The polypeptide may contain up to 75, 50, 25, or 10 conservative amino acid substitutions excluding residues 47, 78, 82, 94, 142, 175, 184, 205, 226, 236, 252, 255, 290, 328, 353, 464, 645, and 710.

In another embodiment, an isolated or recombinant polypeptide that includes the amino acid sequence set forth in SEQ ID NO:13, is provided. SEQ ID NO:13 (see FIG. 20) provides an amino acid sequence of a P450 BM-3 variant. This variant is also designated 21-4G. The polypeptide may contain up to 75, 50, 25, or 10 conservative amino acid substitutions excluding residues 47, 78, 82, 94, 142, 175, 184, 205, 226, 236, 252, 255, 290, 328, 353, 464, 631, and 710.

In another embodiment, an isolated or recombinant polypeptide that includes the amino acid sequence set forth in SEQ ID NO:125, is provided. SEQ ID NO:125 (see FIG. 21B) provides an amino acid sequence of a P450 BM-3 variant. This variant is also designated P450$_{PMO}$. The polypeptide may contain up to 75, 50, 25, or 10 conservative amino acid substitutions excluding residues 47, 52, 74, 78, 82, 94, 142, 175, 184, 188, 205, 226, 236, 252, 255, 290, 328, 353, 366, 443, 464, 698 and 710.

In other embodiments, isolated or recombinant polypeptides of the invention include: (a) a polypeptide comprising the amino acid sequence set forth in SEQ ID NO:7; (b) a polypeptide consisting of the amino acid sequence set forth in SEQ ID NO:7; (c) a polypeptide comprising an amino acid sequence having at least 60%, 70%, 80%, 90%, or 98% sequence identity to the amino acid sequence set forth in SEQ ID NO:7 excluding amino acid residues 47, 78, 82, 94, 142, 175, 184, 205, 226, 236, 252, 255, 290, 328, 353, 464, and 710 of SEQ ID NO:7; or (d) a polypeptide comprising an amino acid sequence that can be optimally aligned with the sequence of SEQ ID NO:7 to generate a similarity score of at least 1830, using the BLOSUM62 matrix, a gap existence penalty of 11, and a gap extension penalty of 1, excluding amino acid residues 47, 78, 82, 94, 142, 175, 184, 205, 226, 236, 252, 255, 290, 328, 353, 464, and 710 of SEQ ID NO:7.

In other embodiments, isolated or recombinant polypeptides of the invention include: (a) a polypeptide comprising the amino acid sequence set forth in SEQ ID NO:8; (b) a polypeptide consisting of the amino acid sequence set forth in SEQ ID NO:8; or (c) a polypeptide comprising an amino acid sequence having at least 60%, 70%, 80%, 90%, or 98% sequence identity to the amino acid sequence set forth in SEQ ID NO:8 excluding amino acid residues 47, 78, 82, 94, 142, 175, 184, 205, 226, 236, 252, 255, 290, 328, 353, 464, and 710 of SEQ ID NO:8.

In other embodiments, isolated or recombinant polypeptides of the invention include: (a) a polypeptide comprising the amino acid sequence set forth in SEQ ID NO:9; (b) a polypeptide consisting of the amino acid sequence set forth in SEQ ID NO:9; or (c) a polypeptide comprising an amino acid sequence having at least 60%, 70%, 80%, 90%, or 98% sequence identity to the amino acid sequence set forth in SEQ ID NO:9 excluding amino acid residues 47, 78, 82, 94, 142, 175, 184, 205, 226, 236, 252, 255, 290, 328, 353, 464, and 710 of SEQ ID NO:9.

In other embodiments, isolated or recombinant polypeptides of the invention include: (a) a polypeptide comprising the amino acid sequence set forth in SEQ ID NO:10; (b) a polypeptide consisting of the amino acid sequence set forth in SEQ ID NO:10; or (c) a polypeptide comprising an amino acid sequence having at least 60%, 70%, 80%, 90%, or 98% sequence identity to the amino acid sequence set forth in SEQ ID NO:10 excluding amino acid residues 47, 78, 82, 94, 142, 175, 184, 205, 226, 236, 252, 255, 290, 328, 353, 464, and 710 of SEQ ID NO:10.

In other embodiments, isolated or recombinant polypeptides of the invention include: (a) a polypeptide comprising the amino acid sequence set forth in SEQ ID NO:11; (b) a polypeptide consisting of the amino acid sequence set forth in SEQ ID NO:11; or (c) a polypeptide comprising an amino acid sequence having at least 60%, 70%, 80%, 90%, or 98% sequence identity to the amino acid sequence set forth in SEQ ID NO:11 excluding amino acid residues 47, 78, 82, 94, 142, 175, 184, 205, 226, 236, 252, 255, 285, 290, 328, 353, 464, and 710 of SEQ ID NO:11.

In other embodiments, isolated or recombinant polypeptides of the invention include: (a) a polypeptide comprising the amino acid sequence set forth in SEQ ID NO:12; (b) a polypeptide consisting of the amino acid sequence set forth in SEQ ID NO:12; or (c) a polypeptide comprising an amino acid sequence having at least 60%, 70%, 80%, 90%, or 98% sequence identity to the amino acid sequence set forth in SEQ ID NO:12 excluding amino acid residues 47, 78, 82, 94, 142, 175, 184, 205, 226, 236, 252, 255, 290, 328, 353, 464, 645, and 710 of SEQ ID NO:12.

In other embodiments, isolated or recombinant polypeptides of the invention include: (a) a polypeptide comprising the amino acid sequence set forth in SEQ ID NO:13; (b) a polypeptide consisting of the amino acid sequence set forth in SEQ ID NO:13; or (c) a polypeptide comprising an amino acid sequence having at least 60%, 70%, 80%, 90%, or 98% sequence identity to the amino acid sequence set forth in SEQ ID NO:13 excluding amino acid residues 47, 78, 82, 94, 142, 175, 184, 205, 226, 236, 252, 255, 290, 328, 353, 464, 631, and 710 of SEQ ID NO:13.

In other embodiments, isolated or recombinant polypeptides of the invention include: (a) a polypeptide comprising the amino acid sequence set forth in SEQ ID NO:125; (b) a polypeptide consisting of the amino acid sequence set forth in SEQ ID NO:125; or (c) a polypeptide comprising an amino acid sequence having at least 60%, 70%, 80%, 90%, or 98% sequence identity to the amino acid sequence set forth in SEQ ID NO:125 excluding amino acid residues residues 47, 52, 74, 78, 82, 94, 142, 175, 184, 188, 205, 226, 236, 252, 255, 290, 328, 353, 366, 443, 464, 698 and 710.

"Sequence identity" herein means the extent to which two nucleotide or amino acid sequences are invariant. "Sequence alignment" means the process of lining up two or more sequences to achieve maximal levels of identity (and, in the case of amino acid sequences, conservation) for the purpose of assessing the degree of similarity. Numerous methods for aligning sequences and assessing similarity/identity are known in the art such as, for example, the Cluster Method, wherein similarity is based on the MEGALIGN algorithm, as well as BLASTN, BLASTP, and FASTA (Lipman and Pearson, 1985; Pearson and Lipman, 1988). When using all of these programs, the preferred settings are those that results in the highest sequence similarity. For example, the "identity" or "percent identity" with respect to a particular pair of aligned amino acid sequences can refer to the percent amino acid sequence identity that is obtained by ClustalW analysis (version W 1.8 available from European Bioinformatics Institute, Cambridge, UK), counting the number of identical matches in the alignment and dividing such number of identical matches by the greater of (i) the length of the aligned sequences, and (ii) 96, and using the following default ClustalW parameters to achieve slow/accurate pairwise alignments—Gap Open Penalty: 10; Gap Extension Penalty: 0.10; Protein weight matrix: Gonnet series; DNA weight matrix: IUB; Toggle Slow/Fast pairwise alignments=SLOW or FULL Alignment.

Two sequences are "optimally aligned" when they are aligned for similarity scoring using a defined amino acid substitution matrix (e.g., BLOSUM62), gap existence penalty and gap extension penalty so as to arrive at the highest score possible for that pair of sequences. Amino acid substitution matrices and their use in quantifying the similarity between two sequences are well-known in the art and described, e.g., in Dayhoff et al. (1978) "A model of evolutionary change in proteins" in "Atlas of Protein Sequence and Structure," Vol. 5, Suppl. 3 (ed. M. O. Dayhoff), pp. 345-352. Natl. Biomed. Res. Found, Washington, D.C. and Henikoff et al. (1992) Proc. Nat'l. Acad. Sci. USA 89: 10915-10919 (each of which is incorporated by reference). The BLOSUM62 matrix (FIG. 10) is often used as a default scoring substitution matrix in sequence alignment protocols such as Gapped BLAST 2.0. The gap existence penalty is imposed for the introduction of a single amino acid gap in one of the aligned sequences, and the gap extension penalty is imposed for each additional empty amino acid position inserted into an already opened gap. The alignment is defined by the amino acids positions of each sequence at which the alignment begins and ends, and optionally by the insertion of a gap or multiple gaps in one or both sequences so as to arrive at the highest possible score. While optimal alignment and scoring can be accomplished manually, the process is facilitated by the use of a computer-implemented alignment algorithm, e.g., gapped BLAST 2.0, described in Altschul et al. (1997) Nucl. Acids Res. 25: 3389-3402 (incorporated by reference herein), and made available to the public at the National Center for Biotechnology Information (NCBI) Website (www.ncbi.nlm.nih.gov). Optimal alignments, including multiple alignments, can be prepared using, e.g., PSI-BLAST, available through the NCB1 website and described by Altschul et al. (1997) Nucl. Acids Res. 25:3389-3402 (incorporated by reference herein).

With respect to an amino acid sequence that is optimally aligned with a reference sequence, an amino acid residue "corresponds to" the position in the reference sequence with which the residue is paired in the alignment. The "position" is denoted by a number that sequentially identifies each amino acid in the reference sequence based on its position relative to the N-terminus. For example, in SEQ ID NO:1, position 1 is T, position 2 is I, position 3 is K, etc. When a test sequence is optimally aligned with SEQ ID NO:1, a residue in the test sequence that aligns with the K at position 3 is said to "correspond to position 3" of SEQ ID NO:1. Owing to deletions, insertion, truncations, fusions, etc., that must be taken into account when determining an optimal alignment, in general the amino acid residue number in a test sequence as determined by simply counting from the N-terminal will not necessarily be the same as the number of its corresponding position in the reference sequence. For example, in a case where there is a deletion in an aligned test sequence, there will be no amino acid that corresponds to a position in the reference sequence at the site of deletion. Where there is an insertion in an aligned reference sequence, that insertion will not correspond to any amino acid position in the reference sequence. In the case of truncations or fusions there can be stretches of amino acids in either the reference or aligned sequence that do not correspond to any amino acid in the corresponding sequence.

In other embodiments, isolated nucleic acid molecules are provided. In one aspect, the invention provides a novel family of isolated or recombinant polynucleotides referred to herein as "P450 polynucleotides" or "P450 nucleic acid molecules." P450 polynucleotide sequences are characterized by the ability to encode a P450 polypeptide. In general, the invention includes any nucleotide sequence that encodes any of the novel P450 polypeptides described herein. In some aspects of the invention, a P450 polynucleotide that encodes a P450 variant polypeptide with activity on alkanes is provided. The terms "polynucleotide," "nucleotide sequence," and "nucleic acid molecule" are used to refer to a polymer of nucleotides (A, C, T, U, G, etc. or naturally occurring or artificial nucleotide analogues), e.g., DNA or RNA, or a representation thereof, e.g., a character string, etc., depending on the relevant context. A given polynucleotide or complementary polynucleotide can be determined from any specified nucleotide sequence.

In one aspect, the P450 polynucleotides comprise recombinant or isolated forms of naturally occurring nucleic acids isolated from an organism, e.g., a bacterial strain. Exemplary P450 polynucleotides include those that encode the wild-type polypeptides set forth in SEQ ID NO: 1, 2, 3, 4, 5, or 6. In another aspect of the invention, P450 polynucleotides are produced by diversifying, e.g., recombining and/or mutating one or more naturally occurring, isolated, or recombinant P450 polynucleotides. As described in more detail elsewhere herein, it is often possible to generate diversified P450 polynucleotides encoding P450 polypeptides with superior functional attributes, e.g., increased catalytic function, increased stability, or higher expression level, than a P450 polynucleotide used as a substrate or parent in the diversification process. Exemplary polynucleotides include those that encode the P450 variant polypeptides set forth in SEQ ID NO: 7, 8, 9, 10, 11, 12, 13 or 125.

The polynucleotides of the invention have a variety of uses in, for example recombinant production (i.e., expression) of the P450 polypeptides of the invention and as substrates for further diversity generation, e.g., recombination reactions or mutation reactions to produce new and/or improved P450 homologues, and the like.

It is important to note that certain specific, substantial and credible utilities of P450 polynucleotides do not require that the polynucleotide encode a polypeptide with substantial P450 activity or even variant P450 activity. For example, P450 polynucleotides that do not encode active enzymes can be valuable sources of parental polynucleotides for use in diversification procedures to arrive at P450 polynucleotide variants, or non-P450 polynucleotides, with desirable functional properties (e.g., high $k_{cat}$ or $k_{cat}/K_m$, low $K_m$, high stability towards heat or other environmental factors, high transcription or translation rates, resistance to proteolytic cleavage, etc.).

P450 polynucleotides, including nucleotide sequences that encode P450 polypeptides and variants thereof, fragments of P450 polypeptides, related fusion proteins, or functional equivalents thereof, are used in recombinant DNA molecules that direct the expression of the P450 polypeptides in appropriate host cells, such as bacterial cells. Due to the inherent degeneracy of the genetic code, other nucleic acid sequences which encode substantially the same or a functionally equivalent amino acid sequence can also be used to clone and express the P450 polynucleotides. The term "host cell", as used herein, includes any cell type which is susceptible to transformation with a nucleic acid construct. The term "transformation" means the introduction of a foreign (i.e., extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence may include regulatory or control sequences, such as start, stop, promoter, signal, secretion, or other sequences used by the genetic machinery of the cell. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

As will be understood by those of skill in the art, it can be advantageous to modify a coding sequence to enhance its expression in a particular host. The genetic code is redundant with 64 possible codons, but most organisms preferentially use a subset of these codons. The codons that are utilized most often in a species are called optimal codons, and those not utilized very often are classified as rare or low-usage codons (see, e.g., Zhang et al. (1991) Gene 105:61-72; incorporated by reference herein). Codons can be substituted to reflect the preferred codon usage of the host, a process sometimes called "codon optimization" or "controlling for species codon bias."

Optimized coding sequences containing codons preferred by a particular prokaryotic or eukaryotic host (see also, Murray et al. (1989) Nucl. Acids Res. 17:477-508; incorporated by reference herein) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, preferred stop codons for *S. cerevisiae* and mammals are UAA and UGA, respectively. The preferred stop codon for monocotyledonous plants is UGA, whereas insects and *E. coli* prefer to use UAA as the stop codon (Dalphin et al. (1996) Nucl. Acids Res. 24: 216-218; incorporated by reference herein). Methodology for optimizing a nucleotide sequence for expression in a plant is provided, for example, in U.S. Pat. No. 6,015,891, and the references cited therein (incorporated herein by reference).

Accordingly, in some embodiments, nucleic acid molecules of the invention include: (a) a nucleic acid molecule which encodes a polypeptide comprising the amino acid sequence set forth in SEQ ID NO:7, 8, 9, 10, 11, 12, 13 or 125; (b) a nucleic acid molecule which encodes a polypeptide consisting of the amino acid sequence set forth in SEQ ID NO:7, 8, 9, 10, 11, 12, 13 or 125; (c) a nucleic acid molecule which encodes a polypeptide comprising residues 1 to about 455 of the amino acid sequence set forth in SEQ ID NO:7 or 11; (d) a nucleic acid molecule which encodes a polypeptide comprising residues about 456 to about 1088 of the amino acid sequence set forth in SEQ ID NO:7, 8, 9, 10, 12, 13 or 125; (e) a nucleic acid molecule comprising the nucleotide sequence set forth in SEQ ID NO:15; (f) a nucleic acid molecule consisting of the nucleotide sequence set forth in SEQ ID NO:15; (g) a nucleic acid molecule comprising the nucleotide sequence set forth in SEQ ID NO:17; (h) a nucleic acid molecule consisting of the nucleotide sequence set forth in SEQ ID NO:17.

In other embodiments, nucleic acid molecules of the invention include: (a) a nucleic acid molecule which encodes a polypeptide comprising residues 1 to about 455 of the amino acid sequence set forth in SEQ ID NO:2 or 3 with the following amino acid residues: 48 and 206 are cysteine (C); 79 and 330 are phenylalanine (F); 83, 143, and 257 are serine (S); 95 and 176 are isoleucine (I); 185, 292, and 355 are valine (V); 227 is arginine (R); 238 is glutamine (Q); and 254 is glycine (G); (b) a nucleic acid molecule which encodes a polypeptide consisting of residues 1 to about 455 of the amino acid sequence set forth in SEQ ID NO:2 or 3 with the following amino acid residues: 48 and 206 are cysteine (C); 79 and 330 are phenylalanine (F); 83, 143, and 257 are serine (S); 95 and 176 are isoleucine (I); 185, 292, and 355 are valine (V); 227 is arginine (R); 238 is glutamine (Q); and 254 is glycine (G); (c) a nucleic acid molecule which encodes a polypeptide comprising residues 1 to about 455 of the amino acid sequence set forth in SEQ ID NO:4 with the following amino acid residues: 49 and 207 are cysteine (C); 80 and 331 are phenylalanine (F); 84, 144, and 258 are serine (S); 96 and 177 are isoleucine (I); 186, 293, and 357 are valine (V); 228 is arginine (R); 239 is glutamine (Q); and 255 is glycine (G); (d) a nucleic acid molecule which encodes a polypeptide consisting of residues 1 to about 455 of the amino acid sequence set forth in SEQ ID NO:4 with the following amino acid residues: 49 and 207 are cysteine (C); 80 and 331 are phenylalanine (F); 84, 144, and 258 are serine (S); 96 and 177 are isoleucine (I); 186, 293, and 357 are valine (V); 228 is arginine (R); 239 is glutamine (Q); and 255 is glycine (G); (e) a nucleic acid molecule which encodes a polypeptide comprising residues 1 to about 455 of the amino acid sequence set forth in SEQ ID NO:5 with the following amino acid residues: 54 and 212 are cysteine (C); 85 and 336 are phenylalanine (F); 89, 149, and 262 are serine (S); 101 and 182 are isoleucine (I); 191, 297, and 361 are valine (V); 232 is arginine (R); 243 is glutamine (Q); and 259 is glycine (G); (f) a nucleic acid molecule which encodes a polypeptide consisting of residues 1 to about 455 of the amino acid sequence set forth in SEQ ID NO:5 with the following amino acid residues: 54 and 212 are cysteine (C); 85 and 336 are phenylalanine (F); 89, 149, and 262 are serine (S); 101 and 182 are isoleucine (I); 191, 297, and 361 are valine (V); 232 is arginine (R); 243 is glutamine (Q); and 259 is glycine (G); (g) a nucleic acid molecule which encodes a polypeptide comprising residues 1 to about 455 of the amino acid sequence set forth in SEQ ID NO:6 with the following amino acid residues: 51 and 208 are cysteine (C); 82 and 337 are phenylalanine (F); 86, 146, and 262 are serine (S); 98 and 179 are isoleucine (I); 188, 296, and 363 are valine (V); 231 is arginine (R); 243 is glutamine (Q); and 258 is glycine (G); and (h) a nucleic acid molecule which encodes a polypeptide consisting of residues 1 to about 455 of the amino acid sequence set forth in SEQ ID NO:6 with the following amino acid residues: 51 and 208 are cysteine (C); 82 and 337 are phenylalanine (F); 86, 146, and 262 are serine (S); 98 and 179 are isoleucine (I); 188, 296, and 363 are valine (V); 231 is arginine (R); 243 is glutamine (Q); and 258 is glycine (G).

In other embodiments, nucleic acid molecules of the invention include: (a) a nucleic acid molecule which encodes a polypeptide comprising the amino acid sequence set forth in SEQ ID NO:2 with the following amino acid residues: 48 and 206 are cysteine (C); 79 and 330 are phenylalanine (F); 83, 143, and 257 are serine (S); 95 and 176 are isoleucine (I); 185, 292, and 355 are valine (V); 227, 287, and 656 are arginine (R); 238 is glutamine (Q); 254 is glycine (G); 475 is glycine (G), arginine (R), tyrosine (Y), or threonine (T); 641 is asparagine (N); 721 is threonine (T); and 980 is leucine; (b) a nucleic acid molecule which encodes a polypeptide consisting of the amino acid sequence set forth in SEQ ID NO:2 with the following amino acid residues: 48 and 206 are cysteine (C); 79 and 330 are phenylalanine (F); 83, 143, and 257 are serine (S); 95 and 176 are isoleucine (I); 185, 292, and 355 are valine (V); 227, 287, and 656 are arginine (R); 238 is glutamine (Q); 254 is glycine (G); 475 is glycine (G), arginine (R), tyrosine (Y), or threonine (T); 641 is asparagine (N); 721 is threonine (T); and 980 is leucine; (c) a nucleic acid molecule which encodes a polypeptide comprising the amino acid sequence set forth in SEQ ID NO:3 with the following amino acid residues: 48 and 206 are cysteine (C); 79 and 330 are phenylalanine (F); 83, 143, and 257 are serine (S); 95 and 176 are isoleucine (I); 185, 292, and 355 are valine (V); 227, 287, and 648 are arginine (R); 238 is glutamine (Q); 254 is glycine (G); 467 is glycine (G), arginine (R), tyrosine (Y), or threonine (T); 634 is asparagine (N); 713 is threonine (T); and 972 is leucine; (d) a nucleic acid molecule which encodes a polypeptide consisting of the amino acid sequence set forth in SEQ ID NO:3 with the following amino acid residues: 48 and 206 are cysteine (C); 79 and 330 are phenylalanine (F); 83, 143, and 257 are serine (S); 95 and 176 are isoleucine (I); 185, 292, and 355 are valine (V); 227, 287, and 648 are arginine (R); 238 is glutamine (Q); 254 is glycine (G); 467 is glycine (G), arginine (R), tyrosine (Y), or threonine (T); 634 is asparagine (N); 713 is threonine (T); and 972 is leucine; (e) a nucleic acid molecule which encodes a polypeptide comprising the amino acid sequence set forth in SEQ ID NO:4 with the following amino acid residues: 49 and 207 are cysteine (C); 80 and 331 are phenylalanine (F); 84, 144, and 258 are serine (S); 96 and 177 are isoleucine (I); 186, 293, and 357 are valine (V); 228, 288, and 659 are arginine (R); 239 is glutamine (Q); and 255 is glycine (G); 477 is glycine (G), arginine (R), tyrosine (Y), or threonine (T); 644 is asparagine (N); 724 is threonine (T); and 983 is leucine; (f) a nucleic acid molecule which encodes a polypeptide consisting of the amino acid sequence set forth in SEQ ID NO:4 with the following amino acid residues: 49 and 207 are cysteine (C); 80 and 331 are phenylalanine (F); 84, 144, and 258 are serine (S); 96 and 177 are isoleucine (I); 186, 293, and 357 are valine (V); 228, 288, and 659 are arginine (R); 239 is glutamine (Q); and 255 is glycine (G); 477 is glycine (G), arginine (R), tyrosine (Y), or threonine (T); 644 is asparagine (N); 724 is threonine (T); and 983 is leucine; (g) a nucleic acid molecule which encodes a polypeptide comprising the amino acid sequence set forth in SEQ ID NO:5 with the following amino acid residues: 54 and 212 are cysteine (C); 85 and 336 are phenylalanine (F); 89, 149, and 262 are serine (S); 101 and 182 are isoleucine (I); 191, 297, and 361 are valine (V); 232, 292, and 656 are arginine (R); 243 is glutamine (Q); and 259 is glycine (G); 472 is glycine (G), arginine (R), tyrosine (Y), or threonine (T); 640 is asparagine (N); 723 is threonine (T); and 985 is leucine; (h) a nucleic acid molecule which encodes a polypeptide consisting of the amino acid sequence set forth in SEQ ID NO:5 with the following amino acid residues: 54 and 212 are cysteine (C); 85 and 336 are phenylalanine (F); 89, 149, and 262 are serine (S); 101 and 182 are isoleucine (I); 191, 297, and 361 are valine (V); 232, 292, and 656 are arginine (R); 243 is glutamine (Q); and 259 is glycine (G); 472 is glycine (G), arginine (R), tyrosine (Y), or threonine (T); 640 is asparagine (N); 723 is threonine (T); and 985 is leucine; (i) a nucleic acid molecule which encodes a polypeptide comprising the amino acid sequence set forth in SEQ ID NO:6 with the following amino acid residues: 51 and 208 are cysteine (C); 82 and 337 are phenylalanine (F); 86, 146, and 262 are serine (S); 98 and 179 are isoleucine (I); 188, 296, and 363 are valine (V); 231, 291, and 664 are arginine (R); 243 is glutamine (Q); and 258 is glycine (G); 480 is glycine (G), arginine (R), tyrosine (Y), or threonine (T); 648 is asparagine (N); 733 is threonine (T); and 997 is leucine; and (j) a nucleic acid molecule which encodes a polypeptide consisting of the amino acid sequence set forth in SEQ ID NO:6 with the following amino acid residues: 51 and 208 are cysteine (C); 82 and 337 are phenylalanine (F); 86, 146, and 262 are serine (S); 98 and 179 are isoleucine (I); 188, 296, and 363 are valine (V); 231, 291, and 664 are arginine (R); 243 is glutamine (Q); and 258 is glycine (G); 480 is glycine (G), arginine (R), tyrosine (Y), or threonine (T); 648 is asparagine (N); 733 is threonine (T); and 997 is leucine.

In one embodiment, an isolated nucleic acid molecule that includes a nucleic acid molecule of the invention and a nucleotide sequence encoding a heterologous polypeptide, is provided.

"Silent variations" are one species of "conservatively modified variations." One of skill will recognize that each codon in a nucleic acid (except AUG, which is ordinarily the only codon for methionine) can be modified by standard techniques to encode a functionally identical polypeptide. Accordingly, each silent variation of a nucleic acid which encodes a polypeptide is implicit in any described sequence. The invention provides each and every possible variation of nucleic acid sequence encoding a polypeptide of the invention that could be made by selecting combinations based on possible codon choices. These combinations are made in accordance with the standard triplet genetic code as applied to the nucleic acid sequence encoding a P450 homologue polypeptide of the invention. All such variations of every nucleic acid herein are specifically provided and described by consideration of the sequence in combination with the genetic code. Any variant can be produced as noted herein.

In general, the invention includes any polypeptide encoded by a modified P450 polynucleotide derived by mutation, recursive sequence recombination, and/or diversification of the polynucleotide sequences described herein. In some aspects of the invention, a P450 polypeptide, such as a heme domain and/or a reductase domain, is modified by single or multiple amino acid substitutions, a deletion, an insertion, or a combination of one or more of these types of modifications. Substitutions can be conservative or non-conservative, can alter function or not, and can add new function. Insertions and deletions can be substantial, such as the case of a truncation of a substantial fragment of the sequence, or in the fusion of additional sequence, either internally or at N or C terminal.

One aspect of the invention pertains to isolated nucleic acid molecules that encode modified P450 polypeptides or biologically active portions thereof. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

A nucleic acid molecule of the present invention, e.g., a nucleic acid molecule that encodes a polypeptide set forth in any of SEQ NOs:1-13 and 125, or having the nucleotide sequence of set forth in any of SEQ ID NOs:15-18, or a portion thereof, can be isolated using standard molecular biology techniques and the sequence information provided herein.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to nucleotide sequences can be prepared by standard synthetic techniques, e.g., using an automated DNA synthesizer. In some embodiments, an isolated nucleic acid molecule of the invention comprises a nucleic acid molecule which is a complement of a nucleotide sequence encoding a polypeptide set forth in any of SEQ NOs:1-13 and 125, or having the nucleotide sequence of set forth in any of SEQ ID NOs:15-18. In still another embodiment, an isolated nucleic acid molecule of the invention comprises a nucleotide sequence which is at least about 50%, 54%, 55%, 60%, 62%, 65%, 70%, 75%, 78%, 80%, 85%, 86%, 90%, 95%, 97%, 98% or more identical to the nucleotide sequence encoding a polypeptide set forth in any of SEQ NOs:1-13 and 125, or having the nucleotide sequence set forth in any of SEQ ID NOs:15-18, or a portion of any of these nucleotide sequences.

In addition to the nucleotide sequences encoding a polypeptide set forth in any of SEQ NOs:1-13, and 125, or having the nucleotide sequence set forth in any of SEQ ID NOs:15-18, it will be appreciated by those skilled in the art that DNA sequence polymorphisms that lead to changes in the amino acid sequences of the proteins may exist within a population. Such genetic polymorphisms may exist among individuals within a population due to natural allelic variation. Such natural allelic variations include both functional and non-functional proteins and can typically result in 1-5% variance in the nucleotide sequence of a gene. Any and all such nucleotide variations and resulting amino acid polymorphisms in genes that are the result of natural allelic variation and that do not alter the functional activity of a protein are intended to be within the scope of the invention.

Accordingly, in another embodiment, an isolated nucleic acid molecule of the invention hybridizes under stringent conditions to a nucleic acid molecule comprising the nucleotide sequence encoding a polypeptide set forth in any of SEQ NOs:1-13 and 125, or having the nucleotide sequence set forth in any of SEQ ID NOs:15-18. In other embodiments, the nucleic acid is at least 30, 50, 100, 150, 200, 250, 300, 350, 400, 450, 500, 550, or 600 nucleotides in length. Nucleic acid molecules are "hybridizable" to each other when at least one strand of one polynucleotide can anneal to another polynucleotide under defined stringency conditions. Stringency of hybridization is determined, e.g., by (a) the temperature at which hybridization and/or washing is performed, and (b) the ionic strength and polarity (e.g., formamide) of the hybridization and washing solutions, as well as other parameters. Hybridization requires that the two polynucleotides contain substantially complementary sequences; depending on the stringency of hybridization, however, mismatches may be tolerated. Typically, hybridization of two sequences at high stringency (such as, for example, in an aqueous solution of 0.5×SSC at 65° C.) requires that the sequences exhibit some high degree of complementarity over their entire sequence. Conditions of intermediate stringency (such as, for example, an aqueous solution of 2×SSC at 65° C.) and low stringency (such as, for example, an aqueous solution of 2×SSC at 55° C.), require correspondingly less overall complementarity between the hybridizing sequences (1×SSC is 0.15 M NaCl, 0.015 M Na citrate). Nucleic acid molecules that hybridize include those which anneal under suitable stringency conditions and which encode polypeptides or enzymes having the same function, such as the ability to catalyze the conversion of an alkane (e.g., methane) to an alcohol (e.g., methanol), of the invention. Further, the term "hybridizes under stringent conditions" is intended to describe conditions for hybridization and washing under which nucleotide sequences at least 30%, 40%, 50%, or 60% homologous to each other typically remain hybridized to each other. Preferably, the conditions are such that sequences at least about 70%, more preferably at least about 80%, even more preferably at least about 85% or 90% homologous to each other typically remain hybridized to each other. In some cases, an isolated nucleic acid molecule of the invention that hybridizes under stringent conditions to a nucleic acid sequence encoding a polypeptide set forth in any of SEQ NOs:1-13, and 125, or having the nucleotide sequence set forth in any of SEQ ID NOs:15-18, corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

The skilled artisan will appreciate that changes can be introduced by mutation into the nucleotide sequences of any nucleic acid sequence encoding a polypeptide set forth in any of SEQ NOs:1-13, and 125, or having the nucleotide sequence set forth in any of SEQ ID NOs:15-18, thereby leading to changes in the amino acid sequence of the encoded proteins. In some cases the alteration will lead to altered function of the polyepeptide. In other cases the change will not alter the functional ability of the encoded polypeptide. In general, substitutions that do not alter the function of a polyeptide include nucleotide substitutions leading to amino acid substitutions at "non-essential" amino acid residues. Generally these substitutions can be made in, for example, in the sequence encoding a polypeptide set forth in any of SEQ NOs:7-13, and 125, or having the nucleotide sequence set forth in any of SEQ ID NOs:15-18, without altering the ability of the enzyme to catalyze the oxidation of an alkane to an alcohol. A "non-essential" amino acid residue is a residue that can be altered from the parent sequence without altering the biological activity of the resulting polypeptide, e.g., catalyzing the conversion of methane to methanol.

Also contemplated are those situations where it is desirable to alter the activity of a parent polypeptide such that the polypeptide has new or increased activity on a particular substrate. It is understood that these amino acid substitutions will generally not constitute "conservative" substitutions. Instead, these substitutions constitute non-conservative substitutions introduced in to a sequence in order to obtain a new or improved activity. For example, the polypeptides set forth in Table 4 (SEQ ID NOs: 1-6) describe specific amino acid substitutions that contribute to the alteration of the activity of a parent polypeptide. SEQ ID NOs: 1-6 are P450 wild-type polypeptides. These polypeptides may also be referred to as "parent" amino acid sequences because substitutions made to their amino acid sequence give rise to modified P450 polypeptides that can have altered or modified activity as compared to the parent sequence (see Table 4). For example, SEQ ID NO:1 provided the parent sequence for the modified P450 polypeptide set forth in SEQ ID NO:7. SEQ ID NO:7 includes amino acid substitutions that impart activities to the SEQ ID NO:7 polypeptide not measurable in the parent polypeptide. Accordingly, the nucleic acid molecule encoding the amino acid sequence of SEQ ID NO:1 provides a "parent" nucleic acid molecule from which mutations can be made to obtain a nucleic acid molecule that encodes a modified polypeptide that includes amino acid substitutions. In general, these mutations provide non-conservative amino acid substitutions at indicated position(s) in a designated sequence.

It is also understood that a modified polypeptide can constitute a "parent" polypeptide from which additional substitutions can be made. Accordingly, a parent polypeptide, and a nucleic acid molecule that encodes a parent polypeptide, includes modified polypeptides and not just "wild-type" sequences. For example, the polypeptide of SEQ ID NO:7 is a modified polypeptide with respect to SEQ ID NO:1 (i.e., the "parent" polypeptide). Similarly, the polypeptide of SEQ ID NO:8 is a modified polypeptide with respect to SEQ ID NO:7. Accordingly, SEQ ID NO:7 is the parent sequence of SEQ ID NO:8. Further, the nucleic acid sequence encoding the polypeptide of SEQ ID NO:7 provides the parent sequence from which mutations can be made to obtain a nucleic acid sequence that encodes the polypeptide of SEQ ID NO:8.

It is also understood that an isolated nucleic acid molecule encoding a polypeptide homologous to the polypeptides if of SEQ ID NOs:1-13, and 125 can be created by introducing one or more nucleotide substitutions, additions or deletions into the nucleotide sequence encoding the particular polypeptide, such that one or more amino acid substitutions, additions or deletions are introduced into the encoded protein. Mutations can be introduced into the nucleic acid sequence by standard techniques, such as site-directed mutagenesis and PCR-mediated mutagenesis. In contrast to those positions where it may be desirable to make a non-conservative amino acid substitutions (see above), in some positions it is preferable to make conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Mutational methods of generating diversity include, for example, site-directed mutagenesis (Ling et al. (1997) "Approaches to DNA mutagenesis: an overview" Anal Biochem. 254(2): 157-178; Dale et al. (1996) "Oligonucleotide-directed random mutagenesis using the phosphorothioate method" Methods Mol. Biol. 57:369-374; Smith (1985) "In vitro mutagenesis" Ann. Rev. Genet. 19:423-462; Botstein & Shortle (1985) "Strategies and applications of in vitro mutagenesis" Science 229:1193-1201; Carter (1986) "Site-directed mutagenesis" Biochem. J. 237:1-7; and Kunkel (1987) "The efficiency of oligonucleotide directed mutagenesis" in Nucleic Acids & Molecular Biology (Eckstein, F. and Lilley, D. M. J. eds., Springer Verlag, Berlin)); mutagenesis using uracil containing templates (Kunkel (1985) "Rapid and efficient site-specific mutagenesis without phenotypic selection" Proc. Natl. Acad. Sci. USA 82:488-492; Kunkel et al. (1987) "Rapid and efficient site-specific mutagenesis without phenotypic selection" Methods in Enzymol. 154, 367-382; and Bass et al. (1988) "Mutant Trp repressors with new DNA-binding specificities" Science 242:240-245); oligonucleotide-directed mutagenesis (Methods in Enzymol. 100: 468-500 (1983); Methods in Enzymol. 154: 329-350 (1987); Zoller & Smith (1982) "Oligonucleotide-directed mutagenesis using M13-derived vectors: an efficient and general procedure for the production of point mutations in any DNA fragment" Nucleic Acids Res. 10:6487-6500; Zoller & Smith (1983) "Oligonucleotide-directed mutagenesis of DNA fragments cloned into M13 vectors" Methods in Enzymol. 100: 468-500; and Zoller & Smith (1987) "Oligonucleotide-directed mutagenesis: a simple method using two oligonucleotide primers and a single-stranded DNA template" Methods in Enzymol. 154:329-350); phosphorothioate-modified DNA mutagenesis (Taylor et al. (1985) "The use of phosphorothioate-modified DNA in restriction enzyme reactions to prepare nicked DNA" Nucl. Acids Res. 13: 8749-8764; Taylor et al. (1985) "The rapid generation of oligonucleotide-directed mutations at high frequency using phosphorothioate-modified DNA" Nucl. Acids Res. 13: 8765-8787; Nakamaye & Eckstein (1986) "Inhibition of restriction endonuclease Nci I cleavage by phosphorothioate groups and its application to oligonucleotide-directed mutagenesis" Nucl. Acids Res. 14: 9679-9698; Sayers et al. (1988) "Y-T Exonucleases in phosphorothioate-based oligonucleotide-directed mutagenesis" Nucl. Acids Res. 16:791-802; and Sayers et al. (1988) "Strand specific cleavage of phosphorothioate-containing DNA by reaction with restriction endonucleases in the presence of ethidium bromide" Nucl. Acids Res. 16: 803-814); mutagenesis using gapped duplex DNA (Kramer et al. (1984) "The gapped duplex DNA approach to oligonucleotide-directed mutation construction" Nucl. Acids Res. 12: 9441-9456; Kramer & Fritz (1987) Methods in Enzymol. "Oligonucleotide-directed construction of mutations via gapped duplex DNA" 154:350-367; Kramer et al. (1988) "Improved enzymatic in vitro reactions in the gapped duplex DNA approach to oligonucleotide-directed construction of mutations" Nucl. Acids Res. 16: 7207; and Fritz et al. (1988) "Oligonucleotide-directed construction of mutations: a gapped duplex DNA procedure without enzymatic reactions in vitro" Nucl. Acids Res. 16: 6987-6999) (each of which is incorporated by reference).

Additional suitable methods include point mismatch repair (Kramer et al. (1984) "Point Mismatch Repair" Cell 38:879-887), mutagenesis using repair-deficient host strains (Carter et al. (1985) "Improved oligonucleotide site-directed mutagenesis using M13 vectors" Nucl. Acids Res. 13: 4431-4443; and Carter (1987) "Improved oligonucleotide-directed mutagenesis using M13 vectors" Methods in Enzymol. 154: 382-403), deletion mutagenesis (Eghtedarzadeh & Henikoff (1986) "Use of oligonucleotides to generate large deletions" Nucl. Acids Res. 14: 5115), restriction-selection and restriction-purification (Wells et al. (1986) "Importance of hydrogen-bond formation in stabilizing the transition state of subtilisin" Phil. Trans. R. Soc. Lond. A 317: 415-423), mutagenesis by total gene synthesis (Nambiar et al. (1984) "Total synthesis and cloning of a gene coding for the ribonuclease S protein" Science 223: 1299-1301; Sakamar and Khorana (1988) "Total synthesis and expression of a gene for the a-subunit of bovine rod outer segment guanine nucleotide-binding protein (transducin)" Nucl. Acids Res. 14: 6361-6372; Wells et al. (1985) "Cassette mutagenesis: an efficient method for generation of multiple mutations at defined sites" Gene 34:315-323; and Grundstrom et al. (1985) "Oligonucleotide-directed mutagenesis by microscale 'shotgun' gene synthesis" Nucl. Acids Res. 13: 3305-3316); double-strand break repair (Mandecki (1986); Arnold (1993) "Protein engineering for unusual environments" Current Opinion in Biotechnology 4:450-455; and "Oligonucleotide-directed double-strand break repair in plasmids of *Escherichia coli*: a method for site-specific mutagenesis" Proc. Natl. Acad. Sci. USA, 83:7177-7181) (each of which is incorporated by reference). Additional details on many of the above methods can be found in Methods in Enzymology Volume 154, which also describes useful controls for trouble-shooting problems with various mutagenesis methods.

Additional details regarding various diversity generating methods can be found in the following U.S. patents, PCT publications, and EPO publications: U.S. Pat. No. 5,605,793 to Stemmer (Feb. 25, 1997), "Methods for In vitro Recombination;" U.S. Pat. No. 5,811,238 to Stemmer et al. (Sep. 22, 1998) "Methods for Generating Polynucleotides having Desired Characteristics by Iterative Selection and Recombination;" U.S. Pat. No. 5,830,721 to Stemmer et al. (Nov. 3, 1998), "DNA Mutagenesis by Random Fragmentation and Reassembly;" U.S. Pat. No. 5,834,252 to Stemmer, et al. (Nov. 10, 1998) "End-Complementary Polymerase Reaction;" U.S. Pat. No. 5,837,458 to Minshull, et al. (Nov. 17, 1998), "Methods and Compositions for Cellular and Metabolic Engineering;" WO 95/22625, Stemmer and Crameri, "Mutagenesis by Random Fragmentation and Reassembly;" WO 96/33207 by Stemmer and Lipschutz "End Complementary Polymerase Chain Reaction;" WO 97/20078 by Stemmer and Crameri "Methods for Generating Polynucleotides having Desired Characteristics by Iterative Selection and Recombination;" WO 97/35966 by Minshull and Stemmer, "Methods and Compositions for Cellular and Metabolic Engineering;" WO 99/41402 by Punnonen et al. "Targeting of Genetic Vaccine Vectors;" WO 99/41383 by Punnonen et al. "Antigen Library Immunization;" WO 99/41369 by Punnonen et al. "Genetic Vaccine Vector Engineering;" WO 99/41368 by Punnonen et al. "Optimization of Immunomodulatory Properties of Genetic Vaccines;" EP 752008 by Stemmer and Crameri, "DNA Mutagenesis by Random Fragmentation and Reassembly;" EP 0932670 by Stemmer "Evolving Cellular DNA Uptake by Recursive Sequence Recombination;" WO 99/23107 by Stemmer et al., "Modification of Virus Tropism and Host Range by Viral Genome Shuffling;" WO 99/21979 by Apt et al., "Human Papillomavirus Vectors;" WO 98/31837 by del Cardayre et al. "Evolution of Whole Cells and Organisms by Recursive Sequence Recombination;" WO 98/27230 by Patten and Stemmer, "Methods and Compositions for Polypeptide Engineering;" WO 98/13487 by Stemmer et al., "Methods for Optimization of Gene Therapy by Recursive Sequence Shuffling and Selection;" WO 00/00632, "Methods for Generating Highly Diverse Libraries;" WO 00/09679, "Methods for Obtaining in vitro Recombined Polynucleotide Sequence Banks and Resulting Sequences;" WO 98/42832 by Arnold et al., "Recombination of Polynucleotide Sequences Using Random or Defined Primers;" WO 99/29902 by Arnold et al., "Method for Creating Polynucleotide and Polypeptide Sequences;" WO 98/41653 by Vind, "An in vitro Method for Construction of a DNA Library;" WO 98/41622 by Borchert et al., "Method for Constructing a Library Using DNA Shuffling;" WO 98/42727 by Pati and Zarling, "Sequence Alterations using Homologous Recombination;" WO 00/18906 by Patten et al., "Shuffling of Codon-Altered Genes;" WO 00/04190 by del Cardayre et al. "Evolution of Whole Cells and Organisms by Recursive Recombination;" WO 00/42561 by Crameri et al., "Oligonucleotide Mediated Nucleic Acid Recombination;" WO 00/42559 by Selifonov and Stemmer "Methods of Populating Data Structures for Use in Evolutionary Simulations;" WO 00/42560 by Selifonov et al., "Methods for Making Character Strings, Polynucleotides & Polypeptides Having Desired Characteristics;" WO 01/23401 by Welch et al., "Use of Codon-Varied Oligonucleotide Synthesis for Synthetic Shuffling;" and WO 01/64864 "Single-Stranded Nucleic Acid Template-Mediated Recombination and Nucleic Acid Fragment Isolation" by Affholter (each of which is incorporated by reference).

Also provided are recombinant constructs comprising one or more of the nucleic acid sequences as broadly described above. The constructs comprise a vector, such as, a plasmid, a cosmid, a phage, a virus, a bacterial artificial chromosome (BAC), a yeast artificial chromosome (YAC), or the like, into which a nucleic acid sequence of the invention has been inserted, in a forward or reverse orientation. In a preferred aspect of this embodiment, the construct further comprises regulatory sequences including, for example, a promoter operably linked to the sequence. Large numbers of suitable vectors and promoters are known to those of skill in the art, and are commercially available.

Accordingly, in other embodiments, vectors that include a nucleic acid molecule of the invention are provided. In other embodiments, host cells transfected with a nucleic acid molecule of the invention, or a vector that includes a nucleic acid molecule of the invention, are provided. Host cells include eucaryotic cells such as yeast cells, insect cells, or animal cells. Host cells also include procaryotic cells such as bacterial cells.

The terms "vector", "vector construct" and "expression vector" mean the vehicle by which a DNA or RNA sequence (e.g. a foreign gene) can be introduced into a host cell, so as to transform the host and promote expression (e.g. transcription and translation) of the introduced sequence. Vectors typically comprise the DNA of a transmissible agent, into which foreign DNA encoding a protein is inserted by restriction enzyme technology. A common type of vector is a "plasmid", which generally is a self-contained molecule of double-stranded DNA that can readily accept additional (foreign) DNA and which can readily introduced into a suitable host cell. A large number of vectors, including plasmid and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g., antibiotic resistance, and one or more expression cassettes.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. A polynucleotide or polypeptide is expressed recombinantly, for example, when it is expressed or produced in a foreign host cell under the control of a foreign or native promoter, or in a native host cell under the control of a foreign promoter.

Polynucleotides provided herein can be incorporated into any one of a variety of expression vectors suitable for expressing a polypeptide. Suitable vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated viruses, retroviruses and many others. Any vector that transduces genetic material into a cell, and, if replication is desired, which is replicable and viable in the relevant host can be used.

Vectors can be employed to transform an appropriate host to permit the host to express an inventive protein or polypeptide. Examples of appropriate expression hosts include: bacterial cells, such as *E. coli, B. subtilis, Streptomyces*, and *Salmonella typhimurium*; fungal cells, such as *Saccharomyces cerevisiae, Pichia pastoris*, and *Neurospora crassa*; insect cells such as *Drosophila* and *Spodoptera frugiperda*; mammalian cells such as CHO, COS, BHK, HEK 293 br Bowes melanoma; or plant cells or explants, etc.

In bacterial systems, a number of expression vectors may be selected depending upon the use intended for the P450 polypeptide. For example, when large quantities of P450 polypeptide or fragments thereof are needed for commercial production or for induction of antibodies, vectors which direct high level expression of fusion proteins that are readily purified can be desirable. Such vectors include, but are not limited to, multifunctional *E. coli* cloning and expression vectors such as BLUESCRIPT (Stratagene), in which the P450 polypeptide coding sequence may be ligated into the vector in-frame with sequences for the amino-terminal Met and the subsequent 7 residues of beta-galactosidase so that a hybrid protein is produced; pIN vectors (Van Heeke & Schuster (1989) J. Biol. Chem. 264: 5503-5509); pET vectors (Novagen, Madison Wis.); and the like.

Similarly, in the yeast *Saccharomyces cerevisiae* a number of vectors containing constitutive or inducible promoters such as alpha factor, alcohol oxidase and PGH may be used for production of the P450 polypeptides of the invention. For reviews, see Ausubel (supra) and Grant et al. (1987) Methods in Enzymology 153:516-544 (incorporated herein by reference).

Also provided are engineered host cells that are transduced (transformed or transfected) with a vector provided herein (e.g., a cloning vector or an expression vector), as well as the production of polypeptides of the invention by recombinant techniques. The vector may be, for example, a plasmid, a viral particle, a phage, etc. The engineered host cells can be cultured in conventional nutrient media modified as appropriate for activating promoters, selecting transformants, or amplifying the P450 homologue gene. Culture conditions, such as temperature, pH and the like, are those previously used with the host cell selected for expression, and will be apparent to those skilled in the art and in the references cited herein, including, e.g., Sambrook, Ausubel and Berger, as well as e.g., Freshney (1994) Culture of Animal Cells: A Manual of Basic Technique, 3rd ed. (Wiley-Liss, New York) and the references cited therein.

In other embodiments, methods for producing a cell that converts an alkane to alcohol, are provided. Such methods generally include: (a) transforming a cell with an isolated nucleic acid molecule encoding a polypeptide comprising an amino acid sequence set forth in SEQ ID NO: 7, 8, 9, 10, 11, 12, 13 or 125; (b) transforming a cell with an isolated nucleic acid molecule encoding a polypeptide of the invention; or (c) transforming a cell with an isolated nucleic acid molecule of the invention.

In other embodiments, methods for selecting a cell that converts an alkane to an alcohol, are provided. The methods generally include: (a) providing a cell containing a nucleic acid construct that includes a nucleotide sequence that encodes a modified cytochrome P450 polypeptide, the nucleotide sequence selected from: (i) a nucleic acid molecule encoding a polypeptide comprising an amino acid sequence set forth in SEQ ID NO: 7, 8, 9, 10, 11, 12, 13 or 125; (ii) a nucleic acid molecule encoding a polypeptide of the invention; or (iii) a nucleic acid molecule of the invention. The methods further include (b) culturing the cell in the presence of a suitable alkane and under conditions where the modified cytochrome P450 is expressed at an effective level; and (c) detecting the production of an alcohol.

In other embodiments, methods for producing an alcohol, are provided. The methods include: (a) providing a cell containing a nucleic acid construct comprising a nucleotide sequence that encodes a modified cytochrome P450 polypeptide, the nucleotide sequence selected from: (i) a nucleic acid molecule encoding a polypeptide comprising an amino acid sequence set forth in SEQ ID NO: 7, 8, 9, 10, 11, 12, 13 or 125; (ii) a nucleic acid molecule encoding a polypeptide of the invention; or (iii) a nucleic acid molecule of the invention. The methods further include (b) culturing the cell in the presence of a suitable alkane and under conditions where the modified cytochrome P450 is expressed at an effective level; and (c) producing an alcohol by hydroxylation of the suitable alkane such as methane ($CH_4$), ethane ($C_2H_6$), propane ($C_3H_8$), butane ($C_4H_{10}$), pentane ($C_5H_{12}$), hexane ($C_6H_{14}$), heptane ($C_8H_{16}$), octane ($C_8H_{18}$), nonane ($C_8H_{20}$), decane ($C_{10}H_{22}$), undecane ($C_{11}H_{24}$), and dodecane ($C_{12}H_{26}$). In general an alcohol produced by a method the invention can include methanol, ethanol, propanol, butanol, pentanol, hexanol, heptanol, octanol, nonanol, decanol, undecanol, and dodecanol.

The cytochrome P450 methane hydroxylase is expressed in its functional form in *Escherichia coli* and the whole cell conversion of methane to methanol using optimized versions of these enzymes in *E. coli* will be possible. As demonstrated in the examples provided herein, *Escherichia coli* over expressing BM-3 enzymes will act as whole cell biocatalysts with relative activities equivalent to the activities of the individual BM-3 catalyst. Substrates used for these whole cell experiments include alkanes, alkenes, and heterocyclic compounds. In the case of methane hydroxylation, the maintenance of the gaseous substrate levels in cultures of whole cells will complicate the process and constitute a large portion of future work with this system. Further, the metabolism of host organisms can be engineered to further increase the levels of NADPH (or NADH for BM-3 variants that accept NADH) available to biocatalysts provided herein.

Examples of whole cell systems that could be used to convert methane to methanol will now be described. The alkane content of natural gas generally comprises about 80% methane and 20% other small alkanes, primarily ethane and propane. Naturally occurring strains of gram negative (e.g. *Pseudomonas*) and gram positive (e.g. Rhodococcus), and even engineered laboratory strains of *E. coli*, can grow using small alcohols as their sole carbon source. Expression of optimized BM-3 based biocatalysts in one of these bacterial strains will allow the bacteria to use the alkane impurities in natural gas as their sole source of carbon and energy (and cofactor regeneration) while converting the methane into methanol. Expression of our BM-3 enzymes in any of these bacteria can be done by standard in the art techniques using muli-host plasmids and shuttle vectors.

Methane generated by the decomposition of biomass in landfills and agricultural waste does not contain other alkanes. To utilize these methane sources with a whole cell system containing our BM-3 biocatalysts, an external carbon and energy source such as glucose must be provided to the host cells to regenerate NADPH. Glucose or similar compounds (with greater NADPH-producing potentials) can be added directly to these whole cell reactions or generated from biomass present in the methane-producing waste. The amount of cofactor a host organism generates from these carbon sources can also be increased by streamlining the cell strain for methane production. Expression of optimized BM-3 enzymes in these bacteria can be done by standard in the art techniques using strain specific plasmids. Modification of *E. coli* strains to optimize NADPH availability can also be performed using standard in the art metabolic engineering techniques such as chromosomal insertion of phage-delivered DNA and recombination of homologous gene fragments from plasmids.

Alternatively, methylotrophs, i.e. methanol-metabolizing yeast (e.g. strains of *Pichia*) and bacterial cell strains (e.g. strains of *Methylobacterium*), can serve as hosts for BM-3 biocatalysts. In this scenario, the engineered BM-3 enzymes supply all of the methanol the hosts need to grow and live while generating excess methanol for production. These cell strains could also be modified genetically to optimize the amount of methanol they can produce. Additionally, since the growth of these methylotrophic strains are dependent on methanol, these strains can be used to identify new enzyme variants with improved activity towards methane. Expression of BM-3 in *Pichia* is possible with standard in the art *Pichia*-specific gene expression plasmids. Expression in methylotrophs is possible with standard in the art techniques using multi-host shuttle vectors.

The methods of the invention can utilize liquid cultures of specific microorganisms for the whole cell bioconversion of methane to methanol, but other host organisms including but not limited to other bacteria, other yeast, and even plants, algae, and fungi could also be used. Plants, algae, and even photosynthesizing bacteria such as cyanobacteria that can convert carbon dioxide and light into sugars (and then NAD(P)H) would be especially valuable as hosts for a BM-3 methane oxidation biocatalyst since these organisms would not require any carbon source other than carbon dioxide. Because methane streams derived from biomass contain about 50% carbon dioxide, these hosts are ideal for methane to methanol processes using landfill and waste generated methane. Expression of BM-3 in plant and fungi is possible with standard in the art DNA transfer techniques specific to these types of cells, such as the use of viral vectors for plants.

As previously discussed, general texts which describe molecular biological techniques useful herein, including the use of vectors, promoters and many other relevant topics, include Berger and Kimmel, Guide to Molecular Cloning Techniques, Methods in Enzymology Volume 152, (Academic Press, Inc., San Diego, Calif.) ("Berger"); Sambrook et al., Molecular Cloning—A Laboratory Manual, 2d ed., Vol. 1-3, Cold Spring Harbor Laboratory, Cold Spring Harbor, N.Y., 1989 ("Sambrook") and Current Protocols in Molecular Biology, F. M. Ausubel et al., eds., Current Protocols, a joint venture between Greene Publishing Associates, Inc. and John Wiley & Sons, Inc., (supplemented through 1999) ("Ausubel") (each of which is incorporated by reference). Examples of protocols sufficient to direct persons of skill through in vitro amplification methods, including the polymerase chain reaction (PCR), the ligase chain reaction (LCR), 0-replicase amplification and other RNA polymerase mediated techniques (e.g., NASBA), e.g., for the production of the homologous nucleic acids of the invention are found in Berger, Sambrook, and Ausubel, as well as in Mullis et al. (1987) U.S. Pat. No. 4,683,202; Innis et al., eds. (1990) PCR Protocols: A Guide to Methods and Applications (Academic Press Inc. San Diego, Calif.) ("Innis"); Arnheim & Levinson (Oct. 1, 1990) C&EN 36-47; The Journal Of NIH Research (1991) 3: 81-94; Kwoh et al. (1989) Proc. Natl. Acad. Sci. USA 86: 1173; Guatelli et al. (1990) Proc. Nat'l. Acad. Sci. USA 87: 1874; Lomell et al. (1989) J. Clin. Chem 35: 1826; Landegren et al. (1988) Science 241: 1077-1080; Van Brunt (1990) Biotechnology 8: 291-294; Wu and Wallace (1989) Gene 4:560; Barringer et al. (1990) Gene 89:117; and Sooknanan and Malek (1995) Biotechnology 13: 563-564 (each of which is incorporated by reference). Improved methods for cloning in vitro amplified nucleic acids are described in Wallace et al., U.S. Pat. No. 5,426,039. Improved methods for amplifying large nucleic acids by PCR are summarized in Cheng et al. (1994) Nature 369: 684-685 and the references cited therein (incorporated by reference herein), in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, e.g., Ausubel, Sambrook and Berger, all supra.

The invention is illustrated in the following examples, which are provided by way of illustration and are not intended to be limiting.

EXAMPLES

Example 1

Ethane Conversion

A catalyst for the selective oxidation under mild conditions of gaseous alkanes into easily transported alcohols allows for the economical exploitation of both local, small natural gas resources and vast, remote reserves. Prior to the present studies, the selective conversion of ethane and methane mainly to their corresponding alcohols was not demonstrated. Provided herein are enzyme-based catalysts that convert ethane to ethanol and methane to methanol with high selectivity and productivity. The enzymes are function at ambient temperature and pressure, use dioxygen from the air as the oxidant, and produce little or no hazardous wastes.

Biological systems have evolved efficient and productive metalloenzymes that convert alkanes into alcohols using dioxygen from the air. Methane monooxygenases (MMO) catalyze the conversion of methane to methanol and thereby enable methanotrophic bacteria to use methane as a source of carbon and energy. Microorganisms that grow on larger gaseous alkanes (ethane, propane, butane) have also been reported and putatively use similar enzymes for the first, alkane oxidation step. The relatively well-studied MMOs have long been a source of inspiration for designers of chemical catalysts. Unfortunately, these structurally complex enzymes have never been functionally expressed in a heterologous organism suitable for bioconversion and process optimization and therefore have proven to be of little practical use themselves for production of alcohols.

The present studies use directed evolution techniques to convert heme-containing medium-chain fatty acid hydroxylases in to hydroxylating catalysts for small alkanes. An exemplary hydroxylase includes cytochrome P450 BM-3 (CYP102A1) which is the third P450 identified in the bacterium *Bacillus megaterium*. P450 BM-3 is a soluble, catalytically self-sufficient fatty acid monoxygenase isolated from *Bacillus megaterium*. It has a multi-domain structure, composed of three domains: one FAD, one FMN and one heme domain, fused on the same 119 kDa polypeptide chain of 1048 residues. Furthermore, despite its bacterial origin, P450 BM-3 has been classified as a class II P450 enzyme, typical of microsomal eukaryotic P450s: it shares 30% sequence identity with microsomal fatty acid co-hydroxylase, 35% sequence identity with microsomal NADPH:P450 reductase, and only 20% homology with other bacterial P450s. Homologues of P450 BM-3 (CYP102A1) have been recognized in other bacteria, including two characterized systems in *Bacillus subtilis*: CYP102A2 and CYP102A3.

Communication between the heme and reductase domains of BM-3 is substrate-dependent and fine-tuned to transfer a pair of electrons from an NADPH cofactor through two reductase-bound flavins and then shuttle the electrons, one at a time, into the hydroxylase domain during catalysis. Engineering the protein for activity on a new substrate such as ethane and/or methane must conserve this regulated communication, and poses significant technical challenges. The engineered enzyme must bind ethane and/or methane, a substrate considerably smaller than a fatty acid, directly above the heme in the active site of the hydroxylase domain. Substrate binding must initiate electron transfer from the reductase domain to the heme domain during catalysis. Once electron transfer occurs, the active iron-oxo species must be capable of breaking the high energy C—H bond in ethane (101.1 kcal mol-1 vs. 95-99 kcal mol-1 for the secondary C—H bonds of the fatty acid substrates of wild type BM-3). Finally, the singly-hydroxylated product must be released from the active site before further oxidation can occur.

Crystal structures of BM-3 heme domain with and without substrate are available while a structure of the reductase domain is not. Furthermore, large conformational changes in both domains during catalysis make it difficult to identify amino acid substitutions which can address all these issues. In the present studies, ethane and/or methane hydroxylases were engineered using an 'evolutionary' strategy in which mutations are accumulated in multiple generations of random mutagenesis and screening. The approach has been to use directed evolution methods to adapt the enzyme to exhibit higher turnover on smaller and smaller alkanes (see e.g., FIG. 1). Through successive rounds of mutagenesis of the heme domain (residues 1-429 of SEQ ID NO:1) the activity of BM-3 towards octane was increased. Screening was initially based on the hydroxylation of the octane surrogate substrate p-nitrophenyl octyl ether. The resulting mutant, 139-3, contained 11 amino acid substitutions distributed throughout the hydroxylase domain and exhibited good activity on octane. It had also acquired a small but appreciable activity on propane, producing 2-propanol and a very small (less than 3%) amount of 1-propanol. Subsequently, the propane-hydroxylating activity of this mutant was increased by randomly mutating its heme domain and screening the resulting libraries for activity towards the (propane surrogate) substrate dimethyl ether. Mutant 9-10A obtained in this way was much more active towards propane than 139-3 and produced significantly more 1-propanol (8%). The increase in 1-propanol was particularly interesting because the propane terminal C—H bond energy (100.4 kcal/mol) is similar to the C—H bond energy of ethane (101.1 kcal/mol).

To obtain an ethane-hydroxylating P450, the directed evolution of 9-10A was initiated. The mutations were targeted to the active site rather than the entire heme domain. Most of these targeted substitutions were not accessible by random point mutagenesis due to the conservative nature of the genetic code. The BM-3 active site consists of a hydrophobic channel located directly above the heme. Guided by the high-resolution crystal structure of P450 BM-3 with bound palmitoylglycine substrate eleven amino acid residues in this channel that lie within five Å of the terminal eight carbons of the bound substrate were chosen for mutagenesis. These residues were targeted because they are likely to contact small alkanes in the active site during catalysis. Saturation mutagenesis libraries constructed for each of these residues were screened for mutants showing improved activity towards dimethyl ether. Single mutants selected from these libraries were then recombined to form a large library containing all possible combinations of the beneficial active-site mutations, and this library was screened for activity towards dimethyl ether. The mutant with the highest activity on propane, 53-5H, was isolated and purified and shown to catalyse thousands of turnovers of propane to propanol at a rate of 370 $min^{-1}$ (see Table 1).

Notably, P450 BM-3 mutant 53-5H also hydroxylates ethane to generate ethanol (see Table 1). 53-5H contains three active-site mutations, A78F, A82S, and A328F, all of which replace alanine with a larger side chain which reduce the volume of the active site and position small alkanes above the heme during catalysis. In addition to its activity towards ethane, 53-5H exhibits the highest regioselectivity (89% 2-octanol) and enantioselectivity (65% S-2-octanol) towards octane yet encountered in any BM-3 variant (see Table 1), further evidence of tighter substrate binding in the engineered active site.

Figure 2:
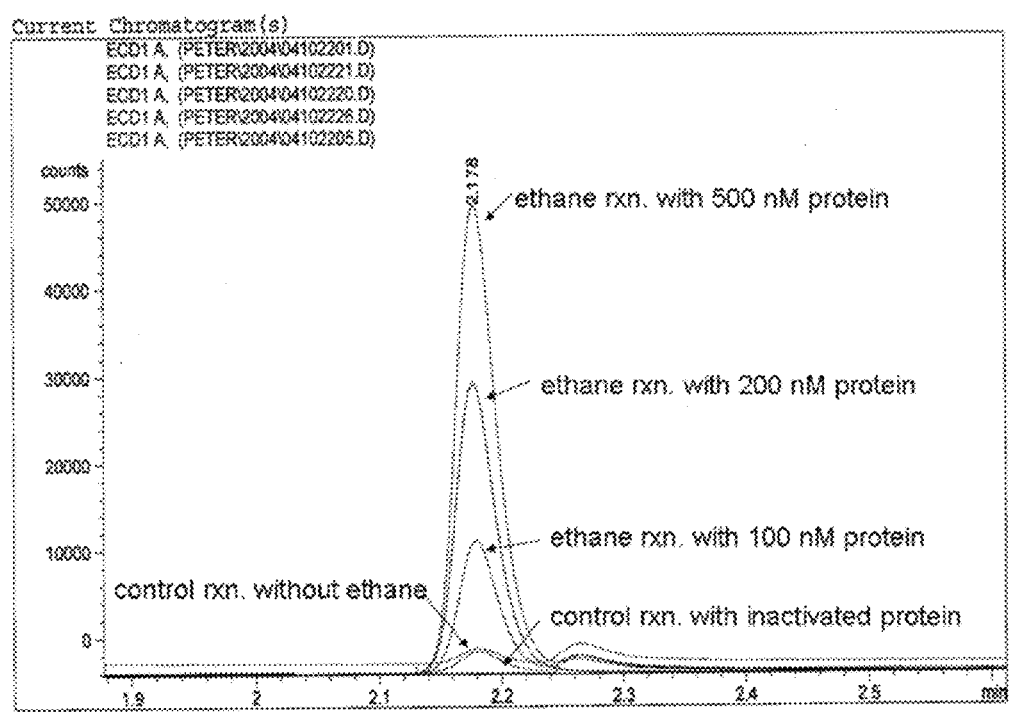
FIG. 2 depicts a gas chromatogram of ethanol reaction mixtures using variant 53-5H as the catalyst. Prior to analysis, ethanol was derivatized to form ethyl nitrite for detection via an electron capture detector (ECD).

Ethane hydroxylation by 53-5H was measured after 12-hour incubations of the enzyme in ethane-saturated buffer containing an ethanol-free NADPH regeneration system (commercial NADPH contains 2-3% ethanol). While the reaction is uncoupled to NADPH oxidation in the presence of ethane (660 $min^{-1}$, see Table 2), 53-5H nevertheless consistently produces at least 50 equivalents of ethanol independent of the starting concentration of enzyme (see FIGS. 2 and 3). Overoxidation was tested by supplying ethanol as a substrate and monitoring ethanol depletion by gas chromatography and the production of acetaldehyde and acetic acid by $^{13}C$ NMR using $^{13}C$-labeled ethanol. No (i.e. less than 10%, the detection limit of these experiments) overoxidation products were detected in these experiments (see FIG. 4). In general, the hydrophobic active sites in P450s assist in the release of singly-hydroxylated products. Alkane-hydroxylating mutants overoxidize longer-chain alkanes such as decane to a higher extent (<7%) than shorter ones such as hexane (<1%). 18 Mutant 53-5H also catalyses the rapid (660 min-1) and efficient (80% coupled) conversion of octane to primarily 2-octanol in the presence of 1% ethanol, demonstrating that ethanol does not inhibit the catalyst. These results demonstrate that the 101.1 kcal/mol C—H bond dissociation energy of ethane does not pose a fundamental barrier to a cytochrome P450 and that a P450-based biocatalyst can cleanly convert ethane into ethanol without undesired side reactions.

Figure 3:
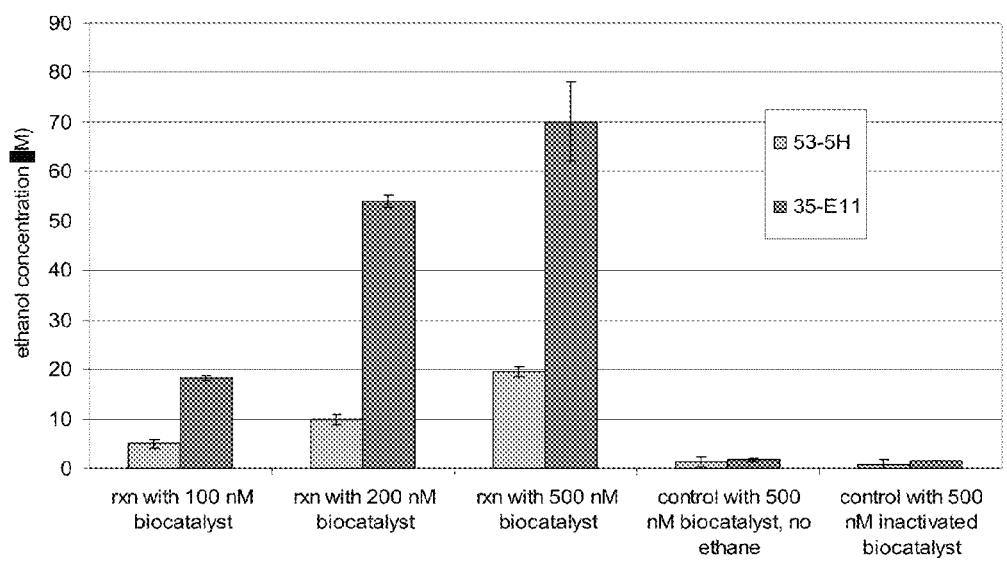
FIG. 3 depicts the conversion of ethane to ethanol using 200 nM protein corresponds to 50 and 250 turnovers per enzyme active site of 53-5H and 35-E11, respectively. Halving or doubling the enzyme concentration yielded approximately correspondingly lower or higher product concentrations, respectively. Control reactions, either without ethane or with inactivated protein, did not contain ethanol concentrations above the background level of 1 µM. Error bars are the standard deviation of three experiments.
Figure 4:
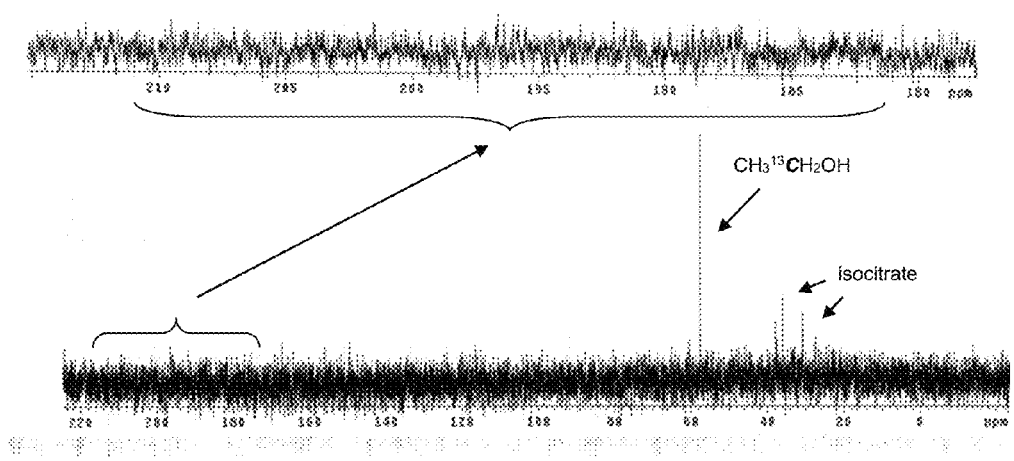
FIG. 4 depicts $^{13}$C-NMR spectrum of singly $^{13}$C-labeled ethanol incubated with 53-5H and NADPH regeneration system. No $^{13}$C-labeled carbonyl peaks due to overoxidation of the ethanol were detectable.

A further round of directed evolution was performed to increase the ethane activity of 53-5H, this time targeting mutations to the reductase domain, including the polypeptide linker that connects it to the heme domain. The amino acid substitution E464G in the linker region increases total turnover in selected BM-3 mutants. Alone this mutation does not enhance the production of ethanol by 53-5H, but further improvement was found upon screening a library of 53-5H containing this mutation and random mutations in the reductase domain for high activity towards dimethyl ether and accompanied by reduced NADPH consumption rates in the absence of substrate. The resulting mutant 35-E11 contains all 15 of the hydroxylase domain substitutions found in 53-5H, the linker mutation E464G, and a new mutation, leading to the substitution I710T, located in the reductase domain. Compared to 53-5H, mutant 35-E11 exhibits a five-fold increase in total turnover of ethane to ethanol (total turnover number (ttn)=250). In a typical reaction with ethane, 200 nM of mutant 35-E11 produces over 50 μM of ethanol (FIG. 3). The rate of product formation by 35-E11 equals that of 53-5H, while the NADPH consumption rate in the presence of ethane has dropped to ~520 min-1 (Table 2). The increased productivity likely reflects a prolonged catalyst lifetime, achieved by reducing non-productive cofactor oxidation, which inactivates the protein by forming various reactive species. Amino acid residue I710 by comparison to the crystal structure of the homologous rat P450 reductase, is located near the FAD cofactor.

Accordingly, provided herein are variant P450s that have been adapted to hydroxylate ever smaller substrates. For example, the wildtype cytochrome P450 BM-3 enzyme is inactive on propane. Evolving it to become an octane hydroxylase, however, generated a small amount of activity towards propane. Similarly, increasing the newly acquired propane activity produced measurable activity towards ethane. Directed evolution has generated a biocatalyst with activity towards ethane. Further, as provided below, additional rounds of directed evolution has generated a BM-3 variant with the ability to convert methane to methanol. This enzyme provides the foundation for a novel biocatalytic route to methanol production from methane.

Reagents:

Unless noted otherwise, chemicals were purchased from Sigma-Aldrich (St. Louis, Mo.). Ethane (99.95%), propane and dimethyl ether (DME) were purchased from Special Gas Services, Inc. (Warren, N.J.) or Advanced Gas Technologies. Ethanol was purchased from AAPER (Shelbyville, Ky.). NADP+ and NADPH were purchased from Roche (Indianapolis, Ind.) or Biocatalytics, Inc. (Pasadena, Calif.). Hexanes (99.94%) were purchased from EMD (Gribbstown, N.J.). Restriction enzymes were purchased from Roche (Indianapolis, Ind.) or New England Biolabs (Beverly, Mass.), Taq DNA polymerase from Roche (Indianapolis, Ind.), Pfu turbo DNA polymerase from Stratagene (La Jolla, Calif.), and T4 DNA ligase from Invitrogen (Carlsbad, Calif.).

Expression and Purification of P450 BM-3:

The genes encoding P450 BM-3 mutants 53-5H (with amino acid substitutions R47C, V78F, A82S, K94I, P142S, T175I, A184V, F205C, S226R, H236Q, E252G, R255S, A290V, A328F, L353V) and 35-E11 (with additional amino acid substitutions E464G and I710T) were expressed and purified as described (Peters et al., J. Am. Chem. Soc. 125: 13442 (2003); incorporated by reference herein). Enzyme concentrations were measured in triplicate from the CO-difference spectra.

Construction of Saturation Mutagenesis Libraries:

Mutations were introduced into mutant 9-10A (with amino acid substitutions R47C, V78A, K94I, P142S, T175I, A184V, F205C, S226R, H236Q, E252G, R255S, A290V, L353V) by PCR overlap extension mutagenesis using Pfu turbo DNA polymerase (Stratagene). The primers for each saturation library contained all possible combinations of bases, NNN (N=A, T, G, or C), at the codon for a particular residue. The recitation of "for" indicates a "forward" primer. Accordingly, the primers in the forward direction for each library were:

```
74NNN-for
                                    (SEQ ID NO: 19)
(5'-GTCAANNNCTTAAATTTGCACG-3')

75NNN-for
                                    (SEQ ID NO: 20)
(5'-GTCAAGCGNNNAAATTTGCACG-3')

78NNN-for
                                    (SEQ ID NO: 21)
(5'-GCTTAAATTTNNNCGTGATTTTGCAGG-3')

81NNN-for
                                    (SEQ ID NO: 22)
(5'-CGTGATNNNGCAGGAGAC-3')

82NNN-for
                                    (SEQ ID NO: 23)
(5'-CGTGATTTTNNNGGAGAC-3')

87NNN-for
                                    (SEQ ID NO: 24)
(5'-GAGACGGGTTANNNACAAGCTGGAC-3')

88NNN-for
                                    (SEQ ID NO: 25)
(5'-GGAGACGGGTTATTTNNNAGCTGGACG-3')

260NNN-for
                                    (SEQ ID NO: 26)
(5'-CAAATTATTNNNTTCTTAATTGCGGGAC-3')

263NNN-for
                                    (SEQ ID NO: 27)
(5'-ACATTCTTANNNGCGGGACACGAAAC-3')

264NNN-for
                                    (SEQ ID NO: 28)
(5'-ACATTCTTAATTNNNGGACACGAAAC-3')

328NNN-for
                                    (SEQ ID NO: 29)
(5'-CCAACTNNNCCTGCGTTTTCC-3')
```

The reverse primers for each of these libraries complement their corresponding forward primers. For each mutation, two separate PCRs were performed, each using a perfectly complementary primer, BamHI-forw (5'-GGAAACAG-GATCCATCGATGC-3') (SEQ ID NO:30) and SacI-rev (5'-GTGAAGGAATACCGCCAAGC-3') (SEQ ID NO:31), at the end of the sequence and a mutagenic primer. The resulting two overlapping fragments that contain the mutations were then annealed in a second PCR to amplify the complete mutated gene. The full gene was then cut with BamHI and SacI restriction enzymes and ligated with T4 ligase (Invitrogen) into pBM-3-WT18-6, previously cut with BamHI and SacI to remove the wild-type gene. The ligation mixtures were then transformed into *E. coli* DH5alpha electrocompetent cells and plated onto Luria-Bertani (LB) agar plates to form single colonies for picking.

Construction of the Active Site Recombination Library:

Improved mutations that were picked up from the saturation mutagenesis libraries were recombined in a combinatorial fashion. Saturation libraries of amino acid positions 74, 81, 263 and 264 did not yield improved mutants so only beneficial mutations at the remaining seven sites were recombined. Mutations were added sequentially using overlap extension PCR with degenerate primers (see above) or a mixture of degenerate primers (mutation sites in the primers are in bold letters). Starting with mutant 9-10A, mutations at amino acid position 78 and 82 were introduced using primers: 78A/T 82A/T/S/F/I/C/G/L/V-for

```
                                          (SEQ ID NO: 32)
(5'GCTTAAATTCRCGCGTGATTTTDBCGGAGACG),
and 78F 82A/T/S/F/I/C/G/L/V-for
                                          (SEQ ID NO: 33)
5'CTTAAATTCTTTCGTGATTTTDBCGGAGACG).
```

Next, mutations at position 260 were introduced using primers:

```
260T-for
                                          (SEQ ID NO: 34)
(5'CAAATTATTACATTCTTAATTGCGGGAC), 260N-for
                                          (SEQ ID NO: 35)
(5'CAAATTATTAACTTCTTAATTGCGGGAC)
and 260L-for
                                          (SEQ ID NO: 36)
(5'CAAATTATTCTTTCTTAATTGCGGGAC).
```

Mutations at position 87 and 88 were introduced using primers:

```
87F/I/V/L 88T for
                                          (SEQ ID NO: 37)
(5'GAGACGGGTTANTYACAAGCTGGAC)
and 87F/I/V/L 88C for
                                          (SEQ ID NO: 38)
(5'GAGACGGGTTANTYTGTAGCTGGAC).
```

Mutations at position 328 were introduced using primers:

```
328A-for
                                          (SEQ ID NO: 39)
(5'CCAACTGCTCCTGCGTTTTCC), 328L/F/V-for
                                          (SEQ ID NO: 40)
(5'CCAACTBTTCCTGCGTTTTCC),
and 328M-for
                                          (SEQ ID NO: 41)
(5'CCAACTATGCCTGCGTTTTCC)
```

Finally, mutations at position 75 were introduced using primers:

```
75L/I-for
                                          (SEQ ID NO: 42)
(5'CTTAAGTCAAGCGMTTAAATTC),
and 75W-for
                                          (SEQ ID NO: 43)
(5'CTTAAGTCAAGCGTGGAAATTC).
```

Sequences of Resulting Ethane Hydroxylating Mutant 53-5H:

Nucleic acid mutations compared to wild-type P450 BM-3 include C142T, T234C, G235T, A237T, G247A, C248G, A249C, A284T, C324T, C427T, C527T, C554T, T617G, C681G, T711G, A758G, C766A, C872T, G985T, C986T, C1060G, and A1119G. Amino acid mutations compared to wild-type P450 BM-3 include R47C, V78F, A82S, K94I, P142S, T175I, A184V, F205C, S226R, H236Q, E252G, R255S, A290V, A328F, and L353V.

Construction of the Reductase Library:

The mutation E465G was found by directed evolution of a different BM-3 variant not reported in this work. To make the reductase library of 53-5H containing this mutation, a random library of the reductase portion of the E465G BM-3 gene (1285 by to 3147 bp) was PCR amplified using the primers Sac1-for (5'-GACTTTGAAGATCATACAAACTAC-GAGCTCG-3') (SEQ ID NO:44) and EcoRI-rev (5'-AG-ATCTGCTCATGTTTGACAGCTTATCATC-GATGAATTC-3') (SEQ ID NO:45), with various concentrations of $MnCl_2$ (0, 50, 100, and 150 µM) added. The amplified DNA was restriction digested using Sac1 and EcoRI and then ligated with T4 ligase into the pCWori plasmid containing the gene for 53-5H with its reductase portion removed with Sac1 and EcoRI. A small library (~100 mutants) from each PCR condition was tested for mutation rate. The 100 µM $MnCl_2$ condition produced the optimal mutation rate of 1-2 mutations per gene, and a larger library containing 2610 members from this condition was picked and screened.

Nucleic acid sequences of resulting ethane hydroxylating mutant 35-E11 (positions given with regard to the coding sequence of wild-type P450 BM-3 nucleic acid sequence) include C142T, T234C, G235T, A237T, G247A, C248G, A249C, A284T, C324T, C427T, C527T, C554T, T617G, C681G, T711G, A758G, C766A, C872T, G985T, C986T, C1060G, A1119G, A1394G, T2132C, and A2313G. Amino acid sequence mutations compared to wild-type P450 BM-3 include R47C, V78F, A82S, K94I, P142S, T175I, A184V, F205C, S226R, H236Q, E252G, R255S, A290V, A328F, L353V, E464G, I710T.

Cell lysates for high throughput screening were prepared as described previously (Peters et al., J. Am. Chem. Soc. 125:13442 (2003); incorporated by rerence herein). High-throughput dimethyl ether (DME) screens were performed in 96 well plates as described previously. Improved mutants were selected based on an increased signal compared to 9-10A (for the saturation mutagenesis libraries) and 1-12G (for the recombination library). Reactions on octane and propane were analyzed by gas chromatography as described.

Reactions on ethane were carried out similarly to those described for propane (Peters et al., J. Am. Chem. Soc. 125: 13442 (2003); incorporated by reference herein). Because commercially-available NADPH contains 2-3% ethanol, an NADPH regeneration system was used. Thereby, the background ethanol concentration was reduced to approximately 1 µM. Ethane hydroxylation reactions were performed in 20 mL glass vials. A 5.0 mL reaction mixture contained 100, 200 or 500 nM purified protein in 0.1 M potassium phosphate buffer (pH 8.0) saturated with ethane and dioxygen. 300 μL of the regeneration system (1.66 mM NADP+, 167 U/mL isocitrate dehydrogenase, 416 mM isocitrate) was added. The vial was immediately topped with a septum, pressurized with 20 psi of ethane and stirred at 25° C. For determination of total turnover, the reaction was allowed to proceed for four hours. For rate determination the reaction was stopped at 0, 15 and 30 min. 50 μL of 5 mM 1-butanol was added to the reaction mixture as an internal standard. Ethanol and 1-butanol were subsequently derivatized to their corresponding alkyl nitrites. Control reactions were performed by repeating these steps without substrate and with inactivated protein, to correct for background levels of ethanol. Reaction buffer saturated with ethane and oxygen did not contain ethanol concentrations above this background. Reactions with ethane and corresponding control reactions without ethane or with inactivated protein were carried out in triplicate. Taking into account the background ethanol concentration of around 1 μM (1.2±0.1 μM for the control reaction without ethane or 0.8±0.1 uM for the control reaction with inactivated P450), the reactions yielded final ethanol concentrations corresponding to total turnover numbers of 50 and 250 for 53-5H and 35-E11, respectively (see e.g., FIGS. 2 and 3).

Gas chromatographic analysis of the ethanol was performed using purchased standards and a five-point calibration curve with 1-butanol as an internal standard. The samples were injected at a volume of 1 μL and analyses were performed at least in triplicate. Ethanol analysis was performed on a Hewlett-Packard 5890 Series II Plus gas chromatograph using an HP-1 column (Agilent Technologies, 30 m length, 0.53 mm ID, 2.65 uM film thickness) connected to an electron capture detector (ECD). The temperature program was: 60° C. injector, 150° C. detector, 35° oven for 3 min, 10° C./min gradient to 60° C., 60° C. gradient to 200° C., and then 200° C. for 5 min.

In addition, overoxidation of ethanol by 53-5H was tested. First, ethanol (20 μM), instead of ethane was used as the substrate under the reaction conditions described above, and no decrease in ethanol concentration was observed within experimental error (±3 uM) over the course of the reaction. Second, NMR (Varian Mercury 300 MHz) spectroscopy was used to monitor reactions of 53-5H with singly $^{13}$C-labeled ethanol (HO—$^{13}$CH$_2$CH$_3$, 57 ppm). Concentrations of $^{13}$C-labeled ethanol as low as 50 μM in the presence of 10 μM P450 (in 0.1M potassium phosphate buffer, pH=8, with 10% deuterium oxide added) could be detected using the 13C channel of the NMR. The longer relaxation rates of the carbonyl carbon atoms in acetaldehyde (206 ppm) and acetic acid (176 ppm) decrease their carbon NMR signal heights by 25-40% in the experiments, making their detection limit approximately 100 μM. Reactions using 10 μM 53-5H, 1 mM $^{13}$C-ethanol, 100 μM NADP+, 50 mM isocitrate, and 10 U/mL isocitrate dehydrogenase were stirred 12 hours at room temperature. Deuterium oxide (10% final concentration) was then added to each reaction, and their NMR spectra (averaging ~20,000 scans each) were recorded. Control reactions using 50 nM of 53-5H from the same batch, 4 mM of octane, 100 μM NADP+, 50 mM isocitrate, and 10 U/mL isocitrate dehydrogenase were also performed and the products characterized to verify that the P450 was fully active. No overoxidation products were detected in these experiments, indicating that, in the presence of 1 mM ethanol, 53-5H catalyzes less than 10 total turnovers of ethanol (see FIG. 4).

Figure 5:
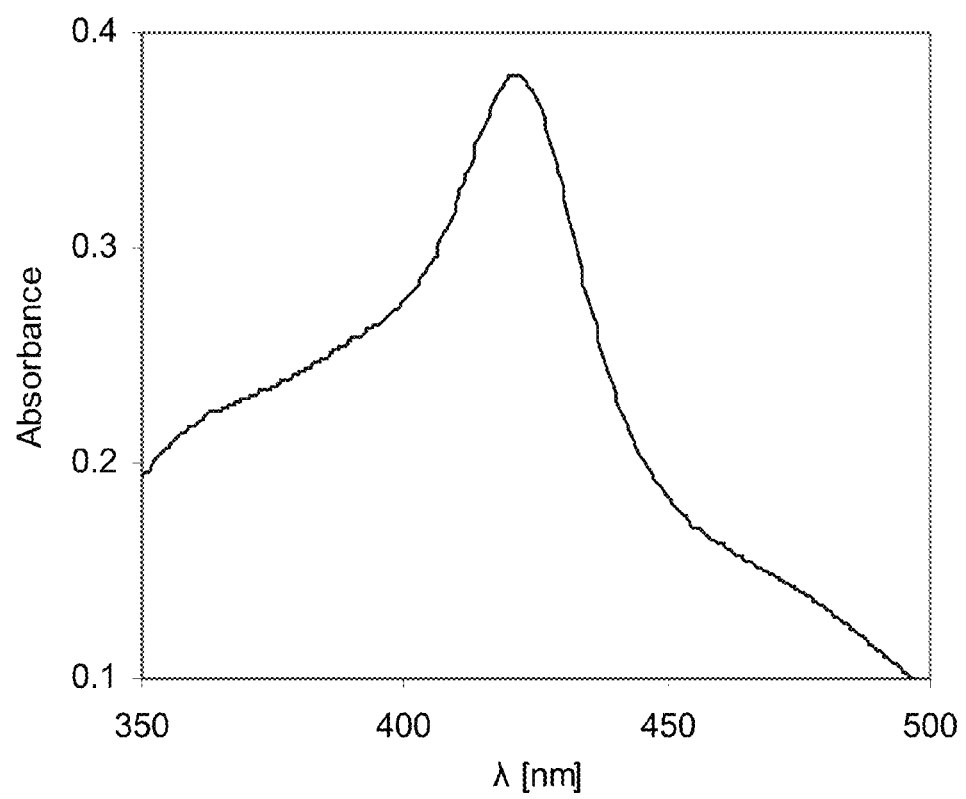

The absorption spectra for 53-5H and 35-E11 were taken using a 3 uM solution of purified P450 in a quartz cuvette. Upon incubation with ethane, no shift in equilibrium from low—($A_{max}$ at 418 nm) to high-spin ($A_{max}$ at 390 nm) configuration of the ferric P450 was observed. Octane, a good substrate, also did not induce a shift. Mutant 35-E11 behaved identically (see FIG. 5). Previously presented mutants, e.g. 9-10A exhibit a significant spin shift upon incubation with good substrates, such as octane.

NADPH oxidation rates were measured over 20 s at 25° C. using a BioSpec-1601 UV-Vis spectrophotometer (Shimadzu, Columbia, Md.) and 1 cm pathlength cuvettes. A 1 mL reaction mixture contained 100 nM P450, 166 μM NADPH and either methane-, ethane- or propane-saturated potassium phosphate buffer (0.1 M, pH 8.0) or 4 mM octane and 1% ethanol in potassium phosphate buffer (0.1M, pH 8.0). The reaction was initiated by the addition of NADPH and the decrease in absorption at 340 nm was monitored. NADPH consumption rates were also measured without substrate (see Table 2).

Octane reactions were performed in presence of 1% ethanol and the results shown in Table 1. Rates of ethanol formation were measured over 30 min using gas chromatography (GC) coupled to an electron capture detector (ECD) and are reported as nmol ethanol/min/nmol enzyme. Errors are at most 10%. Total turnover number (ttn) was measured using GC after completion of the reaction and is reported as nmol product/nmol protein. Errors are at most 10%. Initial rates of propanol and octanol formation were measured over 1 min by GC and are reported as nmol product/min/nmol protein. Errors are at most 15%. The "ee" of 2-octanol (main product) was measured by GC; the favored enantiomer is listed in parenthesis. Wild-type P450 BM-3 primarily produces 3- and 4-octanol. The yields were not sufficient for the determination of ee for wt BM-3. Mutant 9-10A contains amino acid substitutions R47C, V78A K94I, P142S, T175I, A184V, F205C, S226R, H236Q, E252G, R255S, A290V, and L353V.

TABLE 1

| Enzyme | Number of amino acid substitutions | Active site amino acid substitutions | Ethane Rate | Ethane ttn | Propane Rate | Propane ttn | Octane Rate | Octane ttn | Octane % 2-octanol | Octane % ee |
|---|---|---|---|---|---|---|---|---|---|---|
| Wild-type BM-3 | — | — | — | — | — | — | 30 | 150 | 17 | n.d |
| 9-10A | 13 | V78A | — | — | 23 | 1100 | 540 | 3000 | 82 | 50 (S) |
| 53-5H | 15 | V78F, A82S, A328F | 0.4 | 50 | 370 | 5000 | 660 | 8000 | 89 | 65 (S) |
| 35-E11 | 17 | V78F, A82S, A328F | 0.4 | 250 | 210 | 6000 | 420 | 8000 | 89 | 65 (S) |

Table 2 provides NADPH oxidation rates of 53-5H and 35-E11 in presence and absence of substrate. The coupling efficiency is estimated from product formation rate/NADPH oxidation rate. In general, NADPH oxidation rates cannot be measured on the same time scale as ethanol formation rates.

TABLE 2

| | 53-5H | | 35-E11 | |
|---|---|---|---|---|
| | NADPH oxidation rate [min$^{-1}$] | Coupling efficiency [%] | NADPH oxidation rate [min$^{-1}$] | Coupling efficiency [%] |
| no substrate | 540 | | 390 | |
| ethane | 660 | 0.06 | 520 | 0.08 |
| propane | 930 | 40 | 800 | 26 |
| octane | 820 | 80 | 660 | 64 |

Example 2

Methane Conversion

Methane hydroxylase variants were generated by an 'evolutionary' strategy in which mutations were accumulated in multiple generations of random mutagenesis and screening, in essence adapting the enzyme to exhibit higher turnover on smaller and smaller alkanes. In the first generations, the activity of BM-3 towards octane was increased and a small but appreciable activity on propane was acquired. Further evolution led to a variant which is much more active towards propane and, significantly, produced more 1-propanol. The increase in the terminal hydroxylation product was particularly interesting because the propane terminal C—H bond energy (100.4 kcal/mol) is similar to the C—H bond energy of ethane (101.1 kcal/mol).

Continued directed evolution then led to the first ethane-hydroxylating P450 BM-3 as described above. The ethane-hydroxylating P450 BM-3 variant 35-E11 was obtained by improving the electron transfer in the triple active site variant 53-5H as described. Briefly, the active site mutations in 53-5H (V78F, A82S, and A328F) were obtained by screening a library containing all possible combinations of single-site mutations of a BM-3 variant previously evolved for high activity towards propane. The 15 mutations in 53-5H (12 are not in the active site) are located in the heme domain: R47C, V78F, A82S, K94I, P142S, T175I, A184V, F205C, S226R, H236Q, E252G, R255S, A290V, A328F, L353V. While not bound to a particular mechanism of action, it is believed that the active site mutations serve to decrease the size of the active site so that ethane is bound and hydroxylated. Mutant 53-5H has only limited activity towards ethane, producing only about 50 total turnovers before it is inactivated. Variant 35-E11 was obtained by modifying the reductase domain of 53-5H to more efficiently transfer electrons to the active site during catalysis. This variant contains two mutations, one in the linker region connecting the two domains (E464G) and one in the reductase domain (I710T), that improve coupling and increase the total turnovers on ethane to more than 250.

The 35-E11 variant was tested for the ability to convert methane to methanol using the method of Anthon and Barrett (Agric. Food Chem., 52:3749 (2004)). The method was optimized so that it could detect methanol concentrations in water as low as 10 µM. Using this assay the 35-E11 variant was identified as producing methanol from methane.

Libraries of mutants of 35-E11 were screened for phenotypes indicative of either increased product formation on small gaseous substrates slightly larger than methane. Additionally, they were screened for increased coupling of the consumption of NADPH reducing equivalents to product formation. Product formation was determined by measuring total amount of dimethyl ether hydroxylation while increased coupling was determined primarily by decreased background NADPH consumption rates (measured spectrophotometrically at 340 nm in the absence of substrate).

Four libraries of mutants of 35-E11 were constructed. Two saturation mutagenesis libraries were prepared in 35-E11, in which all possible amino acid substitutions were introduced at the positions of two non-heme domain mutations, E464G and I710T. Additionally, two random mutagenesis libraries of 35-E11 were prepared by error-prone PCR such that each library contained an average of 1-2 amino acid mutations. One of these random mutagenesis libraries contained only mutations in the heme domain (residues 1 to about 455) while the other library contained mutations only in the linker between the two domains and the reductase domain (residues about 470 to 1048). These four libraries were screened as described above, and several improved variants (described below) were isolated, sequenced, and purified for further analysis.

Figure 7:
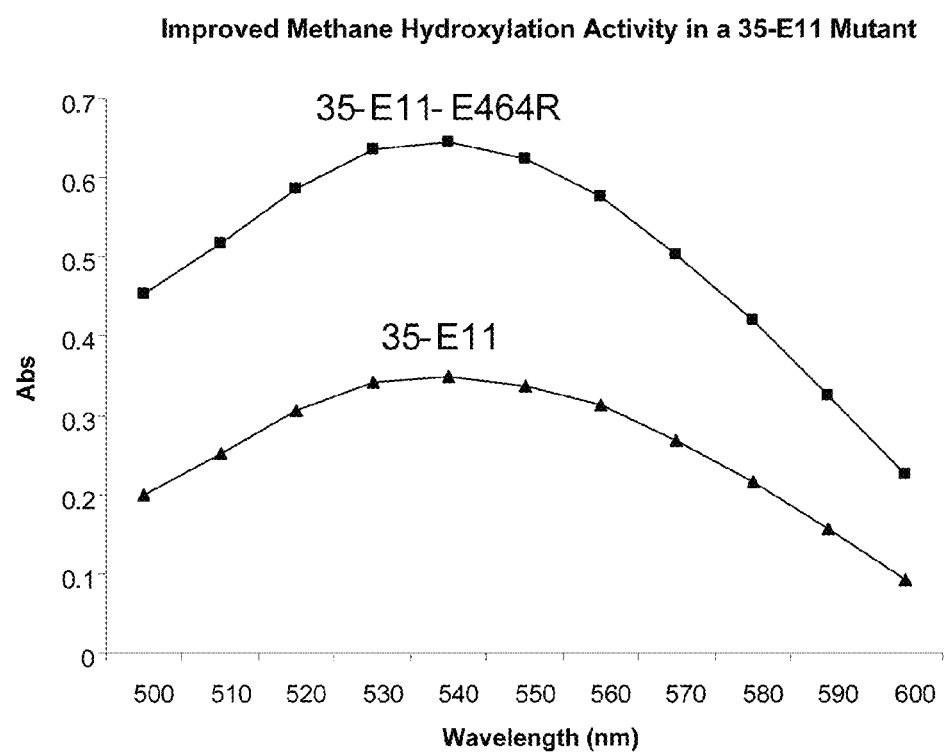
FIG. 7 depicts the spectra of methane reactions of BM-3 variant 35-E11 and the variant 35-E11-E464R after treatment with alcohol oxidase and Purpald. The peak at 550 nm corresponds to methanol produced. Solutions containing all reactants except methane do not absorb in this region when similarly treated.

The mutant BM-3 enzymes described below were purified using published procedures and used as catalysts in small reactions with methane. In glass head space vials containing magnetic stirring bars, BM-3 catalyst was added to 0.1 M potassium phosphate buffer (pH=8) saturated with methane. The vials were then crimped shut and charged to 20 psi with methane. To start the biotransformation, an NADPH regeneration system consisting of NADP+, isocitrate, and isocitric dehydrogenase was added through a syringe. The reaction was allowed to stir 12-15 hours. Methanol production was measured using a coupled enzyme assay. Aliquots of the reaction were transferred to 96-well microtitre plates and reacted with the enzyme alcohol oxidase for 5 minutes at room temperature. Alcohol oxidase converts the methanol produced by the BM-3 variants into formaldehyde which can be detected with the dye Purpald. To detect formaldehyde and quench the alcohol oxidase reaction, a solution of Purpald in 2 M NaOH was added and allowed to react for one hour. The purple color that Purpald forms in the presence of formaldehyde was quantified one hour later by spectrophotometrically reading the well at 550 nm and comparing the absorbance against similarly-treated solutions of BM-3, NADPH regeneration system, and methane-free buffer spiked with known concentrations of methanol. The results of these biotransformations are reported in Table 3 and sample spectra from the colorimetric assay are shown in FIG. 7.

As expected from their relative increase in activity towards the screening substrates, several of the mutants isolated from these libraries have increased activity towards methane. Three of these mutants were isolated from the saturation library of the linker position 464: E464R, E464Y, and E464T. None of these mutants exhibited higher activity towards the screening substrate DME, but all of them had a 30-40% lower NADPH background consumption rate in the screen, indicating that the roughly equivalent production of oxidized DME they produced compared to the parent 35-E11 required less NADPH. This increase in coupling on DME translated to an increase in TTN of methane (from 8 to 11-13). From the heme domain library, mutant 20-D3 was identified for its increased activity towards DME. Even though the background consumption rate of NADPH was increased by an equivalent amount in the screen, more of these reducing equivalents are transferred to the heme domain of this mutant in the presence of substrate, leading to an increase in methanol formation (from 8 to 10 TTN). This mutation, H285R, is located on the surface of the heme domain, near the putative interface between the heme and reductase domains. From the reductase domain library, two mutants, 23-1D and 21-4G, were identified for their decreased background NADPH consumption rates, leading to an increase in methanol formation. The mutations in these variants, Q645R/P968L and D631N, respectively, are located outside of the electron transfer pathway. Their presence, however, gives 35-E11 increased TTN on methane (from 8 to 10-11).

The methane hydroxylation activity reported here is not sufficiently high for a practical process for converting methane to methanol. TTN must be increased, and coupling of methanol production to consumption of the cofactor must be increased, or the enzyme will use too must However, the methods of making mutations and screening the libraries described here can be used to further improve the activity, TTN and coupling.

Whole Cell Catalysis.

Cell mass is generated using a carbon source such as glucose and nitrogen and other nutrients supplied to the cells. At an optimum cell density, expression of the P450 biocatalyst is induced using strategies well known in the art. After optimum biocatalyst expression levels are reached, nitrogen is removed from the medium to prevent further growth of the cell, ensuring that any additional carbon source supplied to the non-growing cells is converted into reducing equivalents for methanol production. Methane and oxygen are then supplied to the culture at saturating levels assisted by mixing with either propeller-type mixing or air-lift mixing. As methanol is accumulated in the culture, portions of the culture are separated from the main reactor, centrifuged to remove cells (which are added back to the main reactor), and the supernatant treated to recover the methanol. The process can be constructed as either a batch or continuous process.

Specifically, the first demonstration of whole cell methanol production using a catalyst based on BM-3 or one of its homologs expressed in a laboratory strain of E. coli will occur in a small fermentor where oxygen and glucose levels can be easily monitored and adjusted. Oxygen levels are particularly important, because in the absence of oxygen, the facultative aerobe E. coli will begin to degrade glucose into ethanol and carbon dioxide. This causes the cell to up-regulate the production of alcohol dehydrogenases that will consume the trace levels of methanol produced by our catalyst. Additionally, the ethanol that accumulates from anaerobic metabolism interferes with our methanol detection assays. To perform the whole cell reaction in the fermentor, a 1 L culture of cells will be grown to high density ($OD_{600}$=1-2) in Terrific Broth containing 1 μg/mL ampicillin (for retention of the PCWori plasmid containing the biocatalyst gene). Catalyst expression will be induced by the addition of 1 mM IPTG and 0.5 mM δ-amino levulinic acid. After 12-24 hours, the culture will be centrifuged to collect the cells containing biocatalyst. After removal of the supernatant, the cells will be resuspended and washed in a nitrogen free minimal medium to remove traces of the terrific broth. The cells in nitrogen free minimal medium will then be added to a fermentor and fed 0.5% glucose. During the reaction, additional glucose will be added to maintain this level. In the fermentor, oxygen will be added to the culture at saturating levels and will be monitored and added during the reaction as needed to maintain these levels. To initiate the reaction, methane will be bubbled through the culture. The lack of nitrogen in the culture forces the cells into a non-growing state, allowing most of the glucose aerobically consumed to be converted into NADPH for the biocatalyst.39 An E. coli cell functioning as an aerobe also has a limited ability to metabolize alcohols, including the methanol product.40 Methanol will be measured in this culture as described for the in vitro reactions in this work.

The present data demonstrates that methane hydroxylation activity can be achieved through modification of various cytochrome P450 enzymes by directed evolution. Since this enzyme can be expressed in heterologous hosts that do not metabolize methanol as it is produced, the invention of this biocatalyst also makes the production of methanol using a whole cell process possible.

Reactions for enzyme-catalyzed conversion of methane to methanol were carried out in 10 mL glass headspace vials. A 470 μL reaction mixture containing 5 μM purified BM-3 variant in 0.1 M potassium phosphate buffer (pH 8.0) was first added to the vial. The vial was immediately topped with a septum, pressurized with 30 psi of methane and shaken at 4° C. for 1 hour. Then 30 μL of an NADPH regeneration system (1.66 mM NADP+, 167 U/mL isocitric dehydrogenase, 416 mM isocitrate) was added to initiate the reaction. For determination of total turnover, the reaction was allowed to proceed for 20 hours at room temperature.

The amount of methanol product formed during the 20 hr methane reaction was quantified colorimetrically with the use of alcohol oxidase and Purpald. 190 μL of the reaction mixture is transferred onto a single cell of a 96 well plate. 10 μL of 0.05 U/μL solution of alcohol oxidase (from *Pichia pastoris*, purchased from Sigma-Aldrich) was added to cell and allowed to incubate at room temperature for 5 minutes. During this time, the alcohol oxidase converts the methanol into formaldehyde. Purpald (168 mM in 2 M NAOH) was then added to form a purple product with the formaldehyde in solution. The purple color was read approximately 1 hour later at 550 nm using a Spectramax Plus microtiter plate reader. The concentration of methanol was determined based on the measure absorbance in comparison to a methanol calibration curve. The methanol calibration curve was generated with several standards. Each standard contained 100 μL of a methanol solution (10, 20, 40, 60, 100 μM) and 90 μL of the methane reaction mixture described above, without the methane pressurization.

Table 3 provides amino acid substitution, screening and activity data for second-generation 35-E11 variants exhibiting methane hydroxylation activity. The relative dimethyl ether (DME) activity was measured, 1 hour after treatment with Purpald, as the average net and absorbance at 550 nm from 8 microtitre plate DME reactions of the mutant compared to 8 equivalent reactions of 35-E11. All values were normalized by measuring the P450 concentration in each well with CO binding. "Asteriks" indicate criteria used to select mutants from libraries for further characterization. The oxidation rate is measured as absorbance change at 340 nm over 1 minute upon the addition of NADPH to 8 microtitre plate wells containing P450-containing cell lysate and compared to 8 equivalent reactions of 35-E11. All values were normalized by measuring the P450 concentration in each well with CO binding. The total turnover number (TTN) was measured as the absorbance at 550 nm of methane reactions with each mutant after treatment with alcohol oxidase and Purpald.

TABLE 3

| Mutant | AA substitutions to 35-E11 | Relative DME activity in screen | Relative background NADPH oxidation rate | Methane TTN |
|---|---|---|---|---|
| 35-E11 | — | 1 | 1 | 8 |
| 35-E11-E464R | E464R | 0.9 | 0.6* | 12 |
| 35-E11-E464Y | E464Y | 0.8 | 0.7* | 13 |
| 35-E11-E464T | E464T | 0.8 | 0.7* | 11 |
| 20-D3 | H285R | 1.7* | 1.6 | 10 |
| 23-1D | Q645R, P968L | 0.7 | 0.8* | 11 |
| 21-4G | D631N | 1.1 | 0.7* | 10 |

Table 4 provides an extensive list of amino acid substitutions in various parental P450 sequences (e.g., SEQ ID NO: 1, 2, 3, 4, 5, and 6).

TABLE 4

| Mutation | Seq. ID No. 1 | Seq. ID No. 2 | Seq. ID No. 3 | Seq. ID No. 4 | Seq. ID No. 5 | Seq. ID No. 6 |
|---|---|---|---|---|---|---|
| Heme Domain Mutation in 35-E11 | R47C | G48C | V48C | D49C | K54C | S51C |
| Active Site Mutation in 35-E11 | V78F | V79F | V79F | V80F | L85F | V82F |
| Active Site Mutation in 35-E11 | A82S | A83S | S83S | G84S | A89S | G86S |
| Heme Domain Mutation in 35-E11 | K94I | P95I | P95I | P96I | P101I | P98I |
| Heme Domain Mutation in 35-E11 | P142S | P143S | A143S | P144S | A149S | V146S |
| Heme Domain Mutation in 35-E11 | T175I | N176I | T176I | T177I | M182I | E179I |
| Heme Domain Mutation in 35-E11 | A184V | A185V | A185V | A186V | A191V | I188V |
| Heme Domain Mutation in 35-E11 | F205C | F206C | F206C | F207C | A212C | L208C |
| Heme Domain Mutation in 35-E11 | S226R | N227R | N227R | S228R | V232R | E231R |
| Heme Domain Mutation in 35-E11 | H236Q | R238Q | L238Q | R239Q | L243Q | A242Q |
| Heme Domain Mutation in 35-E11 | E252G | E254G | E254G | E255G | A259G | V258G |
| Heme Domain Mutation in 35-E11 | R255S | R257S | R257S | R258S | R262S | R262S |
| Heme Domain Mutation in 20-D3 | H285R | D287R | E287R | D288R | G292R | D291R |
| Heme Domain Mutation in 35-E11 | A290V | Y292V | Q292V | Y293V | Y297V | Y296V |
| Active Site Mutation in 35-E11 | A328F | A330F | A330F | A331F | A336F | A337F |
| Heme Domain Mutation in 35-E11 | L353V | I355V | V355V | I357V | I361V | I363V |
| Linker Mutation in 35-E11 and Derivatives | E464G/R/Y/T | E475G/R/Y/T | D467G/R/Y/T | I477G/R/Y/T | S472G/R/Y/T | S480G/R/Y/T |
| Reductase Domain Mutation in 21-4G | D631N | E641N | N634N | E644N | T640N | D648N |
| Reductase Domain Mutation in 23-1D | Q645R | Q656R | T648R | Q659R | R656R | E664R |
| Reductase Domain Mutation in 35-E11 | I710T | N721T | L713T | N724T | L723T | L733T |

TABLE 4-continued

| Mutation | Seq. ID No. 1 | Seq. ID No. 2 | Seq. ID No. 3 | Seq. ID No. 4 | Seq. ID No. 5 | Seq. ID No. 6 |
|---|---|---|---|---|---|---|
| Reductase Domain Mutation in 23-1D | P968L | E980L | E972L | E983L | P985L | D997L |

Example 3

Regiospecific Activity

Biocatalysis provides a useful alternative to classic chemical synthesis due to the inherent specificity of enzymes. Enantioselective catalysts that accept only a single enantiomer or regioisomer of a substrate have been created using directed evolution. The enzymatic, regio- and enantioselective functionalization of achiral compounds, however, is a greater challenge. In particular, the regio- and enantioselective hydroxylation of saturated hydrocarbons remains a problem in chemical synthesis.

As previously noted, cytochrome P450 BM-3 is a soluble protein that contains an hydroxylase domain and a reductase domain on a single polypeptide. Also as previously noted, cytochrome P450 BM-3 variants are provided that exhibit efficient alkane hydroxylase activity. One of these variants, 9-10A, was further modified at eleven active site residues that are in close contact to the substrate and screened for activity. Beneficial mutations were recombined, generating variants that catalyze the hydroxylation of linear alkanes with varying regioselectivities.

Mutant 9-10A exhibits high activity towards alkanes as small as propane. The alkane hydroxylation properties of this mutant are detailed in Tables 5 and 6.

In Table 5 the product distribution is determined as ratio of a specific alcohol product to the total amount of all alcohol products (given in %). The product distribution for ketones was similar to alcohol product distribution. The numbers reported here are the (%) total of all ketones relative to total products (alcohols+ketones). The favored enantiomer is listed in parentheses.

enzyme. Octane reactions contained 10-25 nM P450, 500 uM NADPH, and 4 mM octane in 1% ethanol and potassium phosphate buffer. Propane reactions contained 10-25 nM protein, potassium phosphate buffer saturated with propane, and an NADPH regeneration system containing 100 uM NADP+, 2 U/mL isocitrate dehydrogenase, and 10 mM isocitrate.

TABLE 6

| Mutant | Substrate | Rate of NADPH Consumption $(min^{-1})^{[a]}$ | Rate of Product Formation $(min^{-1})^{[b]}$ | Coupling to NADPH $(\%)^{[c]}$ | Total Turnovers$^{[d]}$ |
|---|---|---|---|---|---|
| 9-10A | octane | 2600 | 540 | 21 | 3000 |
|  | propane | 420 | 23 | 5 | 1100 |

As shown in Table 5 mutant 9-10A hydroxylates octane into a mixture of octanols and ketones. The distribution of these products is different from the distribution produced by wild type BM-3. 9-10A contains 14 mutations in the heme domain, only one of which, V78A, is located in the active site. This data indicates that active site changes, especially multiple changes, may alter product distributions and increase activity. For example, two other active-site mutations, A82L and A328V, shifted the regioselectivity of alkane hydroxylation predominantly to a single, subterminal (w−1) position. Based on these results, active site variants were generated in order to obtain enzymes with altered regioselectivity of hydroxylation and altered substrate specificities.

Screening libraries by spectroscopically monitoring NADPH consumption rates in the presence of the alkane often selects for mutants with NADPH oxidation rates highly uncoupled to product formation. This can be overcome

TABLE 5

| Mutant | Product | Propane | Hexane | % ee | heptane | % ee | Octane | % ee | Nonane | % ee | Decane | % ee |
|---|---|---|---|---|---|---|---|---|---|---|---|---|
| 9-10A | 1-alcohol | 8 | 0 |  | 1 |  | 1 |  | 0 |  | 1 |  |
|  | 2-alcohol | 92 | 6 | 14 (s) | 26 | 7 (S) | 53 | 50 (S) | 39 | 60 (S) | 16 |  |
|  | 3-alcohol |  | 95 | 41 (s) | 41 | 8 (S) | 20 |  | 59 |  | 32 |  |
|  | 4-alcohol |  |  |  | 33 |  | 26 |  | 3 |  | 51 |  |
|  | Ketones |  | <1 |  | 3 |  | 5 |  | 5 |  | 6 |  |

For the data shown in Table 6 the initial NADPH consumption rates were measured over 15 seconds at 340 nm as nmol NADPH/min/nmol protein. Octane reactions contained 100 nM P450, 166 uM NADPH, and 4 mM octane in 1% ethanol and potassium phosphate buffer. Propane reactions contained 200 nM P450, 166 uM NADPH, and propane-saturated potassium phosphate buffer. Errors are at most 10%. Initial rates were measured by GC over 1 minute as nmol total products/min/nmol protein. Octane reactions contained 100 nM P450, 500 uM NADPH, and 4 mM octane in 1% ethanol and potassium phosphate buffer. Propane reactions contained 1 uM P450, 500 uM NADPH, and propane-saturated potassium phosphate buffer. Coupling was determined by ratio of product formation rate to NADPH consumption rate. Total turnover numbers were determined as nmol product/nmol through the use of surrogate substrates that mimic desired substrates, yet yield species when hydroxylated that are easily detected either directly or with the addition of a dye. For example, the screen for the high-throughput identification of mutant BM-3 enzymes with activity towards propane as described previously uses dimethyl ether (DME) as a propane surrogate substrate. Upon hydroxylation, it decomposes into methanol and dye-sensitive formaldehyde. In addition, hexyl methyl ether (HME) may be used as a surrogate for octane. It shares most of the physical properties of octane, including solubility in buffer, size, shape, and strength of its C—H bonds. When HME is hydroxylated at its methoxy carbon, it also produces an equivalent of formaldehyde which is visually detected at concentrations as low as 10 µM with the dye Purpald (see FIG. 25). Hexanal, the aldehyde product formed when the α-carbon of the hexyl group is hydroxylated, is practically unreactive towards Purpald at some concentrations used in the present screens. Formaldehyde is approximately 42 times more sensitive to Purpald than hexanal (see FIG. 26). This disproportionate response makes HME, in contrast to the symmetric ether DME, a regio-selective screen for terminal alkane hydroxylation.

Small libraries of changes at each individual active site position in 9-10A were made to identify changes that either increase its activity towards alkanes or alter its regioselectivity. The 11 key active site residues were chosen for their proximity, i.e. within 5 Angstroms of the 10 carbon atoms closest to the heme cofactor, to the bound fatty acid substrates co-crystallized with BM-3 heme domain in published crystal structures. These active site residues are A74, L75, V78, F81, A82, F87, T88, T260, I263, A264, and A328. For example, crystal structures of wildtype P450 BM-3 with and without substrate reveal large conformational changes upon substrate binding at the active site. The substrate free structure displays an open access channel with 17 to 21 ordered water molecules. Substrate recognition serves as a conformational trigger to close the channel, which dehydrates the active site, increases the redox potential, and allows dioxygen to bind to the heme. In the present studies saturation mutagenesis libraries were made at each of these 11 positions. The libraries were screened for activity towards dimethyl ether (DME) and hexylmethyl ether (HME).

Twenty-one single active site mutants with increased activity towards either of these substrates were isolated. Mutations that improved the activity were found at amino acid positions L75 (I, W), A78 (T, F, S), A82 (T, S, F, I, C, G, L), F87 (I, V, L), T88 (C), T260 (N, L, S) and A328 (L, F, M). The single active site mutants of 9-10A were characterized by their altered regioselectivity towards octane. Each of these mutations produces a characteristic octanol product distribution as a result of their presence altering the active site geometry above the heme cofactor. These 21 different mutants and their regioselectivity towards octane are listed in Table 7. Transformations were carried out using cell lysates. The mutations were generated in variant 9-10A (with amino acid mutations R47C, V78A, K94I, P142S, T175I, A184V, F205C, S226R, H236Q, E252G, R255S, A290V, L353V). "Others" indicates overoxidation products (ketones and aldehydes) with a similar product distribution as the alcohols. "Rate" was measured as nmol octanol/nmol P450/minute. "TTN" was measured as nmol octanol/nmol P450 produced in 4 hour reaction.

TABLE 7

| mutation [b] | 1-ol [%] | 2-ol [%] | 3-ol [%] | 4-ol [%] | Others [c] | rate [d] | ttn [e] |
|---|---|---|---|---|---|---|---|
|  | 0 | 51 | 21 | 27 | 1 | 540 | 3000 |
| L75I | 3 | 42 | 18 | 17 | 20 | 210 | 4500 |
| L75W | 3 | 6 | 18 | 24 | 9 | 200 | 4000 |
| A78T | 4 | 22 | 27 | 45 | 2 | 500 | 4000 |
| A78F | 4 | 37 | 17 | 31 | 11 | 380 | 3000 |
| A78S | 5 | 48 | 18 | 20 | 9 | 260 | 2500 |
| A82T | 5 | 23 | 25 | 44 | 3 | 340 | 2700 |

TABLE 7-continued

| mutation [b] | 1-ol [%] | 2-ol [%] | 3-ol [%] | 4-ol [%] | Others [c] | rate [d] | ttn [e] |
|---|---|---|---|---|---|---|---|
| A82S | 6 | 40 | 19 | 26 | 9 | 300 | 2600 |
| A82F | 4 | 26 | 20 | 48 | 2 | 140 | 3000 |
| A82I | 4 | 11 | 21 | 59 | 5 | 600 | 3500 |
| A82C | 5 | 26 | 26 | 42 | 1 | 200 | 3000 |
| A82G | 7 | 52 | 17 | 23 | 1 | 360 | 2000 |
| F87I | 8 | 70 | 6 | 3 | 13 | 60 | 2600 |
| F87V | 5 | 52 | 13 | 4 | 26 | 240 | 3600 |
| F87L | 7 | 55 | 22 | 12 | 4 | 60 | 2300 |
| T88C | 4 | 51 | 21 | 22 | 2 | 460 | 4000 |
| T260L | 7 | 67 | 11 | 10 | 5 | 260 | 2500 |
| T260S | 6 | 39 | 26 | 29 | 0 | 160 | 3000 |
| T260N | 6 | 29 | 23 | 42 | 0 | 300 | 2500 |
| A328F | 6 | 88 | 4 | 0 | 2 | 40 | 2800 |
| A328M | 24 | 71 | 0 | 0 | 5 | 10 | 700 |
| A328L | 13 | 87 | 0 | 0 | 0 | 20 | 1000 |

The original amino acids and the beneficial mutations described above were recombined to form a library of mutants containing all possible combinations of these mutations. Mutations A82L and A328V were included in this library as they had proven to be important determinants of regioselectivity in previous experiments. Many of the active site mutations are too close to each other on the encoding gene such that standard methods such as DNA shuffling or StEP could not be used to recombine them. Therefore, the recombination library was assembled stepwise using designed oligonucleotide primers containing the mutations. Mutant 1-12G2 was used as a control in the screening procedure. A total of 16 mutants with improved activity towards DME or HME relative to 1-12G were selected for purification and further characterization. Octane was used as a model substrate for alkane hydroxylation and rates of product formation, total turnover number and regioselectivity were determined (Table 8). Mutations were found at amino acid positions 75, 78, 82, 87 and 328. While building the library ten improved members of a partial library were screened and sequenced. All possible amino acids at position 75 and 260 were identified, and four out of eight amino acids at position 78.

Table 8 provides a listing of mutations, product distribution, rates and total turnover numbers of octane hydroxylation reactions catalyzed by BM-3 active site mutants.

Mutations are relative to variant 9-10A (described above). Wild-type has a valine at position 78. The product distribution determined as ratio of a specific alcohol product to the total amount of alcohol products (given in %). The formation of ketones was also observed but is less than 5% of the total amount of product. The initial rates of product formation were measured by GC over 60 s as nmol total products/min/nmol protein. The reactions contained P450 (100 nM), NADPH (500 µM), and octane (4 mM) in ethanol (1%) and potassium phosphate buffer (0.1 M, pH=8.0). The total turnover numbers are determined as nmol product/nmol protein. The reactions contained P450 (25 nM), NADPH (500 µM), and octane (4 mM) in ethanol (1%) and potassium phosphate buffer (0.1 M, pH=8.0).

TABLE 8

| 9-10A | A75 | A78[a] | A82 | F87 | A328 | 4-ol [%] | 3-ol [%] | 2-ol [%] | 1-ol [%] | ttn[c] | rate[d] |
|---|---|---|---|---|---|---|---|---|---|---|---|
| 9-10A | | | | | | 27 | 21 | 51 | 0 | 3000 | 540 |
| 77-9H | | T | G | | L | 0 | 3 | 45 | 52 | 1300 | 160 |
| 1-7D | I | F | G | | L | 1 | 6 | 55 | 38 | 1300 | 220 |
| 68-8F | | F | G | | L | 2 | 8 | 58 | 31 | 1400 | 180 |
| 49-9B | | | G | V | L | 0 | 2 | 76 | 20 | 3800 | 310 |
| 35-7F | | F | S | | L | 1 | 6 | 74 | 18 | 2000 | 200 |
| 1-5G | I | F | S | | L | 1 | 7 | 74 | 17 | 2200 | 380 |
| 13-7C | | T | | | L | 1 | 8 | 74 | 17 | 2600 | 310 |
| 49-1A | | T | G | V | L | 0 | 2 | 81 | 15 | 3700 | 350 |
| 2-4B | I | T | | | L | 1 | 8 | 76 | 14 | 3900 | 320 |
| 12-10C | | | G | V | V | 1 | 6 | 77 | 12 | 3100 | 240 |
| 11-8E | | | | V | L | 0 | 2 | 87 | 8 | 5700 | 550 |
| 41-5B | | F | G | | V | 5 | 15 | 68 | 7 | 1800 | 370 |
| 29-3E | | F | G | | F | 3 | 10 | 79 | 6 | 3200 | 160 |
| 7-11D | | | F | | V | 2 | 13 | 78 | 6 | 2200 | 150 |
| 29-10E | | | F | | F | 1 | 8 | 84 | 5 | 3200 | 140 |
| 53-5H | | F | S | | F | 1 | 5 | 87 | 3 | 7400 | 660 |

The HME screening procedure was used to identify BM-3 variants with a regioselectivity shifted towards the terminal methyl carbon of the alkane chain. In general, mutants with high total turnover of HME in the screen produced more 1-octanol than compared to 1-12G. The total amount of 1-octanol formed (percent of 1-octanol multiplied by ttn) correlates well with the amount of HME converted. For example, mutant 77-9H (see Table 8 above) is not improved relative to 1-12G when considering rates and total turnovers on octane, but this mutant converts octane to 52% 1-octanol, making it highly active towards HME in the screen. The proportion of 1-octanol in the product mixture varies from three to 51%. Single active site mutants that showed significantly different regioselectivities were recombined. Upon recombination and screening for shifts towards terminal hydroxylation all the identified variants are selective for the terminal methyl or penultimate subterminal methylene group. Screening the recombination library e.g. for hydroxylation of the third or fourth carbon of a linear alkane chain may identify variants that exhibit this specific regioselectivity.

The recombination library contains approximately 9,000 different mutants of P450 BM-3, each of which contains a characteristic active site. More than 70% of these were active towards DME or HME. Data provided herein indicate that mutations in the active site can yield variants that hydroxylate complex substrates such as 2-cyclopentyl-benzoxazole with high regio- and enantioselectivity, yielding potentially valuable intermediates for chemical synthesis (see example below).

Application of Active Site Mutations to Homologous Proteins:

Mutant 9-10A described above was acquired by accumulating point mutations in directed evolution experiments. An alternative method for making libraries for directed evolution to obtain P450s with new or altered properties is recombination, or chimeragenesis, in which portions of homologous P450s are swapped to form functional chimeras. Recombining equivalent segments of homologous proteins generates variants in which every amino acid substitution has already proven to be successful in one of the parents. Therefore, the amino acid mutations made in this way are less disruptive, on average, than random mutations. Recently, the structure-based algorithm "SCHEMA" was developed. The algorithm identifies fragments of proteins that can be recombined to minimize disruptive interactions that would prevent the protein from folding into its active form. P450 BM-3 and homologs thereof are soluble fusion proteins consisting of a catalytic heme-domain and an FAD- and FMN-containing NADPH reductase. They require dioxygen and an NADPH cofactor to catalyze substrate hydroxylation. However, the heme domain can utilize hydrogen peroxide via the peroxide "shunt" pathway for catalysis. While this 'peroxygenase' activity is low in CYP102A1, it is enhanced by the amino acid substitution F87A. A similar effect has been shown for the equivalent F88A mutation in CYP102A2.

SCHEMA was used to design chimeras of P450 BM-3 and its homolog CYP102A2 sharing 63% amino acid sequence identity. Fourteen of the seventeen constructed hybrid proteins were able to fold correctly and incorporate the heme cofactor, as determined by CO difference spectra. The folded chimeras exhibited peroxygenase activity. A large library of chimeras made by SCHEMA-guided recombination of BM-3 with its homologs CYP102A2 and CYP102A3 contains more than 3000 new properly folded variants of BM-3. In addition to creating new biocatalysts, these chimeragenesis studies demonstrate that the homologous P450 enzymes CYP102A2 and CYP102A3 are similar enough to BM-3 to recombine in this fashion and still retain a high probability of folding.

Regioselectivity of Variant 77-9H for the Hydroxylation of n-Alkanes:

Mutant 77-9H with the highest selectivity for terminal hydroxylation was characterized in reactions with alkanes of chain length C6 to C10. The product distributions summarized in Table 9 show that mutant 77-9H hydroxylates only octane primarily at the terminal position. Alkanes shorter or longer than octane are hydroxylated mainly at the 2-position. Wildtype BM-3 hydroxylates lauric and palmitic acid at subterminal positions. Lauric acid is hydroxylated mainly (48%) at the ω-1 position, while palmitic acid is hydroxylated at the ω-2 position (48%). On fatty acids, mutant 77-9H shows a similar trend, with selectivity for specific subterminal positions (see Table 10). Residues that contact the terminal eight carbons of the substrate were altered based on the crystal structure with bound palmitoylglycine. Amino acid residues outside this region have not been modified, particularly those interacting with the carboxyl moiety.

TABLE 9

| Substrate | 1-ol [%] | 2-ol [%] | 3-ol [%] | 4-ol [%] | 5-ol [%] |
|---|---|---|---|---|---|
| hexane | 11.4 | 83.8 | 4.9 | | |
| heptane | 21.3 | 74.3 | 4.2 | 0.2 | |
| octane | 51.8 | 45.1 | 2.8 | 0.3 | |

TABLE 9-continued

| Substrate | 1-ol [%] | 2-ol [%] | 3-ol [%] | 4-ol [%] | 5-ol [%] |
|---|---|---|---|---|---|
| nonane | 9.7 | 88.1 | 1.5 | 0.7 | 0.0 |
| decane | 5.5 | 91.8 | 2.0 | 0.7 | 0.0 |

For Table 9 shows product distribution determined as ratio of a specific alcohol product to the total amount of alcohol products (given in %). The formation of ketones was also observed but is less than 10% of the total amount of product.

TABLE 10

| Substrate | ω [%] | ω-1 [%] | ω-2 [%] | ω-3 [%] |
|---|---|---|---|---|
| lauric acid | 7.5 | 52.1 | 2.8 | 37.5 |
| palmitic acid | 8.9 | 5.2 | 83.0 | 3.0 |

Table 10 shows product distributions for hydroxylation of fatty acids catalyzed by cytochrome P450 BM-3 77-9H. Product distribution was determined as ratio of a specific hydroxylation product to the total amount of hydroxylation products (given in %). P450 BM-3 mutant F87A has been reported to support ω-hydroxylation of lauric acid. However, data provided herein shows that the F87A mutation broadens regioselectivity and shifts hydroxylation away from the terminal position. In the present studies, the F87A substitution was engineered into wild-type P450 BM-3 and 9-10A. The distribution of alkane and fatty acid hydroxylation product regioisomers were analyzed. Neither variant supports terminal hydroxylation activity on alkanes (Table 11) or fatty acids (Table 12). Table 11 shows product distributions for hydroxylation of alkanes catalyzed by cytochrome P450 BM-3 variants wt F87A and 9-10A F87A.

TABLE 11

| Mutant | Substrate | 1-ol [%] | 2-ol [%] | 3-ol [%] | 4-ol [%] | 5-ol [%] |
|---|---|---|---|---|---|---|
| wt F87A | hexane | 0 | 54 | 46 | | |
| | heptane | 0 | 36 | 61 | 3 | |
| | octane | 0 | 14 | 43 | 44 | |
| | nonane | 0 | 7 | 20 | 2 | 72 |
| | decane | 0 | 10 | 9 | 0 | 81 |
| 9-10A F87A | hexane | 0 | 42 | 57 | | |
| | heptane | 2 | 62 | 34 | 3 | |
| | octane | 1 | 55 | 37 | 7 | |
| | nonane | 0 | 24 | 46 | 5 | 25 |
| | decane | 0 | 14 | 23 | 1 | 62 |

Table 12 shows product distributions for fatty acid hydroxylation catalyzed by cytochrome P450 BM-3 variants wt F87A and 9-10A F87A.

TABLE 12

| Mutant | Substrate | ω [%] | ω-1 [%] | ω-2 [%] | ω-3 [%] | ω-4 [%] | ω-5 [%] | ω-6 [%] | ω-7 [%] |
|---|---|---|---|---|---|---|---|---|---|
| wt-F87A | lauric acid | 0 | 5 | 9 | 39 | 20 | 27 | 0 | 0 |
| | palmitic acid | 0 | 11 | 36 | 18 | 22 | 13 | 0 | 0 |
| 9-10A-F87A | lauric acid | 0 | 5 | 6 | 28 | 14 | 47 | 0 | 0 |
| | palmitic acid | 0 | 0 | 1 | 1 | 2 | 8 | 20 | 68 |

Total turnover numbers (ttn) and rates of product formation were measured for hydroxylation of the different alkanes by 77-9H (see Table 13). The rates of product formation range from 112 min$^{-1}$ (for heptane) to 742 min$^{-1}$ (for nonane). The highest turnover rates of cytochromes P450 that carry out terminal hydroxylation reactions, however, are an order of magnitude lower than those of 77-9H. Wildtype BM-3 hydroxylates alkanes at rates that are an order of magnitude lower (e.g., 30 min-1 for octane). To determine TTN, the enzyme was diluted to a concentration at which the P450 is neither oxygen-limited nor inactivated due to dialysis of the flavins. The total turnover number was found to be substrate-dependent and generally increases with the alkane chain length. Rates of substrate hydroxylation appear to follow the same trend. It is well known that unproductive dissociation of reduced oxygen species can lead to the formation of superoxide or peroxide, which inactivate the enzyme. Consistent with this is the fact that the enzyme supports the most turnovers on nonane, the substrate for which the coupling efficiency is the highest (66%, Table 13).

TABLE 13

| Substrate | ttn[a] | rate of product formation [min$^{-1}$][b] | rate of NADPH oxidation [min$^{-1}$][c] | coupling efficiency [%][d] |
|---|---|---|---|---|
| hexane | 1800 ± 130 | 251 ± 29 | 1560 ± 60 | 16.1 ± 2.0 |
| heptane | 1730 ± 110 | 112 ± 9 | 1630 ± 20 | 6.9 ± 0.6 |
| octane | 3040 ± 150 | 236 ± 24 | 1630 ± 30 | 14.5 ± 1.7 |
| nonane | 4240 ± 680 | 742 ± 30 | 1150 ± 100 | 65.6 ± 9.3 |
| decane | 2831 ± 225 | 318 ± 47 | 940 ± 50 | 33.4 ± 7.2 |

For Table 13, total turnover numbers were determined as nmol product/nmol protein. The reactions contained P450 (25 nM), an NADPH regeneration system (166 μM NADP+, 6.6 U/mL isocitrate dehydrogenase, 41.6 mM isocitrate) and octane (4 mM) in ethanol (2%) and potassium phosphate buffer (0.1 M, pH 8.0). The rates of product formation were measured by GC over 20 s as nmol total products/min/nmol protein. The reactions contained P450 (200 nM), NADPH (500 μM) and octane (2 mM) in ethanol (2%) and potassium phosphate buffer (0.1 M, pH 8.0). The rates of NADPH oxidation were measured over 20 s at 340 nm as nmol NADPH/min/nmol protein. The reactions contained P450 (200 nM), NADPH (160 μM), and octane (2 mM) in ethanol (2%) and potassium phosphate buffer (0.1 M, pH 8.0). The background NADPH oxidation rate (without substrate) rate was 220/min. The coupling efficiency is the ratio of product formation rate to NADPH oxidation rate.

Wildtype P450 BM-3 tightly regulates electron transfer from the cofactor (NADPH) to the heme. In the absence of substrate, a weakly-bound water molecule acts as the sixth, axial ligand of the heme iron. Substrate replaces this water molecule, perturbing the spin-state equilibrium of the heme iron in favor of the high-spin form and also increases the heme iron reduction potential by approximately 130 mV. These events trigger electron transfer to the substrate bound heme and start the catalytic cycle. However, with mutant BM-3 enzymes and nonnatural substrates, NADPH consumption is not necessarily coupled to the formation of product. Instead, electrons from NADPH reduce heme-bound dioxygen to water or the reactive oxygen species peroxide and superoxide. To determine the coupling efficiency (the fraction of NADPH used for product formation) of mutant 77-9H, rates of NADPH oxidation upon addition of the alkane substrates were measured and compared to product formation rates (Table 13). The rate of product formation is correlated to coupling efficiency, i.e. the more the reaction is coupled to NADPH oxidation, the higher the rate of product formation. The highest coupling efficiency (66%) was observed for nonane.

Linear alkanes are challenging to hydroxylate selectively because they contain no functional groups that help fix their orientation for reaction with the active heme iron-oxo species of cytochrome P450. Model studies with metalloporphyrins show that, absent substrate binding effects, the regioselectivity of n-alkane hydroxylation is determined by the relative bond dissociation energies. Engineering a P450 for terminal hydroxylase activity must therefore override the inherent specificity of the catalytic species for the methylene groups so that only the terminal methyl carbon is activated.

Wildtype cytochrome P450 BM-3 hydroxylates its preferred substrates, medium-chain fatty acids, at subterminal positions. The terminal carbon is not hydroxylated. By screening saturation mutagenesis libraries at 11 active site positions and recombining beneficial mutations a set of P450 BM-3 mutants that exhibit a range of regioselectivities for fatty acid and alkane hydroxylation are provided herein. One mutant, 77-9H, hydroxylates octane at the terminal position with 51% selectivity, but exhibits this selectivity only for octane. The active site of 77-9H is therefore not restricted near the activated oxygen to prevent subterminal hydroxylation. The specificity for the terminal methyl group of octane probably reflects specific interactions between active site residues and octane methylene groups and/or the methyl group at the unreacted end. The hexyl methyl ether substrate used for screening terminal hydroxylation activity has the same chain length as octane. The mutations that enable terminal hydroxylation of HME likely act in a similar fashion to promote terminal hydroxylation of octane.

Recombining Active Site Mutations for Linear, Terminal Alkene Epoxidation:

The target reaction was the selective epoxidation of linear, terminal alkenes. The same saturation mutagenesis libraries were screened to identify single active site mutants that exhibit this activity. Upon recombination of beneficial active site mutations, two mutants were identified that epoxidize linear terminal alkenes with high regioselectivity and opposite enantioselectivity.

Potential Uses of Active Site Recombination Variants for the Regioselective Hydroxylation of Larger Compounds:

The target compound 2-cyclopentlybenzoxazole was hydroxylated by active site mutant 1-12G with high regio- and enantioselectivity (see 'Regio- and Enantio-Selective Alkane Hydroxylation with Engineered Cytochromes P450'—PCT/USO4/18832, incorporated herein by reference). The work presented herein demonstrates that active site mutants are well suited for the preparation of chiral intermediates for chemical synthesis. In this case, the hydroxylated product can be used to as an intermediate in the synthesis of, for example, Carbovir, a carboxylic nucleoside potentially active against human HIV.

The active site mutants 53-5H and 77-9H, as provided herein, were tested for the hydroxylation of 2-cyclopentylbenzoxazole. The regioselectivity for the formation of the 3-(benzoxazol-2-yl)cyclopentanol was even higher than reported for 1-12G. The observed selectivities of 53-5H and 77-9H were 99.4% and 99.9%, respectively. The enantioselectivities were not as high with measured ee values of 55.8% for 53-5H and 1.5% for 77-9H. However, mutants were selected for high regioselectivity and not enantioselectivity.

Direct Conversion of Gaseous Alkanes, Such as Ethane or Propane to their Corresponding Alcohols:

The mutants provided herein indicate that single active site mutants, and combinations thereof, may be used to generate active sites in P450 BM-3 capable of binding a diverse array of substrates, including gaseous alkanes.

The mutant with the highest activity on propane, 53-5H, was shown to catalyze thousands of turnovers of propane to propanol at a rate of 370 min$^{-1}$. This mutant also hydroxylates ethane to generate ethanol 53-5H contains three active-site mutations, A78F, A82S, and A328F, all of which replace alanine with a larger side chain and presumably reduce the volume of the active site and position small alkanes above the heme during catalysis. In addition to its activity towards ethane, 53-5H exhibits the highest regioselectivity (89% 2-octanol) and enantioselectivity (65% S-2-octanol) towards octane of any BM-3 variant identified herein. This information further indicates that tighter substrate binding in the engineered active site occurs in the modified enzymes.

Dehalogenation of Halogenated Alkanes by P450 BM-3 Mutants:

The hydroxylation activity of BM-3 active site mutants on short- and medium-chain alkanes could be potentially useful to carry out the dehalogenation of halogenated alkanes. Accordingly, wild-type P450 BM-3 was used as the starting point for generating active site variants. Alanine at amino acid position 328 was substituted with asparagine, leucine, isoleucine, proline, and valine using standard DNA manipulation techniques. The amino acid sequence of the wild-type enzyme is provided in SEQ ID NO: 1 (see FIG. 8).

The dehalogenation reaction is based on the hydroxylation of the carbon atom carrying the halogen by a spontaneous (base catalyzed) alpha-elimination reaction which leads to the formation of an aldehyde or ketone depending on the starting haloalkane. The expected reaction mechanism for the dehalogenation of a general alpha-haloalkane is described by the scheme:

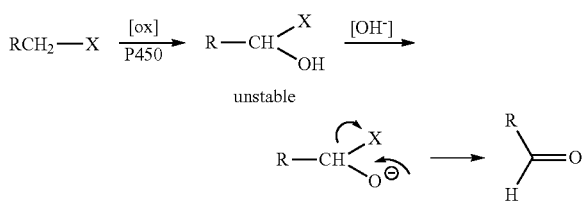

To test the feasibility of this approach, chloromethane was chosen as substrate for the dehalogenation reaction. Compared to other haloalkanes, chloromethane (CM) has the advantage to be moderately soluble in water (0.5 g/100 ml) and to lead to formaldehyde as end product of the hydroxylation/alpha-elimination reaction. Formaldehyde can be then readily detected by colorimetric reaction with Purpald as described previously. To test the reaction, two BM-3 mutants from later rounds of random mutagenesis, 35-E1141 and 20-D3, were incubated in the presence of CM and a cofactor regeneration system based on NADP$^+$, glucose-6-phosphate and glucose-6-phosphate dehydrogenase. Reactions with wild-type P450 BM-3 and without enzyme were included as controls. A specific colorimetric response (see FIG. 27A) was observed only in the presence of the BM-3 mutants.

Figure 29:
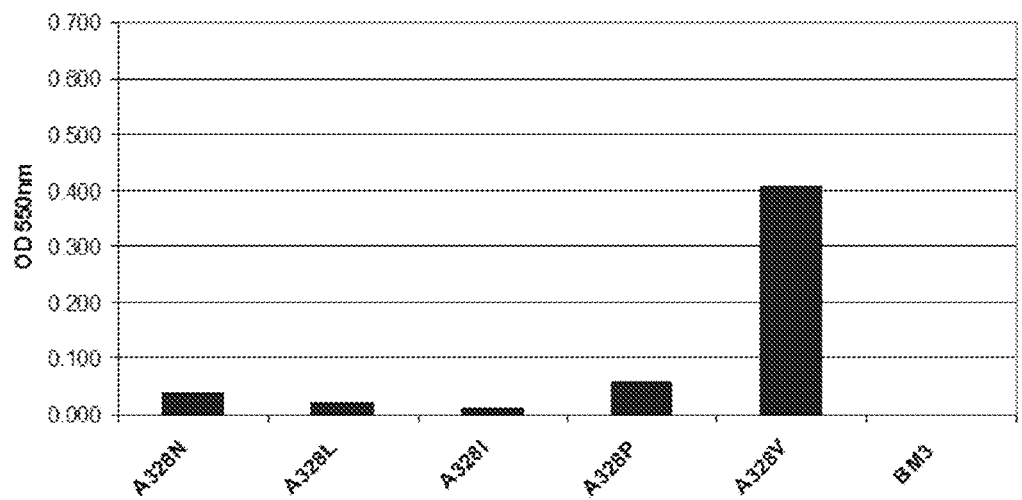
FIG. 29 depicts a colorimetric response for the reaction BM-3 variants substituted at position A328.

The reaction was repeated in the presence of additional BM-3 mutants, including 1-8H, 1-12G2 and the wild-type P450 BM-3 in which A328 was substituted with valine (BM-3-A328V) (FIG. 27B). The total turnover number of BM-3-A328V on CM is considerably higher than that of the other mutants considered in the study, while the wild-type enzyme exhibits no detectable activity (FIG. 28). Wild-type BM-3 was substituted with other amino acid residues at position V328. These mutants, however, are much less active than BM-3-A328V on CM (FIG. 29).

The activity of BM-3-A328V on CM and other substrates such as HME, DME, and propane was further investigated by measuring product formation rate, cofactor consumption and coupling efficiency (Table 14). This mutant was also found to be capable to hydroxylate ethane to ethanol, although only for a total of about 5-10 turnovers. In Table 14 "consumption" rates are expressed as nmol NADPH/nmol enzyme/min and "product formation" rates are expressed as nmol product/nmol enzyme/min.

TABLE 14

| rates | no substrate | HME | DME | Propane | $CH_3Cl$ | ethane |
|---|---|---|---|---|---|---|
| NADPH consumption[a] | 19.9 | 36.3 | 12.5 | n.d. | 16.2 | n.d. |
| product formation[b] | — | 4.3 | 3.0 | 7.0 | 1.1 | n.d. |

TABLE 14-continued

| rates | no substrate | HME | DME | Propane | $CH_3Cl$ | ethane |
|---|---|---|---|---|---|---|
| coupling (%) | — | 11.8 | 24.2 | 8.0 | 6.8 | n.d. |
| TTN | — | n.d. | n.d. | 2300 | 130 | 7 |

Figure 30:
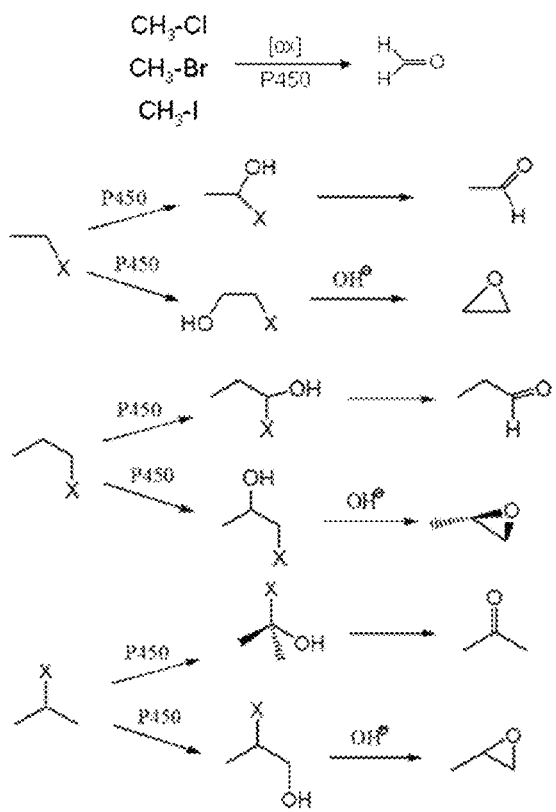
FIG. 30 depicts the chemical structures of products from the hydroxylation/dehalogenation reaction catalyzed by P450 mutants on different kinds of halogenated alkanes.

It is envisioned that the type of dehalogenation reaction described for chloromethane is extendable to other halomethanes such as bromo- and iodomethane as well as longer haloalkanes (e.g., haloethane, 1- and 2-halopropane). The resulting haloalcohols are reactive intermediates which can form the corresponding carbonyl compounds (aldehyde, ketones) or epoxides depending on the regioselectivity of the hydroxylation reaction and the nature of starting compounds (FIG. 30). These reactions are useful for bioremediation as well as for synthetic purposes.

Example 4

Propanol Mutants

Plasmids and Oligonucleotides:

All plasmids are derived from vector pCWori. The encoding sequence (3040 bp) is comprised between BamH I and EcoR I restriction sites under the control of a tac promoter. $P450_{BM3}$ variants 139-3, J, and 35E11 were previously described. Plasmid pCWori 35E11 was used as template for construction of the first library. The sequences of the oligonucleotides that were used throughout this work are indicated in Table 15.

TABLE 15

Oligonucleotides used for library construction.

| # | Primer name (SEQ ID NO:) | Sequence |
|---|---|---|
| 1 | L52I_for (46) | 5'-CGC GCT ACA TAT CAA GTC AGC-3' |
| 2 | L52I_rev (47) | 5'-GCT GAC TTG ATA TGT AGC GCG-3' |
| 3 | M145A_for (48) | 5'-GTA TCG GAA GAC GCG ACA CGT TTA ACG-3' |
| 4 | M145A_rev (49) | 5'-GTA TCG GAA GAC GCG ACA CGT TTA ACG-3' |
| 5 | V340M_for (50) | 5'-GAA GAT ACG ATG CTT GGA GGA G-3' |
| 6 | V340M_rev (51) | 5'-CTC CTC CAA GCA TCG TAT CTT C-3' |
| 7 | I366V_for (52) | 5'-CGT GAT AAA ACA GTT TGG GGA GAC G-3' |
| 8 | I366V_rev (53) | 5'-CGT CTC CCC AAA CTG TTT TAT CAC G-3' |
| 9 | E442K_for (54) | 5'-CGT TAA AAC CTA AAG GCT TTG TGG-3' |
| 10 | E442K_rev (55) | 5'-CCA CAA AGC CTT TAG GTT TTA ACG-3' |
| 11 | L324I_for (56) | 5'-CGA AGC GCT GCG CAT CTG GCC AAC TT-3' |
| 12 | L324I_rev (57) | 5'-AAG TTG GCC AGA TGC GCA GCG CTT CG-3' |
| 13 | S106R_for (58) | 5'-CTTACTTCCAAGGTTCAGTCAGCAGG-3' |
| 14 | S106R_rev (59) | 5'-CCT GCT GAC TGA ACC TTG GAA GTA AG-3' |
| 15 | BamHI_fwd (60) | 5'-CAC AGG AAA CAG GAT CCA TCG ATG CTT AGG-3' |
| 16 | SacI_rev (61) | 5'-CTA GGT GAA GGA ATA CCG CCA AGC GGA-3' |
| 17 | L437NNK_for (62) | 5'-CGA TAT TAA AGA AAC TNN KAC GTT AAA ACC-3' |
| 18 | L437NNK_rev (63) | 5'-GGT TTT AAC GTM NNA GTT TCT TTA ATA TCG-3' |

TABLE 15-continued

Oligonucleotides used for library construction.

| # | Primer name (SEQ ID NO:) | Sequence |
|---|---|---|
| 19 | T438NNK_for (64) | 5'-CGA TAT TAA AGA AAC TTT ANN KTT AAA ACC-3' |
| 20 | T438NNK_rev (65) | 5'-GGT TTT AAM NNT AAA GTT TCT TTA ATA TCG-3' |
| 21 | EcoRI_Rev (66) | 5'-CCG GGC TCA GAT CTG CTC ATG TTT GAC AGC-3' |
| 22 | L181NNK_for (67) | 5'-GGT CCG TGC ANN KGA TGA AGT AAT G-3' |
| 23 | L181NNK_rev (68) | 5'-CAT TAC TTC ATC MNN TGC ACG GAC C-3' |
| 24 | A82NNK_for (69) | 5'-CGT GAT TTT NNK GGA GAC GGG TTA-3' |
| 25 | A82NNK_rev (70) | 5'-TAA CCC GTC TCC MNN AAA ATC ACG-3' |
| 26 | A74NNK_for (71) | 5'-AAC TTA AGT CAA NNK CTT AAA TTC-3' |
| 27 | A74NNK_rev (72) | 5'-GAA TTT AAG MNN TTG ACT TAA GTT-3' |
| 28 | L75NNK_for (73) | 5'-GTC AAG CGN NK AAA TTC TTT CGT G-3' |
| 29 | L75NNK_rev (74) | 5'-CAC GAA AGA ATT TMN NCG CTT GAC-3' |
| 30 | V78NNK_for (75) | 5'-GTC AAG CGC TTA AAT TCN NKC GTG ATT TT-3' |
| 31 | V78NNK_rev (76) | 5'-AAA ATC ACG MNN GAA TTT AAG CGC TTG AC-3' |
| 32 | A328NNK_for (77) | 5'-GGC CAA CTN NKC CTG CGT TTT CC-3' |
| 33 | A328NNK_rev (78) | 5'-GGA AAA CGC AGG MNN AGT TGG CC-3' |
| 34 | A184NNK_for (79) | 5'-GCA CTG GAT GAA NNK ATG AAC AAG-3' |
| 35 | A184NNK_rev (80) | 5'-CTT GTT CAT MNN TTC ATC CAG TGC-3' |
| 36 | L188NNK_for (81) | 5'-GAA CAA GNN KCA GCG AGC AAA TCC-3' |
| 37 | L188NNK_rev (82) | 5'-GGA TTT GCT CGC TGM NNC TTG TTC-3' |
| 38 | I401NNK_fwd (83) | 5'-GCG TGC GTG TNN KGG TCA GCA G-3' |
| 39 | I401NNK_rev (84) | 5'-CTG CTG ACC MNN ACA CGC ACG C-3' |
| 40 | T268NNK_fwd (85) | 5'-GCG GGA CAC GAA NNK ACA AGT GGT C-3' |
| 41 | T268NNK_rev (86) | 5'-GAC CAC TTG TMN NTT CGT GTC CCG C-3' |
| 42 | G265NNK_fwd (87) | 5'-CAT TCT AAT TG CGN NKC ACG AAA CAA CAA GTG-3' |
| 43 | G265NNK_rev (88) | 5'-CAC TTG TTG TTT CGT GMN NCG CAA TTA AGA ATG-3' |
| 44 | A264NNK_fwd (89) | 5'- CA TTC TTA ATT NNK GGA CAC GAA ACA CAA AGT G-3' |
| 45 | A264NNK_rev (90) | 5'-CAC TTG TTG TTT CGT GTC CMN NAA TTA AGA ATG-3' |
| 46 | T260NNK_fwd (91) | 5'-CAA ATT ATT NNK TTC TTA ATT GCG GGA C-3' |
| 47 | T260NNK_rev (92) | 5'-GTC CCG CAA T TA AGA AMN NAA TAA TTT G-3' |
| 48 | L75NNK_fwd (93) | 5'-GTC AAG CGN NKA AAT TTG TAC G-3' |
| 49 | L75NNK_rev (94) | 5'-GTC CCG CAA TTA AGA AMN NAA TAA TTT G-3' |
| 50 | T88NNK_fwd (95) | 5'-GAC GGG TTA TTT NNK AGC TGG ACG CAT G-3' |
| 51 | T88NNK_rev (96) | 5'-GTC CCG CAA TTA AGA AMN NAA TAA TTT G-3' |
| 52 | F87NNK_fwd (97) | 5'-GAC GGG TTA NNK ACA AGC TGG-3' |
| 53 | F87NNK_rev (98) | 5'-CCA GCT TGT MNN TAA CCC GTC-3' |
| 54 | A82G_for (99) | 5'-CGT GAT TTT GGT GGA GAC GGG TTA-3' |
| 55 | A82G_rev (100) | 5'-TAA CCC GTC TCC ACC AAA ATC ACG-3' |

TABLE 15-continued

Oligonucleotides used for library construction.

| # | Primer name (SEQ ID NO:) | Sequence |
|---|---|---|
| 56 | FMN_for (101) | 5'-GCT GGT ACT TGG TAT GAT GCT-3' |
| 57 | FMN_rev (102) | 5'-CCA GAC GGA TTT GCT GTG AT-3' |
| 58 | FAD_for (103) | 5'-CGT GTA ACA GCA AGG TTC GG-3' |
| 59 | FAD_rev (104) | 5'-CTG CTC ATG TTT GAC AGC TTA TC-3' |
| 60 | G443NNK_for (105) | 5'-CGT TAA AAC CTG AAN NKT TTG TGG-3' |
| 61 | G443NNK_rev (106) | 5'-CCA CAA AMN NTT CAG GTT TTA ACG-3' |
| 62 | V445NNK_for (107) | 5'-CCT GAA GGC TTT NNK GTA AAA GCA -3' |
| 63 | V445NNK_rev (108) | 5'-TGC TTT TAC MNN AAA GCC TTC AGG-3' |
| 64 | T480NNK_for (109) | 5'-CGC TCA TAA TNN K CCG CTG CTT GTG-3' |
| 65 | T480NNK_rev (110) | 5'-CAC AAG CAG CGG MNN ATT ATG AGC G-3' |
| 66 | T515NNK_for (111) | 5'-CCG CAG GTC GCA NNK CTT GAT TCA C-3' |
| 67 | T515NNK_rev (112) | 5'-GTG AAT CAA GMN NTG CGA CCT GCG G-3' |
| 68 | P654NNK_for (113) | 5'-GCG GAT ATG NNK CTT GCG AAA ATG-3' |
| 69 | P654NNK_rev (114) | 5'-CAT TTT CGC AAG MNN CAT ATC CGC-3' |
| 70 | T664NNK_for (115) | 5'-GGT GCG TTT TCA NNK AAC GTC GTA GCA-3' |
| 71 | T664NNK_rev (116) | 5'-TGC TAC GAC GTT MNN TGA AAA CGC ACC-3' |
| 72 | D698NNK_for (117) | 5'-CAA GAA GGA NNK CAT TTA GGT G-3' |
| 73 | D698NNK_rev (118) | 5'-CAC CTA AAT GMN NTC CTT CTT G-3' |
| 74 | E1037NNK_for (119) | 5'-CAG CAG CTA GAA NNK AAA GGC CG -3' |
| 75 | E1037NNK_rev (120) | 5'-CGG CCT TTM NNT TCT AGC TGC TG-3' |
| 76 | BMfor_1504 (121) | 5'-GCA GAT ATT GCA ATG AGC AAA GG-3' |
| 77 | BMrev_1504 (122) | 5'-CCT TTG CTC ATT GCA ATA TCT GC-3' |
| 78 | BMfor_2315 (123) | 5'-CGG TCT GCC CGC CGC ATA AAG-3' |
| 79 | BMrev_2315 (124) | 5'-CTT TAT GCG GCG GGC AGA CCG-3' |

Construction of Thermostability Library (HL1):

L52I, S106R, M145A, L324I, V340M, I366V, E442K substitutions were introduced in 35E11 sequence by PCR overlap extension mutagenesis. Multiple mutants were prepared by gene SOEing using PCR products from single mutants. pCWori_35E11 was used as template, BamHI_fwd and SacI_rev as megaprimers, and #1 to #14 as mutagenizing primers. The amplified region (1.5 Kbp) was cloned in pCWori_35E11 using BamH I and Sac I restriction enzymes.

Construction of Random Mutagenesis Library (HL2):

Random mutagenesis library of ETS8 heme domain (BamH I-Sac I region) was created by error-prone PCR using Taq polymerase (Roche, Indianapolis, Ind.), pCWori_ETS8 as template, BamHI_fwd and SacI_rev primers, and different concentrations of MnCl$_2$ (50, 100, 150, 200, 300 µM). Mutation rate was estimated by sequencing of 8 randomly chosen colonies.

Construction of Active Site Libraries (HL3):

Site-saturation (NNK) libraries of positions 437 and 438 were prepared by PCR overlap extension mutagenesis using pCWori_19A12 as template, BamHI_fwd, and EcoRI_rev megaprimers, and #17 to #20 primers. Amplified region (~3.2 Kbp) was cloned in p19A12 using BamH I and EcoR I restriction enzymes. Site-saturation (NNK) libraries of positions 74, 75, 78, 82, 87, 88, 181, 184, 188, 260, 264, 265, 268, 328, and 401 were prepared using BamHI_fwd and SacI_rev megaprimers, and #22 to #53 primers. The amplified region (1.5 Kbp) was cloned in pCWori_35E11 using BamH I and Sac I restriction enzymes.

Construction of Heme Recombination Library (HL4):

Recombination library was prepared recombining single mutants (e.g., A74S, A74Q, V184S, V184T, V184A) from HL3 libraries by SOEing. Sequences of single point mutants from RF-g3 generation served as templates. BamHI_fwd and SacI_rev were used as megaprimers, The amplified region (1.5 Kbp) was cloned in pCWori_35E11 using BamH I and Sac I restriction enzymes.

Construction of Heme Saturation-Recombination Libraries (HL5):

These libraries were prepared by SOEing using gene fragments containing S/NNK in position 74, S/G in position 82, S/T/NNK in position 184 in combinatorial manner. To introduce the 82G mutation primers #54 and #55 were used. To randomize positions 74 and 184, primers #26 and #27 and primers #34 and #35, respectively, were used. To introduce the remaining mutations, plasmids of the corresponding variants were used as templates. For multiple mutants, a second PCR was carried out using purified product from first PCR as template. BamHI_fwd and SacI_rev served as megaprimers. The amplified region (1.5 Kbp) was cloned in pCWori_35E11 using BamH I and Sac I restriction enzymes.

Construction of reductase domain random mutagenesis library (RL1-2).

Random mutagenesis libraries of 35E11 FMN-binding domain (432-720) and FAD-binding domain regions (724-1048) were created by error-prone PCR using Taq polymerase (Roche, Indianapolis, Ind.), pCWori_35E11 as template, FMN_for/FMN_rev and FAD_for/FAD_rev primer pairs, and different concentrations of $MnCl_2$ (100, 200, 300 µM). The amplified region (1.9 Kbp) was cloned in pCWori_35E11 using Sac I and EcoR I restriction enzymes. Mutation rate was estimated by sequencing of 8 randomly chosen colonies.

Construction of reductase domain saturation mutagenesis library (RL3-4).

Site-saturation (NNK) libraries of positions 443, 445, 515, 580, 654, 664, 698, 1037 were prepared by PCR overlap extension mutagenesis using pCWori_11-3 as template, FMN_for, and EcoRI_rev megaprimers, and #60 to #75 primers. Amplified region (1.9 Kbp) was cloned in p11-3 using Sac I and EcoR I restriction enzymes.

Construction of Domain Recombination Library (L9).

A FMN/FAD recombination library was prepared by SOE-ing recombining G443A, P654K, T664G, D698G, and E1037G mutations from RDL3 library, primers #76 to #79, and FMN_for and EcoRI_rev as megaprimers. The reductase domain library was combined to 7-7 heme domain by cloning the amplified region (1.9 Kbp) in pCWori_7-7 using Sac I and EcoR I restriction enzymes.

High-Throughput Screening.

Single colonies were picked and inoculated by a Qpix robot (Genetix, Beaverton, Oreg.) into 1-mL, deep-well plates containing LB ($Amp^+$) medium (400 µL). The plates were incubated at 30° C., 250 rpm, and 80% relative humidity. After 24 h, 50 µL from this pre-culture were used to inoculate a 2-mL, deep-well plates containing 900 µL TB ($Amp^+$) medium per well. Cultures were grown at 37° C., 220 rpm, and 80% relative humidity. As OD at 600 nm reached 1.5, cells were added with 50 µL TB medium containing 10 mM IPTG and 10 mM δ-aminolevulinic acid hydrochloride followed by growth at 30° C. After 24 h, plates were centrifuged at 5000 rpm and stored at −20° C. Cells were resuspended in 500 µL potassium phosphate (KPi) buffer (0.1 M, pH 8.0), containing 0.5 mg/mL lysozyme, 2 units/mL DNaseI, and 10 mM MgCl2. After incubation at 37° C. for 60 min, lysates were centrifuged at 1500 g for 10 minutes. Screening of dimethyl ether (DME) activity was carried out by transferring 20 supernatant to 96-well microtiter plates, adding 130 µl DME-saturated KPi buffer and starting the reaction with 50 µL NADPH (1.0 mM). Formaldehyde produced in the reaction was determined by addition of Purpald (168 mM in 2 M NaOH) and by monitoring absorbance at 550 nM using a Spectramax Plus microtiter plate reader. Mutants with improved DME activity were re-screed in 96-well plates using 8 replicates for each positive clone.

Protein Expression and Purification.

All media and agar were supplemented with 100 µg/ml ampicillin. *E. coli* DH5α cells were transformed with plasmids encoding wild-type $P450_{BM3}$ gene and mutants thereof and grown in TB medium ($Amp^+$). At $OD_{600}$=1.5, cultures were induced with δ-aminolevulinic acid hydrochloride (ALA; 0.5 mM) and IPTG 0.5 mM and grown at 30° C. Cells were harvested after 24 hours by centrifugation at 4000 g. Cell pellets were resuspended in 25 mM Tris pH 8.0 and lysed by sonication. After centrifugation, the supernatant was applied to an ion-exchange column (Toyopearl Super Q-650 resin). After the column was washed with 3 column volumes 25 mM Tris pH 8.0 and 3 column volumes 25 mM Tris 150 mM NaCl pH 8.0, bound protein was eluted with 25 mM Tris 340 mM NaCl pH 8.0. P450-containing fractions were collected and concentrated using a Centriprep 30 (Millipore). The concentrated protein was desalted using a PD-10 desalting column (Pharmacia) and 100 mM KPi pH 8.0 as running buffer. P450 concentration in the purified sample was measured in triplicate from the CO-difference spectra. Protein samples were aliquoted and stored at −80° C.

$T_{50}$ determination. A solution of purified enzyme (1-3 µM) in 100 mM KPi pH 8.0 buffer was transferred on a PCR 96-well plate and incubated for 10 minutes at different temperatures (from 37° C. to 60° C.) in a PCR thermocycler. The plate was then cooled on ice, centrifuged at 1500 g for 10 min. 160 µL of the protein solution was then transferred on a 96-well microtiter plate with 40 µL of sodium hydrosulfite 0.1 M in 1 M KPi pH 8.0. A protein sample incubated at room temperature and one incubated on ice were included in the series. Concentration of folded protein was then determined by measuring CO-binding difference spectra using absorption at 450 and 490 nm and extinction coefficient $\epsilon_{450-490}$=91,000 $M^{-1}$ $cm^{-1}$. CO-binding signals were normalized to protein concentration of the sample incubated at 4° C. $T_{50}$ values were calculated as midpoint inactivation temperatures from nonlinear fitting to the heat-inactivation curves. Experiments were carried out in triplicate.

Determination of NADPH Oxidation Rates.

Initial rates of NADPH oxidation were measured using propane-saturated 100 mM KPi pH 8.0 buffer, purified enzyme at 50-200 nM, and a saturating concentration of NADPH (200 µM). The absorbance decrease at 340 nm was monitored at 25° C. in a BioSpec-1601 UV/VIS spectrophotometer (Shimadzu, Columbia, Md.) for 1 min. Rates were calculated over the first 20 seconds using NADPH extinction coefficient $\epsilon_{340}$=6210 $M^{-1}$ $cm^{-1}$. Rates were determined in triplicate. Coupling values were calculated from the ratio of propanol formation rate to NADPH oxidation rate in the presence of propane.

Reactions on Alkanes.

Reactions with alkanes from pentane to decane were carried out at 3 mL-scale using 100 mM KPi pH 8.0 buffer containing 2% ethanol (to allow alkane solubilization) and purified protein. 2.5 mL KPi buffer were added with 60 µl of 90 mM alkane solution in ethanol (final conc.=1.8 mM), 150 µL enzyme solution at 1 µM (final conc.=50 nM), and 300 µL NADPH regeneration solution (100 units/mL isocitrate dehydrohenase, 70 mg/mL isocitrate, 1.5 mg/ml $NADP^+$). Vials were sealed and stirred for 24 hours at 4° C. 1 mL-aliquot of the reaction was removed, added with 10 µl internal standard (25 mM 1-bromohexane in ethanol), and extracted with 200 µl chloroform (30 sec vortexing, 1 min centrifugation at 10000 g). The organic phase was removed and analyzed by gas chromatography. Reactions with ethane, propane, and butane were carried out as described for longer alkanes with the only difference that alkane-saturated KPi buffer was used. Propane reactions with variants from HL5 and L9 libraries were performed on 1 mL-scale reaction using 20 nM enzyme to reduce oxygen limitation. Propane and butane reactions were analyzed by direct injection of reaction solution on the GC using 1-pentanol as internal standard. Ethane reaction products were functionalized (see below) and analyzed by GC using 1-butanol as internal standard. All measurements were performed in triplicate.

Reactions on Laurate.

$P450_{PMO}$ activity on laurate was tested mixing the substrate (2 mM) with purified protein (up to 0.5 µM) in 100 mM KPi pH 8.0 buffer, and adding NADPH to final concentration of 1 mM. Reaction mixtures were incubated for 5 hours at room temperature under gentle stirring. Analysis of the hydroxylated products was carried out by derivatization with N-methyl-N-trimethylsilylheptafluorobutyramide (Aldrich) followed by GC analysis according to a published procedure. A control experiment was carried out using wild-type $P450_{BM3}$. From the reaction with wild-type $P450_{BM3}$, multiple hydroxylation products were detected, whereas no hydroxylation product could be detected from $P450_{PMO}$ reactions.

Rate Measurements.

Initial rates of product formation were determined at 25° C. in 100 mM KPi pH 8.0 buffer using purified protein (100 nM) and a substrate concentration of 1.6 mM. In a 5 mL-vial, 20 µL of alkane solution (in ethanol) were dissolved in 400 µL KPi buffer, to which 500 µL enzyme solution at 100-200 nM was added. Reaction was initiated by adding 100 µL of 5 mM NADPH solution, followed by stirring at 300 rpm for 1 minute, and quenched by adding 200 µL chloroform and stirring at 800 rpm for 10 sec. Solutions were transferred to an Eppendorf tube, to which internal standard (10 µL 25 mM 1-bromohexane in ethanol) was added. Tubes were vortexed for 10 sec and centrifuged for 30 sec at 10,000 g. Organic phase was removed and analyzed by GC. For propane, reactions were carried out in a 5 mL-scale using 100-400 nM purified enzyme, propane-saturated buffer (propane concentration≈1.6 mM) and a final NADPH concentration of 500 µM. Reactions were stopped by addition of 200 µL $H_2SO_4$ conc. and analyzed by derivatization to alkyl nitrites followed by GC-ECD analysis as described below.

Kinetic Measurements.

A propane concentration range from 1.6 mM to 50 µM (6 data points) was prepared by dilution of a propane-saturated buffer solution (propane solubility in water=1.6 mM). Reactions were carried out in a 5 mL-scale using 100-400 nM purified enzyme and a final NADPH concentration of 1 mM. After 30 seconds, reactions were stopped by addition of 200 µL $H_2SO_4$ conc. and analyzed by GC as described below. Propane leakage during the experiment was neglected in reason of short measuring time. All measurements were performed in triplicate. Kinetic parameters were estimated from least-squares nonlinear regression to the Michaelis-Menten equation, $$v = V_{max} \cdot S/(K_m + S)$$

where v is the initial velocity, S is the substrate concentration, $V_{max}$ is the maximum velocity, and $K_m$ is the apparent Michaelis constant for the substrate.

Products from alkane reactions were identified and quantified by gas chromatography using authentic standards and calibration curves with internal standards. For the reactions with alkanes from pentane to decane, GC analyses were carried out using a Shimadzu GC-17A gas chromatograph, Agilent HP5 column (30 m×0.32 mm×0.1 µm film), 1 µL injection, FID detector, and the following separation program: 250° C. inlet, 250° C. detector, 50° C. oven for 3 min, 5° C./min gradient to 100° C., 25° C./min gradient to 230° C., and 230° C. for 3 min. For butane and propane (TTN) reactions, GC analyses were carried out using a Hewlett-Packard 5890 Series II Plus gas chromatograph, Supelco SPB-1 column (60 m×0.52 mm×0.5 µm film), 0.5 µL injection, FID detector, and the following separation program: 250° C. inlet, 275° C. detector, 80° C. oven for 2 min, 10° C./min gradient to 110° C., 25° C./min gradient to 275° C., and 275° C. for 2.5 min. For ethane and propane (rate) reactions, analysis of reaction mixtures was carried out by derivatization to alkyl nitrites followed by GC-ECD analysis. For laurate, reaction product analysis was carried out by derivatization with N-methyl-N-trimethylsilylheptafluorobutyramide followed by extraction with hexane. Organic solutions were analyzed by FID-GC.

Halomethane Reactions:

Reactions with chloromethane, bromomethane, and iodomethane were carried out in 1 mL-scale using halomethane-saturated buffer (100 mM phosphate pH 8.0) and 50-500 nM purified protein. 900 µL buffer were added with protein, incubated for 15 seconds, and then added with 100 µL NADPH regeneration solution (100 units/mL IDH, 70 mg/mL isocitrate, 1.5 mg/ml NADP+). Solution were sealed and stirred for 30 minutes at 25° C. To reduce background levels of formaldehyde to a minimum, buffers were prepared using HPLC-grade water and autoclaved twice prior to use. Formaldehyde concentration in the reaction solutions was determined through derivatization with o-(2,3,4,5,6-pentafluorobenzyl)hydroxylamine hydrochloride (PFBHA) and gas chromatography. Reaction solutions (1 mL) were transferred in eppendorf tubes and added with 50 µL of PFBHA (Fluka) in formaldehyde-free water (17 mg/mL). Tubes were incubated for 15 minutes at 25° C. (1000 rpm) in a thermoblock. Solutions were added with 10 µL internal standard (25 mM 1-bromohexane), mixed, added with 500 µL hexane, vortexed for 10 sec, and centrifuged at 13,000 rpm for 30 sec. Organic phase was removed, diluted 1/100 v/v, and analyzed on a Shimadzu GC-17A gas chromatograph. Analytical conditions were: Agilent HP1 column (30 m×0.53 mm×2.65 µm film), 1 µL injection, ECD detector. Separation program injection was: 70° C. inlet, 250° C. detector, 45° C. oven for 1 min, 15° C./min gradient to 200° C., 50° C./min gradient to 220° C., and 220° C. for 3 min. Under these conditions, derivatized HCHO (PFBHA carbonyl oxime) elutes at 6.35 min, unreacted PFBHA at 6.88 min. Quantification was carried out using a calibration curve and solutions at known concentration of formaldehyde. Rates were estimated from 30 minute-reactions. Measurements were performed in triplicate.

In multi-component redox systems such as soluble methane monooxygenase and class I cytochrome P450s, the rate of product formation and the extent of coupling efficiency in product oxidation is profoundly influenced by the relative ratio of the individual components in the in vitro reconstituted systems. With sMMO from *Methylosinus trichosporium* OB3b, product yield in propene oxidation varies from 10% to ~100% as the relative concentration of MMOB and MMOR (with respect to MMOH) is changed. With sMMO from *Methylococcus capsulatus* (Bath), coupling in methane oxidation varies according to hydroxylase:reductase ratio with significant uncoupling occurring at stoichiometric concentrations. This relationship was also found to change with the nature of the substrate. Similar observations were made with $P450_{cam}$, a prototypical member of class I P450 systems. When putidaredoxin is added in large stoichiometric excess as compared to the other redox partners, up to 10-fold enhancements of $P450_{cam}$ catalytic rates can be achieved. The $k_{cat}/K_m$ for oxygen consumption in $P450_{cam}$ was also found to be hyperbolically dependent on putidaredoxin concentration. Belonging to prokaryotic class II P450 systems, P450$_{BM3}$ incorporates the hydroxylase domain and the reductase partners in a single polypeptide. The catalytic function of P450$_{BM3}$ is finely regulated through conformational re-arrangements in the heme and reductase domains, possibly involving hinged domain motions. This system enables an easier and unbiased analysis of the evolution of the engineered function without the confounding effects of arbitrarily chosen parameters (e.g. redox system composition), whose role in the natural evolution of enzymes remains unclear.

Figure 35C:
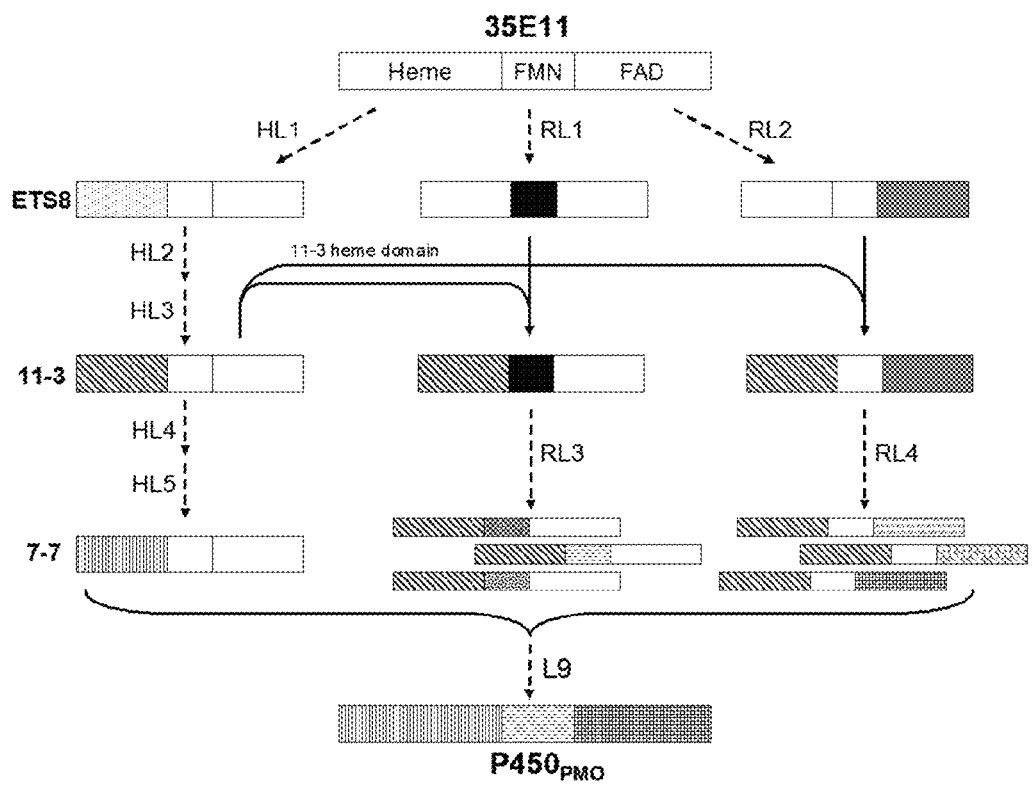

P450$_{BM3}$ fold comprises a heme-, an FMN-, and a FAD-binding domain. Beside the heme domain, mutations in the reductase domains and linker regions are also known to affect the catalytic properties of the enzyme. In order to identify beneficial mutations in each of these enzyme regions, a domain-based engineering strategy was employed (FIG. 35C). While the heme domain was being optimized for propane activity, beneficial mutations in the FMN- and FAD-binding domains were first identified (using 35E11 as background) and subsequently optimized (using heme domain variant 11-3 as background). In the last step, activity-enhancing mutations in the reductase domains were recombined and joined to the heme domain of the most active heme domain variant (7-7). The overall directed evolution process that led to the development of P450$_{PMO}$ from wild-type P450$_{BM3}$ is summarized in FIG. 35A.

Figure 36:
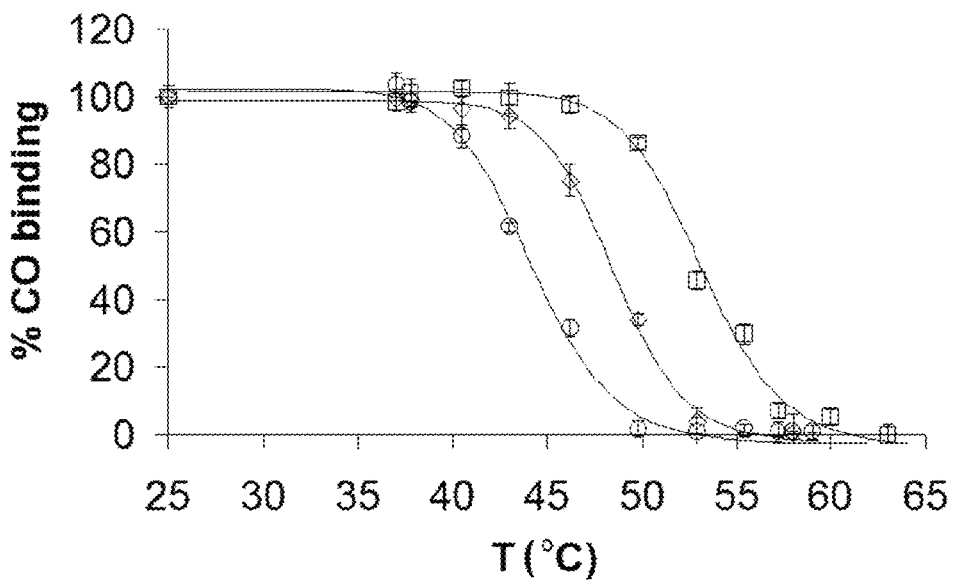
FIG. 36 shows the thermostability of $P450_{BM3}$ variants. Curves corresponding to 35E11 (○), ETS8 (◇), and wild-type $P450_{BM3}$ ( ) are indicated. $T_{50}$ value correspond to mid-point denaturation temperature.
Figure 39:
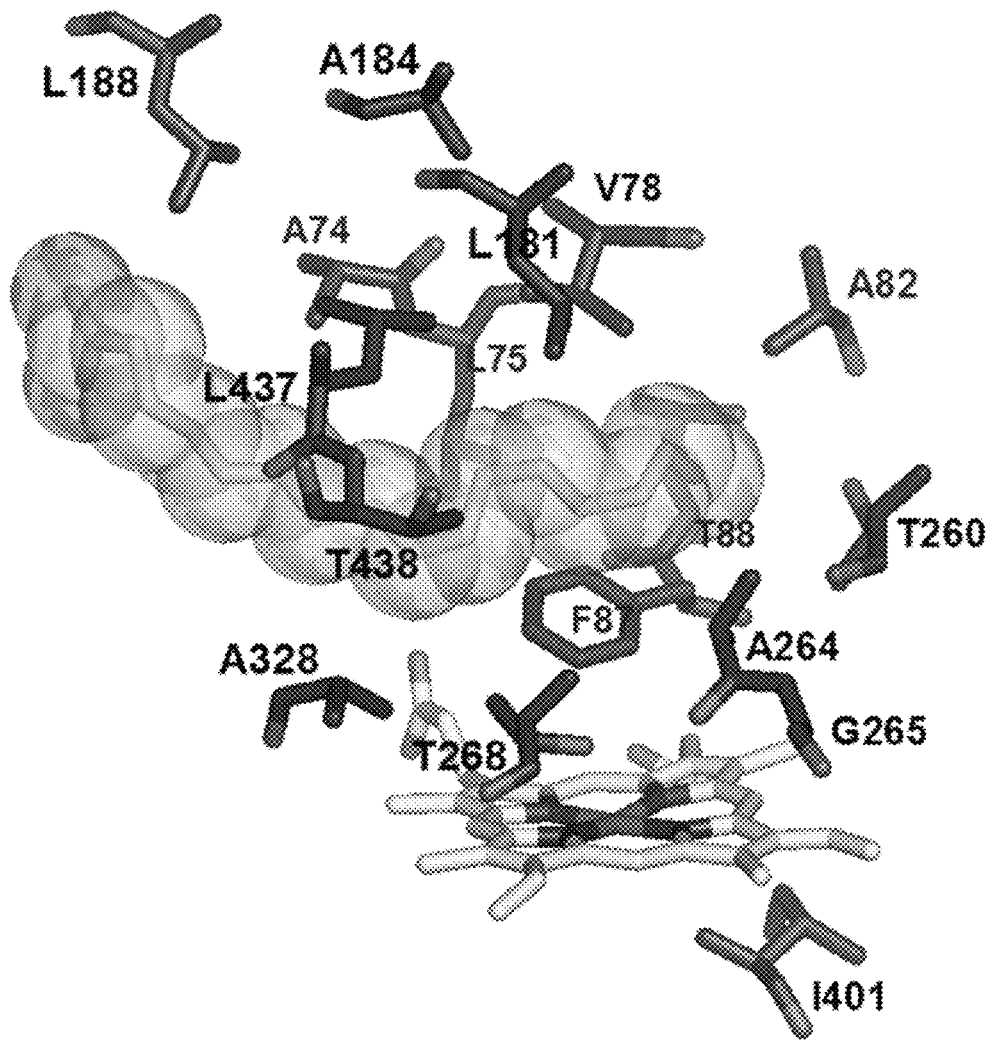
FIG. 39 shows active site engineering. Map of active site residues targeted for saturation mutagenesis on the palmitate-bound structure of $P450_{BM3}$ heme domain (PDB entry 1FAG).

The engineering strategy that led to the development of P450$_{PMO}$ is summarized in FIG. 35. As a first step, we aimed at increasing the thermostability of 35E11 heme domain in order to obtain a more 'evolvable' parent. This choice was motivated by the repeated failure of random and focused mutagenesis libraries to yield improved variants starting from this enzyme and by the analysis of the stability trend from wild-type to 35E11 demonstrated a considerable reduction in stability as a consequence of the accumulated mutations (FIG. 37E). To regain stability and allow further evolution, stabilizing mutations, derived from a thermostable peroxygenase, was tested in single and in combination (Table 16). The effect on enzyme's thermostability of each single mutation or combination thereof on thermosatbility was evaluated by monitoring temperature-dependent inactivation of the enzyme's CO-binding (FIG. 36C). Among 35E11 derivatives, ETS8 was selected as the best candidate for further evolution experiments, in that its higher thermostability ($\Delta T_{50}=+5.1°$ C.) was accompanied by only a 20% decrease in propane activity on propane. Thus, almost half of the stability loss from wild-type to 35E11 ($\Delta T_{50}=-11.6°$ C.) could be recovered in a single step and only two mutations (L52I, I366V). ETS8 was then used as parent for generating a set of heme domain random mutagenesis libraries with mutation rates varying from 2.0-3.5 by mutations/gene. Screening of 3000 members led to two improved variants, 19A12 and 12G7, each carrying a single amino acid mutation (L188P and D182Y, respectively), both located in helix F of P450$_{BM3}$ heme domain (FIG. 35B). 19A12 served as parental sequence for the preparation of a pool of active site libraries, where 17 positions within and in proximity of the enzyme's active site were targeted for saturation mutagenesis (FIG. 39). These positions include residues 74, 75, 78, and 82 in helix B1', 87 and 88 in the helix B1'-helix C linker, 181 184 and 188 in helix F, 260, 264, 265, and 268 in helix I, 328 in helix K-β-2 linker, 401 in helix L, 437 and 438 in the β-4 hairpin. Eleven of these positions were already saturated in a previous round (J→35E11). From the active site libraries, further improvement of propane-hydroxylating activity was achieved in multiple variants, exemplified by variant 11-3. By recombination of the beneficial mutations in these variants, a remarkably more active variant was obtained, i.e. 1-3. Analysis of the mutational pattern in the selected variants from this and the previously screened active site libraries revealed identical positions exploring alternative or novel solutions, suggesting that fine tuning of active site after each mutational step be required for best function on propane. To account for this, a recombination/site-saturation strategy was employed using 1-3 as parent and targeting positions 74, 82, and 184. From these libraries, 7-7 emerged as the most active P450 variant, with three different solutions for each of the targeted positions as compared to 1-3. 7-7 is capable of catalyzing 20,500 turnovers on propane, showing a k$_{cat}$ of 185 min$^{-1}$ and coupling efficiency of about 90% for propane hydroxylation. A list of all the amino acid mutations present in P450$_{PMO}$ and its intermediates is reported in Table 17.

TABLE 16

Thermostabilization of 35E11. S106R and M145A mutations were introduced in ETS2 and ETS7, respectively, resulting in unfolded enzymes. These mutations were therefore not considered for recombination.

| Variant | L52I | L324I | V340M | I366V | E442K | T$_{50}$ (° C.) | $\Delta T_{50}$ (° C.) |
|---|---|---|---|---|---|---|---|
| 35E11 | | | | | | 43.4 ± 0.6 | 0 |
| ETS1 | X | | | | | 44.5 ± 0.3 | 1.1 |
| ETS3 | | X | | | | 43.2 ± 0.1 | −0.3 |
| ETS4 | | | X | | | 46.0 ± 0.1 | 2.6 |
| ETS5 | | | | X | | 47.1 ± 0.1 | 3.7 |
| ETS6 | | | | | X | 45.0 ± 1.4 | 1.6 |
| ETS8 | X | | | X | | 48.5 ± 0.2 | 5.1 |
| ETS9 | X | | | | X | 46.8 ± 0.6 | 3.4 |
| ETS10 | | | X | | X | 44.2 ± 0.1 | 0.8 |
| ETS11 | | | | X | X | 46.6 ± 0.2 | 3.2 |
| ETS12 | X | | | X | X | misfolded | — |
| ETS13 | | | X | X | | misfolded | — |
| ETS14 | X | | X | X | | 46.1 ± 0.6 | 2.7 |
| ETS15 | X | | X | X | X | 47.8 ± 1.3 | 4.4 |
| ETS16 | X | X | | X | | 45.9 ± 0.1 | 2.5 |
| ETS17 | X | X | | X | X | 47.2 ± 0.2 | 3.8 |
| ETS18 | | | X | X | X | 45.5 ± 0.2 | 2.1 |
| ETS19 | | X | X | X | X | 45.6 ± 0.3 | 2.2 |
| ETS20 | | X | X | X | | 44.6 ± 0.2 | 1.2 |
| ETS21 | X | X | X | X | | 45.8 ± 0.1 | 2.4 |
| ETS22 | X | X | X | X | X | 47.0 ± 0.3 | 3.6 |

TABLE 17

Amino acid mutations in the P450$_{BM3}$ variants.

P450$_{BM3}$ variants

| | 139-3 | J | 35E11 | ETS8 | 19A12 | 11-3 | 1-3 | 7-7 | P450$_{PMO}$ |
|---|---|---|---|---|---|---|---|---|---|
| R47 | | | C | C | C | C | C | C | C |
| L52 | | | I | | I | I | I | I | I |
| A74 | | | | | | S | S | E | E |
| V78 | A | A | F | F | F | F | F | F | F |
| A82 | | | S | S | S | S | S | G | G |
| K94 | | | I | I | I | I | I | I | I |
| H138 | Y | | | | | | | | |
| P142 | | | S | S | S | S | S | S | S |
| T175 | I | I | I | I | I | I | I | I | I |
| V178 | I | | | | | | | | |
| A184 | V | V | V | V | V | V | A | V | V |
| L188 | | | | | P | P | P | P | P |
| F205 | | C | C | E | C | C | C | C | C |
| S226 | | R | R | R | R | R | R | R | R |
| H236 | Q | Q | Q | Q | Q | Q | Q | Q | Q |
| E252 | G | G | G | G | G | G | G | G | A |
| R255 | S | S | S | S | S | S | S | S | S |
| A290 | V | V | V | V | V | V | V | V | V |
| A295 | T | | | | | | | | |
| A328 | | | F | F | F | F | F | F | F |
| L353 | V | V | V | V | V | V | V | V | V |
| I366 | | | V | V | V | V | V | V | V |
| G443 | | | | | | | | | A |
| E464 | | | G | G | G | G | G | G | G |
| D698 | | | | | | | | | G |
| I710 | | | T | T | T | T | T | T | T |

Two random mutagenesis libraries were constructed targeting the FMN- and FAD-binding domain regions of 35E11 (RL1 and RL2, respectively; FIG. 35C). Mutation rates ranged from 1.8 to 3.0 by mutations/gene. Screening of about 5,000 members from each library led to the identification of eight beneficial mutations (G443D, V445M, T480M, T515M, P654Q, T664M, D698G, and E1037G). Using 11-3 as parent, these positions were subjected to saturation mutagenesis. Variants with improved activity on propane (as compared to 11-3) were identified in all the libraries except those saturating positions 480 and 515. The amino acid substitutions in the selected variants were G443A, V445R, P654K, T664G, D698G, and E1037G. TTN with propane in these mutants ranged from 20,000 to 25,000 with little or no change in propane oxidation rate. As compared to the parent, most mutants, and in particular 11-3(D698G), show enhanced coupling efficiency for propane hydroxylation. As the last directed evolution step, a recombination library of the mutations in the FMN- and FAD-binding domains was prepared by SOEing and fused to the heme domain of the most active heme domain variant (7-7). The most active variant (P450$_{PMO}$ isolated from this library (L9) contained G443A and D698G mutations in addition to those already present in 7-7. A map of P450$_{PMO}$ mutated sites in the heme domain is given in FIG. 35B.

The structures of P450$_{BM3}$ heme- and FMN-binding domains were obtained using pdb entry 1BU7. P450$_{BM3}$ FAD-binding domain was modeled using rat cytochrome P450 reductase structure, pdb 1AMO. Structural similarity between the two structures is supported by the alignment of the solved structure of P450$_{BM3}$ FAD-binding domain and rat CPR structure. The structures of sMMO components (hydroxylase, 2Fe-2S N-terminal domain of MMO-Reductase, C-terminal FAD-binding domain of MMO-reductase, and MMO regulatory protein) were obtained using pdb entries 1FZH, 1JQ4, 1TVC, and 2MOB, respectively.

Directed evolution was performed on a variant of cytochrome P450$_{BM3}$ (139-3) a self-sufficient hydroxylase from *B. megaterium* that catalyzes the sub-terminal hydroxylation of long-chain ($C_{12}$-$C_{20}$) fatty acids. As described herein the 139-3 P450 was modified to used propane and ethane (35E11). Reflecting the dissimilarity in physico-chemical properties between these small alkanes and the substrates of P450$_{BM3}$ (FIG. 34), coupling in propane and ethane oxidation in the engineered variants was useful.

Because 35E11 was only marginally stable, the engineering strategy described herein (see below) involved an initial stabilization step followed by iterative rounds of mutagenesis and screening. Random, saturation and site-directed mutagenesis methods were used to create libraries of mutants (FIG. 35), which were screened for activity on a propane surrogate, dimethyl ether. Positives were confirmed in a re-screen and purified for further analysis. Reactions with purified enzymes were carried out in sealed vials in the presence of propane-saturated buffer and a cofactor regeneration system. Improvement in propane total turnover number—moles of propanol produced per mole of enzyme—was a selection criterion for taking a mutant to the next round.

Five rounds of directed evolution generated P450$_{PMO}$, a cytochrome P450 that is capable of supporting more than 20,000 turnovers on propane (FIG. 37A) and more than 2,500 turnovers on ethane (Table 18). P450$_{PMO}$ differs from 35E11 at 7 amino acid positions and from wild-type at a total of 23 (~4% of its hydroxylase sequence). To evaluate the overall process of activity refinement from wild-type P450$_{BM3}$ to P450$_{PMO}$, total turnover numbers (TTN), catalytic efficiency ($k_{cat}/K_m$) and coupling efficiencies were measured for P450$_{PMO}$ and all its evolutionary precursors (FIG. 37). Compared to 139-3, where activity on propane emerged (wild-type P450$_{BM3}$ has no detectable propane activity), total turnovers supported by P450$_{PMO}$ increased 100-fold. Kinetic constants ($K_m$, $k_{cat}$) were determined from Michaelis-Menten plots of initial rates of activity on propane at different substrate concentrations. Throughout the variant series, the increase in turnovers on propane accompanied a large decrease in $K_m$ values that went from >30 mM in 139-3 to the ~100-µM range (1-3: 250 µM, P450$_{PMO}$: 170 µM) (FIG. 37C). Despite the much reduced size and polar nature of propane, the P450$_{PMO}$ $K_m$ for propane is similar to that of wild-type enzyme for laurate ($K_m$=210 µM). Catalytic constant $k_{cat}$ increased by a factor of 45 from 139-3 (10 min$^{-1}$) to 19A12 (450 min$^{-1}$) and varied between 400 and 200 min$^{-1}$ in subsequent generations (FIG. 37D). P450$_{PMO}$ has a catalytic efficiency ($k_{cat}/K_m$) of $1.8 \times 10^4$ M$^{-1}$ sec$^{-1}$, or about three orders of magnitude higher than that of the propane oxidizer 139-3 and at least four orders of magnitude better than wild-type BM3.

TTNs for each variant-substrate pair were determined using standardized reaction conditions (identical enzyme and substrate concentration, incubation time, cofactor regeneration system) (Table 18). TTN values were used to assess performance because TTN is a cumulative measure of both catalytic and coupling efficiency and because mutants were selected based on improvement in this property. To facilitate comparison among the variants, TTNs were normalized to the highest value in the series (MTN=Maximal Turnover Number) and plotted for the increasing-sized substrates (FIG. 38). A gradual shift of the enzyme's substrate preference during laboratory evolution is evident from these profiles. The marginal activity of wild-type BM3 on these substrates (MTN=150) is restricted to the long-chain alkanes, where it is a promiscuous function of BM3's high $C_{12}$-$C_{20}$ fatty acid hydroxylase activity. In the first evolutionary intermediates, substrate preference centers on medium-chain alkanes ($C_8$-$C_7$), reflecting their selection for activity on octane. In 35E11, selected for activity on propane, preference still centers on $C_6$-$C_8$ alkanes but now extends towards the shorter ones, including propane. Propane activity becomes prevalent with the transition from variant ETS8 to 19A12. This 'turning point' also coincides with the highest per-mutation stability penalty (FIG. 37F). For example, a single mutation (L188P) separates ETS8 from 19A12. Leucine 188 is located along helix F (FIG. 35B), which together with helix G forms a lid covering the active site, in one of the regions (SRS-2) associated with substrate binding in P450s. Due to its particular conformational requirements and lack of H-bonding amide, proline acts as a 'helix-breaker'. Although not wishing to be bound by any particular theory of operation, the L188P mutation may be associated with a perturbation of the surrounding helical region, which destabilizes the protein fold but at the same time induces a marked change of enzyme's substrate recognition properties. The variants isolated after 19A12 are characterized by higher TTNs on propane and a gradual decrease in relative activity towards the longer alkanes. In $P450_{PMO}$, specificity along the alkane series is increased around propane, showing a 90% drop in activity when even a single methylene unit is added to the substrate.

into the active site. Along the variant series, coupling for propane oxidation increases from 5-15% in the earliest rounds to 90% in $P450_{PMO}$ (FIG. 37B). This is similar to the efficiencies with which wild-type $P450_{BM3}$ oxidizes myristate and palmitate (88% and 93%, respectively).

$T_{50}$ values determined from heat-inactivation curves of heme-dependent CO-binding spectral shift show how mutations accumulated during laboratory evolution affected enzyme stability (FIG. 37E) and enable an estimatation per-mutation stability penalties for each directed evolution round (FIG. 37F). A gradual but continuous decrease in stability both before and after the stabilization step is evident, reflecting the often-observed trade-off between mutational effects on activity and stability. The average impact of each mutational event on enzyme stability varies considerably, however, with the highest stability cost observed for the transition from ETS8 to 19A12. These analyses highlight the importance of the stabilization step after 35E11 and support the proposed relationship between stability and 'evolvability'.

To further investigate the evolution of substrate specificity, kinetic constants for the $C_5$ to $C_8$ alkanes were determined from Michaelis-Menten plots (Table 19). The preference of 35E11 and its evolutionary predecessors for medium-chain alkanes is indicated by their high $C_8/C_5$ specificities (($k_{cat}/K_m$)$_8$/($k_{cat}/K_m$)$_5$~100), where $K_m$ appears to be the major contributing factor. $C_8/C_5$ specificity decreases to ~5 in the immediate precursors of $P450_{PMO}$ and then switches altogether to the smaller alkane, becoming 0.4 in $P450_{PMO}$. In $P450_{PMO}$, catalytic efficiency is highest on propane and decreases along the alkane series, driven by decreasing $k_{cat}$.

TABLE 18

Total turnovers with $P450_{BM3}$ variants with alkanes from ethane to decane.

| Alkane/C atoms | WT | | 139-3 | | J | | 35E11 | |
|---|---|---|---|---|---|---|---|---|
| | TTN | % rel. act. | TTN | % rel. act. | TTN | % rel. act. | TTN | % rel. act. |
| 2 | 0 | 0.0 | 0 | 0.0 | 20 ± 5 | 0.6 | 220 ± 30 | 3.5 |
| 3 | 0 | 0.0 | 200 ± 50 | 9.4 | 750 ± 110 | 21.6 | 4550 ± 350 | 71.7 |
| 4 | 0 | 0.0 | 680 ± 190 | 32.1 | 2790 ± 900 | 80.2 | 5150 ± 104 | 81.1 |
| 5 | 0 | 0.0 | 1020 ± 140 | 48.1 | 3480 ± 412 | 100.0 | 4800 ± 174 | 75.6 |
| 6 | 10 ± 4 | 6.3 | 1940 ± 73 | 91.5 | 3290 ± 642 | 94.5 | 6350 ± 384 | 100.0 |
| 7 | 20 ± 5 | 12.5 | 2120 ± 70 | 100.0 | 2350 ± 220 | 67.5 | 5170 ± 148 | 81.4 |
| 8 | 30 ± 42 | 18.8 | 2060 ± 33 | 97.2 | 2400 ± 119 | 69.0 | 5950 ± 323 | 93.74 |
| 9 | 110 ± 10 | 68.8 | 1110 ± 34 | 52.4 | 1300 ± 320 | 37.4 | 3350 ± 133 | 52.8 |
| 10 | 160 ± 95 | 100.0 | 730 ± 49 | 34.4 | 780 ± 65 | 22.4 | 860 ± 223 | 13.5 |

| Alkane/C atoms | 19A12 | | 11-3 | | 1-3 | | $P450_{PMO}$ | |
|---|---|---|---|---|---|---|---|---|
| | TTN | % rel. act. | TTN | % rel. act. | TTN | % rel. act. | TTN | % rel. act. |
| 2 | 750 ± 80 | 7.1 | 1350 ± 80 | 10.2 | 1750 ± 190 | 10.5 | 2550 ± 280 | 12.4 |
| 3 | 10500 ± 1100 | 100.0 | 13200 ± 1200 | 100.0 | 16600 ± 1500 | 100.0 | 20500 ± 1900 | 100.0 |
| 4 | 8850 ± 850 | 84.3 | 10500 ± 1500 | 79.5 | 8200 ± 900 | 49.4 | 6200 ± 400 | 30.2 |
| 5 | 8590 ± 517 | 81.8 | 9370 ± 268 | 71.0 | 6090 ± 300 | 36.7 | 1000 ± 110 | 4.9 |
| 6 | 7470 ± 631 | 71.1 | 6630 ± 80 | 50.2 | 6350 ± 480 | 38.3 | 2600 ± 205 | 12.7 |
| 7 | 5360 ± 1027 | 51.0 | 5150 ± 263 | 39.0 | 5080 ± 115 | 30.6 | 2990 ± 165 | 14.6 |
| 8 | 2710 ± 108 | 25.8 | 2290 ± 154 | 17.3 | 2020 ± 290 | 12.2 | 1880 ± 60 | 9.2 |
| 9 | 2470 ± 273 | 23.5 | 3330 ± 598 | 25.2 | 2870 ± 510 | 17.3 | 2390 ± 30 | 11.7 |
| 10 | 1170 ± 518 | 16.9 | 515 ± 91 | 3.9 | 1050 ± 100 | 6.3 | 1080 ± 30 | 5.3 |

In the presence of ideal substrates, coupling of product formation to NADPH oxidation approaches 100%, e.g., no side reactions were detected in the P450 active site. Coupling is therefore often used to define how well the substrate fits Table 19.

Kinetic constants for n-alkanes. N.a.=not active. N.m=not measurable.

|  |  | WT | 139-3 | J | 35E11 | 19A12 | 11-3 | 1-3 | P450$_{PMO}$ |
|---|---|---|---|---|---|---|---|---|---|
| Propane | $K_m$ (μM) | n.a. | >30000 | 1450 ± 180 | 820 ± 95 | 475 ± 82 | 340 ± 41 | 250 ± 33 | 170 ± 35 |
|  | $k_{cat}$ (min$^{-1}$) | n.a. | <10 | 45 ± 8 | 245 ± 25 | 450 ± 54 | 455 ± 75 | 320 ± 46 | 185 ± 35 |
|  | $k_{cat}/K_m$ (M$^{-1}$ s$^{-1}$) | — | <1E+01 | 517E+02 | 4.98E+03 | 1.58E+04 | 2.23E+04 | 2.13E+04 | 1.81E+04 |
| Pentane | $K_m$ (μM) | n.a. | 1410 ± 50 | 1290 ± 105 | 1030 ± 57 | 675 ± 74 | 740 ± 69 | 385 ± 43 | 835 ± 117 |
|  | $k_{cat}$ (min$^{-1}$) | n.a. | 98 ± 11 | 215 ± 39 | 760 ± 52 | 1090 ± 125 | 845 ± 95 | 460 ± 85 | 150 ± 14 |
|  | $k_{cat}/K_m$ (M$^{-1}$ s$^{-1}$) | — | 1.12E+03 | 2.78E+03 | 1.23E+04 | 2.69E+04 | 1.90E+04 | 1.99E+04 | 2.99E+03 |
| Hexane | $K_m$ (μM) | n.a. | 435 ± 30 | 295 ± 20 | 370 ± 33 | 685 ± 118 | 395 ± 81 | 150 ± 24 | 430 ± 91 |
|  | $k_{cat}$ (min$^{-1}$) | n.a. | 210 ± 11 | 410 ± 57 | 710 ± 69 | 1310 ± 222 | 910 ± 117 | 315 ± 17 | 85 ± 17 |
|  | $k_{cat}/K_m$ (M$^{-1}$ s$^{-1}$) | — | 8.05E+03 | 2.32E+04 | 3.20E+04 | 3.28E+04 | 3.84E+04 | 3.50E+04 | 3.29E+03 |
| Heptane | $K_m$ (μM) | n.m. | 60 ± 8 | 79 ± 19 | 200 ± 46 | 175 ± 17 | 105 ± 29 | 72 ± 23 | 190 ± 40 |
|  | $k_{cat}$ (min$^{-1}$) | n.m. | 145 ± 12 | 275 ± 57 | 635 ± 83 | 580 ± 125 | 420 ± 76 | 160 ± 35 | 32 ± 5 |
|  | $k_{cat}/K_m$ (M$^{-1}$ s$^{-1}$) | — | 4.03E+04 | 5.73E+04 | 5.29E+04 | 5.52E+04 | 6.67E+04 | 3.81E+04 | 2.75E+03 |
| Octane | $K_m$ (μM) | >5000 | 19 ± 6 | 130 ± 27 | 85 ± 25 | 74 ± 21 | 81 ± 16 | 22 ± 6 | 185 ± 40 |
|  | $k_{cat}$ (min$^{-1}$) | <5 | 190 ± 28 | 520 ± 53 | 390 ± 95 | 205 ± 12 | 235 ± 21 | 100 ± 23 | 13 ± 4 |
|  | $k_{cat}/K_m$ (M$^{-1}$ s$^{-1}$) | <2E+01 | 1.67E+05 | 6.67E+04 | 7.65E+04 | 4.62E+04 | 4.84E+04 | 7.58E+04 | 1.17E+03 |

To evaluate the fate of the enzyme's original function, P450$_{PMO}$ activity was tested on the long-chain fatty acids laurate and palmitate. Despite high catalytic efficiency of wild-type P450$_{BM3}$ with these substrates (1.9×10$^5$ M$^{-1}$ sec$^{-1}$ and 6.0×10$^7$ M$^{-1}$ sec$^{-1}$, respectively), no detectable amounts of hydroxylated fatty acids were observed in the presence of P450$_{PMO}$, demonstrating a loss of these original functions upon re-specialization for propane hydroxylation.

Figure 42:
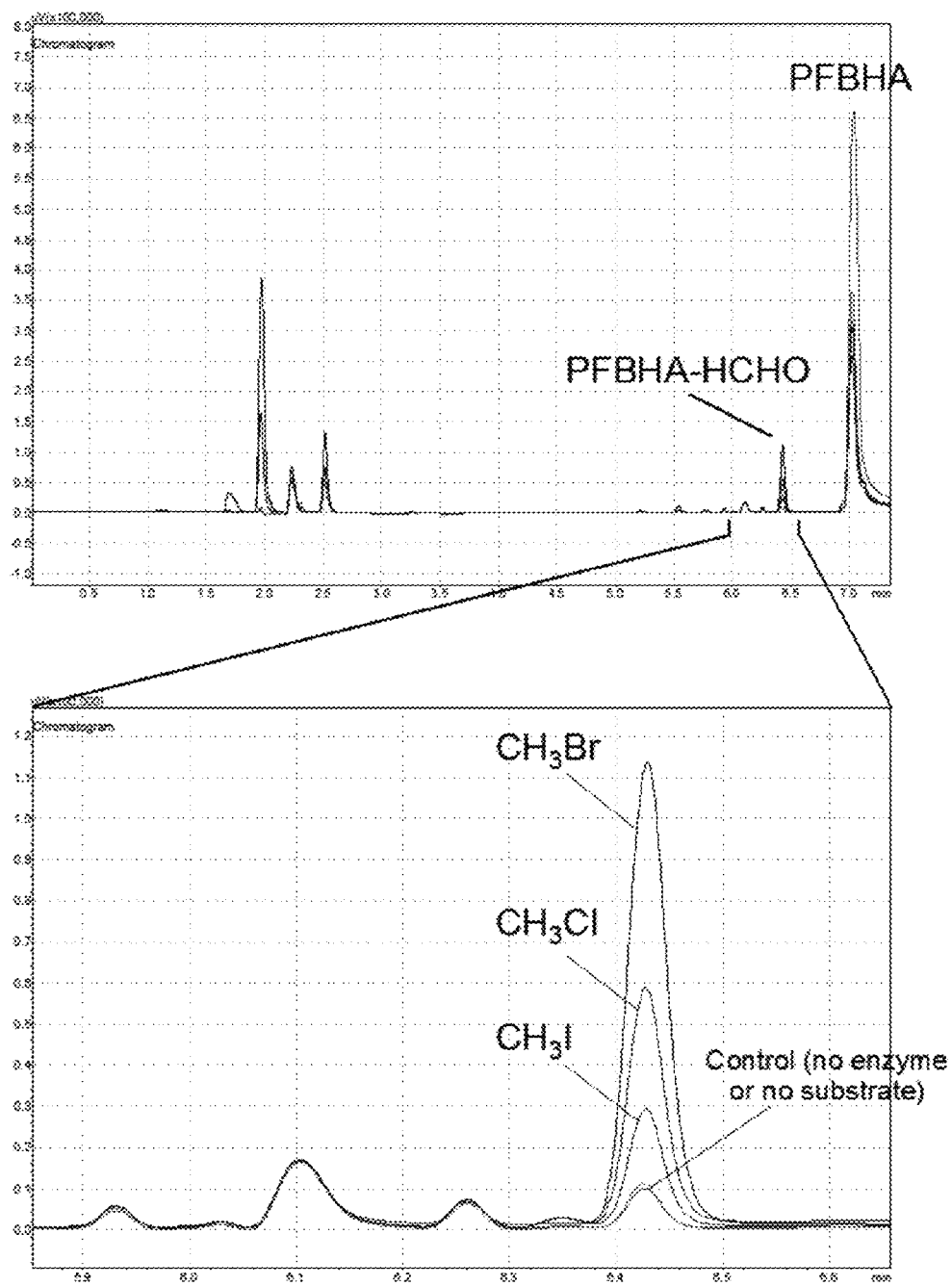
FIG. 42 is a GC chromatogram of PFHA-derivatized formaldehyde from reaction with $P450_{PMO}$ and halogenated methane derivatives, $CH_3Cl$, $CH_3Br$ and $CH_3I$.

Along with activity on propane, P450$_{PMO}$ also hydroxylates ethane (TTN~2,500), despite ethane's higher C—H bond energy (101.0 kcal mol$^{-1}$ versus 98.6 kcal mol$^{-1}$ for propane). P450$_{PMO}$ activity was examined on halogenated derivatives of methane, CH$_3$Cl, CH$_3$Br and CH$_3$I. Halomethanes have molecular sizes and C—H bond energies intermediate between those of methane and propane (FIG. 41), but different reactivity and polarity. All the halomethanes studied except iodomethane are substrates for methane monooxygenase (MMO), which converts them to formaldehyde and HX. Reactions with purified P450 variants and the halomethanes were analyzed for formaldehyde formation (FIG. 42). P450$_{PMO}$ and four of its evolutionary predecessors oxidized bromomethane to formaldehyde. with bromomethane dehalogenase activity that amounts to ~1-5% of the propane activity. Activity on chloromethane was detected at lower levels (0.5-1% of propane activity) and in fewer P450 variants. Iodomethane dehalogenase activity could be detected only in P450$_{PMO}$ and its immediate precursor 1-3 (FIG. 43B). Despite the low turnover rates (0.5-5 min$^{-1}$), the emergence of these activities in P450$_{PMO}$ has important implications. Particularly noteworthy is the iodomethane dehalogenase activity, which is not supported by natural P450s or methane monooxygenase. This compound is only known to be degraded by a small subset of methylotrophic species using enzymes such as corrinoid-dependent methyltransferases that are unrelated to P450s and MMO. With P450$_{PMO}$, an alternative enzymatic strategy for the degradation of this compound has thus emerged, expanding even further the range of known P450 substrates.

The examples set forth above are provided to give those of ordinary skill in the art a complete disclosure and description of how to make and use the embodiments of the devices, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

A number of embodiments of the invention have been described. Nevertheless, it will be understood that various modifications may be made without departing from the spirit and scope of the invention. Accordingly, other embodiments are within the scope of the following claims.

What is claimed is:

1. An isolated polypeptide comprising the amino acid sequence set forth in SEQ ID NO:1 with up to 50 conservative amino acid substitutions excluding residues 47, 52, 74, 78, 82, 94, 142, 175, 184, 188, 205, 226, 236, 252, 255, 290, 328, 353, 366, 464 and 710, wherein if the residue selected from 47, 52, 74, 78, 94, 142, 175, 184, 188, 205, 226, 236, 252, 255, 290, 353, 366, 464 and 710 is substituted the residues have selective substitutions as follows:

(i) at positions selected from the group consisting of 47, 82, 142, 205, 236, 252, 255, and 464 and any combination thereof, an amino acid residue selected from the group consisting of glycine (G), asparagine (N), glutamine (Q), serine (S), threonine (T), tyrosine (Y), and cysteine (C);

(ii) at positions selected from the group consisting of 52, 94, 175, 184, 188, 290, 353, and 366, an amino acid residue selected from alanine (A), valine (V), leucine (L), isoleucine (I), proline (P), and methionine (M);

(iii) at position 226, an amino acid residue selected from the group consisting of lysine (K), and arginine (R);

(iv) at position 78 and 328, an amino acid residue selected from the group consisting of alanine (A), tyrosine (Y), phenylalanine (F), tryptophan (W), and histidine (H), (v) at position 74, an amino acid selected from the group consisting of alanine (A), serine (S), and glutamic acid (E); and (vi) at position 710 of SEQ ID NO:1 a threonine (T) residue;

and which the polypeptide comprises the following mutation(s):

(a) at position 698 a glycine (G) residue, and/or (b) at position 443 an alanine (A) residue;

wherein the polypeptide catalyzes the conversion of a ($C_1$-$C_{12}$)alkane to an alcohol.

2. The polypeptide of claim 1, comprising up to 25 amino acid substitutions.

3. The polypeptide of claim 1, comprising up to 10 amino acid substitutions.

4. The polypeptide of claim 1, comprising up to 5 amino acid substitutions.

5. The polypeptide of claim 1, wherein the alkane is selected from the group consisting of methane ($CH_4$), ethane ($C_2H_6$), propane ($C_3H_8$), butane ($C_4H_{10}$), pentane ($C_5H_{12}$), hexane ($C_6H_{14}$), heptane ($C_7H_{16}$), octane ($C_8H_{18}$), nonane ($C_9H_{20}$), decane ($C_{10}H_{22}$), undecane ($C_{11}H_{24}$), and dodecane ($C_{12}H_{26}$).

6. The polypeptide of claim 1, wherein the alcohol is selected from the group consisting of methanol, ethanol, propanol, butanol, pentanol, hexanol, heptanol, octanol, nonanol, decanol, undecanol, and dodecanol.

7. The polypeptide of claim 1, further comprising at position 285 of SEQ ID NO:1 an amino acid residue selected from the group consisting of lysine (K), arginine (R), and histidine (H).

8. The polypeptide of claim 1, wherein at positions 47 and 205 of SEQ ID NO:1 are cysteine (C) residues.

9. The polypeptide of claim 1, wherein at positions 74, 78, 82, 142 and 255 of SEQ ID NO:1 are serine (S) residues.

10. The polypeptide of claim 1, wherein at positions 52, 94 and 175 of SEQ ID NO:1 are isoleucine (I) residues.

11. The polypeptide of claim 1, wherein at position 74 of SEQ ID NO:1 is a glutamic acid (E) residue.

12. The polypeptide of claim 1, wherein at positions 78 and 328 of SEQ ID NO:1 are phenylalanine (F) residues.

13. The polypeptide of claim 1, wherein at positions 78 and 328 of SEQ ID NO:1 are phenylalanine (E) residues.

14. The polypeptide of claim 1, wherein at positions 82, 252 and 464 of SEQ ID NO:1 are glycine (G) residues.

15. The polypeptide of claim 1, wherein at positions 184, 290, 353 and 366 of SEQ ID NO:1 are valine (V) residues.

16. The polypeptide of claim 1, wherein at position 188 of SEQ ID NO:1 is a proline (P) residue.

17. The polypeptide of claim 1, wherein at position 226 of SEQ ID NO:1 is an arginine (R) residue.

18. The polypeptide of claim 1, wherein at position 235 of SEQ ID NO:1 is a glutamine (Q) residue.

19. The polypeptide of claim 1, wherein at positions 78 and 443 of SEQ ID NO:1 are alanine (A) residues.

20. The polypeptide of claim 1, wherein the polypeptide comprises the amino acid sequence set forth in SEQ ID NO:125.

* * * * *

SEQUENCE LISTING

<160> NUMBER OF SEQ ID NOS: 125

<210> SEQ ID NO 1
<211> LENGTH: 1048
<212> TYPE: PRT
<213> ORGANISM: Bacillus megaterium

<400> SEQUENCE: 1

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45

Thr Arg Tyr Leu Ser Ser Gln Arg Leu Ile Lys Glu Ala Cys Asp Glu
    50                  55                  60

```
Ser Arg Phe Asp Lys Asn Leu Ser Gln Ala Leu Lys Phe Val Arg Asp
 65                  70                  75                  80

Phe Ala Gly Asp Gly Leu Phe Thr Ser Trp Thr His Glu Lys Asn Trp
                 85                  90                  95

Lys Lys Ala His Asn Ile Leu Leu Pro Ser Phe Ser Gln Gln Ala Met
             100                 105                 110

Lys Gly Tyr His Ala Met Met Val Asp Ile Ala Val Gln Leu Val Gln
         115                 120                 125

Lys Trp Glu Arg Leu Asn Ala Asp Glu His Ile Glu Val Pro Glu Asp
130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Thr Ser
                 165                 170                 175

Met Val Arg Ala Leu Asp Glu Ala Met Asn Lys Leu Gln Arg Ala Asn
             180                 185                 190

Pro Asp Asp Pro Ala Tyr Asp Glu Asn Lys Arg Gln Phe Gln Glu Asp
         195                 200                 205

Ile Lys Val Met Asn Asp Leu Val Asp Lys Ile Ile Ala Asp Arg Lys
210                 215                 220

Ala Ser Gly Glu Gln Ser Asp Asp Leu Leu Thr His Met Leu Asn Gly
225                 230                 235                 240

Lys Asp Pro Glu Thr Gly Glu Pro Leu Asp Asp Glu Asn Ile Arg Tyr
                 245                 250                 255

Gln Ile Ile Thr Phe Leu Ile Ala Gly His Glu Thr Thr Ser Gly Leu
             260                 265                 270

Leu Ser Phe Ala Leu Tyr Phe Leu Val Lys Asn Pro His Val Leu Gln
         275                 280                 285

Lys Ala Ala Glu Glu Ala Ala Arg Val Leu Val Asp Pro Val Pro Ser
290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                 325                 330                 335

Glu Asp Thr Val Leu Gly Gly Glu Tyr Pro Leu Glu Lys Gly Asp Glu
             340                 345                 350

Leu Met Val Leu Ile Pro Gln Leu His Arg Asp Lys Thr Ile Trp Gly
         355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                 405                 410                 415

Met Leu Lys His Phe Asp Phe Glu Asp His Thr Asn Tyr Glu Leu Asp
             420                 425                 430

Ile Lys Glu Thr Leu Thr Leu Lys Pro Glu Gly Phe Val Val Lys Ala
         435                 440                 445

Lys Ser Lys Lys Ile Pro Leu Gly Gly Ile Pro Ser Pro Ser Thr Glu
450                 455                 460

Gln Ser Ala Lys Lys Val Arg Lys Lys Ala Glu Asn Ala His Asn Thr
465                 470                 475                 480
```

```
Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
    530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
        595                 600                 605

Phe Glu Gly Thr Tyr Glu Glu Trp Arg Glu His Met Trp Ser Asp Val
    610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
            660                 665                 670

Gln Gln Pro Gly Ser Ala Arg Ser Thr Arg His Leu Glu Ile Glu Leu
        675                 680                 685

Pro Lys Glu Ala Ser Tyr Gln Glu Gly Asp His Leu Gly Val Ile Pro
    690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735

His Leu Pro Leu Ala Lys Thr Val Ser Val Glu Glu Leu Leu Gln Tyr
            740                 745                 750

Val Glu Leu Gln Asp Pro Val Thr Arg Thr Gln Leu Arg Ala Met Ala
        755                 760                 765

Ala Lys Thr Val Cys Pro Pro His Lys Val Glu Leu Glu Ala Leu Leu
    770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
        835                 840                 845

Val Ser Gly Glu Ala Trp Ser Gly Tyr Gly Tyr Lys Gly Ile Ala
    850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
```

```
                          900                 905                 910
Phe Val Gln Ala Arg Lys Gln Leu Lys Glu Gln Gly Gln Ser Leu Gly
                915                 920                 925
Glu Ala His Leu Tyr Phe Gly Cys Arg Ser Pro His Glu Asp Tyr Leu
            930                 935                 940
Tyr Gln Glu Glu Leu Glu Asn Ala Gln Ser Glu Gly Ile Ile Thr Leu
945                 950                 955                 960
His Thr Ala Phe Ser Arg Met Pro Asn Gln Pro Lys Thr Tyr Val Gln
                965                 970                 975
His Val Met Glu Gln Asp Gly Lys Lys Leu Ile Glu Leu Leu Asp Gln
            980                 985                 990
Gly Ala His Phe Tyr Ile Cys Gly Asp Gly Ser Gln Met Ala Pro Ala
            995                 1000                1005
Val Glu Ala Thr Leu Met Lys Ser Tyr Ala Asp Val His Gln Val
    1010                1015                1020
Ser Glu Ala Asp Ala Arg Leu Trp Leu Gln Gln Leu Glu Glu Lys
    1025                1030                1035
Gly Arg Tyr Ala Lys Asp Val Trp Ala Gly
    1040                1045

<210> SEQ ID NO 2
<211> LENGTH: 1060
<212> TYPE: PRT
<213> ORGANISM: Bacillus subtilis

<400> SEQUENCE: 2

Lys Glu Thr Ser Pro Ile Pro Gln Pro Lys Thr Phe Gly Pro Leu Gly
1               5                   10                  15
Asn Leu Pro Leu Ile Asp Lys Asp Lys Pro Thr Leu Ser Leu Ile Lys
                20                  25                  30
Leu Ala Glu Glu Gln Gly Pro Ile Phe Gln Ile His Thr Pro Ala Gly
            35                  40                  45
Thr Thr Ile Val Val Ser Gly His Glu Leu Val Lys Glu Val Cys Asp
        50                  55                  60
Glu Glu Arg Phe Asp Lys Ser Ile Glu Gly Ala Leu Glu Lys Val Arg
65                  70                  75                  80
Ala Phe Ser Gly Asp Gly Leu Phe Thr Ser Trp Thr His Glu Pro Asn
                85                  90                  95
Trp Arg Lys Ala His Asn Ile Leu Met Pro Thr Phe Ser Gln Arg Ala
                100                 105                 110
Met Lys Asp Tyr His Glu Lys Met Val Asp Ile Ala Val Gln Leu Ile
            115                 120                 125
Gln Lys Trp Ala Arg Leu Asn Pro Asn Glu Ala Val Asp Val Pro Gly
        130                 135                 140
Asp Met Thr Arg Leu Thr Leu Asp Thr Ile Gly Leu Cys Gly Phe Asn
145                 150                 155                 160
Tyr Arg Phe Asn Ser Tyr Tyr Arg Glu Thr Pro His Pro Phe Ile Asn
                165                 170                 175
Ser Met Val Arg Ala Leu Asp Glu Ala Met His Gln Met Gln Arg Leu
            180                 185                 190
Asp Val Gln Asp Lys Leu Met Val Arg Thr Lys Arg Gln Phe Arg Tyr
        195                 200                 205
Asp Ile Gln Thr Met Phe Ser Leu Val Asp Ser Ile Ile Ala Glu Arg
    210                 215                 220
```

-continued

Arg Ala Asn Gly Asp Gln Asp Glu Lys Asp Leu Leu Ala Arg Met Leu
225                 230                 235                 240

Asn Val Glu Asp Pro Glu Thr Gly Glu Lys Leu Asp Asp Glu Asn Ile
            245                 250                 255

Arg Phe Gln Ile Ile Thr Phe Leu Ile Ala Gly His Glu Thr Thr Ser
        260                 265                 270

Gly Leu Leu Ser Phe Ala Thr Tyr Phe Leu Leu Lys His Pro Asp Lys
    275                 280                 285

Leu Lys Lys Ala Tyr Glu Glu Val Asp Arg Val Leu Thr Asp Ala Ala
290                 295                 300

Pro Thr Tyr Lys Gln Val Leu Glu Leu Thr Tyr Ile Arg Met Ile Leu
305                 310                 315                 320

Asn Glu Ser Leu Arg Leu Trp Pro Thr Ala Pro Ala Phe Ser Leu Tyr
                325                 330                 335

Pro Lys Glu Asp Thr Val Ile Gly Gly Lys Phe Pro Ile Thr Thr Asn
            340                 345                 350

Asp Arg Ile Ser Val Leu Ile Pro Gln Leu His Arg Asp Arg Asp Ala
        355                 360                 365

Trp Gly Lys Asp Ala Glu Glu Phe Arg Pro Glu Arg Phe Glu His Gln
    370                 375                 380

Asp Gln Val Pro His His Ala Tyr Lys Pro Phe Gly Asn Gly Gln Arg
385                 390                 395                 400

Ala Cys Ile Gly Met Gln Phe Ala Leu His Glu Ala Thr Leu Val Leu
                405                 410                 415

Gly Met Ile Leu Lys Tyr Phe Thr Leu Ile Asp His Glu Asn Tyr Glu
            420                 425                 430

Leu Asp Ile Lys Gln Thr Leu Thr Leu Lys Pro Gly Asp Phe His Ile
        435                 440                 445

Ser Val Gln Ser Arg His Gln Glu Ala Ile His Ala Asp Val Gln Ala
    450                 455                 460

Ala Glu Lys Ala Ala Pro Asp Glu Gln Lys Glu Lys Thr Glu Ala Lys
465                 470                 475                 480

Gly Ala Ser Val Ile Gly Leu Asn Asn Arg Pro Leu Leu Val Leu Tyr
                485                 490                 495

Gly Ser Asp Thr Gly Thr Ala Glu Gly Val Ala Arg Glu Leu Ala Asp
            500                 505                 510

Thr Ala Ser Leu His Gly Val Arg Thr Lys Thr Ala Pro Leu Asn Asp
        515                 520                 525

Arg Ile Gly Lys Leu Pro Lys Glu Gly Ala Val Ile Val Thr Ser
    530                 535                 540

Ser Tyr Asn Gly Lys Pro Pro Ser Asn Ala Gly Gln Phe Val Gln Trp
545                 550                 555                 560

Leu Gln Glu Ile Lys Pro Gly Glu Leu Glu Gly Val His Tyr Ala Val
                565                 570                 575

Phe Gly Cys Gly Asp His Asn Trp Ala Ser Thr Tyr Gln Tyr Val Pro
            580                 585                 590

Arg Phe Ile Asp Glu Gln Leu Ala Glu Lys Gly Ala Thr Arg Phe Ser
        595                 600                 605

Ala Arg Gly Glu Gly Asp Val Ser Gly Asp Phe Glu Gly Gln Leu Asp
    610                 615                 620

Glu Trp Lys Lys Ser Met Trp Ala Asp Ala Ile Lys Ala Phe Gly Leu
625                 630                 635                 640

Glu Leu Asn Glu Asn Ala Asp Lys Glu Arg Ser Thr Leu Ser Leu Gln

```
            645                 650                 655
Phe Val Arg Gly Leu Gly Glu Ser Pro Leu Ala Arg Ser Tyr Glu Ala
            660                 665                 670

Ser His Ala Ser Ile Ala Glu Asn Arg Glu Leu Gln Ser Ala Asp Ser
            675                 680                 685

Asp Arg Ser Thr Arg His Ile Glu Ile Ala Leu Pro Pro Asp Val Glu
690                 695                 700

Tyr Gln Glu Gly Asp His Leu Gly Val Leu Pro Lys Asn Ser Gln Thr
705                 710                 715                 720

Asn Val Ser Arg Ile Leu His Arg Phe Gly Leu Lys Gly Thr Asp Gln
                725                 730                 735

Val Thr Leu Ser Ala Ser Gly Arg Ser Ala Gly His Leu Pro Leu Gly
                740                 745                 750

Arg Pro Val Ser Leu His Asp Leu Leu Ser Tyr Ser Val Glu Val Gln
                755                 760                 765

Glu Ala Ala Thr Arg Ala Gln Ile Arg Glu Leu Ala Ser Phe Thr Val
770                 775                 780

Cys Pro Pro His Arg Arg Glu Leu Glu Glu Leu Ser Ala Glu Gly Val
785                 790                 795                 800

Tyr Gln Glu Gln Ile Leu Lys Lys Arg Ile Ser Met Leu Asp Leu Leu
                805                 810                 815

Glu Lys Tyr Glu Ala Cys Asp Met Pro Phe Glu Arg Phe Leu Glu Leu
                820                 825                 830

Leu Arg Pro Leu Lys Pro Arg Tyr Tyr Ser Ile Ser Ser Ser Pro Arg
                835                 840                 845

Val Asn Pro Arg Gln Ala Ser Ile Thr Val Gly Val Val Arg Gly Pro
850                 855                 860

Ala Trp Ser Gly Arg Gly Glu Tyr Arg Gly Val Ala Ser Asn Asp Leu
865                 870                 875                 880

Ala Glu Arg Gln Ala Gly Asp Asp Val Val Met Phe Ile Arg Thr Pro
                885                 890                 895

Glu Ser Arg Phe Gln Leu Pro Lys Asp Pro Glu Thr Pro Ile Ile Met
                900                 905                 910

Val Gly Pro Gly Thr Gly Val Ala Pro Phe Arg Gly Phe Leu Gln Ala
                915                 920                 925

Arg Asp Val Leu Lys Arg Glu Gly Lys Thr Leu Gly Glu Ala His Leu
930                 935                 940

Tyr Phe Gly Cys Arg Asn Asp Arg Asp Phe Ile Tyr Arg Asp Glu Leu
945                 950                 955                 960

Glu Arg Phe Glu Lys Asp Gly Ile Val Thr Val His Thr Ala Phe Ser
                965                 970                 975

Arg Lys Glu Gly Met Pro Lys Thr Tyr Val Gln His Leu Met Ala Asp
                980                 985                 990

Gln Ala Asp Thr Leu Ile Ser Ile Leu Asp Arg Gly Gly Arg Leu Tyr
                995                 1000                1005

Val Cys Gly Asp Gly Ser Lys Met Ala Pro Asp Val Glu Ala Ala
    1010                1015                1020

Leu Gln Lys Ala Tyr Gln Ala Val His Gly Thr Gly Glu Gln Glu
    1025                1030                1035

Ala Gln Asn Trp Leu Arg His Leu Gln Asp Thr Gly Met Tyr Ala
    1040                1045                1050

Lys Asp Val Trp Ala Gly Ile
    1055                1060
```

<210> SEQ ID NO 3
<211> LENGTH: 1053
<212> TYPE: PRT
<213> ORGANISM: Bacillus subtilis

<400> SEQUENCE: 3

```
Lys Gln Ala Ser Ala Ile Pro Gln Pro Lys Thr Tyr Gly Pro Leu Lys
1               5                   10                  15

Asn Leu Pro His Leu Glu Lys Glu Gln Leu Ser Gln Ser Leu Trp Arg
            20                  25                  30

Ile Ala Asp Glu Leu Gly Pro Ile Phe Arg Phe Asp Phe Pro Gly Val
        35                  40                  45

Ser Ser Val Phe Val Ser Gly His Asn Leu Val Ala Glu Val Cys Asp
    50                  55                  60

Glu Lys Arg Phe Asp Lys Asn Leu Gly Lys Gly Leu Gln Lys Val Arg
65                  70                  75                  80

Glu Phe Gly Gly Asp Gly Leu Phe Thr Ser Trp Thr His Glu Pro Asn
                85                  90                  95

Trp Gln Lys Ala His Arg Ile Leu Leu Pro Ser Phe Ser Gln Lys Ala
            100                 105                 110

Met Lys Gly Tyr His Ser Met Met Leu Asp Ile Ala Thr Gln Leu Ile
        115                 120                 125

Gln Lys Trp Ser Arg Leu Asn Pro Asn Glu Glu Ile Asp Val Ala Asp
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Ser Gln His Pro Phe Ile Thr
                165                 170                 175

Ser Met Leu Arg Ala Leu Lys Glu Ala Met Asn Gln Ser Lys Arg Leu
            180                 185                 190

Gly Leu Gln Asp Lys Met Met Val Lys Thr Lys Leu Gln Phe Gln Lys
        195                 200                 205

Asp Ile Glu Val Met Asn Ser Leu Val Asp Arg Met Ile Ala Glu Arg
    210                 215                 220

Lys Ala Asn Pro Asp Glu Asn Ile Lys Asp Leu Leu Ser Leu Met Leu
225                 230                 235                 240

Tyr Ala Lys Asp Pro Val Thr Gly Glu Thr Leu Asp Asp Glu Asn Ile
                245                 250                 255

Arg Tyr Gln Ile Ile Thr Phe Leu Ile Ala Gly His Glu Thr Thr Ser
            260                 265                 270

Gly Leu Leu Ser Phe Ala Ile Tyr Cys Leu Leu Thr His Pro Glu Lys
        275                 280                 285

Leu Lys Lys Ala Gln Glu Glu Ala Asp Arg Val Leu Thr Asp Asp Thr
    290                 295                 300

Pro Glu Tyr Lys Gln Ile Gln Gln Leu Lys Tyr Ile Arg Met Val Leu
305                 310                 315                 320

Asn Glu Thr Leu Arg Leu Tyr Pro Thr Ala Pro Ala Phe Ser Leu Tyr
                325                 330                 335

Ala Lys Glu Asp Thr Val Leu Gly Gly Glu Tyr Pro Ile Ser Lys Gly
            340                 345                 350

Gln Pro Val Thr Val Leu Ile Pro Lys Leu His Arg Asp Gln Asn Ala
        355                 360                 365

Trp Gly Pro Asp Ala Glu Asp Phe Arg Pro Glu Arg Phe Glu Asp Pro
```

```
            370                 375                 380
Ser Ser Ile Pro His His Ala Tyr Lys Pro Phe Gly Asn Gly Gln Arg
385                 390                 395                 400

Ala Cys Ile Gly Met Gln Phe Ala Leu Gln Glu Ala Thr Met Val Leu
                405                 410                 415

Gly Leu Val Leu Lys His Phe Glu Leu Ile Asn His Thr Gly Tyr Glu
                420                 425                 430

Leu Lys Ile Lys Glu Ala Leu Thr Ile Lys Pro Asp Asp Phe Lys Ile
                435                 440                 445

Thr Val Lys Pro Arg Lys Thr Ala Ala Ile Asn Val Gln Arg Lys Glu
            450                 455                 460

Gln Ala Asp Ile Lys Ala Glu Thr Lys Pro Lys Glu Thr Lys Pro Lys
465                 470                 475                 480

His Gly Thr Pro Leu Leu Val Leu Phe Gly Ser Asn Leu Gly Thr Ala
                485                 490                 495

Glu Gly Ile Ala Gly Glu Leu Ala Ala Gln Gly Arg Gln Met Gly Phe
                500                 505                 510

Thr Ala Glu Thr Ala Pro Leu Asp Asp Tyr Ile Gly Lys Leu Pro Glu
            515                 520                 525

Glu Gly Ala Val Val Ile Val Thr Ala Ser Tyr Asn Gly Ala Pro Pro
530                 535                 540

Asp Asn Ala Ala Gly Phe Val Glu Trp Leu Lys Glu Leu Glu Glu Gly
545                 550                 555                 560

Gln Leu Lys Gly Val Ser Tyr Ala Val Phe Gly Cys Gly Asn Arg Ser
                565                 570                 575

Trp Ala Ser Thr Tyr Gln Arg Ile Pro Arg Leu Ile Asp Asp Met Met
                580                 585                 590

Lys Ala Lys Gly Ala Ser Arg Leu Thr Ala Ile Gly Glu Gly Asp Ala
                595                 600                 605

Ala Asp Asp Phe Glu Ser His Arg Glu Ser Trp Glu Asn Arg Phe Trp
            610                 615                 620

Lys Glu Thr Met Asp Ala Phe Asp Ile Asn Glu Ile Ala Gln Lys Glu
625                 630                 635                 640

Asp Arg Pro Ser Leu Ser Ile Thr Phe Leu Ser Glu Ala Thr Glu Thr
                645                 650                 655

Pro Val Ala Lys Ala Tyr Gly Ala Phe Glu Gly Ile Val Leu Glu Asn
                660                 665                 670

Arg Glu Leu Gln Thr Ala Ala Ser Thr Arg Ser Thr Arg His Ile Glu
                675                 680                 685

Leu Glu Ile Pro Ala Gly Lys Thr Tyr Lys Glu Gly Asp His Ile Gly
            690                 695                 700

Ile Leu Pro Lys Asn Ser Arg Glu Leu Val Gln Arg Val Leu Ser Arg
705                 710                 715                 720

Phe Gly Leu Gln Ser Asn His Val Ile Lys Val Ser Gly Ser Ala His
                725                 730                 735

Met Ala His Leu Pro Met Asp Arg Pro Ile Lys Val Val Asp Leu Leu
                740                 745                 750

Ser Ser Tyr Val Glu Leu Gln Glu Pro Ala Ser Arg Leu Gln Leu Arg
            755                 760                 765

Glu Leu Ala Ser Tyr Thr Val Cys Pro Pro His Gln Lys Glu Leu Glu
        770                 775                 780

Gln Leu Val Ser Asp Asp Gly Ile Tyr Lys Glu Gln Val Leu Ala Lys
785                 790                 795                 800
```

-continued

Arg Leu Thr Met Leu Asp Phe Leu Glu Asp Tyr Pro Ala Cys Glu Met
                805                 810                 815

Pro Phe Glu Arg Phe Leu Ala Leu Leu Pro Ser Leu Lys Pro Arg Tyr
            820                 825                 830

Tyr Ser Ile Ser Ser Ser Pro Lys Val His Ala Asn Ile Val Ser Met
        835                 840                 845

Thr Val Gly Val Val Lys Ala Ser Ala Trp Ser Gly Arg Gly Glu Tyr
    850                 855                 860

Arg Gly Val Ala Ser Asn Tyr Leu Ala Glu Leu Asn Thr Gly Asp Ala
865                 870                 875                 880

Ala Ala Cys Phe Ile Arg Thr Pro Gln Ser Gly Phe Gln Met Pro Asn
                885                 890                 895

Asp Pro Glu Thr Pro Met Ile Met Val Gly Pro Gly Thr Gly Ile Ala
            900                 905                 910

Pro Phe Arg Gly Phe Ile Gln Ala Arg Ser Val Leu Lys Lys Glu Gly
        915                 920                 925

Ser Thr Leu Gly Glu Ala Leu Leu Tyr Phe Gly Cys Arg Arg Pro Asp
    930                 935                 940

His Asp Asp Leu Tyr Arg Glu Glu Leu Asp Gln Ala Glu Gln Asp Gly
945                 950                 955                 960

Leu Val Thr Ile Arg Arg Cys Tyr Ser Arg Val Glu Asn Glu Pro Lys
                965                 970                 975

Gly Tyr Val Gln His Leu Leu Lys Gln Asp Thr Gln Lys Leu Met Thr
            980                 985                 990

Leu Ile Glu Lys Gly Ala His Ile Tyr Val Cys Gly Asp Gly Ser Gln
        995                 1000                1005

Met Ala Pro Asp Val Glu Arg Thr Leu Arg Leu Ala Tyr Glu Ala
    1010                1015                1020

Glu Lys Ala Ala Ser Gln Glu Glu Ser Ala Val Trp Leu Gln Lys
    1025                1030                1035

Leu Gln Asp Gln Arg Arg Tyr Val Lys Asp Val Trp Thr Gly Met
    1040                1045                1050

<210> SEQ ID NO 4
<211> LENGTH: 1065
<212> TYPE: PRT
<213> ORGANISM: Bacillus cereus

<400> SEQUENCE: 4

Met Asp Lys Lys Val Ser Ala Ile Pro Gln Pro Lys Tyr Gly Pro
1               5                   10                  15

Leu Gly Asn Leu Pro Leu Ile Asp Lys Asp Lys Pro Thr Leu Ser Phe
            20                  25                  30

Ile Lys Ile Ala Glu Glu Tyr Gly Pro Ile Phe Gln Ile Gln Thr Leu
        35                  40                  45

Ser Asp Thr Ile Ile Val Ile Ser Gly His Glu Leu Val Ala Glu Val
    50                  55                  60

Cys Asp Glu Thr Arg Phe Asp Lys Ser Ile Glu Gly Ala Leu Ala Lys
65                  70                  75                  80

Val Arg Ala Phe Ala Gly Asp Gly Leu Phe Thr Ser Glu Thr Gln Glu
                85                  90                  95

Pro Asn Trp Lys Lys Ala His Asn Ile Leu Met Pro Thr Phe Ser Gln
            100                 105                 110

Arg Ala Met Lys Asp Tyr His Ala Met Met Val Asp Ile Ala Val Gln

-continued

```
            115                 120                 125
Leu Val Gln Lys Trp Ala Arg Leu Asn Pro Asn Glu Asn Val Asp Val
        130                 135                 140
Pro Glu Asp Met Thr Arg Leu Thr Leu Asp Thr Ile Gly Leu Cys Gly
145                 150                 155                 160
Phe Asn Tyr Arg Phe Asn Ser Phe Tyr Arg Glu Thr Pro His Pro Phe
                165                 170                 175
Ile Thr Ser Met Thr Arg Ala Leu Asp Glu Ala Met His Gln Leu Gln
                180                 185                 190
Arg Leu Asp Ile Glu Asp Lys Leu Met Trp Arg Thr Lys Arg Gln Phe
                195                 200                 205
Gln His Asp Ile Gln Ser Met Phe Ser Leu Val Asp Asn Ile Ile Ala
            210                 215                 220
Glu Arg Lys Ser Ser Gly Asn Gln Glu Asn Asp Leu Leu Ser Arg
225                 230                 235                 240
Met Leu His Val Gln Asp Pro Glu Thr Gly Glu Lys Leu Asp Asp Glu
                245                 250                 255
Asn Ile Arg Phe Gln Ile Ile Thr Phe Leu Ile Ala Gly His Glu Thr
                260                 265                 270
Thr Ser Gly Leu Leu Ser Phe Ala Ile Tyr Phe Leu Leu Lys Asn Pro
            275                 280                 285
Asp Lys Leu Lys Lys Ala Tyr Glu Glu Val Asp Arg Val Leu Thr Asp
        290                 295                 300
Pro Thr Pro Thr Tyr Gln Gln Val Met Lys Leu Lys Tyr Ile Arg Met
305                 310                 315                 320
Ile Leu Asn Glu Ser Leu Arg Leu Trp Pro Thr Ala Pro Ala Phe Ser
                325                 330                 335
Leu Tyr Ala Lys Glu Asp Thr Val Ile Gly Gly Lys Tyr Pro Ile Lys
                340                 345                 350
Lys Gly Glu Asp Arg Ile Ser Val Leu Ile Pro Gln Leu His Arg Asp
            355                 360                 365
Lys Asp Ala Trp Gly Asp Asn Val Glu Glu Phe Gln Pro Glu Arg Phe
        370                 375                 380
Glu Asp Leu Asp Lys Val Pro His His Ala Tyr Lys Pro Phe Gly Asn
385                 390                 395                 400
Gly Gln Arg Ala Cys Ile Gly Met Gln Phe Ala Leu His Glu Ala Thr
                405                 410                 415
Leu Val Met Gly Met Leu Leu Gln His Phe Glu Phe Ile Asp Tyr Glu
                420                 425                 430
Asp Tyr Gln Leu Asp Val Lys Gln Thr Leu Thr Leu Lys Pro Gly Asp
            435                 440                 445
Phe Lys Ile Arg Ile Val Pro Arg Asn Gln Asn Ile Ser His Thr Thr
        450                 455                 460
Val Leu Ala Pro Thr Glu Glu Lys Leu Lys Asn His Glu Ile Lys Gln
465                 470                 475                 480
Gln Val Gln Lys Thr Pro Ser Ile Ile Gly Ala Asp Asn Leu Ser Leu
                485                 490                 495
Leu Val Leu Tyr Gly Ser Asp Thr Gly Val Ala Glu Gly Ile Ala Arg
                500                 505                 510
Glu Leu Ala Asp Thr Ala Ser Leu Glu Gly Val Gln Thr Glu Val Ala
            515                 520                 525
Ala Leu Asn Asp Arg Ile Gly Ser Leu Pro Lys Glu Gly Ala Val Leu
        530                 535                 540
```

```
Ile Val Thr Ser Ser Tyr Asn Gly Lys Pro Pro Ser Asn Ala Gly Gln
545                 550                 555                 560

Phe Val Gln Trp Leu Glu Glu Leu Lys Pro Asp Glu Leu Lys Gly Val
            565                 570                 575

Gln Tyr Ala Val Phe Gly Cys Gly Asp His Asn Trp Ala Ser Thr Tyr
            580                 585                 590

Gln Arg Ile Pro Arg Tyr Ile Asp Glu Gln Met Ala Gln Lys Gly Ala
        595                 600                 605

Thr Arg Phe Ser Thr Arg Gly Glu Ala Asp Ala Ser Gly Asp Phe Glu
        610                 615                 620

Glu Gln Leu Glu Gln Trp Lys Glu Ser Met Trp Ser Asp Ala Met Lys
625                 630                 635                 640

Ala Phe Gly Leu Glu Leu Asn Lys Asn Met Glu Lys Glu Arg Ser Thr
                645                 650                 655

Leu Ser Leu Gln Phe Val Ser Arg Leu Gly Gly Ser Pro Leu Ala Arg
            660                 665                 670

Thr Tyr Glu Ala Val Tyr Ala Ser Ile Leu Glu Asn Arg Glu Leu Gln
        675                 680                 685

Ser Ser Ser Ser Glu Arg Ser Thr Arg His Ile Glu Ile Ser Leu Pro
690                 695                 700

Glu Gly Ala Thr Tyr Lys Glu Gly Asp His Leu Gly Val Leu Pro Ile
705                 710                 715                 720

Asn Ser Glu Lys Asn Val Asn Arg Ile Leu Lys Arg Phe Gly Leu Asn
                725                 730                 735

Gly Lys Asp Gln Val Ile Leu Ser Ala Ser Gly Arg Ser Val Asn His
            740                 745                 750

Ile Pro Leu Asp Ser Pro Val Arg Leu Tyr Asp Leu Leu Ser Tyr Ser
        755                 760                 765

Val Glu Val Gln Glu Ala Ala Thr Arg Ala Gln Ile Arg Glu Met Val
        770                 775                 780

Thr Phe Thr Ala Cys Pro Pro His Lys Lys Glu Leu Glu Ser Leu Leu
785                 790                 795                 800

Glu Asp Gly Val Tyr His Glu Gln Ile Leu Lys Lys Arg Ile Ser Met
                805                 810                 815

Leu Asp Leu Leu Glu Lys Tyr Glu Ala Cys Glu Ile Arg Phe Glu Arg
            820                 825                 830

Phe Leu Glu Leu Leu Pro Ala Leu Lys Pro Arg Tyr Tyr Ser Ile Ser
        835                 840                 845

Ser Ser Pro Leu Ile Ala Gln Asp Arg Leu Ser Ile Thr Val Gly Val
850                 855                 860

Val Asn Ala Pro Ala Trp Ser Gly Glu Gly Thr Tyr Glu Gly Val Ala
865                 870                 875                 880

Ser Asn Tyr Leu Ala Gln Arg His Asn Lys Asp Glu Ile Ile Cys Phe
                885                 890                 895

Ile Arg Thr Pro Gln Ser Asn Phe Gln Leu Pro Glu Asn Pro Glu Thr
            900                 905                 910

Pro Ile Ile Met Val Gly Pro Gly Thr Gly Ile Ala Pro Phe Arg Gly
        915                 920                 925

Phe Leu Gln Ala Arg Arg Val Gln Lys Gln Lys Gly Met Asn Leu Gly
        930                 935                 940

Glu Ala His Leu Tyr Phe Gly Cys Arg His Pro Glu Lys Asp Tyr Leu
945                 950                 955                 960
```

```
Tyr Arg Thr Glu Leu Glu Asn Asp Glu Arg Asp Gly Leu Ile Ser Leu
            965                 970                 975

His Thr Ala Phe Ser Arg Leu Gly His Pro Lys Thr Tyr Val Gln
        980                 985                 990

His Val Ile Lys Glu Asp Arg Met Asn Leu Ile Ser Leu Leu Asp Asn
        995                 1000                1005

Gly Ala His Leu Tyr Ile Cys Gly Asp Gly Ser Lys Met Ala Pro
        1010                1015                1020

Asp Val Glu Asp Thr Leu Cys Gln Ala Tyr Gln Glu Ile His Glu
        1025                1030                1035

Val Ser Glu Gln Glu Ala Arg Asn Trp Leu Asp Arg Leu Gln Asp
        1040                1045                1050

Glu Gly Arg Tyr Gly Lys Asp Val Trp Ala Gly Ile
        1055                1060                1065

<210> SEQ ID NO 5
<211> LENGTH: 1063
<212> TYPE: PRT
<213> ORGANISM: Ralstonia sp.

<400> SEQUENCE: 5

Ser Thr Ala Thr Pro Ala Ala Leu Glu Pro Ile Pro Arg Asp Pro
1               5                   10                  15

Gly Trp Pro Ile Phe Gly Asn Leu Phe Gln Ile Thr Pro Gly Glu Val
            20                  25                  30

Gly Gln His Leu Leu Ala Arg Ser Arg His His Asp Gly Ile Phe Glu
        35                  40                  45

Leu Asp Phe Ala Gly Lys Arg Val Pro Phe Val Ser Ser Val Ala Leu
    50                  55                  60

Ala Ser Glu Leu Cys Asp Ala Thr Arg Phe Arg Lys Ile Ile Gly Pro
65                  70                  75                  80

Pro Leu Ser Tyr Leu Arg Asp Met Ala Gly Asp Gly Leu Phe Thr Ala
                85                  90                  95

His Ser Asp Glu Pro Asn Trp Gly Cys Ala His Arg Ile Leu Met Pro
            100                 105                 110

Ala Phe Ser Gln Arg Ala Met Lys Ala Tyr Phe Asp Val Met Leu Arg
        115                 120                 125

Val Ala Asn Arg Leu Val Asp Lys Trp Asp Arg Gln Gly Pro Asp Ala
    130                 135                 140

Asp Ile Ala Val Ala Asp Asp Met Thr Arg Leu Thr Leu Asp Thr Ile
145                 150                 155                 160

Ala Leu Ala Gly Phe Gly Tyr Asp Phe Ala Ser Phe Ala Ser Asp Glu
                165                 170                 175

Leu Asp Pro Phe Val Met Ala Met Val Gly Ala Leu Gly Glu Ala Met
            180                 185                 190

Gln Lys Leu Thr Arg Leu Pro Ile Gln Asp Arg Phe Met Gly Arg Ala
        195                 200                 205

His Arg Gln Ala Ala Glu Asp Ile Ala Tyr Met Arg Asn Leu Val Asp
    210                 215                 220

Asp Val Ile Arg Gln Arg Val Ser Pro Thr Ser Gly Met Asp Leu
225                 230                 235                 240

Leu Asn Leu Met Leu Glu Ala Arg Asp Pro Glu Thr Asp Arg Arg Leu
                245                 250                 255

Asp Asp Ala Asn Ile Arg Asn Gln Val Ile Thr Phe Leu Ile Ala Gly
            260                 265                 270
```

```
His Glu Thr Thr Ser Gly Leu Leu Thr Phe Ala Leu Tyr Glu Leu Leu
            275                 280                 285

Arg Asn Pro Gly Val Leu Ala Gln Ala Tyr Ala Glu Val Asp Thr Val
        290                 295                 300

Leu Pro Gly Asp Ala Leu Pro Val Tyr Ala Asp Leu Ala Arg Met Pro
305                 310                 315                 320

Val Leu Asp Arg Val Leu Lys Glu Thr Leu Arg Leu Trp Pro Thr Ala
                325                 330                 335

Pro Ala Phe Ala Val Ala Pro Phe Asp Asp Val Val Leu Gly Gly Arg
                340                 345                 350

Tyr Arg Leu Arg Lys Asp Arg Arg Ile Ser Val Val Leu Thr Ala Leu
                355                 360                 365

His Arg Asp Pro Lys Val Trp Ala Asn Pro Glu Arg Phe Asp Ile Asp
        370                 375                 380

Arg Phe Leu Pro Glu Asn Glu Ala Lys Leu Pro Ala His Ala Tyr Met
385                 390                 395                 400

Pro Phe Gly Gln Gly Glu Arg Ala Cys Ile Gly Arg Gln Phe Ala Leu
                405                 410                 415

Thr Glu Ala Lys Leu Ala Leu Ala Leu Met Leu Arg Asn Phe Ala Phe
                420                 425                 430

Gln Asp Pro His Asp Tyr Gln Phe Arg Leu Lys Glu Thr Leu Thr Ile
                435                 440                 445

Lys Pro Asp Gln Phe Val Leu Arg Val Arg Arg Arg Pro His Glu
        450                 455                 460

Arg Phe Val Thr Arg Gln Ala Ser Gln Ala Val Ala Asp Ala Ala Gln
465                 470                 475                 480

Thr Asp Val Arg Gly His Gly Gln Ala Met Thr Val Leu Cys Ala Ser
                485                 490                 495

Ser Leu Gly Thr Ala Arg Glu Leu Ala Glu Gln Ile His Ala Gly Ala
                500                 505                 510

Ile Ala Ala Gly Phe Asp Ala Lys Leu Ala Asp Leu Asp Asp Ala Val
        515                 520                 525

Gly Val Leu Pro Thr Ser Gly Leu Val Val Val Ala Ala Thr Tyr
                530                 535                 540

Asn Gly Arg Ala Pro Asp Ser Ala Arg Lys Phe Glu Ala Met Leu Asp
545                 550                 555                 560

Ala Asp Asp Ala Ser Gly Tyr Arg Ala Asn Gly Met Arg Leu Ala Leu
                565                 570                 575

Leu Gly Cys Gly Asn Ser Gln Trp Ala Thr Tyr Gln Ala Phe Pro Arg
                580                 585                 590

Arg Val Phe Asp Phe Phe Ile Thr Ala Gly Ala Val Pro Leu Leu Pro
                595                 600                 605

Arg Gly Glu Ala Asp Gly Asn Gly Asp Phe Asp Gln Ala Ala Glu Arg
        610                 615                 620

Trp Leu Ala Gln Leu Trp Gln Ala Leu Gln Ala Asp Gly Ala Gly Thr
625                 630                 635                 640

Gly Gly Leu Gly Val Asp Val Gln Val Arg Ser Met Ala Ala Ile Arg
                645                 650                 655

Ala Glu Thr Leu Pro Ala Gly Thr Gln Ala Phe Thr Val Leu Ser Asn
                660                 665                 670

Asp Glu Leu Val Gly Asp Pro Ser Gly Leu Trp Asp Phe Ser Ile Glu
                675                 680                 685
```

Ala Pro Arg Thr Ser Thr Arg Asp Ile Arg Leu Gln Leu Pro Pro Gly
690                 695                 700

Ile Thr Tyr Arg Thr Gly Asp His Ile Ala Val Trp Pro Gln Asn Asp
705                 710                 715                 720

Ala Gln Leu Val Ser Glu Leu Cys Glu Arg Leu Asp Leu Asp Pro Asp
            725                 730                 735

Ala Gln Ala Thr Ile Ser Ala Pro His Gly Met Gly Arg Gly Leu Pro
            740                 745                 750

Ile Asp Gln Ala Leu Pro Val Arg Gln Leu Leu Thr His Phe Ile Glu
        755                 760                 765

Leu Gln Asp Val Val Ser Arg Gln Thr Leu Arg Ala Leu Ala Gln Ala
    770                 775                 780

Thr Arg Cys Pro Phe Thr Lys Gln Ser Ile Glu Gln Leu Ala Ser Asp
785                 790                 795                 800

Asp Ala Glu His Gly Tyr Ala Thr Lys Val Val Ala Arg Arg Leu Gly
                805                 810                 815

Ile Leu Asp Val Leu Val Glu His Pro Ala Ile Ala Leu Thr Leu Gln
            820                 825                 830

Glu Leu Leu Ala Cys Thr Val Pro Met Arg Pro Arg Leu Tyr Ser Ile
        835                 840                 845

Ala Ser Ser Pro Leu Val Ser Pro Asp Val Ala Thr Leu Leu Val Gly
    850                 855                 860

Thr Val Cys Ala Pro Ala Leu Ser Gly Arg Gly Gln Phe Arg Gly Val
865                 870                 875                 880

Ala Ser Thr Trp Leu Gln His Leu Pro Pro Gly Ala Arg Val Ser Ala
                885                 890                 895

Ser Ile Arg Thr Pro Asn Pro Pro Phe Ala Pro Asp Pro Asp Pro Ala
            900                 905                 910

Ala Pro Met Leu Leu Ile Gly Pro Gly Thr Gly Ile Ala Pro Phe Arg
        915                 920                 925

Gly Phe Leu Glu Glu Arg Ala Leu Arg Lys Met Ala Gly Asn Ala Val
    930                 935                 940

Thr Pro Ala Gln Leu Tyr Phe Gly Cys Arg His Pro Gln His Asp Trp
945                 950                 955                 960

Leu Tyr Arg Glu Asp Ile Glu Arg Trp Ala Gly Gln Gly Val Val Glu
                965                 970                 975

Val His Pro Ala Tyr Ser Val Val Pro Asp Ala Pro Arg Tyr Val Gln
            980                 985                 990

Asp Leu Leu Trp Gln Arg Arg Glu Gln Val Trp Ala Gln Val Arg Asp
        995                 1000                1005

Gly Ala Thr Ile Tyr Val Cys Gly Asp Gly Arg Arg Met Ala Pro
    1010                1015                1020

Ala Val Arg Gln Thr Leu Ile Glu Ile Gly Met Ala Gln Gly Gly
    1025                1030                1035

Met Thr Asp Lys Ala Ala Ser Asp Trp Phe Gly Gly Leu Val Ala
    1040                1045                1050

Gln Gly Arg Tyr Arg Gln Asp Val Phe Asn
    1055                1060

<210> SEQ ID NO 6
<211> LENGTH: 1077
<212> TYPE: PRT
<213> ORGANISM: Bradyrhizobium japonicum

<400> SEQUENCE: 6

-continued

```
Ser Ser Lys Asn Arg Leu Asp Pro Ile Pro Gln Pro Pro Thr Lys Pro
1               5                   10                  15

Val Val Gly Asn Met Leu Ser Leu Asp Ser Ala Ala Pro Val Gln His
                20                  25                  30

Leu Thr Arg Leu Ala Lys Glu Leu Gly Pro Ile Phe Trp Leu Asp Met
            35                  40                  45

Met Gly Ser Pro Ile Val Val Ser Gly His Asp Leu Val Asp Glu
    50                  55                  60

Leu Ser Asp Glu Lys Arg Phe Asp Lys Thr Val Arg Gly Ala Leu Arg
65                  70                  75                  80

Arg Val Arg Ala Val Gly Gly Asp Gly Leu Phe Thr Ala Asp Thr Arg
                85                  90                  95

Glu Pro Asn Trp Ser Lys Ala His Asn Ile Leu Leu Gln Pro Phe Gly
                100                 105                 110

Asn Arg Ala Met Gln Ser Tyr His Pro Ser Met Val Asp Ile Ala Glu
                115                 120                 125

Gln Leu Val Gln Lys Trp Glu Arg Leu Asn Ala Asp Asp Glu Ile Asp
        130                 135                 140

Val Val His Asp Met Thr Ala Leu Thr Leu Asp Thr Ile Gly Leu Cys
145                 150                 155                 160

Gly Phe Asp Tyr Arg Phe Asn Ser Phe Tyr Arg Arg Asp Tyr His Pro
                165                 170                 175

Phe Val Glu Ser Leu Val Arg Ser Leu Glu Thr Ile Met Met Thr Arg
                180                 185                 190

Gly Leu Pro Phe Glu Gln Ile Trp Met Gln Lys Arg Arg Lys Thr Leu
                195                 200                 205

Ala Glu Asp Val Ala Phe Met Asn Lys Met Val Asp Glu Ile Ile Ala
        210                 215                 220

Glu Arg Arg Lys Ser Ala Glu Gly Ile Asp Asp Lys Lys Asp Met Leu
225                 230                 235                 240

Ala Ala Met Met Thr Gly Val Asp Arg Ser Thr Gly Glu Gln Leu Asp
                245                 250                 255

Asp Val Asn Ile Arg Tyr Gln Ile Asn Thr Phe Leu Ile Ala Gly His
                260                 265                 270

Glu Thr Thr Ser Gly Leu Leu Ser Tyr Thr Leu Tyr Ala Leu Leu Lys
        275                 280                 285

His Pro Asp Ile Leu Lys Lys Ala Tyr Asp Glu Val Asp Arg Val Phe
        290                 295                 300

Gly Pro Asp Val Asn Ala Lys Pro Thr Tyr Gln Gln Val Thr Gln Leu
305                 310                 315                 320

Thr Tyr Ile Thr Gln Ile Leu Lys Glu Ala Leu Arg Leu Trp Pro Pro
                325                 330                 335

Ala Pro Ala Tyr Gly Ile Ser Pro Leu Ala Asp Glu Thr Ile Gly Gly
                340                 345                 350

Gly Lys Tyr Lys Leu Arg Lys Gly Thr Phe Ile Thr Ile Leu Val Thr
                355                 360                 365

Ala Leu His Arg Asp Pro Ser Val Trp Gly Pro Asn Pro Asp Ala Phe
        370                 375                 380

Asp Pro Glu Asn Phe Ser Arg Glu Ala Glu Lys Arg Pro Ile Asn
385                 390                 395                 400

Ala Trp Lys Pro Phe Gly Asn Gly Gln Arg Ala Cys Ile Gly Arg Gly
                405                 410                 415
```

```
Phe Ala Met His Glu Ala Ala Leu Ala Leu Gly Met Ile Leu Gln Arg
            420                 425                 430
Phe Lys Leu Ile Asp His Gln Arg Tyr Gln Met His Leu Lys Glu Thr
        435                 440                 445
Leu Thr Met Lys Pro Glu Gly Phe Lys Ile Lys Val Arg Pro Arg Ala
450                 455                 460
Asp Arg Glu Arg Gly Ala Tyr Gly Gly Pro Val Ala Ala Val Ser Ser
465                 470                 475                 480
Ala Pro Arg Ala Pro Arg Gln Pro Thr Ala Arg Pro Gly His Asn Thr
                485                 490                 495
Pro Met Leu Val Leu Tyr Gly Ser Asn Leu Gly Thr Ala Glu Glu Leu
            500                 505                 510
Ala Thr Arg Met Ala Asp Leu Ala Glu Ile Asn Gly Phe Ala Val His
        515                 520                 525
Leu Gly Ala Leu Asp Glu Tyr Val Gly Lys Leu Pro Gln Glu Gly Gly
    530                 535                 540
Val Leu Ile Ile Cys Ala Ser Tyr Asn Gly Ala Pro Pro Asp Asn Ala
545                 550                 555                 560
Thr Gln Phe Val Lys Trp Leu Gly Ser Asp Leu Pro Lys Asp Ala Phe
                565                 570                 575
Ala Asn Val Arg Tyr Ala Val Phe Gly Cys Gly Asn Ser Asp Trp Ala
            580                 585                 590
Ala Thr Tyr Gln Ser Val Pro Arg Phe Ile Asp Glu Gln Leu Ser Gly
        595                 600                 605
His Gly Ala Arg Ala Val Tyr Pro Arg Gly Glu Gly Asp Ala Arg Ser
    610                 615                 620
Asp Leu Asp Gly Gln Phe Gln Lys Trp Phe Pro Ala Ala Ala Gln Val
625                 630                 635                 640
Ala Thr Lys Glu Phe Gly Ile Asp Trp Asn Phe Thr Arg Thr Ala Glu
                645                 650                 655
Asp Asp Pro Leu Tyr Ala Ile Glu Pro Val Ala Val Thr Ala Val Asn
            660                 665                 670
Thr Ile Val Ala Gln Gly Gly Ala Val Ala Met Lys Val Leu Val Asn
        675                 680                 685
Asp Glu Leu Gln Asn Lys Ser Gly Ser Asn Pro Ser Glu Arg Ser Thr
    690                 695                 700
Arg His Ile Glu Val Gln Leu Pro Ser Asn Ile Thr Tyr Arg Val Gly
705                 710                 715                 720
Asp His Leu Ser Val Val Pro Arg Asn Asp Pro Thr Leu Val Asp Ser
                725                 730                 735
Val Ala Arg Arg Phe Gly Phe Leu Pro Ala Asp Gln Ile Arg Leu Gln
            740                 745                 750
Val Ala Glu Gly Arg Arg Ala Gln Leu Pro Val Gly Glu Ala Val Ser
        755                 760                 765
Val Gly Arg Leu Leu Ser Glu Phe Val Glu Leu Gln Gln Val Ala Thr
    770                 775                 780
Arg Lys Gln Ile Gln Ile Met Ala Glu His Thr Arg Cys Pro Val Thr
785                 790                 795                 800
Lys Pro Lys Leu Leu Ala Phe Val Gly Glu Glu Ala Glu Pro Ala Glu
                805                 810                 815
Arg Tyr Arg Thr Glu Ile Leu Ala Met Arg Lys Ser Val Tyr Asp Leu
            820                 825                 830
Leu Leu Glu Tyr Pro Ala Cys Glu Leu Pro Phe His Val Tyr Leu Glu
```

```
                    835                 840                 845
Met Leu Ser Leu Leu Ala Pro Arg Tyr Tyr Ser Ile Ser Ser Ser Pro
    850                 855                 860
Ser Val Asp Pro Ala Arg Cys Ser Ile Thr Val Gly Val Val Glu Gly
865                 870                 875                 880
Pro Ala Ala Ser Gly Arg Gly Val Tyr Lys Gly Ile Cys Ser Asn Tyr
                885                 890                 895
Leu Ala Asn Arg Arg Ala Ser Asp Ala Ile Tyr Ala Thr Val Arg Glu
                900                 905                 910
Thr Lys Ala Gly Phe Arg Leu Pro Asp Asp Ser Ser Val Pro Ile Ile
                915                 920                 925
Met Ile Gly Pro Gly Thr Gly Leu Ala Pro Phe Arg Gly Phe Leu Gln
    930                 935                 940
Glu Arg Ala Ala Arg Lys Ala Lys Gly Ala Ser Leu Gly Pro Ala Met
945                 950                 955                 960
Leu Phe Phe Gly Cys Arg His Pro Asp Gln Asp Phe Leu Tyr Ala Asp
                965                 970                 975
Glu Leu Lys Ala Leu Ala Ala Ser Gly Val Thr Glu Leu Phe Thr Ala
                980                 985                 990
Phe Ser Arg Ala Asp Gly Pro Lys  Thr Tyr Val Gln His  Val Leu Ala
                995                 1000                1005
Ala Gln Lys Asp Lys Val Trp  Pro Leu Ile Glu Gln  Gly Ala Ile
    1010                1015                1020
Ile Tyr Val Cys Gly Asp Gly  Gly Gln Met Glu Pro  Asp Val Lys
    1025                1030                1035
Ala Ala Leu Val Ala Ile Arg  His Glu Lys Ser Gly  Ser Asp Thr
    1040                1045                1050
Ala Thr Ala Ala Arg Trp Ile  Glu Glu Met Gly Ala  Thr Asn Arg
    1055                1060                1065
Tyr Val Leu Asp Val Trp Ala  Gly Gly
    1070                1075

<210> SEQ ID NO 7
<211> LENGTH: 1048
<212> TYPE: PRT
<213> ORGANISM: Artificial Sequence
<220> FEATURE:
<223> OTHER INFORMATION: mutant P450 35-E11 protein sequence

<400> SEQUENCE: 7

Thr Ile Lys Glu Met Pro Gln Pro Lys Thr Phe Gly Glu Leu Lys Asn
1               5                   10                  15
Leu Pro Leu Leu Asn Thr Asp Lys Pro Val Gln Ala Leu Met Lys Ile
                20                  25                  30
Ala Asp Glu Leu Gly Glu Ile Phe Lys Phe Glu Ala Pro Gly Cys Val
            35                  40                  45
Thr Arg Tyr Leu Ser Ser Gln Arg Leu Ile Lys Glu Ala Cys Asp Glu
        50                  55                  60
Ser Arg Phe Asp Lys Asn Leu Ser Gln Ala Leu Lys Phe Arg Asp
65                  70                  75                  80
Phe Ser Gly Asp Gly Leu Phe Thr Ser Trp Thr His Glu Ile Asn Trp
                85                  90                  95
Lys Lys Ala His Asn Ile Leu Leu Pro Ser Phe Ser Gln Gln Ala Met
                100                 105                 110
Lys Gly Tyr His Ala Met Met Val Asp Ile Ala Val Gln Leu Val Gln
```

```
            115                 120                 125
Lys Trp Glu Arg Leu Asn Ala Asp Glu His Ile Glu Val Ser Glu Asp
130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
                180                 185                 190

Pro Asp Asp Pro Ala Tyr Asp Glu Asn Lys Arg Gln Cys Gln Glu Asp
                195                 200                 205

Ile Lys Val Met Asn Asp Leu Val Asp Lys Ile Ile Ala Asp Arg Lys
            210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
                260                 265                 270

Leu Ser Phe Ala Leu Tyr Phe Leu Val Lys Asn Pro His Val Leu Gln
                275                 280                 285

Lys Val Val Glu Glu Ala Ala Arg Val Leu Val Asp Pro Val Pro Ser
            290                 295                 300

Tyr Lys Gln Val Lys Gln Leu Lys Tyr Val Gly Met Val Leu Asn Glu
305                 310                 315                 320

Ala Leu Arg Leu Trp Pro Thr Phe Pro Ala Phe Ser Leu Tyr Ala Lys
                325                 330                 335

Glu Asp Thr Val Leu Gly Gly Glu Tyr Pro Leu Glu Lys Gly Asp Glu
                340                 345                 350

Val Met Val Leu Ile Pro Gln Leu His Arg Asp Lys Thr Ile Trp Gly
                355                 360                 365

Asp Asp Val Glu Glu Phe Arg Pro Glu Arg Phe Glu Asn Pro Ser Ala
            370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
                420                 425                 430

Ile Lys Glu Thr Leu Thr Leu Lys Pro Glu Gly Phe Val Val Lys Ala
            435                 440                 445

Lys Ser Lys Lys Ile Pro Leu Gly Gly Ile Pro Ser Pro Ser Thr Gly
450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
                500                 505                 510

Val Ala Thr Leu Asp Ser His Ala Gly Asn Leu Pro Arg Glu Gly Ala
            515                 520                 525

Val Leu Ile Val Thr Ala Ser Tyr Asn Gly His Pro Pro Asp Asn Ala
530                 535                 540
```

```
Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
            595                 600                 605

Phe Glu Gly Thr Tyr Glu Glu Trp Arg Glu His Met Trp Ser Asp Val
        610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
            660                 665                 670

Gln Gln Pro Gly Ser Ala Arg Ser Thr Arg His Leu Glu Ile Glu Leu
            675                 680                 685

Pro Lys Glu Ala Ser Tyr Gln Glu Gly Asp His Leu Gly Val Ile Pro
        690                 695                 700

Arg Asn Tyr Glu Gly Thr Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735

His Leu Pro Leu Ala Lys Thr Val Ser Val Glu Leu Leu Gln Tyr
                740                 745                 750

Val Glu Leu Gln Asp Pro Val Thr Arg Thr Gln Leu Arg Ala Met Ala
            755                 760                 765

Ala Lys Thr Val Cys Pro Pro His Lys Val Glu Leu Glu Ala Leu Leu
    770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
                820                 825                 830

Ser Ser Pro Arg Val Asp Glu Lys Gln Ala Ser Ile Thr Val Ser Val
        835                 840                 845

Val Ser Gly Glu Ala Trp Ser Gly Tyr Gly Glu Tyr Lys Gly Ile Ala
        850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
            915                 920                 925

Glu Ala His Leu Tyr Phe Gly Cys Arg Ser Pro His Glu Asp Tyr Leu
        930                 935                 940

Tyr Gln Glu Glu Leu Glu Asn Ala Gln Ser Glu Gly Ile Ile Thr Leu
945                 950                 955                 960
```

-continued

```
His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
        995                 1000                1005

Val Glu Ala Thr Leu Met Lys Ser Tyr Ala Asp Val His Gln Val
    1010                1015                1020

Ser Glu Ala Asp Ala Arg Leu Trp Leu Gln Gln Leu Glu Glu Lys
    1025                1030                1035

Gly Arg Tyr Ala Lys Asp Val Trp Ala Gly
    1040                1045

<210> SEQ ID NO 8
<211> LENGTH: 1048
<212> TYPE: PRT
<213> ORGANISM: Artificial sequence
<220> FEATURE:
<223> OTHER INFORMATION: mutant P450 35-E11-E464R protein sequence

<400> SEQUENCE: 8

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Cys Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Phe Phe Arg Asp
65                  70                  75                  80

Phe Ser Gly Asp Gly Leu Phe Thr Ser Trp Thr His Glu Ile Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Cys Gln Glu Asp
        195                 200                 205

Ile Lys Val Met Asn Asp Leu Val Asp Lys Ile Ile Ala Asp Arg Lys
    210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
            260                 265                 270
```

-continued

```
Leu Ser Phe Ala Leu Tyr Phe Leu Val Lys Asn Pro His Val Leu Gln
        275                 280                 285
Lys Val Val Glu Glu Ala Ala Arg Val Leu Val Asp Pro Val Pro Ser
    290                 295                 300
Tyr Lys Gln Val Lys Gln Leu Lys Tyr Val Gly Met Val Leu Asn Glu
305                 310                 315                 320
Ala Leu Arg Leu Trp Pro Thr Phe Pro Ala Phe Ser Leu Tyr Ala Lys
                325                 330                 335
Glu Asp Thr Val Leu Gly Gly Glu Tyr Pro Leu Glu Lys Gly Asp Glu
            340                 345                 350
Val Met Val Leu Ile Pro Gln Leu His Arg Asp Lys Thr Ile Trp Gly
        355                 360                 365
Asp Asp Val Glu Glu Phe Arg Pro Glu Arg Phe Glu Asn Pro Ser Ala
    370                 375                 380
Ile Pro Gln His Ala Phe Lys Pro Phe Gly Asn Gly Gln Arg Ala Cys
385                 390                 395                 400
Ile Gly Gln Gln Phe Ala Leu His Glu Ala Thr Leu Val Leu Gly Met
                405                 410                 415
Met Leu Lys His Phe Asp Phe Glu Asp His Thr Asn Tyr Glu Leu Asp
            420                 425                 430
Ile Lys Glu Thr Leu Thr Leu Lys Pro Glu Gly Phe Val Val Lys Ala
        435                 440                 445
Lys Ser Lys Lys Ile Pro Leu Gly Gly Ile Pro Ser Pro Ser Thr Arg
    450                 455                 460
Gln Ser Ala Lys Lys Val Arg Lys Lys Ala Glu Asn Ala His Asn Thr
465                 470                 475                 480
Pro Leu Leu Val Leu Tyr Gly Ser Asn Met Gly Thr Ala Glu Gly Thr
                485                 490                 495
Ala Arg Asp Leu Ala Asp Ile Ala Met Ser Lys Gly Phe Ala Pro Gln
            500                 505                 510
Val Ala Thr Leu Asp Ser His Ala Gly Asn Leu Pro Arg Glu Gly Ala
        515                 520                 525
Val Leu Ile Val Thr Ala Ser Tyr Asn Gly His Pro Pro Asp Asn Ala
    530                 535                 540
Lys Gln Phe Val Asp Trp Leu Asp Gln Ala Ser Ala Asp Glu Val Lys
545                 550                 555                 560
Gly Val Arg Tyr Ser Val Phe Gly Cys Gly Asp Lys Asn Trp Ala Thr
                565                 570                 575
Thr Tyr Gln Lys Val Pro Ala Phe Ile Asp Glu Thr Leu Ala Ala Lys
            580                 585                 590
Gly Ala Glu Asn Ile Ala Asp Arg Gly Glu Ala Asp Ala Ser Asp Asp
        595                 600                 605
Phe Glu Gly Thr Tyr Glu Glu Trp Arg Glu His Met Trp Ser Asp Val
    610                 615                 620
Ala Ala Tyr Phe Asn Leu Asp Ile Glu Asn Ser Glu Asp Asn Lys Ser
625                 630                 635                 640
Thr Leu Ser Leu Gln Phe Val Asp Ser Ala Asp Met Pro Leu Ala
                645                 650                 655
Lys Met His Gly Ala Phe Ser Thr Asn Val Val Ala Ser Lys Glu Leu
            660                 665                 670
Gln Gln Pro Gly Ser Ala Arg Ser Thr Arg His Leu Glu Ile Glu Leu
        675                 680                 685
Pro Lys Glu Ala Ser Tyr Gln Glu Gly Asp His Leu Gly Val Ile Pro
```

```
                690             695             700
Arg Asn Tyr Glu Gly Thr Val Asn Arg Val Thr Ala Arg Phe Gly Leu
705             710             715             720

Asp Ala Ser Gln Gln Ile Arg Leu Glu Ala Glu Glu Lys Leu Ala
            725             730             735

His Leu Pro Leu Ala Lys Thr Val Ser Val Glu Leu Leu Gln Tyr
            740             745             750

Val Glu Leu Gln Asp Pro Val Thr Arg Thr Gln Leu Arg Ala Met Ala
            755             760             765

Ala Lys Thr Val Cys Pro Pro His Lys Val Glu Leu Glu Ala Leu Leu
770             775             780

Glu Lys Gln Ala Tyr Lys Glu Gln Val Leu Ala Lys Arg Leu Thr Met
785             790             795             800

Leu Glu Leu Leu Glu Lys Tyr Pro Ala Cys Glu Met Lys Phe Ser Glu
                805             810             815

Phe Ile Ala Leu Leu Pro Ser Ile Arg Pro Arg Tyr Tyr Ser Ile Ser
                820             825             830

Ser Ser Pro Arg Val Asp Glu Lys Gln Ala Ser Ile Thr Val Ser Val
            835             840             845

Val Ser Gly Glu Ala Trp Ser Gly Tyr Gly Glu Tyr Lys Gly Ile Ala
            850             855             860

Ser Asn Tyr Leu Ala Glu Leu Gln Glu Gly Asp Thr Ile Thr Cys Phe
865             870             875             880

Ile Ser Thr Pro Gln Ser Glu Phe Thr Leu Pro Lys Asp Pro Glu Thr
                885             890             895

Pro Leu Ile Met Val Gly Pro Gly Thr Gly Val Ala Pro Phe Arg Gly
                900             905             910

Phe Val Gln Ala Arg Lys Gln Leu Lys Glu Gln Gly Gln Ser Leu Gly
            915             920             925

Glu Ala His Leu Tyr Phe Gly Cys Arg Ser Pro His Glu Asp Tyr Leu
930             935             940

Tyr Gln Glu Glu Leu Glu Asn Ala Gln Ser Glu Gly Ile Ile Thr Leu
945             950             955             960

His Thr Ala Phe Ser Arg Met Pro Asn Gln Pro Lys Thr Tyr Val Gln
                965             970             975

His Val Met Glu Gln Asp Gly Lys Leu Ile Glu Leu Leu Asp Gln
            980             985             990

Gly Ala His Phe Tyr Ile Cys Gly Asp Gly Ser Gln Met Ala Pro Ala
            995             1000             1005

Val Glu Ala Thr Leu Met Lys Ser Tyr Ala Asp Val His Gln Val
    1010             1015             1020

Ser Glu Ala Asp Ala Arg Leu Trp Leu Gln Gln Leu Glu Glu Lys
    1025             1030             1035

Gly Arg Tyr Ala Lys Asp Val Trp Ala Gly
    1040             1045

<210> SEQ ID NO 9
<211> LENGTH: 1048
<212> TYPE: PRT
<213> ORGANISM: Artificial sequence
<220> FEATURE:
<223> OTHER INFORMATION: mutant P450 35-E11-E464Y protein sequence

<400> SEQUENCE: 9

Thr Ile Lys Glu Met Pro Gln Pro Lys Thr Phe Gly Glu Leu Lys Asn
```

-continued

```
  1               5                  10                 15
Leu Pro Leu Leu Asn Thr Asp Lys Pro Val Gln Ala Leu Met Lys Ile
              20                  25                 30
Ala Asp Glu Leu Gly Glu Ile Phe Lys Phe Glu Ala Pro Gly Cys Val
              35                  40                 45
Thr Arg Tyr Leu Ser Ser Gln Arg Leu Ile Lys Glu Ala Cys Asp Glu
 50                  55                 60
Ser Arg Phe Asp Lys Asn Leu Ser Gln Ala Leu Lys Phe Phe Arg Asp
 65                  70                 75                 80
Phe Ser Gly Asp Gly Leu Phe Thr Ser Trp Thr His Glu Ile Asn Trp
              85                  90                 95
Lys Lys Ala His Asn Ile Leu Leu Pro Ser Phe Ser Gln Gln Ala Met
             100                 105                110
Lys Gly Tyr His Ala Met Met Val Asp Ile Ala Val Gln Leu Val Gln
             115                 120                125
Lys Trp Glu Arg Leu Asn Ala Asp Glu His Ile Glu Val Ser Glu Asp
             130                 135                140
Met Thr Arg Leu Thr Leu Asp Thr Ile Gly Leu Cys Gly Phe Asn Tyr
145                 150                 155                160
Arg Phe Asn Ser Phe Tyr Arg Asp Gln Pro His Pro Phe Ile Ile Ser
             165                 170                175
Met Val Arg Ala Leu Asp Glu Val Met Asn Lys Leu Gln Arg Ala Asn
             180                 185                190
Pro Asp Asp Pro Ala Tyr Asp Glu Asn Lys Arg Gln Cys Gln Glu Asp
             195                 200                205
Ile Lys Val Met Asn Asp Leu Val Asp Lys Ile Ile Ala Asp Arg Lys
210                 215                 220
Ala Arg Gly Glu Gln Ser Asp Asp Leu Leu Thr Gln Met Leu Asn Gly
225                 230                 235                240
Lys Asp Pro Glu Thr Gly Glu Pro Leu Asp Asp Gly Asn Ile Ser Tyr
             245                 250                255
Gln Ile Ile Thr Phe Leu Ile Ala Gly His Glu Thr Thr Ser Gly Leu
             260                 265                270
Leu Ser Phe Ala Leu Tyr Phe Leu Val Lys Asn Pro His Val Leu Gln
             275                 280                285
Lys Val Val Glu Glu Ala Ala Arg Val Leu Val Asp Pro Val Pro Ser
             290                 295                300
Tyr Lys Gln Val Lys Gln Leu Lys Tyr Val Gly Met Val Leu Asn Glu
305                 310                 315                320
Ala Leu Arg Leu Trp Pro Thr Phe Pro Ala Phe Ser Leu Tyr Ala Lys
             325                 330                335
Glu Asp Thr Val Leu Gly Gly Glu Tyr Pro Leu Glu Lys Gly Asp Glu
             340                 345                350
Val Met Val Leu Ile Pro Gln Leu His Arg Asp Lys Thr Ile Trp Gly
             355                 360                365
Asp Asp Val Glu Glu Phe Arg Pro Glu Arg Phe Glu Asn Pro Ser Ala
             370                 375                380
Ile Pro Gln His Ala Phe Lys Pro Phe Gly Asn Gly Gln Arg Ala Cys
385                 390                 395                400
Ile Gly Gln Gln Phe Ala Leu His Glu Ala Thr Leu Val Leu Gly Met
             405                 410                415
Met Leu Lys His Phe Asp Phe Glu Asp His Thr Asn Tyr Glu Leu Asp
             420                 425                430
```

```
Ile Lys Glu Thr Leu Thr Leu Lys Pro Glu Gly Phe Val Lys Ala
        435                 440                 445

Lys Ser Lys Lys Ile Pro Leu Gly Gly Ile Pro Ser Pro Ser Thr Tyr
450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
                500                 505                 510

Val Ala Thr Leu Asp Ser His Ala Gly Asn Leu Pro Arg Glu Gly Ala
            515                 520                 525

Val Leu Ile Val Thr Ala Ser Tyr Asn Gly His Pro Pro Asp Asn Ala
            530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
            595                 600                 605

Phe Glu Gly Thr Tyr Glu Glu Trp Arg Glu His Met Trp Ser Asp Val
                610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Asp Met Pro Leu Ala
                645                 650                 655

Lys Met His Gly Ala Phe Ser Thr Asn Val Val Ala Ser Lys Glu Leu
                660                 665                 670

Gln Gln Pro Gly Ser Ala Arg Ser Thr Arg His Leu Glu Ile Glu Leu
            675                 680                 685

Pro Lys Glu Ala Ser Tyr Gln Glu Gly Asp His Leu Gly Val Ile Pro
            690                 695                 700

Arg Asn Tyr Glu Gly Thr Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735

His Leu Pro Leu Ala Lys Thr Val Ser Val Glu Glu Leu Leu Gln Tyr
                740                 745                 750

Val Glu Leu Gln Asp Pro Val Thr Arg Thr Gln Leu Arg Ala Met Ala
            755                 760                 765

Ala Lys Thr Val Cys Pro Pro His Lys Val Glu Leu Glu Ala Leu Leu
    770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
            835                 840                 845
```

```
Val Ser Gly Glu Ala Trp Ser Gly Tyr Gly Glu Tyr Lys Gly Ile Ala
    850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
                900                 905                 910

Phe Val Gln Ala Arg Lys Gln Leu Lys Glu Gln Gly Gln Ser Leu Gly
                915                 920                 925

Glu Ala His Leu Tyr Phe Gly Cys Arg Ser Pro His Glu Asp Tyr Leu
            930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
                980                 985                 990

Gly Ala His Phe Tyr Ile Cys Gly Asp Gly Ser Gln Met Ala Pro Ala
            995                 1000                1005

Val Glu Ala Thr Leu Met Lys Ser Tyr Ala Asp Val His Gln Val
    1010            1015                1020

Ser Glu Ala Asp Ala Arg Leu Trp Leu Gln Gln Leu Glu Glu Lys
    1025            1030                1035

Gly Arg Tyr Ala Lys Asp Val Trp Ala Gly
    1040            1045

<210> SEQ ID NO 10
<211> LENGTH: 1048
<212> TYPE: PRT
<213> ORGANISM: Artificial sequence
<220> FEATURE:
<223> OTHER INFORMATION: mutant P450 35-E11-E464T protein sequence

<400> SEQUENCE: 10

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
                20                  25                  30

Ala Asp Glu Leu Gly Glu Ile Phe Lys Phe Glu Ala Pro Gly Cys Val
            35                  40                  45

Thr Arg Tyr Leu Ser Ser Gln Arg Leu Ile Lys Glu Ala Cys Asp Glu
50                  55                  60

Ser Arg Phe Asp Lys Asn Leu Ser Gln Ala Leu Lys Phe Phe Arg Asp
65                  70                  75                  80

Phe Ser Gly Asp Gly Leu Phe Thr Ser Trp Thr His Glu Ile Asn Trp
                85                  90                  95

Lys Lys Ala His Asn Ile Leu Leu Pro Ser Phe Ser Gln Gln Ala Met
                100                 105                 110

Lys Gly Tyr His Ala Met Met Val Asp Ile Ala Val Gln Leu Val Gln
            115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160
```

```
Arg Phe Asn Ser Phe Tyr Arg Asp Gln Pro His Pro Phe Ile Ile Ser
            165                 170                 175

Met Val Arg Ala Leu Asp Glu Val Met Asn Lys Leu Gln Arg Ala Asn
        180                 185                 190

Pro Asp Asp Pro Ala Tyr Asp Glu Asn Lys Arg Gln Cys Gln Glu Asp
    195                 200                 205

Ile Lys Val Met Asn Asp Leu Val Asp Lys Ile Ile Ala Asp Arg Lys
210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Val Val Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Thr Phe Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Ile Trp Gly
        355                 360                 365

Asp Asp Val Glu Glu Phe Arg Pro Glu Arg Phe Glu Asn Pro Ser Ala
    370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
        435                 440                 445

Lys Ser Lys Lys Ile Pro Leu Gly Gly Ile Pro Ser Pro Ser Thr Thr
    450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
    530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
```

-continued

```
            580                 585                 590
Gly Ala Glu Asn Ile Ala Asp Arg Gly Glu Ala Asp Ala Ser Asp Asp
                595                 600                 605

Phe Glu Gly Thr Tyr Glu Glu Trp Arg Glu His Met Trp Ser Asp Val
    610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Asp Met Pro Leu Ala
                645                 650                 655

Lys Met His Gly Ala Phe Ser Thr Asn Val Val Ala Ser Lys Glu Leu
                660                 665                 670

Gln Gln Pro Gly Ser Ala Arg Ser Thr Arg His Leu Glu Ile Glu Leu
            675                 680                 685

Pro Lys Glu Ala Ser Tyr Gln Glu Gly Asp His Leu Gly Val Ile Pro
        690                 695                 700

Arg Asn Tyr Glu Gly Thr Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735

His Leu Pro Leu Ala Lys Thr Val Ser Val Glu Glu Leu Leu Gln Tyr
                740                 745                 750

Val Glu Leu Gln Asp Pro Val Thr Arg Thr Gln Leu Arg Ala Met Ala
            755                 760                 765

Ala Lys Thr Val Cys Pro Pro His Lys Val Glu Leu Glu Ala Leu Leu
        770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
                820                 825                 830

Ser Ser Pro Arg Val Asp Glu Lys Gln Ala Ser Ile Thr Val Ser Val
            835                 840                 845

Val Ser Gly Glu Ala Trp Ser Gly Tyr Gly Glu Tyr Lys Gly Ile Ala
        850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
            915                 920                 925

Glu Ala His Leu Tyr Phe Gly Cys Arg Ser Pro His Glu Asp Tyr Leu
        930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
        995                 1000                1005
```

```
Val Glu Ala Thr Leu Met Lys Ser Tyr Ala Asp Val His Gln Val
    1010            1015                1020

Ser Glu Ala Asp Ala Arg Leu Trp Leu Gln Gln Leu Glu Glu Lys
    1025            1030                1035

Gly Arg Tyr Ala Lys Asp Val Trp Ala Gly
    1040            1045

<210> SEQ ID NO 11
<211> LENGTH: 1048
<212> TYPE: PRT
<213> ORGANISM: Artificial sequence
<220> FEATURE:
<223> OTHER INFORMATION: mutant P450 20-D3 protein sequence

<400> SEQUENCE: 11

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Cys Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Phe Phe Arg Asp
65                  70                  75                  80

Phe Ser Gly Asp Gly Leu Phe Thr Ser Trp Thr His Glu Ile Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Cys Gln Glu Asp
        195                 200                 205

Ile Lys Val Met Asn Asp Leu Val Asp Lys Ile Ala Asp Arg Lys
    210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro Arg Val Leu Gln
        275                 280                 285

Lys Val Val Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320
```

```
Ala Leu Arg Leu Trp Pro Thr Phe Pro Ala Phe Ser Leu Tyr Ala Lys
            325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Ile Trp Gly
            355                 360                 365

Asp Asp Val Glu Glu Phe Arg Pro Glu Arg Phe Glu Asn Pro Ser Ala
            370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
            435                 440                 445

Lys Ser Lys Lys Ile Pro Leu Gly Gly Ile Pro Ser Pro Ser Thr Gly
450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
            515                 520                 525

Val Leu Ile Val Thr Ala Ser Tyr Asn Gly His Pro Pro Asp Asn Ala
            530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
            595                 600                 605

Phe Glu Gly Thr Tyr Glu Glu Trp Arg Glu His Met Trp Ser Asp Val
            610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
            660                 665                 670

Gln Gln Pro Gly Ser Ala Arg Ser Thr Arg His Leu Glu Ile Glu Leu
            675                 680                 685

Pro Lys Glu Ala Ser Tyr Gln Glu Gly Asp His Leu Gly Val Ile Pro
            690                 695                 700

Arg Asn Tyr Glu Gly Thr Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735
```

-continued

His Leu Pro Leu Ala Lys Thr Val Ser Val Glu Glu Leu Leu Gln Tyr
                740                 745                 750

Val Glu Leu Gln Asp Pro Val Thr Arg Thr Gln Leu Arg Ala Met Ala
            755                 760                 765

Ala Lys Thr Val Cys Pro Pro His Lys Val Glu Leu Glu Ala Leu Leu
        770                 775                 780

Glu Lys Gln Ala Tyr Lys Glu Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
        835                 840                 845

Val Ser Gly Glu Ala Trp Ser Gly Tyr Gly Glu Tyr Lys Gly Ile Ala
850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
        915                 920                 925

Glu Ala His Leu Tyr Phe Gly Cys Arg Ser Pro His Glu Asp Tyr Leu
930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
        995                 1000                1005

Val Glu Ala Thr Leu Met Lys Ser Tyr Ala Asp Val His Gln Val
    1010                1015                1020

Ser Glu Ala Asp Ala Arg Leu Trp Leu Gln Gln Leu Glu Glu Lys
    1025                1030                1035

Gly Arg Tyr Ala Lys Asp Val Trp Ala Gly
    1040                1045

<210> SEQ ID NO 12
<211> LENGTH: 1048
<212> TYPE: PRT
<213> ORGANISM: Artificial sequence
<220> FEATURE:
<223> OTHER INFORMATION: Mutant P450 23-1D protein sequence

<400> SEQUENCE: 12

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Cys Val
        35                  40                  45

-continued

```
Thr Arg Tyr Leu Ser Ser Gln Arg Leu Ile Lys Glu Ala Cys Asp Glu
         50                  55                  60

Ser Arg Phe Asp Lys Asn Leu Ser Gln Ala Leu Lys Phe Phe Arg Asp
 65                  70                  75                  80

Phe Ser Gly Asp Gly Leu Phe Thr Ser Trp Thr His Glu Ile Asn Trp
                 85                  90                  95

Lys Lys Ala His Asn Ile Leu Leu Pro Ser Phe Ser Gln Gln Ala Met
                100                 105                 110

Lys Gly Tyr His Ala Met Met Val Asp Ile Ala Val Gln Leu Val Gln
                115                 120                 125

Lys Trp Glu Arg Leu Asn Ala Asp Glu His Ile Glu Val Ser Glu Asp
130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
                180                 185                 190

Pro Asp Asp Pro Ala Tyr Asp Glu Asn Lys Arg Gln Cys Gln Glu Asp
                195                 200                 205

Ile Lys Val Met Asn Asp Leu Val Asp Lys Ile Ile Ala Asp Arg Lys
210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
                260                 265                 270

Leu Ser Phe Ala Leu Tyr Phe Leu Val Lys Asn Pro His Val Leu Gln
                275                 280                 285

Lys Val Val Glu Glu Ala Ala Arg Val Leu Val Asp Pro Val Pro Ser
                290                 295                 300

Tyr Lys Gln Val Lys Gln Leu Lys Tyr Val Gly Met Val Leu Asn Glu
305                 310                 315                 320

Ala Leu Arg Leu Trp Pro Thr Phe Pro Ala Phe Ser Leu Tyr Ala Lys
                325                 330                 335

Glu Asp Thr Val Leu Gly Gly Glu Tyr Pro Leu Glu Lys Gly Asp Glu
                340                 345                 350

Val Met Val Leu Ile Pro Gln Leu His Arg Asp Lys Thr Ile Trp Gly
                355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
                420                 425                 430

Ile Lys Glu Thr Leu Thr Leu Lys Pro Glu Gly Phe Val Val Lys Ala
                435                 440                 445

Lys Ser Lys Lys Ile Pro Leu Gly Gly Ile Pro Ser Pro Ser Thr Gly
450                 455                 460

Gln Ser Ala Lys Lys Val Arg Lys Lys Ala Glu Asn Ala His Asn Thr
```

```
            465                 470                 475                 480
        Pro Leu Val Leu Tyr Gly Ser Asn Met Gly Thr Ala Glu Gly Thr
                        485                 490                 495

Ala Arg Asp Leu Ala Asp Ile Ala Met Ser Lys Gly Phe Ala Pro Gln
                        500                 505                 510

Val Ala Thr Leu Asp Ser His Ala Gly Asn Leu Pro Arg Glu Gly Ala
                        515                 520                 525

Val Leu Ile Val Thr Ala Ser Tyr Asn Gly His Pro Pro Asp Asn Ala
                        530                 535                 540

Lys Gln Phe Val Asp Trp Leu Asp Gln Ala Ser Ala Asp Glu Val Lys
        545                 550                 555                 560

Gly Val Arg Tyr Ser Val Phe Gly Cys Gly Asp Lys Asn Trp Ala Thr
                            565                 570                 575

Thr Tyr Gln Lys Val Pro Ala Phe Ile Asp Glu Thr Leu Ala Ala Lys
                        580                 585                 590

Gly Ala Glu Asn Ile Ala Asp Arg Gly Glu Ala Asp Ala Ser Asp Asp
                        595                 600                 605

Phe Glu Gly Thr Tyr Glu Trp Arg Glu His Met Trp Ser Asp Val
                    610                 615                 620

Ala Ala Tyr Phe Asn Leu Asp Ile Glu Asn Ser Glu Asp Asn Lys Ser
        625                 630                 635                 640

Thr Leu Ser Leu Arg Phe Val Asp Ser Ala Ala Asp Met Pro Leu Ala
                        645                 650                 655

Lys Met His Gly Ala Phe Ser Thr Asn Val Val Ala Ser Lys Glu Leu
                        660                 665                 670

Gln Gln Pro Gly Ser Ala Arg Ser Thr Arg His Leu Glu Ile Glu Leu
                        675                 680                 685

Pro Lys Glu Ala Ser Tyr Gln Glu Gly Asp His Leu Gly Val Ile Pro
                        690                 695                 700

Arg Asn Tyr Glu Gly Thr Val Asn Arg Val Thr Ala Arg Phe Gly Leu
        705                 710                 715                 720

Asp Ala Ser Gln Gln Ile Arg Leu Glu Ala Glu Glu Lys Leu Ala
                        725                 730                 735

His Leu Pro Leu Ala Lys Thr Val Ser Val Glu Glu Leu Leu Gln Tyr
                        740                 745                 750

Val Glu Leu Gln Asp Pro Val Thr Arg Thr Gln Leu Arg Ala Met Ala
                        755                 760                 765

Ala Lys Thr Val Cys Pro Pro His Lys Val Glu Leu Glu Ala Leu Leu
                        770                 775                 780

Glu Lys Gln Ala Tyr Lys Glu Gln Val Leu Ala Lys Arg Leu Thr Met
        785                 790                 795                 800

Leu Glu Leu Leu Glu Lys Tyr Pro Ala Cys Glu Met Lys Phe Ser Glu
                        805                 810                 815

Phe Ile Ala Leu Leu Pro Ser Ile Arg Pro Arg Tyr Tyr Ser Ile Ser
                        820                 825                 830

Ser Ser Pro Arg Val Asp Glu Lys Gln Ala Ser Ile Thr Val Ser Val
                        835                 840                 845

Val Ser Gly Glu Ala Trp Ser Gly Tyr Gly Glu Tyr Lys Gly Ile Ala
                        850                 855                 860

Ser Asn Tyr Leu Ala Glu Leu Gln Glu Gly Asp Thr Ile Thr Cys Phe
        865                 870                 875                 880

Ile Ser Thr Pro Gln Ser Glu Phe Thr Leu Pro Lys Asp Pro Glu Thr
                        885                 890                 895
```

-continued

```
Pro Leu Ile Met Val Gly Pro Gly Thr Gly Val Ala Pro Phe Arg Gly
                900                 905                 910

Phe Val Gln Ala Arg Lys Gln Leu Lys Glu Gln Gly Gln Ser Leu Gly
                915                 920                 925

Glu Ala His Leu Tyr Phe Gly Cys Arg Ser Pro His Glu Asp Tyr Leu
                930                 935                 940

Tyr Gln Glu Glu Leu Glu Asn Ala Gln Ser Glu Gly Ile Ile Thr Leu
945                 950                 955                 960

His Thr Ala Phe Ser Arg Met Leu Asn Gln Pro Lys Thr Tyr Val Gln
                965                 970                 975

His Val Met Glu Gln Asp Gly Lys Lys Leu Ile Glu Leu Leu Asp Gln
                980                 985                 990

Gly Ala His Phe Tyr Ile Cys Gly Asp Gly Ser Gln Met Ala Pro Ala
                995                 1000                1005

Val Glu Ala Thr Leu Met Lys Ser Tyr Ala Asp Val His Gln Val
            1010                1015                1020

Ser Glu Ala Asp Ala Arg Leu Trp Leu Gln Gln Leu Glu Glu Lys
            1025                1030                1035

Gly Arg Tyr Ala Lys Asp Val Trp Ala Gly
            1040                1045

<210> SEQ ID NO 13
<211> LENGTH: 1048
<212> TYPE: PRT
<213> ORGANISM: Artificial sequence
<220> FEATURE:
<223> OTHER INFORMATION: Mutant P450 21-4G protein sequence

<400> SEQUENCE: 13

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
                20                  25                  30

Ala Asp Glu Leu Gly Glu Ile Phe Lys Phe Glu Ala Pro Gly Cys Val
                35                  40                  45

Thr Arg Tyr Leu Ser Ser Gln Arg Leu Ile Lys Glu Ala Cys Asp Glu
                50                  55                  60

Ser Arg Phe Asp Lys Asn Leu Ser Gln Ala Leu Lys Phe Phe Arg Asp
65                  70                  75                  80

Phe Ser Gly Asp Gly Leu Phe Thr Ser Trp Thr His Glu Ile Asn Trp
                85                  90                  95

Lys Lys Ala His Asn Ile Leu Leu Pro Ser Phe Ser Gln Gln Ala Met
                100                 105                 110

Lys Gly Tyr His Ala Met Met Val Asp Ile Ala Val Gln Leu Val Gln
                115                 120                 125

Lys Trp Glu Arg Leu Asn Ala Asp Glu His Ile Glu Val Ser Glu Asp
                130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
                180                 185                 190

Pro Asp Asp Pro Ala Tyr Asp Glu Asn Lys Arg Gln Cys Gln Glu Asp
                195                 200                 205
```

```
Ile Lys Val Met Asn Asp Leu Val Asp Lys Ile Ile Ala Asp Arg Lys
    210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
                260                 265                 270

Leu Ser Phe Ala Leu Tyr Phe Leu Val Lys Asn Pro His Val Leu Gln
        275                 280                 285

Lys Val Val Glu Glu Ala Ala Arg Val Leu Val Asp Pro Val Pro Ser
290                 295                 300

Tyr Lys Gln Val Lys Gln Leu Lys Tyr Val Gly Met Val Leu Asn Glu
305                 310                 315                 320

Ala Leu Arg Leu Trp Pro Thr Phe Pro Ala Phe Ser Leu Tyr Ala Lys
                325                 330                 335

Glu Asp Thr Val Leu Gly Gly Glu Tyr Pro Leu Glu Lys Gly Asp Glu
                340                 345                 350

Val Met Val Leu Ile Pro Gln Leu His Arg Asp Lys Thr Ile Trp Gly
        355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
                420                 425                 430

Ile Lys Glu Thr Leu Thr Leu Lys Pro Glu Gly Phe Val Val Lys Ala
        435                 440                 445

Lys Ser Lys Lys Ile Pro Leu Gly Gly Ile Pro Ser Pro Ser Thr Gly
450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
                500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
                580                 585                 590

Gly Ala Glu Asn Ile Ala Asp Arg Gly Glu Ala Asp Ala Ser Asp Asp
        595                 600                 605

Phe Glu Gly Thr Tyr Glu Glu Trp Arg Glu His Met Trp Ser Asp Val
610                 615                 620
```

-continued

Ala Ala Tyr Phe Asn Leu Asn Ile Glu Asn Ser Glu Asp Asn Lys Ser
625                 630                 635                 640

Thr Leu Ser Leu Gln Phe Val Asp Ser Ala Ala Asp Met Pro Leu Ala
        645                 650                 655

Lys Met His Gly Ala Phe Ser Thr Asn Val Val Ala Ser Lys Glu Leu
        660                 665                 670

Gln Gln Pro Gly Ser Ala Arg Ser Thr Arg His Leu Glu Ile Glu Leu
    675                 680                 685

Pro Lys Glu Ala Ser Tyr Gln Glu Gly Asp His Leu Gly Val Ile Pro
690                 695                 700

Arg Asn Tyr Glu Gly Thr Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735

His Leu Pro Leu Ala Lys Thr Val Ser Val Glu Glu Leu Leu Gln Tyr
                740                 745                 750

Val Glu Leu Gln Asp Pro Val Thr Arg Thr Gln Leu Arg Ala Met Ala
            755                 760                 765

Ala Lys Thr Val Cys Pro Pro His Lys Val Glu Leu Glu Ala Leu Leu
770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
        835                 840                 845

Val Ser Gly Glu Ala Trp Ser Gly Tyr Gly Glu Tyr Lys Gly Ile Ala
    850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
        915                 920                 925

Glu Ala His Leu Tyr Phe Gly Cys Arg Ser Pro His Glu Asp Tyr Leu
930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
        995                 1000                1005

Val Glu Ala Thr Leu Met Lys Ser Tyr Ala Asp Val His Gln Val
        1010                1015                1020

Ser Glu Ala Asp Ala Arg Leu Trp Leu Gln Gln Leu Glu Glu Lys
        1025                1030                1035

Gly Arg Tyr Ala Lys Asp Val Trp Ala Gly

<210> SEQ ID NO 14
<211> LENGTH: 862
<212> TYPE: PRT
<213> ORGANISM: Artificial sequence
<220> FEATURE:
<223> OTHER INFORMATION: P450 reductase consensus sequence

<400> SEQUENCE: 14

```
Ile Ile Pro Gln Pro Lys Thr Phe Gly Leu Gly Asn Leu Pro Leu Leu
1               5                   10                  15

Asp Asp Lys Pro Gln Ser Leu Ile Lys Ile Ala Asp Glu Leu Gly Pro
            20                  25                  30

Ile Phe Ile Asp Pro Gly Thr Ile Phe Val Ser Gly His Leu Val Glu
        35                  40                  45

Val Cys Asp Glu Ser Arg Phe Asp Lys Ile Ala Leu Lys Val Arg Asp
    50                  55                  60

Phe Ala Gly Asp Gly Leu Phe Thr Ser Trp Thr His Glu Pro Asn Trp
65                  70                  75                  80

Lys Lys Ala His Asn Ile Leu Leu Pro Ser Phe Ser Gln Arg Ala Met
                85                  90                  95

Lys Gly Tyr His Ala Met Met Val Asp Ile Ala Val Gln Leu Val Gln
            100                 105                 110

Lys Trp Glu Arg Leu Asn Pro Asp Glu Ile Asp Val Glu Asp Met Thr
        115                 120                 125

Arg Leu Thr Leu Asp Thr Ile Gly Leu Cys Gly Phe Asn Tyr Arg Phe
    130                 135                 140

Asn Ser Phe Tyr Arg Asp Pro His Pro Phe Ile Ser Met Val Arg Ala
145                 150                 155                 160

Leu Asp Glu Ala Met Asn Leu Gln Arg Leu Ile Asp Asp Lys Met Arg
                165                 170                 175

Lys Arg Gln Phe Gln Glu Asp Ile Met Asn Leu Val Asp Ile Ile Ala
            180                 185                 190

Glu Arg Lys Ala Gly Asp Gln Asp Leu Leu Ser Met Leu Gly Lys Asp
        195                 200                 205

Pro Glu Thr Gly Glu Leu Asp Asp Glu Asn Ile Arg Tyr Gln Ile Ile
    210                 215                 220

Thr Phe Leu Ile Ala Gly His Glu Thr Thr Ser Gly Leu Leu Ser Phe
225                 230                 235                 240

Ala Leu Tyr Phe Leu Leu Lys Asn Pro Asp Val Leu Lys Lys Ala Tyr
                245                 250                 255

Glu Glu Val Asp Arg Val Leu Asp Pro Thr Tyr Lys Gln Val Gln Leu
            260                 265                 270

Lys Tyr Ile Met Val Leu Asn Glu Ala Leu Arg Leu Trp Pro Thr Ala
        275                 280                 285

Pro Ala Phe Ser Leu Tyr Ala Lys Glu Asp Thr Val Leu Gly Gly Tyr
    290                 295                 300

Pro Ile Lys Gly Asp Ile Ser Val Leu Ile Pro Gln Leu His Arg Asp
305                 310                 315                 320

Lys Ile Trp Gly Asp Glu Phe Arg Pro Glu Arg Phe Glu Ser Ile
                325                 330                 335

Pro His Ala Tyr Lys Pro Phe Gly Asn Gly Gln Arg Ala Cys Ile Gly
            340                 345                 350

Gln Phe Ala Leu His Glu Ala Thr Leu Val Leu Gly Met Met Leu Lys
```

```
              355                 360                 365
His Phe Asp Phe Ile Asp His Tyr Glu Leu Asp Ile Lys Glu Thr Leu
370                 375                 380

Thr Leu Lys Pro Glu Phe Ile Lys Val Lys Arg Lys Ala Pro Gly Lys
385                 390                 395                 400

Ser Ala His Asn Thr Pro Leu Leu Val Leu Tyr Gly Ser Asn Leu Gly
                405                 410                 415

Thr Ala Glu Gly Ile Ala Arg Glu Leu Ala Asp Ala Gly Phe Val Ala
                420                 425                 430

Leu Asp Asp His Ile Gly Leu Pro Lys Glu Gly Ala Val Leu Ile Val
                435                 440                 445

Thr Ala Ser Tyr Asn Gly Pro Pro Asp Asn Ala Gln Phe Val Trp Leu
450                 455                 460

Asp Asp Glu Leu Lys Gly Val Arg Tyr Ala Val Phe Gly Cys Gly Asp
465                 470                 475                 480

Asn Trp Ala Ser Thr Tyr Gln Lys Val Pro Arg Phe Ile Asp Glu Leu
                485                 490                 495

Ala Ala Lys Gly Ala Ile Ala Arg Gly Glu Ala Asp Ala Ser Asp Phe
                500                 505                 510

Glu Gly Glu Trp Lys Met Trp Ser Asp Phe Gly Leu Asp Ile Asp Asp
                515                 520                 525

Arg Ser Thr Leu Ser Leu Gln Phe Val Ala Asp Ser Pro Leu Ala Lys
530                 535                 540

Tyr Gly Ala Val Leu Asn Arg Glu Leu Gln Ala Ser Arg Ser Thr Arg
545                 550                 555                 560

His Ile Glu Ile Leu Pro Thr Tyr Lys Glu Gly Asp His Leu Gly Val
                565                 570                 575

Leu Pro Arg Asn Leu Val Asn Arg Val Arg Phe Gly Leu Ala Gln Ile
                580                 585                 590

Arg Leu Ser Ala Leu Ala His Leu Pro Leu Ala Lys Val Ser Val Asp
                595                 600                 605

Leu Leu Ser Tyr Val Glu Leu Gln Asp Ala Thr Arg Gln Leu Arg Met
610                 615                 620

Ala Ala Thr Val Cys Pro Pro His Lys Glu Leu Glu Ala Leu Leu Asp
625                 630                 635                 640

Tyr Lys Glu Gln Val Leu Ala Lys Arg Leu Ser Met Leu Asp Leu Leu
                645                 650                 655

Glu Lys Tyr Pro Ala Cys Glu Met Phe Phe Leu Ala Leu Leu Pro Ser
                660                 665                 670

Leu Lys Pro Arg Tyr Tyr Ser Ile Ser Ser Ser Pro Arg Val Ala Ser
                675                 680                 685

Ile Thr Val Gly Val Val Gly Pro Ala Trp Ser Arg Gly Glu Tyr
                690                 695                 700

Lys Gly Val Ala Ser Asn Tyr Leu Ala Glu Leu Gln Gly Asp Ile Cys
705                 710                 715                 720

Phe Ile Arg Thr Pro Gln Ser Phe Leu Pro Asp Pro Glu Thr Pro Ile
                725                 730                 735

Ile Met Val Gly Pro Gly Thr Gly Ile Ala Pro Phe Arg Gly Phe Leu
                740                 745                 750

Gln Ala Arg Val Leu Lys Gly Ser Leu Gly Glu Ala His Leu Tyr Phe
                755                 760                 765

Gly Cys Arg Pro Asp Asp Tyr Leu Tyr Arg Glu Glu Leu Glu Asn Asp
770                 775                 780
```

```
Gly Ile Ile Thr Leu His Thr Ala Phe Ser Arg Met Glu Pro Lys Thr
785                 790                 795                 800

Tyr Val Gln His Val Leu Gln Asp Lys Leu Ile Leu Leu Asp Gln Gly
            805                 810                 815

Ala His Ile Tyr Val Cys Gly Asp Gly Ser Gln Met Ala Pro Asp Val
        820                 825                 830

Glu Ala Thr Leu Met Ala Tyr Asp Val His Gly Val Ser Glu Glu Ala
    835                 840                 845

Trp Leu Leu Asp Gly Arg Tyr Ala Lys Asp Val Trp Ala Gly
850                 855                 860

<210> SEQ ID NO 15
<211> LENGTH: 3147
<212> TYPE: DNA
<213> ORGANISM: Artificial sequence
<220> FEATURE:
<223> OTHER INFORMATION: Mutant P450 53-5H DNA sequence

<400> SEQUENCE: 15
```

| | |
|---|---:|
| atgacaatta aagaaatgcc tcagccaaaa acgtttggag agcttaaaaa tttaccgtta | 60 |
| ttaaacacag ataaaccggt tcaagctttg atgaaaattg cggatgaatt aggagaaatc | 120 |
| tttaaattcg aggcgcctgg ttgtgtaacg cgctacttat caagtcagcg tctaattaaa | 180 |
| gaagcatgcg atgaatcacg ctttgataaa aacttaagtc aagcgcttaa attctttcgt | 240 |
| gattttagcg gagacgggtt atttacaagc tggacgcatg aaataaattg gaaaaaagcg | 300 |
| cataatatct tacttccaag ctttagtcag caggcaatga aggctatca tgcgatgatg | 360 |
| gtcgatatcg ccgtgcagct tgttcaaaag tgggagcgtc taaatgcaga tgagcatatt | 420 |
| gaagtatcgg aagacatgac acgtttaacg cttgatacaa ttggtctttg cggctttaac | 480 |
| tatcgcttta acagctttta ccgagatcag cctcatccat ttattataag tatggtccgt | 540 |
| gcactggatg aagtaatgaa caagctgcag cgagcaaatc cagacgaccc agcttatgat | 600 |
| gaaaacaagc gccagtgtca agaagatatc aaggtgatga acgacctagt agataaaatt | 660 |
| attgcagatc gcaaagcaag gggtgaacaa agcgatgatt tattaacgca gatgctaaac | 720 |
| ggaaaagatc cagaaacggg tgagccgctt gatgacggga acattagcta tcaaattatt | 780 |
| acattcttaa ttgcgggaca cgaaacaaca agtggtcttt tatcatttgc gctgtatttc | 840 |
| ttagtgaaaa atccacatgt attacaaaaa gtagcagaag aagcagcacg agttctagta | 900 |
| gatcctgttc aagctacaa acaagtcaaa cagcttaaat atgtcggcat ggtcttaaac | 960 |
| gaagcgctgc gcttatggcc aactttttcct gcgttttccc tatatgcaaa agaagatacg | 1020 |
| gtgcttggag gagaatatcc tttagaaaaa ggcgacgaag taatggttct gattcctcag | 1080 |
| cttcaccgtg ataaaacaat tgggggagac gatgtggagg agttccgtcc agagcgtttt | 1140 |
| gaaaatccaa gtgcgattcc gcagcatgcg tttaaaccgt tggaaacggt tcagcgtgcg | 1200 |
| tgtatcggtc agcagttcgc tcttcatgaa gcaacgctgg tacttggtat gatgctaaaa | 1260 |
| cactttgact ttgaagatca tacaaactac gagctcgata ttaaagaaac tttaacgtta | 1320 |
| aaacctgaag gctttgtggt aaaagcaaaa tcgaaaaaaa ttccgcttgg cggtattcct | 1380 |
| tcacctagca ctgaacagtc tgctaaaaaa gtacgcaaaa aggcagaaaa cgctcataat | 1440 |
| acgccgctgc ttgtgctata cggttcaaat atgggaacag ctgaaggaac ggcgcgtgat | 1500 |
| ttagcagata ttgcaatgag caaaggattt gcaccgcagg tcgcaacgct tgattcacac | 1560 |
| gccggaaatc ttccgcgcga aggagctgta ttaattgtaa cggcgtctta taacggtcat | 1620 |

-continued

```
ccgcctgata acgcaaagca atttgtcgac tggttagacc aagcgtctgc tgatgaagta    1680
aaaggcgttc gctactccgt atttggatgc ggcgataaaa actgggctac tacgtatcaa    1740
aaagtgcctg cttttatcga tgaaacgctt gccgctaaag gggcagaaaa catcgctgac    1800
cgcggtgaag cagatgcaag cgacgacttt gaaggcacat atgaagaatg gcgtgaacat    1860
atgtggagtg acgtagcagc ctactttaac ctcgacattg aaaacagtga agataataaa    1920
tctactcttt cacttcaatt tgtcgacagc gccgcggata tgccgcttgc gaaaatgcac    1980
ggtgcgtttt caacgaacgt cgtagcaagc aaagaacttc aacagccagg cagtgcacga    2040
agcacgcgac atcttgaaat tgaacttcca aaagaagctt cttatcaaga aggagatcat    2100
ttaggtgtta ttcctcgcaa ctatgaagga atagtaaacc gtgtaacagc aaggttcggc    2160
ctagatgcat cacagcaaat ccgtctggaa gcagaagaag aaaaattagc tcatttgcca    2220
ctcgctaaaa cagtatccgt agaagagctt ctgcaatacg tggagcttca agatcctgtt    2280
acgcgcacgc agcttcgcgc aatggctgct aaaacggtct gcccgccgca taaagtagag    2340
cttgaagcct tgcttgaaaa gcaagcctac aaagaacaag tgctggcaaa acgtttaaca    2400
atgcttgaac tgcttgaaaa ataccccggcg tgtgaaatga aattcagcga atttatcgcc    2460
cttctgccaa gcatacgccc gcgctattac tcgatttctt catcacctcg tgtcgatgaa    2520
aaacaagcaa gcatcacggt cagcgttgtc tcaggagaag cgtggagcgg atatggagaa    2580
tataaaggaa ttgcgtcgaa ctatcttgcc gagctgcaag aaggagatac gattacgtgc    2640
tttatttcca caccgcagtc agaatttacg ctgccaaaag accctgaaac gccgcttatc    2700
atggtcggac cgggaacagg cgtcgcgccg tttagaggct tgtgcaggc gcgcaaacag    2760 ctaaaagaac aaggacagtc acttggagaa gcacatttat acttcggctg ccgttcaccct    2820 catgaagact atctgtatca agaagagctt gaaaacgccc aaagcgaagg catcattacg    2880
cttcataccg cttttctcg catgccaaat cagccgaaaa catacgttca gcacgtaatg    2940
gaacaagacg gcaagaaatt gattgaactt cttgatcaag gagcgcactt ctatatttgc    3000
ggagacggaa gccaaatggc acctgccgtt gaagcaacgc ttatgaaaag ctatgctgac    3060
gttcaccaag tgagtgaagc agacgctcgc ttatggctgc agcagctaga agaaaaaggc    3120
cgatacgcaa aagacgtgtg ggctggg                                       3147
```

<210> SEQ ID NO 16
<211> LENGTH: 4500
<212> TYPE: DNA
<213> ORGANISM: Artificial sequence
<220> FEATURE:
<223> OTHER INFORMATION: pCWORI-53-H DNA sequence

<400> SEQUENCE: 16

```
atgacaatta agaaatgcc tcagccaaaa acgtttggag agcttaaaaa tttaccgtta      60
ttaaacacag ataaaccggt tcaagctttg atgaaaattg cggatgaatt aggagaaatc    120
tttaaattcg aggcgcctgg ttgtgtaacg cgctacttat caagtcagcg tctaattaaa    180
gaagcatgcg atgaatcacg ctttgataaa aacttaagtc aagcgcttaa attctttcgt    240
gattttagcg gagacgggtt atttacaagc tggacgcatg aaataaattg gaaaaaagcg    300
cataatatct tacttccaag ctttagtcag caggcaatga aggctatca tgcgatgatg    360 gtcgatatcg ccgtgcagct tgttcaaaag tgggagcgtc taaatgcaga tgagcatatt    420
gaagtatcgg aagacatgac acgtttaacg cttgatacaa ttggtctttg cggctttaac    480
```

```
tatcgcttta acagctttta ccgagatcag cctcatccat ttattataag tatggtccgt    540
gcactggatg aagtaatgaa caagctgcag cgagcaaatc cagacgaccc agcttatgat    600
gaaaacaagc gccagtgtca agaagatatc aaggtgatga acgacctagt agataaaatt    660
attgcagatc gcaaagcaag gggtgaacaa agcgatgatt tattaacgca gatgctaaac    720
ggaaaagatc cagaaacggg tgagccgctt gatgacggga acattagcta tcaaattatt    780
acattcttaa ttgcgggaca cgaaacaaca agtggtcttt tatcatttgc gctgtatttc    840
ttagtgaaaa atccacatgt attacaaaaa gtagcagaag aagcagcacg agttctagta    900
gatcctgttc caagctacaa acaagtcaaa cagcttaaat atgtcggcat ggtcttaaac    960
gaagcgctgc gcttatggcc aacttttcct gcgttttccc tatatgcaaa agaagatacg    1020
gtgcttggag gagaatatcc tttagaaaaa ggcgacgaag taatggttct gattcctcag    1080
cttcaccgtg ataaaacaat ttggggagac gatgtggagg agttccgtcc agagcgtttt    1140
gaaaatccaa gtgcgattcc gcagcatgcg tttaaaccgt ttggaaacgg tcagcgtgcg    1200
tgtatcggtc agcagttcgc tcttcatgaa gcaacgctgg tacttggtat gatgctaaaa    1260
cactttgact ttgaagatca tacaaactac gagctcgata ttaaagaaac tttaacgtta    1320
aaacctgaag gctttgtggt aaaagcaaaa tcgaaaaaaa ttccgcttgg cggtattcct    1380
tcacctagca ctgaacagtc tgctaaaaaa gtacgcaaaa aggcagaaaa cgctcataat    1440
acgccgctgc ttgtgctata cggttcaaat atgggaacag ctgaaggaac ggcgcgtgat    1500
ttagcagata ttgcaatgag caaaggattt gcaccgcagg tcgcaacgct tgattcacac    1560
gccgaaaatc ttccgcgcga aggagctgta ttaattgtaa cggcgtctta taacggtcat    1620
ccgcctgata acgcaaagca atttgtcgac tggttagacc aagcgtctgc tgatgaagta    1680
aaaggcgttc gctactccgt atttggatgc ggcgataaaa actgggctac tacgtatcaa    1740
aaagtgcctg cttttatcga tgaaacgctt gccgctaaag gggcagaaaa catcgctgac    1800
cgcggtgaag cagatgcaag cgacgacttt gaaggcacat atgaagaatg gcgtgaacat    1860
atgtggagtg acgtagcagc ctactttaac ctcgacattg aaaacagtga agataataaa    1920
tctactcttt cacttcaatt tgtcgacagc gccgcggata tgccgcttgc gaaaatgcac    1980
ggtgcgtttt caacgaacgt cgtagcaagc aaagaacttc aacagccagg cagtgcacga    2040
agcacgcgac atcttgaaat tgaacttcca aaagaagctt cttatcaaga aggagatcat    2100
ttaggtgtta ttcctcgcaa ctatgaagga atagtaaacc gtgtaacagc aaggttcggc    2160
ctagatgcat cacagcaaat ccgtctggaa gcagaagaag aaaaattagc tcatttgcca    2220
ctcgctaaaa cagtatccgt agaagagctt ctgcaatacg tggagcttca agatcctgtt    2280
acgcgcacgc agcttcgcgc aatggctgct aaaacggtct gcccgccgca taaagtagag    2340
cttgaagcct tgcttgaaaa gcaagcctac aaagaacaag tgctggcaaa acgtttaaca    2400
atgcttgaac tgcttgaaaa ataccccggcg tgtgaaatga aattcagcga atttatcgcc    2460
cttctgccaa gcatacgccc gcgctattac tcgatttctt catcacctcg tgtcgatgaa    2520
aaacaagcaa gcatcacggt cagcgttgtc tcaggagaag cgtggagcgg atatggagaa    2580
tataaaggaa ttgcgtcgaa ctatcttgcc gagctgcaag aaggagatac gattacgtgc    2640
tttatttcca caccgcagtc agaatttacg ctgccaaaag accctgaaac gccgcttatc    2700
atggtcggac cgggaacagg cgtcgcgccg tttagaggct ttgtgcaggc gcgcaaacag    2760
ctaaaagaac aaggacagtc acttggagaa gcacatttat acttcggctg ccgttcacct    2820
catgaagact atctgtatca agaagagctt gaaaacgccc aaagcgaagg catcattacg    2880
```

```
cttcataccg cttttttctcg catgccaaat cagccgaaaa catacgttca gcacgtaatg   2940
gaacaagacg gcaagaaatt gattgaactt cttgatcaag gagcgcactt ctatatttgc   3000
ggagacggaa gccaaatggc acctgccgtt gaagcaacgc ttatgaaaag ctatgctgac   3060
gttcaccaag tgagtgaagc agacgctcgc ttatggctgc agcagctaga agaaaaaggc   3120
cgatacgcaa aagacgtgtg ggctgggtaa gaattcatcg atgataagct gtcaaacatg   3180
agcagatctg agcccgccta atgagcgggc ttttttttca gatctgcttg aagacgaaag   3240
ggcctcgtga tacgcctatt tttataggtt aatgtcatga taataatggt ttcttagcgt   3300
caaagcaacc atagtacgcg ccctgtagcg gcgcattaag cgcggcgggt gtggtggtta   3360
cgcgcagcgt gaccgctaca cttgccagcg ccctagcgcc cgctcctttc gctttcttcc   3420
cttcctttct cgccacgttc gccggctttc ccgtcaagc tctaaatcgg gggctccctt   3480
tagggttccg atttagtgct ttacggcacc tcgaccccaa aaaacttgat ttgggtgatg   3540
gttcacgtag tgggccatcg ccctgataga cggttttttcg ccctttgacg ttggagtcca   3600
cgttctttaa tagtggactc ttgttccaaa ctggaacaac actcaaccct atctcgggct   3660
attcttttga tttataaggg attttgccga tttcggccta ttggttaaaa aatgagctga   3720
tttaacaaaa atttaacgcg aattttaaca aaatattaac gtttacaatt tcaggtggca   3780
cttttcgggg aaatgtgcgc ggaacccta tttgtttatt tttctaaata cattcaaata   3840
tgtatccgct catgagacaa taaccctgat aaatgcttca ataatattga aaaggaaga   3900 gtatgagtat tcaacatttc cgtgtcgccc ttattccctt ttttgcggca ttttgccttc   3960 ctgttttgc tcacccagaa acgctggtga agtaaaaga tgctgaagat cagttgggtg   4020
cacgagtggg ttcatcgaa ctggatctca acagcggtaa gatccttgag agttttcgcc   4080
ccgaagaacg ttttccaatg atgagcactt ttaaagttct gctatgtggc gcggtattat   4140
cccgtgttga cgccgggcaa gagcaactcg gtcgccgcat acactattct cagaatgact   4200
tggttgagta ctcaccagtc acagaaaagc atcttacgga tggcatgaca gtaagagaat   4260
tatgcagtgc tgccataacc atgagtgata acactgcggc caacttactt ctgacaacga   4320
tcggaggacc gaaggagcta accgcttttt tggttgagta ctcaccagtc acagaaaagc   4380
atcttacgga tggcatgaca gtaagagaat tatgcagtgc tgccataacc atgagtgata   4440
acactgcggc caacttactt ctgacaacga tcggaggacc gaaggagcta accgcttttt   4500
```

<210> SEQ ID NO 17
<211> LENGTH: 3147
<212> TYPE: DNA
<213> ORGANISM: Artificial sequence
<220> FEATURE:
<223> OTHER INFORMATION: Mutant P450 35-E11 DNA sequence

<400> SEQUENCE: 17

```
atgacaatta aagaaatgcc tcagccaaaa acgtttggag agcttaaaaa tttaccgtta    60
ttaaacacag ataaaccggt tcaagctttg atgaaaattg cggatgaatt aggagaaatc   120
tttaaattcg aggcgcctgg ttgtgtaacg cgctacttat caagtcagcg tctaattaaa   180
gaagcatgcg atgaatcacg ctttgataaa aacttaagtc aagcgcttaa attctttcgt   240
gattttagcg gagacgggtt atttacaagc tggacgcatg aaataaattg gaaaaagcg   300 cataatatct tacttccaag cttttagtcag caggcaatga aaggctatca tgcgatgatg   360
gtcgatatcg ccgtgcagct tgttcaaaag tgggagcgtc taaatgcaga tgagcatatt   420
```

```
gaagtatcgg aagacatgac acgtttaacg cttgatacaa ttggtctttg cggctttaac    480
tatcgcttta acagctttta ccgagatcag cctcatccat ttattataag tatggtccgt    540
gcactggatg aagtaatgaa caagctgcag cgagcaaatc cagacgaccc agcttatgat    600
gaaaacaagc gccagtgtca agaagatatc aaggtgatga cgacctagt agataaaatt     660 attgcagatc gcaaagcaag gggtgaacaa agcgatgatt tattaacgca gatgctaaac    720
ggaaaagatc cagaaacggg tgagccgctt gatgacggga acattagcta tcaaattatt    780
acattcttaa ttgcgggaca cgaaacaaca agtggtcttt tatcatttgc gctgtatttc    840
ttagtgaaaa atccacatgt attacaaaaa gtagcagaag aagcagcacg agttctagta    900
gatcctgttc caagctacaa acaagtcaaa cagcttaaat atgtcggcat ggtcttaaac    960
gaagcgctgc gcttatggcc aactttcct gcgttttccc tatatgcaaa agaagatacg    1020
gtgcttggag gagaatatcc tttagaaaaa ggcgacgaag taatggttct gattcctcag    1080
cttcaccgtg ataaaacaat ttggggagac gatgtggagg agttccgtcc agagcgtttt    1140
gaaaatccaa gtgcgattcc gcagcatgcg tttaaaccgt ttggaaacgg tcagcgtgcg    1200
tgtatcggtc agcagttcgc tcttcatgaa gcaacgctgg tacttggtat gatgctaaaa    1260
cactttgact ttgaagatca tacaaactac gagctcgata ttaaagaaac tttaacgtta    1320
aaacctgaag gctttgtggt aaaagcaaaa tcgaaaaaaa ttccgcttgg cggtattcct    1380
tcacctagca ctggacagtc tgctaaaaaa gtacgcaaaa aggcagaaaa cgctcataat    1440
acgccgctgc ttgtgctata cggttcaaat atgggaacag ctgaaggaac ggcgcgtgat    1500
ttagcagata ttgcaatgag caaaggattt gcaccgcagg tcgcaacgct tgattcacac    1560
gccggaaatc ttccgcgcga aggagctgta ttaattgtaa cggcgtctta taacggtcat    1620
ccgcctgata acgcaaagca atttgtcgac tggttagacc aagcgtctgc tgatgaagta    1680
aaaggcgttc gctactccgt atttggatgc ggcgataaaa actgggctac tacgtatcaa    1740
aaagtgcctg cttttatcga tgaaacgctt gccgctaaag gggcagaaaa catcgctgac    1800
cgcggtgaag cagatgcaag cgacgacttt gaaggcacat atgaagaatg cgtgaacat     1860 atgtggagtg acgtagcagc ctactttaac ctcgacattg aaaacagtga agataataaa    1920
tctactcttt cacttcaatt tgtcgacagc gccgcggata tgccgcttgc gaaaatgcac    1980
ggtgcgtttt caacgaacgt cgtagcaagc aaagaacttc aacagccagg cagtgcacga    2040
agcacgcgac atcttgaaat tgaacttcca aaagaagctt cttatcaaga aggagatcat    2100
ttaggtgtta ttcctcgcaa ctatgaagga acagtaaacc gtgtaacagc aaggttcggc    2160
ctagatgcat cacagcaaat ccgtctggaa gcagaagaag aaaaattagc tcatttgcca    2220
ctcgctaaaa cagtatccgt agaagagctt ctgcaatacg tggagcttca agatcctgtt    2280
acgcgcacgc agcttcgcgc aatggctgct aagacggtct gcccgccgca taagtagag    2340 cttgaagcct tgcttgaaaa gcaagcctac aagaacaag tgctggcaaa acgtttaaca    2400
atgcttgaac tgcttgaaaa ataccccggcg tgtgaaatga aattcagcga atttatcgcc    2460
cttctgccaa gcatacgccc gcgctattac tcgatttctt catcacctcg tgtcgatgaa    2520
aaacaagcaa gcatcacggt cagcgttgtc tcaggagaag cgtggagcgg atatggagaa    2580
tataaaggaa ttgcgtcgaa ctatcttgcc gagctgcaag aaggagatac gattacgtgc    2640 tttattcca caccgcagtc agaatttacg ctgccaaaag accctgaaac gccgcttatc    2700
atggtcggac cgggaacagg cgtcgcgccg tttagaggct ttgtgcaggc gcgcaaacag    2760
ctaaaagaac aaggacagtc acttggagaa gcacatttat acttcggctg ccgttcacct    2820
```

```
catgaagact atctgtatca agaagagctt gaaaacgccc aaagcgaagg catcattacg    2880
cttcataccg cttttttctcg catgccaaat cagccgaaaa catacgttca gcacgtaatg    2940
gaacaagacg gcaagaaatt gattgaactt cttgatcaag gagcgcactt ctatatttgc    3000
ggagacggaa gccaaatggc acctgccgtt gaagcaacgc ttatgaaaag ctatgctgac    3060
gttcaccaag tgagtgaagc agacgctcgc ttatggctgc agcagctaga agaaaaggc    3120 cgatacgcaa aagacgtgtg ggctggg                                         3147

<210> SEQ ID NO 18
<211> LENGTH: 8060
<212> TYPE: DNA
<213> ORGANISM: Artificial sequence
<220> FEATURE:
<223> OTHER INFORMATION: pCWORI-35-E11 DNA sequence

<400> SEQUENCE: 18
atgacaatta agaaaatgcc tcagccaaaa acgtttggag agcttaaaaa tttaccgtta      60
ttaaacacag ataaaccggt tcaagctttg atgaaaattg cggatgaatt aggagaaatc     120
tttaaattcg aggcgcctgg ttgtgtaacg cgctacttat caagtcagcg tctaattaaa     180
gaagcatgcg atgaatcacg ctttgataaa aacttaagtc aagcgcttaa attctttcgt     240
gattttagcg gagacgggtt atttacaagc tggacgcatg aaataaattg gaaaaaagcg     300
cataatatct tacttccaag cttttagtcag caggcaatga aaggctatca tgcgatgatg     360
gtcgatatcg ccgtgcagct tgttcaaaag tgggagcgtc taaatgcaga tgagcatatt     420
gaagtatcgg aagacatgac acgtttaacg cttgatacaa ttggtctttg cggctttaac     480
tatcgcttta acagcttttta ccgagatcag cctcatccat ttattataag tatggtccgt     540
gcactggatg aagtaatgaa caagctgcag cgagcaaatc cagacgaccc agcttatgat     600
gaaaacaagc gccagtgtca agaagatatc aaggtgatga acgacctagt agataaaatt     660
attgcagatc gcaaagcaag gggtgaacaa agcgatgatt tattaacgca gatgctaaac     720
ggaaaagatc cagaaacggg tgagccgctt gatgacggga acattagcta tcaaattatt     780
acattcttaa ttgcgggaca cgaaacaaca agtggtcttt tatcatttgc gctgtatttc     840
ttagtgaaaa atccacatgt attacaaaaa gtagcagaag aagcagcacg agttctagta     900
gatcctgttc caagctacaa acaagtcaaa cagcttaaat atgtcggcat ggtcttaaac     960
gaagcgctgc gcttatggcc aacttttcct gcgttttccc tatatgcaaa agaagatacg    1020
gtgcttggag gagaatatcc tttagaaaaa ggcgacgaag taatggttct gattcctcag    1080
cttcaccgtg ataaaacaat ttggggagac gatgtggagg agttccgtcc agagcgtttt    1140
gaaaatccaa gtgcgattcc gcagcatgcg tttaaaccgt ttggaaacgg tcagcgtgcg    1200
tgtatcggtc agcagttcgc tcttcatgaa gcaacgctgg tacttggtat gatgctaaaa    1260
cactttgact tgaagatca tacaaactac gagctcgata ttaaagaaac tttaacgtta    1320
aaacctgaag gctttgtggt aaaagcaaaa tcgaaaaaaa ttccgcttgg cggtattcct    1380
tcacctagca ctggacagtc tgctaaaaaa gtacgcaaaa aggcagaaaa cgctcataat    1440
acgccgctgc ttgtgctata cggttcaaat atgggaacag ctgaaggaac ggcgcgtgat    1500
ttagcagata ttgcaatgag caaaggattt gcaccgcagg tcgcaacgct tgattcacac    1560
gccggaaatc ttccgcgcga aggagctgta ttaattgtaa cggcgtctta taacggtcat    1620
ccgcctgata acgcaaagca atttgtcgac tggttagacc aagcgtctgc tgatgaagta    1680
```

```
aaaggcgttc gctactccgt atttggatgc ggcgataaaa actgggctac tacgtatcaa    1740
aaagtgcctg cttttatcga tgaaacgctt gccgctaaag gggcagaaaa catcgctgac    1800
cgcggtgaag cagatgcaag cgacgacttt gaaggcacat atgaagaatg cgtgaacat     1860 atgtggagtg acgtagcagc ctactttaac ctcgacattg aaaacagtga agataataaa    1920
tctactcttt cacttcaatt tgtcgacagc gccgcggata tgccgcttgc gaaaatgcac    1980
ggtgcgtttt caacgaacgt cgtagcaagc aaagaacttc aacagccagg cagtgcacga    2040
agcacgcgac atcttgaaat tgaacttcca aaagaagctt cttatcaaga aggagatcat    2100
ttaggtgtta ttcctcgcaa ctatgaagga acagtaaacc gtgtaacagc aaggttcggc    2160
ctagatgcat cacagcaaat ccgtctggaa gcagaagaag aaaaattagc tcatttgcca    2220
ctcgctaaaa cagtatccgt agaagagctt ctgcaatacg tggagcttca agatcctgtt    2280
acgcgcacgc agcttcgcgc aatggctgct aagacggtct gcccgccgca taaagtagag    2340
cttgaagcct tgcttgaaaa gcaagcctac aaagaacaag tgctggcaaa acgtttaaca    2400
atgcttgaac tgcttgaaaa atacccggcg tgtgaaatga aattcagcga atttatcgcc    2460
cttctgccaa gcatacgccc gcgctattac tcgatttctt catcacctcg tgtcgatgaa    2520
aaacaagcaa gcatcacggt cagcgttgtc tcaggagaag cgtggagcgg atatggagaa    2580
tataaaggaa ttgcgtcgaa ctatcttgcc gagctgcaag aaggagatac gattacgtgc    2640
tttatttcca caccgcagtc agaatttacg ctgccaaaag accctgaaac gccgcttatc    2700
atggtcggac cgggaacagg cgtcgcgccg tttagaggct tgtgcaggc gcgcaaacag     2760 ctaaaagaac aaggacagtc acttggagaa gcacatttat acttcggctg ccgttcacct    2820
catgaagact atctgtatca agaagagctt gaaaacgccc aaagcgaagg catcattacg    2880
cttcataccg cttttctcg catgccaaat cagccgaaaa catacgttca gcacgtaatg      2940
gaacaagacg gcaagaaatt gattgaactt cttgatcaag gagcgcactt ctatatttgc    3000
ggagacggaa gccaaatggc aacctgccgtt gaagcaacgc ttatgaaaag ctatgctgac   3060
gttcaccaag tgagtgaagc agacgctcgc ttatggctgc agcagctaga agaaaaaggc    3120
cgatacgcaa aagacgtgtg ggctgggtaa gaattcatcg atgataagct gtcaaacatg    3180
agcagatctg agcccgccta atgagcgggc ttttttttca gatctgcttg aagacgaaag    3240
ggcctcgtga tacgcctatt tttataggtt aatgtcatga taataatggt ttcttagcgt    3300
caaagcaacc atagtacgcg ccctgtagcg gcgcattaag cgcggcgggt gtggtggtta    3360
cgcgcagcgt gaccgctaca cttgccagcg ccctagcgcc cgctcctttc gctttcttcc    3420
cttcctttct cgccacgttc gccggctttc cccgtcaagc tctaaatcgg gggctccctt    3480
tagggttccg atttagtgct ttacggcacc tcgaccccaa aaaacttgat tgggtgatg     3540 gttcacgtag tgggccatcg ccctgataga cggtttttcg ccctttgacg ttggagtcca    3600
cgttctttaa tagtggactc ttgttccaaa ctggaacaac actcaaccct atctcgggct    3660
attcttttga tttataaggg attttgccga tttcggccta ttggttaaaa aatgagctga    3720
tttaacaaaa atttaacgcg aattttaaca aaatattaac gtttacaatt tcaggtggca    3780
cttttcgggg aaatgtgcgc ggaaccccta tttgtttatt tttctaaata cattcaaata    3840
tgtatccgct catgagacaa taaccctgat aaatgcttca ataatattga aaaggaaga    3900 gtatgagtat tcaacatttc cgtgtcgccc ttattccctt ttttgcggca ttttgccttc    3960 ctgttttgc tcacccagaa acgctggtga agtaaaaga tgctgaagat cagttgggtg     4020
cacgagtggg ttacatcgaa ctggatctca acagcggtaa gatccttgag agttttcgcc    4080
```

```
ccgaagaacg ttttccaatg atgagcactt ttaaagttct gctatgtggc gcggtattat    4140
cccgtgttga cgccgggcaa gagcaactcg gtcgccgcat acactattct cagaatgact    4200
tggttgagta ctcaccagtc acagaaaagc atcttacgga tggcatgaca gtaagagaat    4260
tatgcagtgc tgccataacc atgagtgata acactgcggc caacttactt ctgacaacga    4320
tcggaggacc gaaggagcta accgcttttt tgcacaacat gggggatcat gtaactcgcc    4380
ttgatcgttg ggaaccggag ctgaatgaag ccataccaaa cgacgagcgt gacaccacga    4440
tgcctgcagc aatggcaaca acgttgcgca aactattaac tggcgaacta cttactctag    4500
cttcccggca acaattaata gactggatgg aggcggataa agttgcagga ccacttctgc    4560
gctcggccct tccggctggc tggtttattg ctgataaatc tggagccggt gagcgtgggt    4620
ctcgcggtat cattgcagca ctggggccag atggtaagcc ctcccgtatc gtagttatct    4680
acacgacggg gagtcaggca actatggatg aacgaaatag acagatcgct gagataggtg    4740
cctcactgat taagcattgg taactgtcag accaagttta ctcatatata ctttagattg    4800
atttaaaact tcatttttaa tttaaaagga tctaggtgaa gatcctttt gataatctca    4860 tgaccaaaat cccttaacgt gagttttcgt tccactgagc gtcagacccc gtagaaaaga    4920
tcaaaggatc ttcttgagat ccttttttc tgcgcgtaat ctgctgcttg caaacaaaaa    4980
aaccaccgct accagcggtg gtttgtttgc cggatcaaga gctaccaact cttttccga    5040 aggtaactgg cttcagcaga gcgcagatac caaatactgt ccttctagtg tagccgtagt    5100
taggccacca cttcaagaac tctgtagcac cgcctacata cctcgctctg ctaatcctgt    5160
taccagtggc tgctgccagt ggcgataagt cgtgtcttac cgggttggac tcaagacgat    5220
agttaccgga taaggcgcag cggtcgggct gaacggggg ttcgtgcaca cagcccagct    5280
tggagcgaac gacctacacc gaactgagat acctacagcg tgagctatga gaaagcgcca    5340
cgcttcccga agggagaaag gcggacaggt atccggtaag cggcagggtc ggaacaggag    5400
agcgcacgag ggagcttcca gggggaaacg cctggtatct ttatagtcct gtcgggtttc    5460
gccacctctg acttgagcgt cgatttttgt gatgctcgtc agggggggcgg agcctatgga    5520 aaaacgccag caacgcggcc ttttttacggt tcctggcctt ttgctggcct tttgctcaca    5580
tgttctttcc tgcgttatcc cctgattctg tggataaccg tattaccgcc tttgagtgag    5640
ctgataccgc tcgccgcagc cgaacgaccg agcgcagcga gtcagtgagc gaggaagcgg    5700
aagagcgcct gatgcggtat tttctcctta cgcatctgtg cggtatttca caccgcatat    5760
atggtgcact ctcagtacaa tctgctctga tgccgcatag ttaagccagt atacactccg    5820
ctatcgctac gtgactgggt catggctgcg ccccgacacc cgccaacacc cgctgacgcg    5880
ccctgacggg cttgtctgct cccggcatcc gcttacagac aagctgtgac cgtctccggg    5940
agctgcatgt gtcagaggtt ttcaccgtca tcaccgaaac gcgcgaggca gaacgccatc    6000
aaaaataatt cgcgtctggc cttcctgtag ccagctttca tcaacattaa atgtgagcga    6060
gtaacaaccc gtcggattct ccgtgggaac aaacggcgga ttgaccgtaa tgggataggt    6120
tacgttggtg tagatgggcg catcgtaacc gtgcatctgc cagtttgagg ggacgacgac    6180
agtatcggcc tcaggaagat cgcactccag ccagctttcc ggcaccgctt ctggtgccgg    6240
aaaccaggca aagcgccatt cgccattcag gctgcgcaac tgttgggaag ggcgatcgt    6300 gcgggcctct tcgctattac gccagctggc gaaagggggga tgtgctgcaa ggcgattaag    6360
ttgggtaacg ccagggtttt cccagtcacg acgttgtaaa acgacggcca gtgaatccgt    6420
```

```
aatcatggtc atagctgttt cctgtgtgaa attgttatcc gctcacaatt ccacacaaca    6480
tacgagccgg aagcataaag tgtaaagcct ggggtgccta atgagtgagc taactcacat    6540
taattgcgtt gcgctcactg cccgctttcc agtcgggaaa cctgtcgtgc cagctgcatt    6600
aatgaatcgg ccaacgcgcg gggagaggcg gtttgcgtat tgggcgccag ggtggttttt    6660
cttttcacca gtgagacggg caacagctga ttgcccttca ccgcctggcc ctgagagagt    6720
tgcagcaagc ggtccacgct ggtttgcccc agcaggcgaa atcctgtttt gatggtggtt    6780
aacggcggga tataacatga gctgtcttcg gtatcgtcgt atcccactac cgagatatcc    6840
gcaccaacgc gcagcccgga ctcggtaatg gcgcgcattg cgcccagcgc catctgatcg    6900
ttggcaacca gcatcgcagt gggaacgatg ccctcattca gcatttgcat ggtttgttga    6960
aaaccggaca tggcactcca gtcgccttcc cgttccgcta tcggctgaat ttgattgcga    7020
gtgagatatt tatgccagcc agccagacgc agacgcgccg agacagaact taatgggccc    7080
gctaacagcg cgatttgctg gtgacccaat gcgaccagat gctccacgcc cagtcgcgta    7140
ccgtcttcat gggagaaaat aatactgttg atgggtgtct ggtcagagac atcaagaaat    7200
aacgccggaa cattagtgca ggcagcttcc acagcaatgg catcctggtc atccagcgga    7260
tagttaatga tcagcccact gacgcgttgc gcgagaagat tgtgcaccgc cgctttacag    7320
gcttcgacgc cgcttcgttc taccatcgac accaccacgc tggcacccag ttgatcggcg    7380
cgagatttaa tcgccgcgac aatttgcgac ggcgcgtgca gggccagact ggaggtggca    7440
acgccaatca gcaacgactg tttgcccgcc agttgttgtg ccacgcggtt gggaatgtaa    7500
ttcagctccg ccatcgccgc ttccactttt tcccgcgttt tcgcagaaac gtggctggcc    7560
tggttcacca cgcgggaaac ggtctgataa gagacaccgg catactctgc gacatcgtat    7620
aacgttactg gtttcacatt caccaccctg aattgactct cttccgggcg ctatcatgcc    7680
ataccgcgaa aggttttgcg ccattcgatg gtgtcctggc acgacaggtt tcccgactgg    7740
aaagcgggca gtgagcgcaa cgcaattaat gtgagttagc tcactcatta ggcaccccag    7800
gctttacact ttatgcttcc ggctcgtata atgtgtggaa ttgtgagcgg ataacaattt    7860
cacacaggaa acaggatcga tccatcgatg agcttactcc ccatcccccct gttgacaatt    7920 aatcatcggc tcgtataatg tgtggaattg tgagcggata acaatttcac acaggaaaca    7980
ggatcagctt actccccatc cccctgttga caattaatca tcggctcgta taatgtgtgg    8040
aattgtgagc ggataacaat                                                8060

<210> SEQ ID NO 19
<211> LENGTH: 22
<212> TYPE: DNA
<213> ORGANISM: Artificial sequence
<220> FEATURE:
<223> OTHER INFORMATION: Forward primer
<220> FEATURE:
<221> NAME/KEY: misc_feature
<222> LOCATION: (6)..(8)
<223> OTHER INFORMATION: n is a, c, g, or t

<400> SEQUENCE: 19
gtcaannnct taaatttgca cg                                              22

<210> SEQ ID NO 20
<211> LENGTH: 22
<212> TYPE: DNA
<213> ORGANISM: Artificial sequence
<220> FEATURE:
<223> OTHER INFORMATION: Forward primer
```

```
<220> FEATURE:
<221> NAME/KEY: misc_feature
<222> LOCATION: (9)..(11)
<223> OTHER INFORMATION: n is a, c, g, or t

<400> SEQUENCE: 20
gtcaagcgnn naaatttgca cg                                              22

<210> SEQ ID NO 21
<211> LENGTH: 27
<212> TYPE: DNA
<213> ORGANISM: Artificial sequence
<220> FEATURE:
<223> OTHER INFORMATION: Forward primer
<220> FEATURE:
<221> NAME/KEY: misc_feature
<222> LOCATION: (11)..(13)
<223> OTHER INFORMATION: n is a, c, g, or t

<400> SEQUENCE: 21
gcttaaattt nnncgtgatt ttgcagg                                         27

<210> SEQ ID NO 22
<211> LENGTH: 18
<212> TYPE: DNA
<213> ORGANISM: Artificial sequence
<220> FEATURE:
<223> OTHER INFORMATION: Forward primer
<220> FEATURE:
<221> NAME/KEY: misc_feature
<222> LOCATION: (7)..(9)
<223> OTHER INFORMATION: n is a, c, g, or t

<400> SEQUENCE: 22
cgtgatnnng caggagac                                                   18

<210> SEQ ID NO 23
<211> LENGTH: 18
<212> TYPE: DNA
<213> ORGANISM: Artificial sequence
<220> FEATURE:
<223> OTHER INFORMATION: Forward primer
<220> FEATURE:
<221> NAME/KEY: misc_feature
<222> LOCATION: (10)..(12)
<223> OTHER INFORMATION: n is a, c, g, or t

<400> SEQUENCE: 23
cgtgattttn nnggagac                                                   18

<210> SEQ ID NO 24
<211> LENGTH: 25
<212> TYPE: DNA
<213> ORGANISM: Artificial sequence
<220> FEATURE:
<223> OTHER INFORMATION: Forward primer
<220> FEATURE:
<221> NAME/KEY: misc_feature
<222> LOCATION: (12)..(14)
<223> OTHER INFORMATION: n is a, c, g, or t

<400> SEQUENCE: 24
gagacgggtt annnacaagc tggac                                           25

<210> SEQ ID NO 25
<211> LENGTH: 27
<212> TYPE: DNA
<213> ORGANISM: Artificial sequence
<220> FEATURE:
```

```
<223> OTHER INFORMATION: Forward primer
<220> FEATURE:
<221> NAME/KEY: misc_feature
<222> LOCATION: (16)..(18)
<223> OTHER INFORMATION: n is a, c, g, or t

<400> SEQUENCE: 25
ggagacgggt tatttnnnag ctggacg                                      27

<210> SEQ ID NO 26
<211> LENGTH: 28
<212> TYPE: DNA
<213> ORGANISM: Artificial sequence
<220> FEATURE:
<223> OTHER INFORMATION: Forward primer
<220> FEATURE:
<221> NAME/KEY: misc_feature
<222> LOCATION: (10)..(12)
<223> OTHER INFORMATION: n is a, c, g, or t

<400> SEQUENCE: 26
caaattattn nnttcttaat tgcgggac                                     28

<210> SEQ ID NO 27
<211> LENGTH: 26
<212> TYPE: DNA
<213> ORGANISM: Artificial sequence
<220> FEATURE:
<223> OTHER INFORMATION: Forward primer
<220> FEATURE:
<221> NAME/KEY: misc_feature
<222> LOCATION: (10)..(12)
<223> OTHER INFORMATION: n is a, c, g, or t

<400> SEQUENCE: 27
acattcttan nngcgggaca cgaaac                                       26

<210> SEQ ID NO 28
<211> LENGTH: 26
<212> TYPE: DNA
<213> ORGANISM: Artificial sequence
<220> FEATURE:
<223> OTHER INFORMATION: Forward primer
<220> FEATURE:
<221> NAME/KEY: misc_feature
<222> LOCATION: (13)..(15)
<223> OTHER INFORMATION: n is a, c, g, or t

<400> SEQUENCE: 28
acattcttaa ttnnnggaca cgaaac                                       26

<210> SEQ ID NO 29
<211> LENGTH: 21
<212> TYPE: DNA
<213> ORGANISM: Artificial sequence
<220> FEATURE:
<223> OTHER INFORMATION: Forward primer
<220> FEATURE:
<221> NAME/KEY: misc_feature
<222> LOCATION: (7)..(9)
<223> OTHER INFORMATION: n is a, c, g, or t

<400> SEQUENCE: 29
ccaactnnnc ctgcgttttc c                                            21

<210> SEQ ID NO 30
<211> LENGTH: 21
<212> TYPE: DNA
<213> ORGANISM: Artificial sequence
```

```
<220> FEATURE:
<223> OTHER INFORMATION: Forward primer

<400> SEQUENCE: 30
ggaaacagga tccatcgatg c                                              21

<210> SEQ ID NO 31
<211> LENGTH: 20
<212> TYPE: DNA
<213> ORGANISM: Artificial sequence
<220> FEATURE:
<223> OTHER INFORMATION: Forward primer

<400> SEQUENCE: 31
gtgaaggaat accgccaagc                                                20

<210> SEQ ID NO 32
<211> LENGTH: 32
<212> TYPE: DNA
<213> ORGANISM: Artificial sequence
<220> FEATURE:
<223> OTHER INFORMATION: Forward primer

<400> SEQUENCE: 32
gcttaaattc rcgcgtgatt ttdbcggaga cg                                  32

<210> SEQ ID NO 33
<211> LENGTH: 31
<212> TYPE: DNA
<213> ORGANISM: Artificial sequence
<220> FEATURE:
<223> OTHER INFORMATION: Forward primer

<400> SEQUENCE: 33
cttaaattct ttcgtgattt tdbcggagac g                                   31

<210> SEQ ID NO 34
<211> LENGTH: 28
<212> TYPE: DNA
<213> ORGANISM: Artificial sequence
<220> FEATURE:
<223> OTHER INFORMATION: Forward primer

<400> SEQUENCE: 34
caaattatta cattcttaat tgcgggac                                       28

<210> SEQ ID NO 35
<211> LENGTH: 28
<212> TYPE: DNA
<213> ORGANISM: Artificial sequence
<220> FEATURE:
<223> OTHER INFORMATION: Forward primer

<400> SEQUENCE: 35
caaattatta acttcttaat tgcgggac                                       28

<210> SEQ ID NO 36
<211> LENGTH: 28
<212> TYPE: DNA
<213> ORGANISM: Artificial sequence
<220> FEATURE:
<223> OTHER INFORMATION: Forward primer

<400> SEQUENCE: 36
caaattattc ttttcttaat tgcgggac                                       28
```

<210> SEQ ID NO 37
<211> LENGTH: 25
<212> TYPE: DNA
<213> ORGANISM: Artificial sequence
<220> FEATURE:
<223> OTHER INFORMATION: Forward primer
<220> FEATURE:
<221> NAME/KEY: misc_feature
<222> LOCATION: (12)..(12)
<223> OTHER INFORMATION: n is a, c, g, or t

<400> SEQUENCE: 37
gagacgggtt antyacaagc tggac                                    25

<210> SEQ ID NO 38
<211> LENGTH: 25
<212> TYPE: DNA
<213> ORGANISM: Artificial sequence
<220> FEATURE:
<223> OTHER INFORMATION: Forward primer
<220> FEATURE:
<221> NAME/KEY: misc_feature
<222> LOCATION: (12)..(12)
<223> OTHER INFORMATION: n is a, c, g, or t

<400> SEQUENCE: 38
gagacgggtt antytgtagc tggac                                    25

<210> SEQ ID NO 39
<211> LENGTH: 21
<212> TYPE: DNA
<213> ORGANISM: Artificial sequence
<220> FEATURE:
<223> OTHER INFORMATION: Forward primer

<400> SEQUENCE: 39
ccaactgctc ctgcgttttc c                                        21

<210> SEQ ID NO 40
<211> LENGTH: 21
<212> TYPE: DNA
<213> ORGANISM: Artificial sequence
<220> FEATURE:
<223> OTHER INFORMATION: Forward primer

<400> SEQUENCE: 40
ccaactbttc ctgcgttttc c                                        21

<210> SEQ ID NO 41
<211> LENGTH: 21
<212> TYPE: DNA
<213> ORGANISM: Artificial sequence
<220> FEATURE:
<223> OTHER INFORMATION: Forward primer

<400> SEQUENCE: 41
ccaactatgc ctgcgttttc c                                        21

<210> SEQ ID NO 42
<211> LENGTH: 22
<212> TYPE: DNA
<213> ORGANISM: Artificial sequence
<220> FEATURE:
<223> OTHER INFORMATION: Forward primer

<400> SEQUENCE: 42
cttaagtcaa gcgmttaaat tc                                       22

<210> SEQ ID NO 43
<211> LENGTH: 22
<212> TYPE: DNA
<213> ORGANISM: Artificial sequence
<220> FEATURE:
<223> OTHER INFORMATION: Forward primer

<400> SEQUENCE: 43
cttaagtcaa gcgtggaaat tc                                         22

<210> SEQ ID NO 44
<211> LENGTH: 31
<212> TYPE: DNA
<213> ORGANISM: Artificial sequence
<220> FEATURE:
<223> OTHER INFORMATION: Forward primer

<400> SEQUENCE: 44
gactttgaag atcatacaaa ctacgagctc g                               31

<210> SEQ ID NO 45
<211> LENGTH: 39
<212> TYPE: DNA
<213> ORGANISM: Artificial sequence
<220> FEATURE:
<223> OTHER INFORMATION: Reverse primer

<400> SEQUENCE: 45
agatctgctc atgtttgaca gcttatcatc gatgaattc                       39

<210> SEQ ID NO 46
<211> LENGTH: 21
<212> TYPE: DNA
<213> ORGANISM: Artificial sequence
<220> FEATURE:
<223> OTHER INFORMATION: Forward primer

<400> SEQUENCE: 46
cgcgctacat atcaagtcag c                                          21

<210> SEQ ID NO 47
<211> LENGTH: 21
<212> TYPE: DNA
<213> ORGANISM: Artificial sequence
<220> FEATURE:
<223> OTHER INFORMATION: Reverse primer

<400> SEQUENCE: 47
gctgacttga tatgtagcgc g                                          21

<210> SEQ ID NO 48
<211> LENGTH: 27
<212> TYPE: DNA
<213> ORGANISM: Artificial sequence
<220> FEATURE:
<223> OTHER INFORMATION: Forward primer

<400> SEQUENCE: 48
gtatcggaag acgcgacacg tttaacg                                    27

<210> SEQ ID NO 49
<211> LENGTH: 27
<212> TYPE: DNA
<213> ORGANISM: Artificial sequence
<220> FEATURE:

```
<223> OTHER INFORMATION: Reverse primer

<400> SEQUENCE: 49
gtatcggaag acgcgacacg tttaacg                                27

<210> SEQ ID NO 50
<211> LENGTH: 22
<212> TYPE: DNA
<213> ORGANISM: Artificial sequence
<220> FEATURE:
<223> OTHER INFORMATION: Forward primer

<400> SEQUENCE: 50
gaagatacga tgcttggagg ag                                     22

<210> SEQ ID NO 51
<211> LENGTH: 22
<212> TYPE: DNA
<213> ORGANISM: Artificial sequence
<220> FEATURE:
<223> OTHER INFORMATION: Reverse primer

<400> SEQUENCE: 51
ctcctccaag catcgtatct tc                                     22

<210> SEQ ID NO 52
<211> LENGTH: 25
<212> TYPE: DNA
<213> ORGANISM: Artificial sequence
<220> FEATURE:
<223> OTHER INFORMATION: Forward primer

<400> SEQUENCE: 52
cgtgataaaa cagtttgggg agacg                                  25

<210> SEQ ID NO 53
<211> LENGTH: 25
<212> TYPE: DNA
<213> ORGANISM: Artificial sequence
<220> FEATURE:
<223> OTHER INFORMATION: Reverse primer

<400> SEQUENCE: 53
cgtctcccca aactgtttta tcacg                                  25

<210> SEQ ID NO 54
<211> LENGTH: 24
<212> TYPE: DNA
<213> ORGANISM: Artificial sequence
<220> FEATURE:
<223> OTHER INFORMATION: Forward primer

<400> SEQUENCE: 54
cgttaaaacc taaaggcttt gtgg                                   24

<210> SEQ ID NO 55
<211> LENGTH: 24
<212> TYPE: DNA
<213> ORGANISM: Artificial sequence
<220> FEATURE:
<223> OTHER INFORMATION: Reverse primer

<400> SEQUENCE: 55
ccacaaagcc tttaggtttt aacg                                   24
```

-continued

```
<210> SEQ ID NO 56
<211> LENGTH: 26
<212> TYPE: DNA
<213> ORGANISM: Artificial sequence
<220> FEATURE:
<223> OTHER INFORMATION: Forward primer

<400> SEQUENCE: 56
cgaagcgctg cgcatctggc caactt                                              26

<210> SEQ ID NO 57
<211> LENGTH: 26
<212> TYPE: DNA
<213> ORGANISM: Artificial sequence
<220> FEATURE:
<223> OTHER INFORMATION: Reverse primer

<400> SEQUENCE: 57
aagttggcca gatgcgcagc gcttcg                                              26

<210> SEQ ID NO 58
<211> LENGTH: 26
<212> TYPE: DNA
<213> ORGANISM: Artificial sequence
<220> FEATURE:
<223> OTHER INFORMATION: Forward primer

<400> SEQUENCE: 58
cttacttcca aggttcagtc agcagg                                              26

<210> SEQ ID NO 59
<211> LENGTH: 26
<212> TYPE: DNA
<213> ORGANISM: Artificial sequence
<220> FEATURE:
<223> OTHER INFORMATION: Reversse primer

<400> SEQUENCE: 59
cctgctgact gaaccttgga agtaag                                              26

<210> SEQ ID NO 60
<211> LENGTH: 30
<212> TYPE: DNA
<213> ORGANISM: Artificial sequence
<220> FEATURE:
<223> OTHER INFORMATION: Forward primer

<400> SEQUENCE: 60
cacaggaaac aggatccatc gatgcttagg                                          30

<210> SEQ ID NO 61
<211> LENGTH: 27
<212> TYPE: DNA
<213> ORGANISM: Artificial sequence
<220> FEATURE:
<223> OTHER INFORMATION: Reverse primer

<400> SEQUENCE: 61
ctaggtgaag gaataccgcc aagcgga                                             27

<210> SEQ ID NO 62
<211> LENGTH: 30
<212> TYPE: DNA
<213> ORGANISM: Artificial sequence
<220> FEATURE:
<223> OTHER INFORMATION: Forward primer
<220> FEATURE:
```

```
<221> NAME/KEY: misc_feature
<222> LOCATION: (17)..(18)
<223> OTHER INFORMATION: n is a, c, g, or t

<400> SEQUENCE: 62
cgatattaaa gaaactnnka cgttaaaacc                                    30

<210> SEQ ID NO 63
<211> LENGTH: 30
<212> TYPE: DNA
<213> ORGANISM: Artificial sequence
<220> FEATURE:
<223> OTHER INFORMATION: Reverse primer
<220> FEATURE:
<221> NAME/KEY: misc_feature
<222> LOCATION: (13)..(14)
<223> OTHER INFORMATION: n is a, c, g, or t

<400> SEQUENCE: 63
ggttttaacg tmnnagtttc tttaatatcg                                    30

<210> SEQ ID NO 64
<211> LENGTH: 30
<212> TYPE: DNA
<213> ORGANISM: Artificial sequence
<220> FEATURE:
<223> OTHER INFORMATION: Forward primer
<220> FEATURE:
<221> NAME/KEY: misc_feature
<222> LOCATION: (20)..(21)
<223> OTHER INFORMATION: n is a, c, g, or t

<400> SEQUENCE: 64
cgatattaaa gaaactttan nkttaaaacc                                    30

<210> SEQ ID NO 65
<211> LENGTH: 30
<212> TYPE: DNA
<213> ORGANISM: Artificial sequence
<220> FEATURE:
<223> OTHER INFORMATION: Reverse primer
<220> FEATURE:
<221> NAME/KEY: misc_feature
<222> LOCATION: (10)..(11)
<223> OTHER INFORMATION: n is a, c, g, or t

<400> SEQUENCE: 65
ggttttaamn ntaaagtttc tttaatatcg                                    30

<210> SEQ ID NO 66
<211> LENGTH: 30
<212> TYPE: DNA
<213> ORGANISM: Artificial sequence
<220> FEATURE:
<223> OTHER INFORMATION: Reverse primer

<400> SEQUENCE: 66
ccgggctcag atctgctcat gtttgacagc                                    30

<210> SEQ ID NO 67
<211> LENGTH: 25
<212> TYPE: DNA
<213> ORGANISM: Artificial sequence
<220> FEATURE:
<223> OTHER INFORMATION: Forward primer
<220> FEATURE:
<221> NAME/KEY: misc_feature
<222> LOCATION: (11)..(12)
<223> OTHER INFORMATION: n is a, c, g, or t
```

-continued

<400> SEQUENCE: 67
ggtccgtgca nnkgatgaag taatg                                              25

<210> SEQ ID NO 68
<211> LENGTH: 25
<212> TYPE: DNA
<213> ORGANISM: Artificial sequence
<220> FEATURE:
<223> OTHER INFORMATION: Reverse primer
<220> FEATURE:
<221> NAME/KEY: misc_feature
<222> LOCATION: (14)..(15)
<223> OTHER INFORMATION: n is a, c, g, or t

<400> SEQUENCE: 68
cattacttca tcmnntgcac ggacc                                              25

<210> SEQ ID NO 69
<211> LENGTH: 24
<212> TYPE: DNA
<213> ORGANISM: Artificial sequence
<220> FEATURE:
<223> OTHER INFORMATION: Forward primer
<220> FEATURE:
<221> NAME/KEY: misc_feature
<222> LOCATION: (10)..(11)
<223> OTHER INFORMATION: n is a, c, g, or t

<400> SEQUENCE: 69
cgtgattttn nkggagacgg gtta                                               24

<210> SEQ ID NO 70
<211> LENGTH: 24
<212> TYPE: DNA
<213> ORGANISM: Artificial sequence
<220> FEATURE:
<223> OTHER INFORMATION: Reverse primer
<220> FEATURE:
<221> NAME/KEY: misc_feature
<222> LOCATION: (14)..(15)
<223> OTHER INFORMATION: n is a, c, g, or t

<400> SEQUENCE: 70
taacccgtct ccmnnaaaat cacg                                               24

<210> SEQ ID NO 71
<211> LENGTH: 24
<212> TYPE: DNA
<213> ORGANISM: Artificial sequence
<220> FEATURE:
<223> OTHER INFORMATION: Forward primer
<220> FEATURE:
<221> NAME/KEY: misc_feature
<222> LOCATION: (13)..(14)
<223> OTHER INFORMATION: n is a, c, g, or t

<400> SEQUENCE: 71
aacttaagtc aannkcttaa attc                                               24

<210> SEQ ID NO 72
<211> LENGTH: 24
<212> TYPE: DNA
<213> ORGANISM: Artificial sequence
<220> FEATURE:
<223> OTHER INFORMATION: Reverse primer
<220> FEATURE:
<221> NAME/KEY: misc_feature
<222> LOCATION: (11)..(12)

<223> OTHER INFORMATION: n is a, c, g, or t

<400> SEQUENCE: 72
gaatttaagm nnttgactta agtt                                            24

<210> SEQ ID NO 73
<211> LENGTH: 24
<212> TYPE: DNA
<213> ORGANISM: Artificial sequence
<220> FEATURE:
<223> OTHER INFORMATION: Forward primer
<220> FEATURE:
<221> NAME/KEY: misc_feature
<222> LOCATION: (9)..(10)
<223> OTHER INFORMATION: n is a, c, g, or t

<400> SEQUENCE: 73
gtcaagcgnn kaaattcttt cgtg                                            24

<210> SEQ ID NO 74
<211> LENGTH: 24
<212> TYPE: DNA
<213> ORGANISM: Artificial sequence
<220> FEATURE:
<223> OTHER INFORMATION: Reverse primer
<220> FEATURE:
<221> NAME/KEY: misc_feature
<222> LOCATION: (15)..(16)
<223> OTHER INFORMATION: n is a, c, g, or t

<400> SEQUENCE: 74
cacgaaagaa tttmnncgct tgac                                            24

<210> SEQ ID NO 75
<211> LENGTH: 29
<212> TYPE: DNA
<213> ORGANISM: Artificial sequence
<220> FEATURE:
<223> OTHER INFORMATION: Forward primer
<220> FEATURE:
<221> NAME/KEY: misc_feature
<222> LOCATION: (18)..(19)
<223> OTHER INFORMATION: n is a, c, g, or t

<400> SEQUENCE: 75
gtcaagcgct taaattcnnk cgtgatttt                                       29

<210> SEQ ID NO 76
<211> LENGTH: 29
<212> TYPE: DNA
<213> ORGANISM: Artificial sequence
<220> FEATURE:
<223> OTHER INFORMATION: Reverse primer
<220> FEATURE:
<221> NAME/KEY: misc_feature
<222> LOCATION: (11)..(12)
<223> OTHER INFORMATION: n is a, c, g, or t

<400> SEQUENCE: 76
aaaatcacgm nngaatttaa gcgcttgac                                       29

<210> SEQ ID NO 77
<211> LENGTH: 23
<212> TYPE: DNA
<213> ORGANISM: Artificial sequence
<220> FEATURE:
<223> OTHER INFORMATION: Forward primer
<220> FEATURE:
<221> NAME/KEY: misc_feature

```
<222> LOCATION: (9)..(10)
<223> OTHER INFORMATION: n is a, c, g, or t

<400> SEQUENCE: 77
ggccaactnn kcctgcgttt tcc                                              23

<210> SEQ ID NO 78
<211> LENGTH: 23
<212> TYPE: DNA
<213> ORGANISM: Artificial sequence
<220> FEATURE:
<223> OTHER INFORMATION: Reverse primer
<220> FEATURE:
<221> NAME/KEY: misc_feature
<222> LOCATION: (14)..(15)
<223> OTHER INFORMATION: n is a, c, g, or t

<400> SEQUENCE: 78
ggaaaacgca ggmnnagttg gcc                                              23

<210> SEQ ID NO 79
<211> LENGTH: 24
<212> TYPE: DNA
<213> ORGANISM: Artificial sequence
<220> FEATURE:
<223> OTHER INFORMATION: Forward primer
<220> FEATURE:
<221> NAME/KEY: misc_feature
<222> LOCATION: (13)..(14)
<223> OTHER INFORMATION: n is a, c, g, or t

<400> SEQUENCE: 79
gcactggatg aannkatgaa caag                                             24

<210> SEQ ID NO 80
<211> LENGTH: 24
<212> TYPE: DNA
<213> ORGANISM: Artificial sequence
<220> FEATURE:
<223> OTHER INFORMATION: Reverse primer
<220> FEATURE:
<221> NAME/KEY: misc_feature
<222> LOCATION: (11)..(12)
<223> OTHER INFORMATION: n is a, c, g, or t

<400> SEQUENCE: 80
cttgttcatm nnttcatcca gtgc                                             24

<210> SEQ ID NO 81
<211> LENGTH: 24
<212> TYPE: DNA
<213> ORGANISM: Artificial sequence
<220> FEATURE:
<223> OTHER INFORMATION: Forward primer
<220> FEATURE:
<221> NAME/KEY: misc_feature
<222> LOCATION: (8)..(9)
<223> OTHER INFORMATION: n is a, c, g, or t

<400> SEQUENCE: 81
gaacaagnnk cagcgagcaa atcc                                             24

<210> SEQ ID NO 82
<211> LENGTH: 24
<212> TYPE: DNA
<213> ORGANISM: Artificial sequence
<220> FEATURE:
<223> OTHER INFORMATION: Reverse primer
<220> FEATURE:
```

```
<221> NAME/KEY: misc_feature
<222> LOCATION: (16)..(17)
<223> OTHER INFORMATION: n is a, c, g, or t

<400> SEQUENCE: 82
ggatttgctc gctgmnnctt gttc                                          24

<210> SEQ ID NO 83
<211> LENGTH: 22
<212> TYPE: DNA
<213> ORGANISM: Artificial sequence
<220> FEATURE:
<223> OTHER INFORMATION: Forward primer
<220> FEATURE:
<221> NAME/KEY: misc_feature
<222> LOCATION: (11)..(12)
<223> OTHER INFORMATION: n is a, c, g, or t

<400> SEQUENCE: 83
gcgtgcgtgt nnkggtcagc ag                                            22

<210> SEQ ID NO 84
<211> LENGTH: 22
<212> TYPE: DNA
<213> ORGANISM: Artificial sequence
<220> FEATURE:
<223> OTHER INFORMATION: Reverse primer
<220> FEATURE:
<221> NAME/KEY: misc_feature
<222> LOCATION: (11)..(12)
<223> OTHER INFORMATION: n is a, c, g, or t

<400> SEQUENCE: 84
ctgctgaccm nnacacgcac gc                                            22

<210> SEQ ID NO 85
<211> LENGTH: 25
<212> TYPE: DNA
<213> ORGANISM: Artificial sequence
<220> FEATURE:
<223> OTHER INFORMATION: Forward primer
<220> FEATURE:
<221> NAME/KEY: misc_feature
<222> LOCATION: (13)..(14)
<223> OTHER INFORMATION: n is a, c, g, or t

<400> SEQUENCE: 85
gcgggacacg aannkacaag tggtc                                         25

<210> SEQ ID NO 86
<211> LENGTH: 25
<212> TYPE: DNA
<213> ORGANISM: Artificial sequence
<220> FEATURE:
<223> OTHER INFORMATION: Reverse primer
<220> FEATURE:
<221> NAME/KEY: misc_feature
<222> LOCATION: (12)..(13)
<223> OTHER INFORMATION: n is a, c, g, or t

<400> SEQUENCE: 86
gaccacttgt mnnttcgtgt cccgc                                         25

<210> SEQ ID NO 87
<211> LENGTH: 33
<212> TYPE: DNA
<213> ORGANISM: Artificial sequence
<220> FEATURE:
<223> OTHER INFORMATION: Forward primer
```

```
<220> FEATURE:
<221> NAME/KEY: misc_feature
<222> LOCATION: (15)..(16)
<223> OTHER INFORMATION: n is a, c, g, or t

<400> SEQUENCE: 87
cattcttaat tgcgnnkcac gaaacaacaa gtg                             33

<210> SEQ ID NO 88
<211> LENGTH: 33
<212> TYPE: DNA
<213> ORGANISM: Artificial sequence
<220> FEATURE:
<223> OTHER INFORMATION: Reverse primer
<220> FEATURE:
<221> NAME/KEY: misc_feature
<222> LOCATION: (18)..(19)
<223> OTHER INFORMATION: n is a, c, g, or t

<400> SEQUENCE: 88
cacttgttgt ttcgtgmnnc gcaattaaga atg                             33

<210> SEQ ID NO 89
<211> LENGTH: 33
<212> TYPE: DNA
<213> ORGANISM: Artificial sequence
<220> FEATURE:
<223> OTHER INFORMATION: Forward primer
<220> FEATURE:
<221> NAME/KEY: misc_feature
<222> LOCATION: (12)..(13)
<223> OTHER INFORMATION: n is a, c, g, or t

<400> SEQUENCE: 89
cattcttaat tnnkggacac gaaacaacaa gtg                             33

<210> SEQ ID NO 90
<211> LENGTH: 33
<212> TYPE: DNA
<213> ORGANISM: Artificial sequence
<220> FEATURE:
<223> OTHER INFORMATION: Reverse primer
<220> FEATURE:
<221> NAME/KEY: misc_feature
<222> LOCATION: (21)..(22)
<223> OTHER INFORMATION: n is a, c, g, or t

<400> SEQUENCE: 90
cacttgttgt ttcgtgtccm nnaattaaga atg                             33

<210> SEQ ID NO 91
<211> LENGTH: 28
<212> TYPE: DNA
<213> ORGANISM: Artificial sequence
<220> FEATURE:
<223> OTHER INFORMATION: Forward primer
<220> FEATURE:
<221> NAME/KEY: misc_feature
<222> LOCATION: (10)..(11)
<223> OTHER INFORMATION: n is a, c, g, or t

<400> SEQUENCE: 91
caaattattn nkttcttaat tgcgggac                                   28

<210> SEQ ID NO 92
<211> LENGTH: 28
<212> TYPE: DNA
<213> ORGANISM: Artificial sequence
<220> FEATURE:
```

```
<223> OTHER INFORMATION: Reverse primer
<220> FEATURE:
<221> NAME/KEY: misc_feature
<222> LOCATION: (18)..(19)
<223> OTHER INFORMATION: n is a, c, g, or t

<400> SEQUENCE: 92
gtcccgcaat taagaamnna ataatttg                                        28

<210> SEQ ID NO 93
<211> LENGTH: 22
<212> TYPE: DNA
<213> ORGANISM: Artificial sequence
<220> FEATURE:
<223> OTHER INFORMATION: Forward primer
<220> FEATURE:
<221> NAME/KEY: misc_feature
<222> LOCATION: (9)..(10)
<223> OTHER INFORMATION: n is a, c, g, or t

<400> SEQUENCE: 93
gtcaagcgnn kaaatttgta cg                                              22

<210> SEQ ID NO 94
<211> LENGTH: 28
<212> TYPE: DNA
<213> ORGANISM: Artificial sequence
<220> FEATURE:
<223> OTHER INFORMATION: Reverse primer
<220> FEATURE:
<221> NAME/KEY: misc_feature
<222> LOCATION: (18)..(19)
<223> OTHER INFORMATION: n is a, c, g, or t

<400> SEQUENCE: 94
gtcccgcaat taagaamnna ataatttg                                        28

<210> SEQ ID NO 95
<211> LENGTH: 28
<212> TYPE: DNA
<213> ORGANISM: Artificial sequence
<220> FEATURE:
<223> OTHER INFORMATION: Forward primer
<220> FEATURE:
<221> NAME/KEY: misc_feature
<222> LOCATION: (13)..(14)
<223> OTHER INFORMATION: n is a, c, g, or t

<400> SEQUENCE: 95
gacgggttat ttnnkagctg gacgcatg                                        28

<210> SEQ ID NO 96
<211> LENGTH: 28
<212> TYPE: DNA
<213> ORGANISM: Artificial sequence
<220> FEATURE:
<223> OTHER INFORMATION: Reverse primer
<220> FEATURE:
<221> NAME/KEY: misc_feature
<222> LOCATION: (18)..(19)
<223> OTHER INFORMATION: n is a, c, g, or t

<400> SEQUENCE: 96
gtcccgcaat taagaamnna ataatttg                                        28

<210> SEQ ID NO 97
<211> LENGTH: 21
<212> TYPE: DNA
<213> ORGANISM: Artificial sequence
```

```
<220> FEATURE:
<223> OTHER INFORMATION: Forward primer
<220> FEATURE:
<221> NAME/KEY: misc_feature
<222> LOCATION: (10)..(11)
<223> OTHER INFORMATION: n is a, c, g, or t

<400> SEQUENCE: 97
gacgggttan nkacaagctg g                                              21

<210> SEQ ID NO 98
<211> LENGTH: 21
<212> TYPE: DNA
<213> ORGANISM: Artificial sequence
<220> FEATURE:
<223> OTHER INFORMATION: Reverse primer
<220> FEATURE:
<221> NAME/KEY: misc_feature
<222> LOCATION: (11)..(12)
<223> OTHER INFORMATION: n is a, c, g, or t

<400> SEQUENCE: 98
ccagcttgtm nntaacccgt c                                              21

<210> SEQ ID NO 99
<211> LENGTH: 24
<212> TYPE: DNA
<213> ORGANISM: Artificial sequence
<220> FEATURE:
<223> OTHER INFORMATION: Forward primer

<400> SEQUENCE: 99
cgtgattttg gtggagacgg gtta                                           24

<210> SEQ ID NO 100
<211> LENGTH: 24
<212> TYPE: DNA
<213> ORGANISM: Artificial sequence
<220> FEATURE:
<223> OTHER INFORMATION: Reverse primer

<400> SEQUENCE: 100
taacccgtct ccaccaaaat cacg                                           24

<210> SEQ ID NO 101
<211> LENGTH: 21
<212> TYPE: DNA
<213> ORGANISM: Artificial sequence
<220> FEATURE:
<223> OTHER INFORMATION: Forward primer

<400> SEQUENCE: 101
gctggtactt ggtatgatgc t                                              21

<210> SEQ ID NO 102
<211> LENGTH: 20
<212> TYPE: DNA
<213> ORGANISM: Artificial sequence
<220> FEATURE:
<223> OTHER INFORMATION: Reverse primer

<400> SEQUENCE: 102
ccagacggat ttgctgtgat                                                20

<210> SEQ ID NO 103
<211> LENGTH: 20
<212> TYPE: DNA
```

```
<213> ORGANISM: Artificial sequence
<220> FEATURE:
<223> OTHER INFORMATION: Forward primer

<400> SEQUENCE: 103
cgtgtaacag caaggttcgg                                              20

<210> SEQ ID NO 104
<211> LENGTH: 23
<212> TYPE: DNA
<213> ORGANISM: Artificial sequence
<220> FEATURE:
<223> OTHER INFORMATION: Reverse primer

<400> SEQUENCE: 104
ctgctcatgt ttgacagctt atc                                          23

<210> SEQ ID NO 105
<211> LENGTH: 24
<212> TYPE: DNA
<213> ORGANISM: Artificial sequence
<220> FEATURE:
<223> OTHER INFORMATION: Forward primer
<220> FEATURE:
<221> NAME/KEY: misc_feature
<222> LOCATION: (15)..(16)
<223> OTHER INFORMATION: n is a, c, g, or t

<400> SEQUENCE: 105
cgttaaaacc tgaannkttt gtgg                                         24

<210> SEQ ID NO 106
<211> LENGTH: 24
<212> TYPE: DNA
<213> ORGANISM: Artificial sequence
<220> FEATURE:
<223> OTHER INFORMATION: Reverse primer
<220> FEATURE:
<221> NAME/KEY: misc_feature
<222> LOCATION: (9)..(10)
<223> OTHER INFORMATION: n is a, c, g, or t

<400> SEQUENCE: 106
ccacaaamnn ttcaggtttt aacg                                         24

<210> SEQ ID NO 107
<211> LENGTH: 24
<212> TYPE: DNA
<213> ORGANISM: Artificial sequence
<220> FEATURE:
<223> OTHER INFORMATION: Forward primer
<220> FEATURE:
<221> NAME/KEY: misc_feature
<222> LOCATION: (13)..(14)
<223> OTHER INFORMATION: n is a, c, g, or t

<400> SEQUENCE: 107
cctgaaggct ttnnkgtaaa agca                                         24

<210> SEQ ID NO 108
<211> LENGTH: 24
<212> TYPE: DNA
<213> ORGANISM: Artificial sequence
<220> FEATURE:
<223> OTHER INFORMATION: Reverse primer
<220> FEATURE:
<221> NAME/KEY: misc_feature
<222> LOCATION: (11)..(12)
<223> OTHER INFORMATION: n is a, c, g, or t
```

```
<400> SEQUENCE: 108
tgcttttacm nnaaagcctt cagg                                              24

<210> SEQ ID NO 109
<211> LENGTH: 25
<212> TYPE: DNA
<213> ORGANISM: Artificial sequence
<220> FEATURE:
<223> OTHER INFORMATION: Forward primer
<220> FEATURE:
<221> NAME/KEY: misc_feature
<222> LOCATION: (11)..(12)
<223> OTHER INFORMATION: n is a, c, g, or t

<400> SEQUENCE: 109
cgctcataat nnkccgctgc ttgtg                                             25

<210> SEQ ID NO 110
<211> LENGTH: 25
<212> TYPE: DNA
<213> ORGANISM: Artificial sequence
<220> FEATURE:
<223> OTHER INFORMATION: Reverse primer
<220> FEATURE:
<221> NAME/KEY: misc_feature
<222> LOCATION: (14)..(15)
<223> OTHER INFORMATION: n is a, c, g, or t

<400> SEQUENCE: 110
cacaagcagc ggmnnattat gagcg                                             25

<210> SEQ ID NO 111
<211> LENGTH: 25
<212> TYPE: DNA
<213> ORGANISM: Artificial sequence
<220> FEATURE:
<223> OTHER INFORMATION: Forward primere
<220> FEATURE:
<221> NAME/KEY: misc_feature
<222> LOCATION: (13)..(14)
<223> OTHER INFORMATION: n is a, c, g, or t

<400> SEQUENCE: 111
ccgcaggtcg cannkcttga ttcac                                             25

<210> SEQ ID NO 112
<211> LENGTH: 25
<212> TYPE: DNA
<213> ORGANISM: Artificial sequence
<220> FEATURE:
<223> OTHER INFORMATION: Reverse primer
<220> FEATURE:
<221> NAME/KEY: misc_feature
<222> LOCATION: (12)..(13)
<223> OTHER INFORMATION: n is a, c, g, or t

<400> SEQUENCE: 112
gtgaatcaag mnntgcgacc tgcgg                                             25

<210> SEQ ID NO 113
<211> LENGTH: 24
<212> TYPE: DNA
<213> ORGANISM: Artificial sequence
<220> FEATURE:
<223> OTHER INFORMATION: Forward primer
<220> FEATURE:
<221> NAME/KEY: misc_feature
<222> LOCATION: (10)..(11)
```

```
<223> OTHER INFORMATION: n is a, c, g, or t

<400> SEQUENCE: 113
gcggatatgn nkcttgcgaa aatg                                                24

<210> SEQ ID NO 114
<211> LENGTH: 24
<212> TYPE: DNA
<213> ORGANISM: Artificial sequence
<220> FEATURE:
<223> OTHER INFORMATION: Reverse primer
<220> FEATURE:
<221> NAME/KEY: misc_feature
<222> LOCATION: (14)..(15)
<223> OTHER INFORMATION: n is a, c, g, or t

<400> SEQUENCE: 114
cattttcgca agmnncatat ccgc                                                24

<210> SEQ ID NO 115
<211> LENGTH: 27
<212> TYPE: DNA
<213> ORGANISM: Artificial sequence
<220> FEATURE:
<223> OTHER INFORMATION: forward primer
<220> FEATURE:
<221> NAME/KEY: misc_feature
<222> LOCATION: (13)..(14)
<223> OTHER INFORMATION: n is a, c, g, or t

<400> SEQUENCE: 115
ggtgcgtttt cannkaacgt cgtagca                                             27

<210> SEQ ID NO 116
<211> LENGTH: 27
<212> TYPE: DNA
<213> ORGANISM: Artificial sequence
<220> FEATURE:
<223> OTHER INFORMATION: Reverse primer
<220> FEATURE:
<221> NAME/KEY: misc_feature
<222> LOCATION: (14)..(15)
<223> OTHER INFORMATION: n is a, c, g, or t

<400> SEQUENCE: 116
tgctacgacg ttmnntgaaa acgcacc                                             27

<210> SEQ ID NO 117
<211> LENGTH: 22
<212> TYPE: DNA
<213> ORGANISM: Artificial sequence
<220> FEATURE:
<223> OTHER INFORMATION: Forward primer
<220> FEATURE:
<221> NAME/KEY: misc_feature
<222> LOCATION: (10)..(11)
<223> OTHER INFORMATION: n is a, c, g, or t

<400> SEQUENCE: 117
caagaaggan nkcatttagg tg                                                  22

<210> SEQ ID NO 118
<211> LENGTH: 22
<212> TYPE: DNA
<213> ORGANISM: Artificial sequence
<220> FEATURE:
<223> OTHER INFORMATION: Reverse primer
<220> FEATURE:
<221> NAME/KEY: misc_feature
```

```
<222> LOCATION: (12)..(13)
<223> OTHER INFORMATION: n is a, c, g, or t

<400> SEQUENCE: 118
cacctaaatg mnntccttct tg                                              22

<210> SEQ ID NO 119
<211> LENGTH: 23
<212> TYPE: DNA
<213> ORGANISM: Artificial sequence
<220> FEATURE:
<223> OTHER INFORMATION: Forward primer
<220> FEATURE:
<221> NAME/KEY: misc_feature
<222> LOCATION: (13)..(14)
<223> OTHER INFORMATION: n is a, c, g, or t

<400> SEQUENCE: 119
cagcagctag aannkaaagg ccg                                             23

<210> SEQ ID NO 120
<211> LENGTH: 23
<212> TYPE: DNA
<213> ORGANISM: Artificial sequence
<220> FEATURE:
<223> OTHER INFORMATION: Reverse primer
<220> FEATURE:
<221> NAME/KEY: misc_feature
<222> LOCATION: (10)..(11)
<223> OTHER INFORMATION: n is a, c, g, or t

<400> SEQUENCE: 120
cggcctttmn nttctagctg ctg                                             23

<210> SEQ ID NO 121
<211> LENGTH: 23
<212> TYPE: DNA
<213> ORGANISM: Artificial sequence
<220> FEATURE:
<223> OTHER INFORMATION: Forward primer

<400> SEQUENCE: 121
gcagatattg caatgagcaa agg                                             23

<210> SEQ ID NO 122
<211> LENGTH: 23
<212> TYPE: DNA
<213> ORGANISM: Artificial sequence
<220> FEATURE:
<223> OTHER INFORMATION: Reverse primer

<400> SEQUENCE: 122
cctttgctca ttgcaatatc tgc                                             23

<210> SEQ ID NO 123
<211> LENGTH: 21
<212> TYPE: DNA
<213> ORGANISM: Artificial sequence
<220> FEATURE:
<223> OTHER INFORMATION: Forward primer

<400> SEQUENCE: 123
cggtctgccc gccgcataaa g                                               21

<210> SEQ ID NO 124
<211> LENGTH: 21
<212> TYPE: DNA
```

<213> ORGANISM: Artificial sequence
<220> FEATURE:
<223> OTHER INFORMATION: Reverse primer

<400> SEQUENCE: 124
ctttatgcgg cgggcagacc g                                       21

<210> SEQ ID NO 125
<211> LENGTH: 1048
<212> TYPE: PRT
<213> ORGANISM: Artificial sequence
<220> FEATURE:
<223> OTHER INFORMATION: Mutant P450PMO protein sequence

<400> SEQUENCE: 125

```
Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Cys Val
        35                  40                  45

Thr Arg Tyr Ile Ser Ser Gln Arg Leu Ile Lys Glu Ala Cys Asp Glu
    50                  55                  60

Ser Arg Phe Asp Lys Asn Leu Ser Gln Glu Leu Lys Phe Phe Arg Asp
65                  70                  75                  80

Phe Gly Gly Asp Gly Leu Phe Thr Ser Trp Thr His Glu Ile Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Pro Gln Arg Ala Asn
            180                 185                 190

Pro Asp Asp Pro Ala Tyr Asp Glu Asn Lys Arg Gln Cys Gln Glu Asp
        195                 200                 205

Ile Lys Val Met Asn Asp Leu Val Asp Lys Ile Ile Ala Asp Arg Lys
    210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Val Val Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Thr Phe Pro Ala Phe Ser Leu Tyr Ala Lys
```

-continued

```
                325                 330                 335
Glu Asp Thr Val Leu Gly Gly Glu Tyr Pro Leu Glu Lys Gly Asp Glu
            340                 345                 350
Val Met Val Leu Ile Pro Gln Leu His Arg Asp Lys Thr Val Trp Gly
            355                 360                 365
Asp Asp Val Glu Glu Phe Arg Pro Glu Arg Phe Glu Asn Pro Ser Ala
            370                 375                 380
Ile Pro Gln His Ala Phe Lys Pro Phe Gly Asn Gly Gln Arg Ala Cys
385                 390                 395                 400
Ile Gly Gln Gln Phe Ala Leu His Glu Ala Thr Leu Val Leu Gly Met
                405                 410                 415
Met Leu Lys His Phe Asp Phe Glu Asp His Thr Asn Tyr Glu Leu Asp
            420                 425                 430
Ile Lys Glu Thr Leu Thr Leu Lys Pro Glu Ala Phe Val Val Lys Ala
            435                 440                 445
Lys Ser Lys Lys Ile Pro Leu Gly Gly Ile Pro Ser Pro Ser Thr Gly
450                 455                 460
Gln Ser Ala Lys Lys Val Arg Lys Lys Ala Glu Asn Ala His Asn Thr
465                 470                 475                 480
Pro Leu Leu Val Leu Tyr Gly Ser Asn Met Gly Thr Ala Glu Gly Thr
                485                 490                 495
Ala Arg Asp Leu Ala Asp Ile Ala Met Ser Lys Gly Phe Ala Pro Gln
            500                 505                 510
Val Ala Thr Leu Asp Ser His Ala Gly Asn Leu Pro Arg Glu Gly Ala
            515                 520                 525
Val Leu Ile Val Thr Ala Ser Tyr Asn Gly His Pro Pro Asp Asn Ala
            530                 535                 540
Lys Gln Phe Val Asp Trp Leu Asp Gln Ala Ser Ala Asp Glu Val Lys
545                 550                 555                 560
Gly Val Arg Tyr Ser Val Phe Gly Cys Gly Asp Lys Asn Trp Ala Thr
                565                 570                 575
Thr Tyr Gln Lys Val Pro Ala Phe Ile Asp Glu Thr Leu Ala Ala Lys
            580                 585                 590
Gly Ala Glu Asn Ile Ala Asp Arg Gly Glu Ala Asp Ala Ser Asp Asp
            595                 600                 605
Phe Glu Gly Thr Tyr Glu Glu Trp Arg Glu His Met Trp Ser Asp Val
            610                 615                 620
Ala Ala Tyr Phe Asn Leu Asp Ile Glu Asn Ser Glu Asp Asn Lys Ser
625                 630                 635                 640
Thr Leu Ser Leu Gln Phe Val Asp Ser Ala Ala Asp Met Pro Leu Ala
                645                 650                 655
Lys Met His Gly Ala Phe Ser Thr Asn Val Val Ala Ser Lys Glu Leu
            660                 665                 670
Gln Gln Pro Gly Ser Ala Arg Ser Thr Arg His Leu Glu Ile Glu Leu
            675                 680                 685
Pro Lys Glu Ala Ser Tyr Gln Glu Gly Gly His Leu Gly Val Ile Pro
            690                 695                 700
Arg Asn Tyr Glu Gly Thr Val Asn Arg Val Thr Ala Arg Phe Gly Leu
705                 710                 715                 720
Asp Ala Ser Gln Gln Ile Arg Leu Glu Ala Glu Glu Lys Leu Ala
                725                 730                 735
His Leu Pro Leu Ala Lys Thr Val Ser Val Glu Glu Leu Leu Gln Tyr
            740                 745                 750
```

```
Val Glu Leu Gln Asp Pro Val Thr Arg Thr Gln Leu Arg Ala Met Ala
        755                 760                 765

Ala Lys Thr Val Cys Pro Pro His Lys Val Glu Leu Glu Ala Leu Leu
    770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
            805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
        835                 840                 845

Val Ser Gly Glu Ala Trp Ser Gly Tyr Gly Glu Tyr Lys Gly Ile Ala
    850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
                900                 905                 910

Phe Val Gln Ala Arg Lys Gln Leu Lys Glu Gln Gly Gln Ser Leu Gly
            915                 920                 925

Glu Ala His Leu Tyr Phe Gly Cys Arg Ser Pro His Glu Asp Tyr Leu
    930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
                980                 985                 990

Gly Ala His Phe Tyr Ile Cys Gly Asp Gly Ser Gln Met Ala Pro Ala
        995                 1000                1005

Val Glu Ala Thr Leu Met Lys Ser Tyr Ala Asp Val His Gln Val
    1010                1015                1020

Ser Glu Ala Asp Ala Arg Leu Trp Leu Gln Gln Leu Glu Glu Lys
    1025                1030                1035

Gly Arg Tyr Ala Lys Asp Val Trp Ala Gly
    1040                1045
```